United States Patent
Bernstein et al.

(10) Patent No.: US 9,834,755 B2
(45) Date of Patent: Dec. 5, 2017

(54) COMPOSITIONS AND METHODS FOR ENHANCED GENERATION OF HEMATOPOIETIC STEM/PROGENITOR CELLS

(71) Applicants: FRED HUTCHINSON CANCER RESEARCH CENTER, Seattle, WA (US); NOVARTIS INSTITUTE FOR FUNCTIONAL GENOMICS, INC., San Diego, CA (US)

(72) Inventors: Irwin D. Bernstein, Seattle, WA (US); Anthony E. Boitano, San Diego, CA (US); Michael Cooke, San Diego, CA (US); Colleen Delaney, Seattle, WA (US)

(73) Assignees: Fred Hutchinson Cancer Research Center, Seattle, WA (US); Novartis AG, Basel (CH)

( * ) Notice: Subject to any disclaimer, the term of this patent is extended or adjusted under 35 U.S.C. 154(b) by 452 days.

(21) Appl. No.: 14/363,748

(22) PCT Filed: Dec. 7, 2012

(86) PCT No.: PCT/US2012/068599
§ 371 (c)(1),
(2) Date: Jun. 6, 2014

(87) PCT Pub. No.: WO2013/086436
PCT Pub. Date: Jun. 13, 2013

(65) Prior Publication Data
US 2014/0369973 A1 Dec. 18, 2014

Related U.S. Application Data

(60) Provisional application No. 61/568,573, filed on Dec. 8, 2011.

(51) Int. Cl.
*A61K 35/28* (2015.01)
*C12N 5/0789* (2010.01)
*A61K 35/12* (2015.01)

(52) U.S. Cl.
CPC ............ *C12N 5/0647* (2013.01); *A61K 35/28* (2013.01); *A61K 2035/124* (2013.01); *C12N 2501/125* (2013.01); *C12N 2501/145* (2013.01); *C12N 2501/2303* (2013.01); *C12N 2501/2306* (2013.01); *C12N 2501/26* (2013.01); *C12N 2501/38* (2013.01); *C12N 2501/42* (2013.01); *C12N 2501/60* (2013.01); *C12N 2501/999* (2013.01)

(58) Field of Classification Search
None
See application file for complete search history.

(56) References Cited

U.S. PATENT DOCUMENTS

| | | | |
|---|---|---|---|
| 5,648,464 A | 7/1997 | Artavanis-Tsakonas et al. | |
| 5,780,300 A | 7/1998 | Artavanis-Tsakonas et al. | |
| 5,849,869 A | 12/1998 | Artavanis-Tsakonas et al. | |
| 5,856,441 A | 1/1999 | Artavanis-Tsakonas et al. | |
| 7,399,633 B2 * | 7/2008 | Bernstein ........... G01N 33/5094 435/372 |
| 2004/0067583 A1 | 4/2004 | Bernstein et al. | |
| 2010/0183564 A1 | 7/2010 | Boitano et al. | |

FOREIGN PATENT DOCUMENTS

| | | |
|---|---|---|
| WO | WO9219734 A1 | 11/1992 |
| WO | WO9312141 A1 | 6/1993 |
| WO | WO9627610 | 9/1996 |
| WO | WO9701571 A1 | 1/1997 |
| WO | WO0028987 A1 | 5/2000 |
| WO | WO0035446 A1 | 6/2000 |
| WO | WO0066112 A1 | 11/2000 |
| WO | WO0117349 A1 | 3/2001 |
| WO | WO0121180 A1 | 3/2001 |
| WO | WO0134585 A1 | 5/2001 |
| WO | WO0139773 A1 | 6/2001 |
| WO | WO0189457 A2 | 11/2001 |
| WO | WO0249413 A2 | 6/2002 |
| WO | WO02085343 | 10/2002 |
| WO | WO03103686 | 12/2003 |

(Continued)

OTHER PUBLICATIONS

Boitano, Anthony; et al; "Aryl Hydrocarbon Receptor Antagonists Promote the Expansion of Human Hematopoietic Stem Cells" Science, 329, 1345-1348, 2010.*
Boitano, Anthony E; et al; "Aryl Hydrocarbon Receptor Antagonists Promote the Expansion of Human Hematopoietic Stem Cells" Science, 329, 1345-1348, 2010.*
Smith, Kayla J; et al; "Identification of a High-Affinity Ligand That Exhibits Complete Aryl Hydrocarbon Receptor Antagonism" The Journal of Pharmacology and Experimental Therapeutics, 338, 318-327, 2011.*

(Continued)

*Primary Examiner* — David Berke-Schlessel
(74) *Attorney, Agent, or Firm* — C. Rachal Winger

(57) ABSTRACT

The present invention relates to methods, kits and compositions for expansion of hematopoietic stem/progenitor cells and providing hematopoietic function to human patients in need thereof. In one aspect, it relates to kits and compositions comprising a Notch agonist and an aryl hydrocarbon receptor antagonist. Also provided herein are methods for expanding the hematopoietic stem/progenitor cells using kits and compositions comprising a Notch agonist and an aryl hydrocarbon receptor antagonist. The hematopoietic stem/progenitor cells expanded using the disclosed kits, compositions and methods include human umbilical cord blood stem/progenitor cells, placental cord blood stem/progenitor cells and peripheral blood stem cells. The present invention also relates to administering hematopoietic stem/progenitor cells expanded using a combination of a Notch agonist and an aryl hydrocarbon receptor antagonist to a patient for short-term and/or long-term in vivo repopulation benefits.

22 Claims, 21 Drawing Sheets

(56) References Cited

FOREIGN PATENT DOCUMENTS

Figure 1:
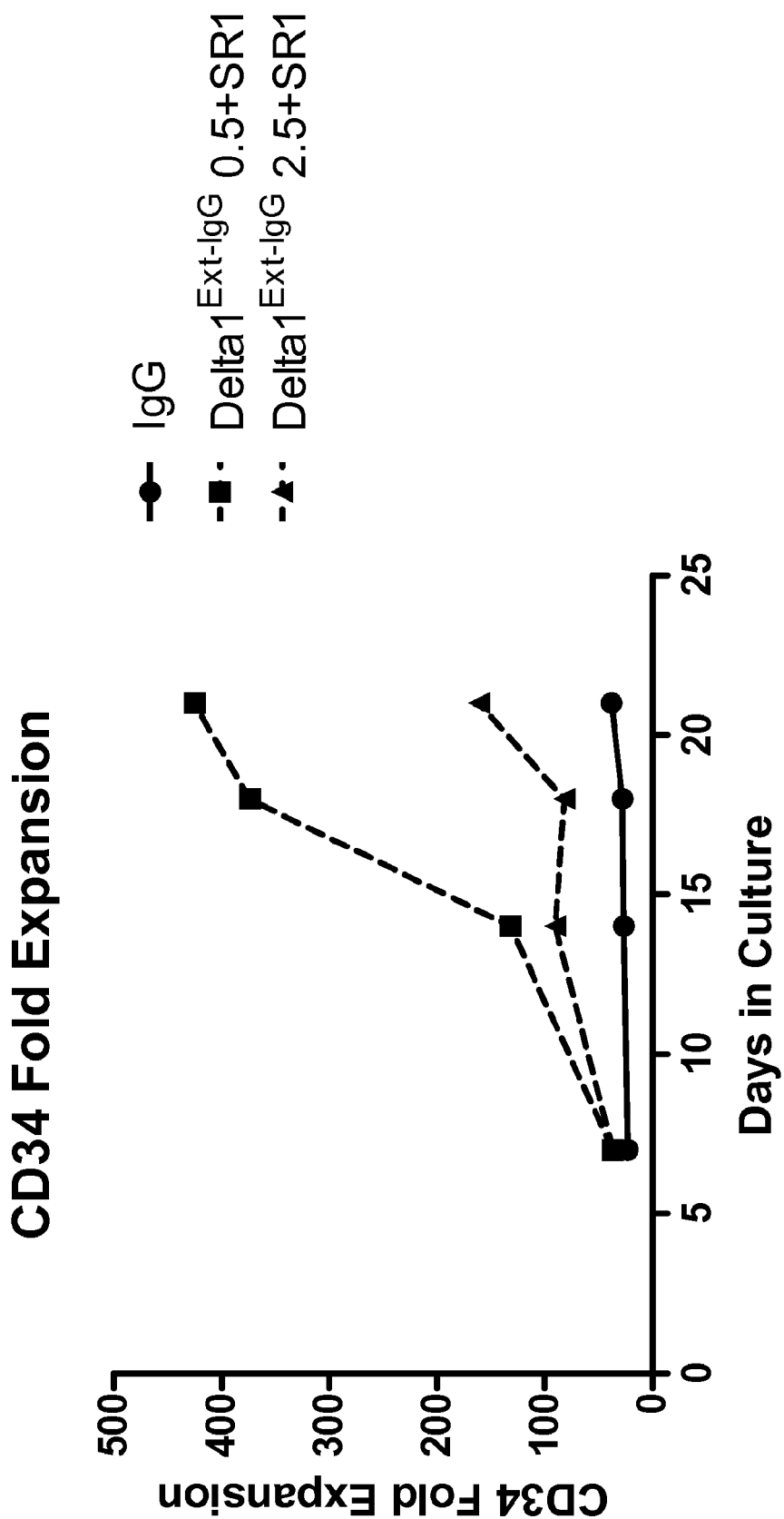

| WO | WO2004054515 | | 7/2004 |
|---|---|---|---|
| WO | WO2006047569 | A2 | 5/2006 |
| WO | WO2007009120 | | 1/2007 |
| WO | WO2007022269 | | 2/2007 |
| WO | WO2007095594 | A2 | 8/2007 |
| WO | WO2007145227 | A1 | 12/2007 |
| WO | WO2008028645 | | 3/2008 |
| WO | WO2008073748 | | 6/2008 |
| WO | WO2010059401 | A2 | 5/2010 |

OTHER PUBLICATIONS

Smith, Angela R; Wagner, John E; "Alternative haematopoietic stem cell sources for transplantation: place of umbilical cord blood" British Journal of Haematology, 147, 246-261, 2009.*
Zatloukalova, et al., "beta-Naphthoflavone and 3'-methoxy-4'-nitroflavone exert ambiguous effects on Ah receptor-dependent cell proliferation and gene expression in rat liver 'stem-like' cells," Biochem. Pharmacol., vol. 73, No. 10, 2007, pp. 1622-1634.
Zhang, et al., "Angiopoietin-like 5 and IGFBP2 stimulate ex vivo expansion of human cord blood hematopoietic stem cells as assayed by NOD/SCID transplantation," Blood, vol. 111, No. 7, 2008, pp. 3415-3423.
Alam, et al., "Notch signaling drives IL-22 secretion in CD4+ T cells by stimulating the aryl hydrocarbon receptor," PNAS, vol. 107, No. 13, 2010, pp. 5943-5948.
Artavanis-Tsakonas and Simpson, "Choosing a cell fate: a view from the Notch locus," Trends Genet., vol. 7, 1991, pp. 403-408.
Artavanis-Tsakonas et al., "Notch Signaling," Science, vol. 268, 1995, pp. 225-232.
Artavanis-Tsakonas et al., "Notch signaling: cell fate control and signal integration in development," Science, vol. 284, No. 5415, 1999, pp. 770-776.
Barker et al., "Transplantation of 2 partially HLA-matched umbilical cord blood units to enhance engraftment in adults with hematologic malignancy," Blood, vol. 105, No. 3, 2005, pp. 1343-1347.
Boitano, et al, "Aryl hydrocarbon receptor antagonists promote the expansion of human hematopoietic stem cells," Science, vol. 329, No. 5997, 2010, pp. 1345-1348.
Carlesso, et al., "Notch1-induced delay of human hematopoietic progenitor cell differentiation is associated with altered cell cycle kinetics," Blood, Vol. 93, No. 3, 1999, pp. 838-848.
Dahlberg, et al., "Ex vivo expansion of human hematopoietic stem and progenitor cells," Blood, vol. 117, No. 23, 2011, pp. 6083-6090.
Dao, et al., "Adhesion to fibronectin maintains regenerative capacity during ex vivo culture and transduction of human hematopoietic stem and progenitor cells," Blood, vol. 92, No. 12, 1998, pp. 4612-4621.
De Lima, et al., "Mesenchymal Stem Cell (MSC) Based Cord Blood (CB) Expansion (Exp) Leads to Rapid Engraftment of Platelets and Neutrophils," Blood, vol. 116, 2010, Abstract 362.
De Lima M, et al., "Transplantation of ex vivo expanded cord blood cells using the copper chelator tetraethylenepentamine: a phase I/II clinical trial," Bone Marrow Transplant., vol. 41, No. 9, 2008, pp. 771-778.
Deftos, et al., "Correlating notch signaling with thymocyte maturation," Immunity, vol. 9, No. 6, 1998, pp. 777-786.
Delaney, et al., "Dose-dependent effects of the Notch ligand Delta1 on ex vivo differentiation and in vivo marrow repopulating ability of cord blood cells," Blood, vol. 106, No. 8, 2005, pp. 2693-2699.
Delaney, et al., "Notch-mediated expansion of human cord blood progenitor cells capable of rapid myeloid reconstitution," Nature Med., vol. 16, No. 2, 2010, pp. 232-236.
Go, et al., "Cell proliferation control by Notch signaling in Drosophila development," Development, vol. 125, No. 11, 1998, pp. 2031-2040.
Gray, et al., "Human ligands of the Notch receptor," Am. J. Path., vol. 154, No. 3, 1999, pp. 785-794.

Himburg, et al., "Pleiotrophin regulates the expansion and regeneration of hematopoietic stem cells," Nature Medicine, vol. 16, No. 4, 2010, pp. 475-482.
International Report on Patentability dated Jun. 19, 2014 in International Application No. PCT/US12/68599.
Jaleco, et al., "Differential effects of Notch ligands Delta-1 and Jagged-1 in human lymphoid differentiation," J. Exp. Med., vol. 194, No. 7, 2001, pp. 991-1002.
Jarriault, et al., "Delta-1 activation of notch-1 signaling results in HES-1 transactivation," Mol. Cell. Biol., vol. 18, No. 12, 1998, pp. 7423-7431.
Jehn, et al., "Cutting edge: protective effects of notch-1 on TCR-induced apoptosis," J. Immunol., vol. 162, No. 2, 1999, pp. 635-638.
Jones, et al., "Stromal expression of Jagged 1 promotes colony formation by fetal hematopoietic progenitor cells," Blood, vol. 92, No. 5, 1998, pp. 1505-1511.
Kopan, et al., "The canonical Notch signaling pathway: unfolding the activation mechanism," Cell, vol. 137, No. 2, 2009, pp. 216-233.
Lehar, et al., "Notch ligands Delta1 and Jagged1 transmit distinct signals to T-cell precursors," Blood, vol. 105, No. 4, 2005, pp. 1440-1447.
Li, et al., "The human homolog of rat Jagged1 expressed by marrow stroma inhibits differentiation of 32D cells through interaction with Notch1," Immunity, vol. 8, No. 1, 1998, pp. 43-55.
Majeti, et al., "Identification of a hierarchy of multipotent progenitors in human cord blood," Cell Stem Cell, vol. 1, No. 6, 2007, pp. 635-645.
Manz, et al., "Prospective isolation of human clonogenic common myeloid progenitors," PNAS, vol. 99, No. 18, 2002, pp. 11872-11877.
McNiece, et al., "Ex vivo expansion of cord blood mononuclear cells on mesenchymal stem cells," Cytotherapy, vol. 6, No. 4, 2004, pp. 311-317.
Milner, et al., "A human homologue of the Drosophila developmental gene, Notch, is expressed in CD34+ hematopoietic precursors," Blood, vol. 83, No. 8, 1994, pp. 2057-2062.
Ohishi, et al., "Delta-1 enhances marrow and thymus repopulating ability of human CD34(+)CD38(−) cord blood cells," J. Clin. Invest., vol. 110, No. 8, 2002, pp. 1165-1174.
Ohishi, et al., "Monocytes express high amounts of Notch and undergo cytokine specific apoptosis following interaction with the Notch ligand, Delta-1," Blood, vol. 95, No. 9, 2000, pp. 2847-2854.
Pearce, et al., "Interaction of the aryl hydrocarbon receptor ligand 6-methyl-1,3,8-trichlorodibenzofuran with estrogen receptor alpha," Cancer Res., vol. 64, No. 8, 2004, pp. 2889-2897.
Peled, et al., "Nicotinamide, a SIRT 1 inhibitor, inhibits differentiation and facilitates expansion of hematopoietic progenitor cells with enhanced bone marrow homing and engraftment," Exp. Hematol., vol. 40, No. 4, 2012, pp. 342-355.
Peled, et al., "Pre-clinical development of cord blood-derived progenitor cell graft expanded ex vivo with cytokines and the polyamine copper chelator tetraethylenepentamine," Cytotherapy, vol. 6, No. 4, 2004, pp. 344-355.
Pui, et al., "Notch1 expression in early lymphopoiesis influences B versus T lineage determination," Immunity, vol. 11, No. 3, 1999, pp. 299-308.
Radtke, et al., "Deficient T Cell Fate Specification in Mice with an Induced Inactivation of Notch1," Immunity, vol. 10, No. 5, 1999, pp. 547-558.
Rebay, et al., "Specific EGF repeats of Notch mediate interactions with Delta and Serrate: implications for Notch as a multifunctional receptor," Cell, vol. 67, No. 4, 1991, pp. 687-699.
Robey, et al., "An activated form of Notch influences the choice between CD4 and CD8 T cell lineages," Cell, vol. 87, No. 3, 1996, pp. 483-492.
Savouret, et al., "The aryl hydrocarbon receptor and its xenobiotic ligands: a fundamental trigger for cardiovascular diseases," Nutr. Metab. Cardiovasc. Dis., vol. 13, No. 2, 2003, pp. 104-113.
Schlondorff and Blobel, "Metalloprotease-disintegrins: modular proteins capable of promoting cell-cell interactions and triggering signals by protein-ectodomain shedding," J. Cell Sci., vol. 112, Pt. 21, 1999, pp. 3603-3617.

(56) References Cited

OTHER PUBLICATIONS

Simpson, "Developmental genetics. The Notch connection," Nature, vol. 375, 1995, pp. 736-737.

Simpson, "Introduction: Notch signalling and choice of cell fates in development," Semin. Cell Dev. Biol., vol. 9, No. 6, 1998, pp. 581-582.

Singh, et al., "Aryl hydrocarbon receptor-null allele mice have hematopoietic stem/progenitor cells with abnormal characteristics and functions," Stem Cells Dev., vol. 20, No. 5, 2011, pp. 769-784.

Search Report dated Apr. 3, 2013 in International Application No. PCT/US12/68599.

Tomita, et al., "The bHLH gene Hes1 is essential for expansion of early T cell precursors," Genes Dev., vol. 13, No. 9, 1999, pp. 1203-1210.

Varnum-Finney, et al., "Combined effects of Notch signaling and cytokines induce a multiple log increase in precursors with lymphoid and myeloid reconstituting ability," Blood, vol. 101, No. 5, 1993, pp. 1784-1789.

Varnum-Finney, et al., "Immobilization of Notch ligand, Delta-1, is required for induction of notch signaling," J. Cell Science, vol. 113, Part 23, 2000, pp. 4313-4318.

Varnum-Finney, et al., "The Notch ligand, Jagged-1, influences the development of primitive hematopoietic precursor cells," Blood, vol. 91, No. 11, 1998, pp. 4084-4991.

Walker, et al., "The Notch/Jagged pathway inhibits proliferation of human hematopoietic progenitors in vitro," Stem Cells, vol. 17, No. 3, 1999, pp. 162-171.

Washburn, et al., "Notch activity influences the alphabeta versus gammadelta T cell lineage decision," Cell, vol. 88, No. 6, 1997, pp. 833-843.

Dontu, et al., "Open Access Role of Notch signaling in cell-fate determination of human mammary stem/progenitor cells", Breast Cancer Res., vol. 6, 2004, 11 pages.

Office Action dated Feb. 21, 2017 for European Patent Application No. 12806795.6.

Office Action dated Jun. 16, 2017 in Australian Application No. 2012347534.

\* cited by examiner

COMPOSITIONS AND METHODS FOR ENHANCED GENERATION OF HEMATOPOIETIC STEM/PROGENITOR CELLS

PRIORITY BENEFIT

This application claims priority to U.S. provisional application No. 61/568,573, filed on Dec. 8, 2011, which is incorporated herein by reference in its entirety.

STATEMENT REGARDING FEDERALLY SPONSORED RESEARCH OR DEVELOPMENT

This invention was made with government support under Grant No. 5R01HL080245, Ruth L. Kirschstein National Research Service Awards Nos. T32CA009351 and K12CA076930, and National Heart, Lung and Blood Institute Grants Nos. U01HL100395 and R01HL080245, all awarded by the National Institutes of Health. The government has certain rights in the invention.

1. FIELD OF THE INVENTION

The present invention relates to methods, kits and compositions for expansion of hematopoietic stem/progenitor cells and providing hematopoietic function to human patients in need thereof. In one aspect, it relates to kits and compositions comprising a Notch agonist and an aryl hydrocarbon receptor antagonist. Also provided herein are methods for expanding the hematopoietic stem/progenitor cells using kits and compositions comprising a Notch agonist and an aryl hydrocarbon receptor antagonist. The hematopoietic stem/progenitor cells expanded using the disclosed kits, compositions and methods include human umbilical cord blood stem/progenitor cells, placental cord blood stem/progenitor cells and peripheral blood stem cells. The present invention also relates to administering hematopoietic stem/progenitor cells expanded using a combination of a Notch agonist and an aryl hydrocarbon receptor antagonist to a patient for short-term and/or long-term in vivo repopulation benefits.

2. BACKGROUND OF THE INVENTION

Hematopoietic stem cells (HSC) have therapeutic potential as a result of their capacity to restore blood and immune cells in transplant recipients. Specifically, autologous or allogeneic transplantation of HSC can be used for the treatment of patients with inherited immunodeficient and autoimmune diseases and diverse hematopoietic disorders to reconstitute the hematopoietic cell lineages and immune system defense. Human bone marrow transplantation methods are currently used as therapies for leukemia, lymphoma, and other life-threatening diseases. For these procedures, a large number of stem cells must be isolated to ensure that there are enough HSC for engraftment. The number of HSC available for treatment is a clinical limitation. See U.S. Patent Publication No. 2010/0183564.

Prolonged pancytopenia is common following intensive chemotherapy regimens, myeloablative and reduced intensity regimens for hematopoietic cell transplantation (HCT), and exposure to acute ionizing radiation. Of particular concern is prolonged neutropenia, which results in a significant risk of infection despite improved antimicrobial therapy and increases morbidity and mortality. Thus, novel therapies that can abrogate prolonged pancytopenia/neutropenia following high dose chemotherapy and/or radiation, and potentially facilitate more rapid hematopoietic recovery, are needed.

2.1 Hematopoietic Stem Cells

The hematopoietic stem cell is pluripotent and ultimately gives rise to all types of terminally differentiated blood cells. The hematopoietic stem cell can self-renew, or it can differentiate into more committed progenitor cells, which progenitor cells are irreversibly determined to be ancestors of only a few types of blood cell. For instance, the hematopoietic stem cell can differentiate into (i) myeloid progenitor cells, which myeloid progenitor cells ultimately give rise to monocytes and macrophages, neutrophils, basophils, eosinophils, erythrocytes, megakaryocytes/platelets, dendritic cells, or (ii) lymphoid progenitor cells, which lymphoid progenitor cells ultimately give rise to T-cells, B-cells, and lymphocyte-like cells called natural killer cells (NK-cells). Once the stem cell differentiates into a myeloid progenitor cell, its progeny cannot give rise to cells of the lymphoid lineage, and, similarly, lymphoid progenitor cells cannot give rise to cells of the myeloid lineage. For a general discussion of hematopoiesis and hematopoietic stem cell differentiation, see Chapter 17, Differentiated Cells and the Maintenance of Tissues, Alberts et al., 1989, Molecular Biology of the Cell, 2nd Ed., Garland Publishing, New York, N.Y.; Chapter 2 of Regenerative Medicine, Department of Health and Human Services, August 2006, and Chapter 5 of Hematopoietic Stem Cells, 2009, Stem Cell Information, Department of Health and Human Services.

In vitro and in vivo assays have been developed to characterize hematopoietic stem cells, for example, the spleen colony forming (CFU-S) assay and reconstitution assays in immune-deficient mice. Further, presence or absence of cell surface protein markers defined by monoclonal antibody recognition have been used to recognize and isolate hematopoietic stem cells. Such markers include, but are not limited to, Lin, CD34, CD38, CD43, CD45RO, CD45RA, CD59, CD90, CD109, CD117, CD133, CD166, and HLA DR, and combinations thereof. See Chapter 2 of Regenerative Medicine, Department of Health and Human Services, August 2006, and the references cited therein.

2.2 Notch Pathway

Members of the Notch family encode large transmembrane proteins that play central roles in cell-cell interactions and cell-fate decisions during early development in a number of invertebrate systems (Simpson, 1995, Nature 375: 736-7; Artavanis-Tsakonis et al., 1995, Science. 268:225-232; Simpson, 1998, Semin. Cell Dev. Biol. 9:581-2; Go et al., 1998, Development. 125:2031-2040; Artavanis-Tsakonas and Simpson, 1991, Trends Genet. 7:403-408). The Notch receptor is part of a highly conserved pathway that enables a variety of cell types to choose between alternative differentiation pathways based on those taken by immediately neighboring cells. This receptor appears to act through an undefined common step that controls the progression of uncommitted cells toward the differentiated state by inhibiting their competence to adopt one of two alternative fates, thereby allowing the cell either to delay differentiation, or in the presence of the appropriate developmental signal, to commit to differentiate along the non-inhibited pathway.

Genetic and molecular studies have led to the identification of a group of genes which define distinct elements of the Notch signaling pathway. While the identification of these various elements has come exclusively from *Drosophila* using genetic tools as the initial guide, subsequent analyses have lead to the identification of homologous proteins in vertebrate species including humans. The molecular relationships between the known Notch pathway elements as well as their subcellular localization are depicted in Artavanis-Tsakonas et al., 1995, Science 268:225-232; Artavanis-Tsakonas et al., 1999, Science 284:770-776; and in Kopan et al., 2009, Cell 137:216-233. Proteins of the Delta family and proteins of the Serrate (including Jagged, the mammalian homolog of Serrate) family are extracellular ligands of Notch. The portion of Delta and Serrate responsible for binding to Notch is called the DSL domain, which domain is located in the extracellular domain of the protein. Epidermal growth factor-like repeats (ELRs) 11 and 12 in the extracellular domain of Notch are responsible for binding to Delta, Serrate and Jagged. See Artavanis-Tsakonas et al., 1995, Science 268:225-232 and Kopan et al., 2009, Cell 137:216-233.

2.3 Notch Pathway in Hematopoiesis

Evidence of Notch-1 mRNA expression in human $CD34^+$ precursors has led to speculation for a role for Notch signaling in hematopoiesis (Milner et al., 1994, Blood 3:2057-62). This is further supported by the demonstration that Notch-1 and -2 proteins are present in hematopoietic precursors, and, in higher amounts, in T cells, B cells, and monocytes, and by the demonstration of Jagged-1 protein in hematopoietic stroma (Ohishi et al., 2000, Blood 95:2847-2854; Varnum-Finney et al., 1998, Blood 91:4084-91; Li et al., 1998, Immunity 8:43-55).

The clearest evidence for a physiologic role of Notch signaling has come from studies of T cell development which showed that activated Notch-1 inhibited B cell maturation but permitted T cell maturation (Pui et al., 1999, Immunity 11:299-308). In contrast, inactivation of Notch-1 or inhibition of Notch-mediated signaling by knocking out HES-1 inhibited T cell development but permitted B cell maturation (Radtke et al., 1999, Immunity 10: 47-58; Tomita et al., 1999, Genes Dev. 13:1203-10). These opposing effects of Notch-1 on B and T cell development raise the possibility that Notch-1 regulates fate decisions by a common lymphoid progenitor cell.

Other studies in transgenic mice have shown that activated Notch-1 affects the proportion of cells assuming a CD4 vs. CD8 phenotype as well as an $\alpha\beta$ vs. $\gamma\delta$ cell-fate (Robey et al., 1996. Cell 87:483-92; Washburn et al 1997. Cell 88:833-43). Although this may reflect an effect on fate decisions by a common precursor, more recent studies have suggested that these effects may result from an anti-apoptotic effect of Notch-1 that enables the survival of differentiating T cells that would otherwise die (Deftos et al., 1998, Immunity 9:777-86; Jehn et al., 1999, J Immunol. 162:635-8).

Studies have also shown that the differentiation of isolated hematopoietic precursor cells can be inhibited by ligand-induced Notch signaling. Co-culture of murine marrow precursor cells ($Lin^-$ $Sca-1^+$ $c-kit^+$) with 3T3 cells expressing human Jagged-1 led to a 2 to 3 fold increase in the formation of primitive precursor cell populations (Varnum-Finney et al., 1998, Blood 91:4084-4991; Jones et al., 1998, Blood 92:1505-11). Incubation of sorted precursors with beads coated with the purified extracellular domain of human Jagged-1 also led to enhanced generation of precursor cells (Varnum-Finney et al., 1998, Blood 91:4084-91).

In a study of human $CD34^+$ cells, expression of the intracellular domain of Notch-1 or exposure to cells that overexpressed Jagged-2 also led to enhanced generation of precursor cells and prolonged maintenance of CD34 expression (Carlesso et al., 1999, Blood 93:838-48). In another study, the effects of Jagged-1-expressing cells on $CD34^+$ cells were influenced by the cytokines present in the cultures; in the absence of added growth factors, the interaction with cell-bound Jagged-1 led to maintenance of $CD34^+$ cells in a non-proliferating, undifferentiated state, whereas the addition of c-kit ligand led to a 2-fold increase in erythroid colony-forming cells (Walker et al., 1999, Stem Cells 17:162-71).

2.4 Expansion and Engraftment of Hematopoietic Stem/Progenitor Cells

There is a need for successful expansion of human stem/progenitor cells (HSPC). This has particular immediate relevance for cord blood (CB) transplants where the stem cell dose in a single cord blood unit is often inadequate for a larger child or adult recipient and double cord blood transplantation (dCBT) is required. Despite dCBT for these individuals, engraftment is often delayed for more than 3 weeks leaving the recipient susceptible to infection resulting in increased morbidity and mortality (see Barker et al., 2005, Blood. 105 (3): 1343-1347). Thus successful ex vivo generation of both short- and long-term repopulating HSPC, including CB HSPC, has both biological relevance for better understanding HSPC self-renewal and clear clinical impact.

Past efforts have attempted to expand HSPC using soluble cytokine mediated methodologies; however, these attempts have demonstrated limited clinical efficacy (see Shpall et al., 2002, Biol Blood Marrow Transplant. 8(7): 368-376; de Lima et al., 2008, Blood. 112: Abstract 154; Jaroscak et al., 2003, Blood. 101(12): 5061-5067).

Varnum-Finney et al., 1993, Blood 101:1784-1789 demonstrated that activation of endogenous Notch receptors in mouse marrow precursor cells by an immobilized Notch ligand revealed profound effects on the growth and differentiation of the precursor cells, and that a multilog increase in the number of precursor cells with short-term lymphoid and myeloid repopulating ability was observed.

Delaney et al., 2005, Blood 106:2693-2699 and Ohishi et al., 2002, J. Clin. Invest. 110:1165-1174 demonstrated that incubation of human cord blood progenitors in the presence of an immobilized Notch ligand generated an approximate 100-fold increase in the number of $CD34^+$ cells with enhanced repopulating ability as determined in an immunodeficient mouse model. See also U.S. Pat. No. 7,399,633 B2.

Delaney et al., 2010, Nature Med. 16(2): 232-236 demonstrated that a population of $CD34^+$ cells obtained from a frozen cord blood sample, which population had been cultured in the presence of a Notch ligand (resulting in a greater than 100 fold increase in the number of $CD34^+$ cells), repopulated immunodeficient mice with markedly enhanced kinetics and magnitude, and provided more rapid myeloid engraftment in humans in a clinical phase 1 myeloablative cord blood transplant trial.

Expansion techniques for cord blood stem cells have been described. See, e.g., U.S. Pat. No. 7,399,633 B2 to Bernstein et al., and Delaney et al., 2010, Nature Med. 16(2): 232-236. Delaney et al. reported rapid engraftment after infusion of previously cryopreserved cord blood stem cells which had been selected on the basis of HLA matching, and which had been expanded ex vivo.

International Patent Publication No. WO 2006/047569 A2 discloses methods for expanding myeloid progenitor cells that do not typically differentiate into cells of the lymphoid lineage, and which can be MHC-mismatched with respect to the recipient of the cells.

International Patent Publication No. WO 2007/095594 A2 discloses methods for facilitating engraftment of hematopoietic stem cells by administering myeloid progenitor cells in conjunction with the hematopoietic stem cell graft, for example, where the hematopoietic stem cell graft is suboptimal because it has more than one MHC mismatch with respect to the cells of the recipient patient.

U.S. Pat. No. 5,004,681 to Boyse et al. discloses the use of human cord blood stem cells for hematopoietic reconstitution.

U.S. Patent Publication No. 2010/0183564 to Boitano et al. discloses methods and compositions for expanding HSPC populations using an agent capable of down-regulating the activity and/or expression of aryl hydrocarbon receptor and/or a downstream effector of aryl hydrocarbon receptor pathway.

International Patent Publication No. WO 2011/127470 A1 discloses methods and compositions for providing hematopoietic function to a human patient, by selecting an expanded human umbilical cord blood stem/progenitor cell sample without taking into account the HLA-type of the expanded human cord blood stem cell/progenitor sample or the HLA-type of the patient, and administering the selected expanded human cord blood stem/progenitor cell sample to the patient; as well as methods for obtaining the expanded human cord blood stem cell/progenitor cell samples; and banks of frozen expanded human cord blood stem cell/progenitor cell samples, and methods for producing such banks.

International Patent Publication No. WO 2011/127472 A1 discloses methods and compositions for providing hematopoietic function to a human patient, by selecting a pool of expanded human umbilical cord blood stem/progenitor cell samples for administration to a patient, wherein the samples in the pool collectively do not mismatch the patient at more than 2 of the HLA antigens or alleles typed in the patient, and administering the selected pool of expanded human cord blood stem/progenitor cell samples to the patient; as well as methods for obtaining the pools of expanded human cord blood stem cell/progenitor cell samples; and banks of frozen pools of expanded human umbilical cord blood stem cell/progenitor cell samples, and methods for producing such banks.

2.5 Effects of Aryl Hydrocarbon Receptor Antagonist on Cell Expansion and Engraftment Boitano et al. described enhanced ex vivo expansion of CD34$^+$ cord blood HSPC with StemRegenin1 (SR1), an aryl hydrocarbon receptor (AhR) antagonist that acts at least in part by preventing cellular differentiation resulting in HSC expansion (see Boitano et al., 2010, Science 329(5997): 1345-1348). Specifically, Boitano et al. demonstrated that culturing HSPC with SR1 leads to a 50-fold increase in CD34$^+$ cells and a 17-fold increase in the number of cells with the ability to repopulate immunodeficient mice. Boitano et al further demonstrated that these SR1-mediated effects are direct result of inhibition of AhR present on HSPC.

Citation or identification of any reference in Section 2 or any other section of this application shall not be construed as an admission that such reference is available as prior art to the present invention.

3. SUMMARY OF THE INVENTION

The present invention relates to methods and compositions for expansion of hematopoietic stem/progenitor cells ex vivo by methods comprising using a Notch agonist, such as any of the Notch agonists as described in U.S. Pat. No. 7,399,633 incorporated by reference herein in its entirety (e.g., an extracellular domain of a Notch ligand (such as Delta or Serrate) or a Notch-binding fragment thereof), in combination with using an aryl hydrocarbon receptor antagonist, such as any of the aryl hydrocarbon receptor antagonists as described in U.S. Patent Publication No. 2010/0183564 incorporated by reference herein in its entirety (e.g., a compound of Formula I as depicted below, such as 4-(2-(2-(benzo[b]thiophen-3-yl)-9-isopropyl-9H-purin-6-ylamino)ethyl)phenol (StemRegenin1, "SR1")). The expanded hematopoietic stem/progenitor cells can be administered to a patient in need thereof to provide hematopoietic function to the patient.

Compositions and methods for expansion of precursor cells such as hematopoietic stem/progenitor cells, said method comprising culturing the precursor cells in the presence of a Notch agonist, as well as uses of such expanded cells, are described in U.S. Pat. No. 7,399,633 to Bernstein et al. In a specific embodiment, as described in U.S. Pat. No. 7,399,633 to Bernstein et al., the Notch agonist is an extracellular domain of a Notch ligand (e.g., Delta$^{ext-IgG}$) immobilized on a solid support for expansion of hematopoietic stem/progenitor cells. The entire disclosure of U.S. Pat. No. 7,399,633 is hereby incorporated by reference herein in its entirety.

Compositions and methods for expansion of hematopoietic stem/progenitor cells, said method comprising culturing the hematopoietic stem/progenitor cells in the presence of an agent capable of antagonizing the activity and/or expression of aryl hydrocarbon receptor and/or downstream effector of aryl hydrocarbon receptor pathway, as well as uses of such expanded cells, are described in U.S. Patent Publication No. 2010/0183564 to Boitano et al. In a specific embodiment, as described in U.S. Patent Publication No. 2010/0183564 to Boitano et al., 4-(2-(2-(benzo[b]thiophen-3-yl)-9-isopropyl-9H-purin-6-ylamino)ethyl)phenol (Stem Regenin1, "SR1") is used for expansion of hematopoietic stem/progenitor cells. The entire disclosure of U.S. Patent Publication No. 2010/0183564 is hereby incorporated by reference herein in its entirety.

The present invention describes methods, kits and compositions comprising a combination of a Notch agonist and an aryl hydrocarbon receptor antagonist, and uses of such compositions and combinations. In certain embodiments, the Notch agonist is an extracellular domain of a Notch ligand (e.g., Delta or Serrate) or a Notch-binding fragment thereof. In preferred embodiments, the Notch agonist is an extracellular domain of a human or rodent (e.g., rat) Notch ligand (e.g., human or rodent Delta, or human or rodent Jagged) or a Notch-binding fragment thereof. Preferably, the Notch agonist is the extracellular domain of Delta or Serrate/Jagged (or a Notch-binding portion thereof) fused to a fusion partner. The fusion partners can be, but are not limited to, an Fc domain of IgG or tags that contain an antigenic determinant such as a myc tag. In a preferred embodiment, the Notch agonist is Delta$^{ext-IgG}$.

In some embodiments, the Notch agonist is immobilized on a solid phase in contact with the HSPC. In specific embodiments, SR1 is in a fluid medium contacting the HSPC.

In specific embodiments, described herein are kits and compositions comprising HSPC, an immobilized extracellular domain of a Notch ligand (preferably fused to a fusion partner) in contact with the HSPC, and SR1 in contact with the HSPC. In specific embodiments, the extracellular domain of a Notch ligand (e.g., Delta$^{ext-IgG}$) is immobilized on a solid phase, on which HSPC are cultured, whereas SR1 is in a fluid medium contacting the HSPC.

In one aspect, disclosed herein are methods for expansion of hematopoietic stem/progenitor cells using the described kits and compositions comprising a Notch agonist and an aryl hydrocarbon receptor antagonist. In preferred embodiments, disclosed herein are methods for expansion of hematopoietic stem/progenitor cells using a combination of an extracellular domain of a Notch ligand (e.g., Delta$^{ext-IgG}$) and SR1. Hematopoietic stem/progenitor cells that may be expanded using the disclosed compositions include, but are not limited to, human umbilical cord blood stem/progenitor cells, placental cord blood stem/progenitor cells, peripheral blood stem/progenitor cells (e.g., mobilized peripheral blood stem/progenitor cells) and bone marrow stem/progenitor cells.

In another aspect, disclosed herein are methods of treatment comprising administering the expanded hematopoietic stem/progenitor cells disclosed herein to a patient in need thereof. In one embodiment, the patient is a human. The hematopoietic stem/progenitor cells expanded using the methods described herein can be effectively used for short term in vivo repopulation/engraftment. In particular, the hematopoietic stem/progenitor cells expanded using the methods described herein can be effectively used for early myeloid repopulation and neutrophil engraftment in treated patients. Further, the hematopoietic stem/progenitor cells expanded using the methods described herein can be effectively used for long term in vivo repopulation/engraftment. In particular, the hematopoietic stem/progenitor cells expanded using the methods described herein can be effectively used for multi-lineage, sustained in vivo repopulation. In one aspect, disclosed herein are methods of treatment comprising administering the expanded hematopoietic stem/progenitor cells disclosed herein to a patient in need of short-term and/or long-term in vivo repopulation.

Preferably, the combination of a Notch agonist and an aryl hydrocarbon receptor antagonist (e.g., the combination of an immobilized extracellular domain of a Delta, a Serrate, or a Jagged protein with SR1) has synergistic or additive activities upon HSPC engraftment and/or expansion.

In certain embodiments, described herein are methods of expanding hematopoietic stem/progenitor cells comprising culturing isolated hematopoietic stem/progenitor cells ex vivo in the presence of a composition comprising a Notch agonist and an aryl hydrocarbon receptor antagonist, thereby producing an expanded hematopoietic stem/progenitor cell sample. In one embodiment, the isolated hematopoietic stem/progenitor cells are human. In some embodiments, during the culturing step, hematopoietic stem/progenitor cells are cultured in the presence of an immobilized Notch agonist that is the extracellular domain of a Notch ligand, preferably fused to a fusion partner, and in the presence of an aryl hydrocarbon receptor antagonist (e.g., in a fluid contacting the cells). In specific embodiments, during the culturing step, hematopoietic stem/progenitor cells are cultured on a solid phase coated with the Notch agonist, and the aryl hydrocarbon receptor antagonist is in a fluid contacting the cells. In some embodiments, the isolated HSPC are expanded in the presence of one or more growth factors, two or more growth factors, three or more growth factors, or four or more growth factors (e.g., in a fluid medium). For example, the growth factors can be selected from stem cell factor (SCF), Flt-3 ligand (Flt-3), Interleukin-6 (IL-6), Interleukin-3 (IL-3), Interleukin-11 (IL-11), thrombopoietin (TPO), Granulocyte-macrophage colony stimulating factor (GM-CSF), or granulocyte colony stimulating factor (G-CSF). In one embodiment, the isolated HSPC are expanded in the presence of IL-6, Flt-3, SCF and TPO (e.g., in a fluid medium). In another embodiment, the isolated HSPC are expanded in the presence of IL-6, Flt-3, SCF, TPO and IL-3 (e.g., in a fluid medium).

In specific embodiments, the Notch agonist used in the methods of expanding HSPC described herein is the extracellular domain of a Delta, a Jagged or a Serrate protein, fused to an Fc region of an IgG (or fused to another fusion partner such as a myc or other epitope). In one embodiment, the Notch agonist is Delta 1$^{ext-IgG}$. In some embodiments, Delta$^{ext-IgG}$ is applied to the solid phase at a concentration between about 0.2 and 20 μg/ml, between about 1.25 and 10 μg/ml, or between about 2 and 6 μg/ml. In some embodiments of the compositions for expansion of hematopoietic stem/progenitor cells in which (e.g., Delta1$^{ext-IgG}$) Delta$^{ext-IgG}$ (e.g., Delta1$^{ext-IgG}$) is immobilized on a solid phase, Delta$^{ext-IgG}$ (e.g., Delta1$^{ext-IgG}$) has been applied to the solid phase at a concentration between about 0.2 and 20 μg/ml, between about 1.25 and 10 μg/ml, or between about 2 and 6 μg/ml.

In specific embodiments, the aryl hydrocarbon receptor antagonist used in the methods of expanding HSPC described herein is a compound of Formula I:

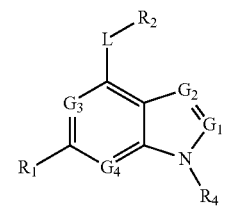

in which:

$G_1$ is selected from N and $CR_3$;

$G_2$, $G_3$ and $G_4$ are independently selected from CH and N; with the proviso that at least 1 of $G_3$ and $G_4$ is N; with the proviso that $G_1$ and $G_2$ are not both N;

L is selected from —NR$_{5a}$(CH$_2$)$_{0-3}$—, —NR$_{5a}$CH(C(O)OCH$_3$)CH$_2$—, —NR$_{5a}$(CH$_2$)$_2$NR$_{5b}$—, —NR$_{5a}$(CH$_2$)$_2$S—, —NR$_{5a}$CH$_2$CH(CH$_3$)CH$_2$—, —NR$_{5a}$CH$_2$CH(OH)— and —NR$_{5a}$CH(CH$_3$)CH$_2$—; wherein R$_{5a}$ and R$_{5b}$ are independently selected from hydrogen and C$_{1-4}$alkyl;

R$_1$ is selected from hydrogen, phenyl, thiophenyl, furanyl, 1H-benzoimidazolyl, isoquinolinyl, 1H-imidazopyridinyl, benzothiophenyl, pyrimidinyl, 1H-pyrazolyl, pyridinyl, 1H-imidazolyl, pyrrolidinyl, pyrazinyl, pyridazinyl, 1H-pyrrolyl and thiazolyl; wherein said phenyl, thiophenyl, furanyl, 1H-benzoimidazolyl, isoquinolinyl, 1H-imidazopyridinyl, benzothiophenyl, pyrimidinyl, 1H-pyrazolyl, pyridinyl, 1H-imidazolyl, pyrrolidinyl, pyrazinyl, pyridazinyl, 1H-pyrrolyl or thiazolyl of R$_1$ can be optionally substituted by 1 to 3 radicals independently selected from cyano, hydroxy, C$_{1-4}$alkyl, C$_{1-4}$alkoxy, halo, halo-substituted-C$_{1-4}$alkyl, halo-substituted-C$_{1-4}$alkoxy, hydroxy, amino, —C(O)R$_{8a}$, —S(O)$_{0-2}$R$_{8a}$, —C(O)OR$_{8a}$ and —C(O)NR$_{8a}$R$_{8b}$; wherein R$_{8a}$ and R$_{8b}$ are independently selected from hydrogen and C$_{1-4}$alkyl; with the proviso that R$_1$ and R$_3$ are not both hydrogen;

R$_2$ is selected from —S(O)$_2$NR$_{6a}$R$_{6b}$, —NR$_{9a}$C(O)R$_{9b}$, —NR$_{6a}$C(O)NR$_{6b}$R$_{6c}$, phenyl, 1H-pyrrolopyridin-3-yl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl and 1H-indazolyl; wherein R$_{6a}$, R$_{6b}$ and R$_{6c}$ are independently selected from hydrogen and C$_{1-4}$alkyl; wherein said phenyl, 1H-pyrrolopyridin-3-yl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl or 1H-indazolyl of R$_2$ is optionally substituted with 1 to 3 radicals independently selected from hydroxy, halo, methyl, methoxy, amino, —O(CH$_2$)$_n$NR$_{7a}$R$_{7b}$, —S(O)$_2$NR$_{7a}$R$_{7b}$, —OS(O)$_2$NR$_{7a}$R$_{7b}$ and —NR$_{7a}$S(O)$_2$R$_{7b}$; wherein R$_{7a}$ and R$_{7b}$ are independently selected from hydrogen and C$_{1-4}$alkyl;

R$_3$ is selected from hydrogen, C$_{1-4}$alkyl and biphenyl; and R$_4$ is selected from C$_{1-10}$alkyl, prop-1-en-2-yl, cyclohexyl, cyclopropyl, 2-(2-oxopyrrolidin-1-yl)ethyl, oxetan-3-yl, benzhydryl, tetrahydro-2H-pyran-3-yl, tetrahydro-2H-pyran-4-yl, phenyl, tetrahydrofuran-3-yl, benzyl, (4-pentyl-phenyl)(phenyl)methyl and 1-(1-(2-oxo-6,9,12-trioxa-3-azatetradecan-14-yl)-1H-1,2,3-triazol-4-yl)ethyl; wherein said alkyl, cyclopropyl, cyclohexyl, 2-(2-oxopyrrolidin-1-yl)ethyl, oxetan-3-yl, oxetan-2-yl, benzhydryl, tetrahydro-2H-pyran-2-yl, tetrahydro-2H-pyran-3-yl, tetrahydro-2H-pyran-4-yl, phenyl, tetrahydrofuran-3-yl, tetrahydrofuran-2-yl, benzyl, (4-pentylphenyl)(phenyl)methyl or 1-(1-(2-oxo-6,9,12-trioxa-3-azatetradecan-14-yl)-1H-1,2,3-triazol-4-yl) ethyl can be optionally substituted with 1 to 3 radicals independently selected from hydroxy, C$_{1-4}$alkyl and halo-substituted-C$_{1-4}$alkyl; or a salt thereof.

In one embodiment, the aryl hydrocarbon receptor antagonist used in the methods of expanding HSPC described herein is 4-(2-(2-(benzo[b]thiophen-3-yl)-9-isopropyl-9H-purin-6-ylamino)ethyl)phenol (i.e., "SR1"). In particular embodiments, the aryl hydrocarbon receptor antagonist used in the methods of expanding HSPC described herein is SR1, and the Notch agonist is an immobilized extracellular domain of Delta1 (e.g., Delta1$^{ext-IgG}$).

In certain embodiments, the isolated HSPC are expanded in the presence of a fibronectin or a fragment thereof (e.g., CH-296). For example, the isolated HSPC can be expanded in the presence of an immobilized fibronectin or a fragment thereof (e.g., immobilized on the same solid phase as the Notch agonist, or immobilized on a solid phase that is different from the solid phase on which the Notch agonist is immobilized).

In some embodiments, the isolated hematopoietic stem/progenitor cells used in the methods of the invention are derived from umbilical cord blood and/or placental cord blood (e.g., form a single human collected at birth of said human, or from a pool of two or more different humans at birth). In other embodiments, the isolated hematopoietic stem/progenitor cells are derived from peripheral blood (e.g., mobilized peripheral blood stem cells). In yet other embodiments, the isolated hematopoietic stem/progenitor cells are derived from bone marrow. In some embodiments, the isolated hematopoietic stem/progenitor cells are derived from a single human, while in other embodiments, the isolated HSPC are derived from two or more humans (where the two or more humans can be, but are not limited to, humans of the same race or humans of the same ethnicity).

In certain embodiments, the percentage of CD34$^+$ cells in the expanded hematopoietic stem/progenitor cell sample, obtained using the methods described herein, is higher than the percentage of CD34$^+$ cells in the isolated hematopoietic stem/progenitor cells prior to expansion. In particular embodiments, the percentage of CD34$^+$ cells in the expanded hematopoietic stem/progenitor cell sample, obtained using the methods described herein, is higher than the percentage of CD34$^+$ cells in a sample of the hematopoietic stem/progenitor cells expanded using a Notch agonist alone and/or an aryl hydrocarbon receptor antagonist alone.

In particular embodiments, the percentage of CD34$^+$CD90$^+$ cells in the expanded hematopoietic stem/progenitor cell sample, obtained using the methods described herein, is higher than the percentage of CD34$^+$CD90$^+$ cells in a sample of the hematopoietic stem/progenitor cells expanded using a Notch agonist alone and/or an aryl hydrocarbon receptor antagonist alone.

In particular embodiments, the percentage of Lin$^-$CD34$^+$CD38$^-$CD45RA$^-$CD90$^+$ cells in the expanded hematopoietic stem/progenitor cell sample, obtained using the methods described herein, is higher than the percentage of Lin$^-$CD34$^+$CD38$^-$CD45RA$^-$CD90$^+$ cells in a sample of the hematopoietic stem/progenitor cells expanded using a Notch agonist alone and/or an aryl hydrocarbon receptor antagonist alone.

In particular embodiments, the percentage of CD34$^+$ cells in the expanded hematopoietic stem/progenitor cell sample obtained using the methods described herein is either the same or lower than the percentage of CD34$^+$ cells in a sample of the hematopoietic stem/progenitor cells expanded using an aryl hydrocarbon receptor antagonist alone, but the percentage of CD34$^+$CD90$^+$ (e.g., Lin$^-$CD34$^+$CD38$^-$CD45RA$^-$CD90$^+$) cells in the expanded hematopoietic stem/progenitor cell sample obtained using the methods described herein is higher than the percentage of CD34$^+$90$^+$ (e.g., Lin$^-$CD34$^+$CD38$^-$CD45RA$^-$CD90$^+$) cells in a sample of the hematopoietic stem/progenitor cells expanded using a Notch agonist alone and/or an aryl hydrocarbon receptor antagonist alone. In a specific embodiment, the ratio of the total number of CD34$^+$CD90$^+$ (e.g., Lin$^-$CD34$^+$CD38$^-$CD45RA$^-$CD90$^+$) cells to the total number of CD34$^+$ cells in the expanded hematopoietic stem/progenitor cell sample, obtained using the methods described herein, is higher than such ratio in the isolated hematopoietic stem/progenitor cells prior to expansion. In another specific embodiment, the ratio of the total number of CD34$^+$CD90$^+$ (e.g., Lin$^-$CD34$^+$CD38$^-$CD45RA$^-$CD90$^+$) cells to the total number of CD34$^+$ cells in the expanded hematopoietic stem/progenitor cell sample, obtained using the methods described herein, is higher than such ratio in a sample of the hematopoietic stem/progenitor cells expanded using a Notch agonist alone and/or an aryl hydrocarbon receptor antagonist alone.

In specific embodiments, the percentage of CD34$^-$CD14$^+$ cells in the expanded hematopoietic stem/progenitor cell sample, obtained using the methods described herein, is lower than the percentage of CD34$^-$CD14$^+$ cells in the isolated hematopoietic stem/progenitor cells prior to expansion. In particular embodiments, the percentage of CD34$^-$CD14$^+$ cells in the expanded hematopoietic stem/progenitor cell sample, obtained using the methods described herein, is lower than the percentage of CD34$^-$CD14$^+$ cells in a sample of the hematopoietic stem/progenitor cells expanded using a Notch agonist alone and/or an aryl hydrocarbon receptor antagonist alone.

In some embodiments, the percentage of mature myeloid CD14$^+$ and/or CD15$^+$ cells in the expanded hematopoietic stem/progenitor cell sample, obtained using the methods described herein, is lower than the percentage of mature myeloid CD14$^+$ and/or CD15$^+$ cells in a sample of the hematopoietic stem/progenitor cells expanded using an aryl hydrocarbon receptor antagonist alone.

In certain embodiments, the expanded hematopoietic stem/progenitor cell sample, obtained using the methods described herein, has an improved in vivo repopulating ability relative to a sample of the hematopoietic stem/progenitor cells expanded using a Notch agonist alone and/or an aryl hydrocarbon receptor antagonist alone. In one embodiment, the expanded hematopoietic stem/progenitor cell sample is capable of enhanced generation of short-term in vivo repopulating cells relative to a sample of the hematopoietic stem/progenitor cells expanded using a Notch agonist alone and/or an aryl hydrocarbon receptor antagonist alone. In another embodiment, the expanded hematopoietic stem/progenitor cell sample is capable of enhanced generation of multi-lineage long-term in vivo repopulating cells relative to a sample of the hematopoietic stem/progenitor cells expanded using a Notch agonist alone and/or an aryl hydrocarbon receptor antagonist alone. In yet another embodiment, the expanded hematopoietic stem/progenitor cell sample is capable of improved engraftment of $CD45^+$ cells relative to a sample of the hematopoietic stem/progenitor cells expanded using a Notch agonist alone and/or an aryl hydrocarbon receptor antagonist alone. In one embodiment, the expanded hematopoietic stem/progenitor cell sample is capable of improved engraftment of $CD45^+CD33^+$ cells relative to a sample of the hematopoietic stem/progenitor cells expanded using a Notch agonist alone and/or an aryl hydrocarbon receptor antagonist alone. In another embodiment, the expanded hematopoietic stem/progenitor cell sample is capable of improved engraftment of $CD45^+CD34^+$ cells relative to a sample of the hematopoietic stem/progenitor cells expanded using a Notch agonist alone and/or an aryl hydrocarbon receptor antagonist alone. In a specific embodiment, the expanded hematopoietic stem/progenitor cell sample is capable of improved early or short-term engraftment of $CD45^+CD34^+$ cells and/or $CD45^+CD33^+$ cells relative to a sample of the hematopoietic stem/progenitor cells expanded using a Notch agonist alone and/or an aryl hydrocarbon receptor antagonist alone. In specific embodiments, the expanded hematopoietic stem/progenitor cell sample is capable of improved early or short-term engraftment of $CD45^+CD34^+CD33^-$ cells and/or $CD45^+CD34^+CD33^+$ cells relative to a sample of the hematopoietic stem/progenitor cells expanded using a Notch agonist alone and/or an aryl hydrocarbon receptor antagonist alone. In a particular embodiment, the expanded hematopoietic stem/progenitor cell sample is capable of improved early or short-term engraftment of $CD45^+CD14^+CD15^+$ cells relative to a sample of the hematopoietic stem/progenitor cells expanded using a Notch agonist alone and/or an aryl hydrocarbon receptor antagonist alone. In certain embodiments, the expanded hematopoietic stem/progenitor cell sample is capable of improved long-term total human engraftment, such as improved long-term engraftment of $CD45^+$ cells, relative to a sample of the hematopoietic stem/progenitor cells expanded using a Notch agonist alone and/or an aryl hydrocarbon receptor antagonist alone. In yet another embodiment, the expanded hematopoietic stem/progenitor cell sample is capable of improved long-term engraftment of $CD45^+CD19^+$ cells relative to a sample of the hematopoietic stem/progenitor cells expanded using a Notch agonist alone and/or an aryl hydrocarbon receptor antagonist alone. In one embodiment, the expanded hematopoietic stem/progenitor cell sample is capable of improved long-term engraftment of $CD45^+CD19^+CD33^-$ cells relative to a sample of the hematopoietic stem/progenitor cells expanded using a Notch agonist alone and/or an aryl hydrocarbon receptor antagonist alone. In one embodiment, the expanded hematopoietic stem/progenitor cell sample is capable of improved long-term engraftment due to lymphocyte repopulation relative to a sample of the hematopoietic stem/progenitor cells expanded using a Notch agonist alone and/or an aryl hydrocarbon receptor antagonist alone.

In a specific embodiment, described herein are methods of expanding human hematopoietic stem/progenitor cells comprising culturing isolated hematopoietic stem/progenitor cells ex vivo on a solid phase coated with Delta1$^{ext-IgG}$ and CH-296, and further in the presence of a medium comprising an aryl hydrocarbon receptor antagonist and four or more growth factors; wherein the aryl hydrocarbon antagonist is 4-(2-(2-(benzo[b]thiophen-3-yl)-9-isopropyl-9H-purin-6-ylamino)ethyl)phenol; and wherein the four or more growth factors are selected from IL6, TPO, Flt-3 ligand, CSF and IL3; thereby producing an expanded hematopoietic stem/progenitor cell sample.

Also described herein are hematopoietic stem/progenitor cell samples expanded using any of the methods disclosed herein.

Further embodiments of the invention include methods for providing hematopoietic function to a patient in need thereof, comprising administering to a patient the expanded hematopoietic stem/progenitor cell sample obtained using any of the methods described herein. Other embodiments of the invention include methods for providing hematopoietic function to a patient in need thereof, comprising carrying out any of the methods for expansion of hematopoietic stem/progenitor cells described herein, and administering to a patient the expanded hematopoietic stem/progenitor cells (the expanded hematopoietic stem/progenitor cell sample) thereby obtained. In preferred embodiments, the patient treated in accordance with the invention is human. In some embodiments, the expanded hematopoietic stem/progenitor cell sample, obtained using the methods described herein, is derived from hematopoietic stem/progenitor cells isolated from one or two patients (e.g., human patients). In some embodiments, the expanded hematopoietic stem/progenitor cell sample, obtained using the methods described herein, is derived from hematopoietic stem/progenitor cells isolated from a single human at birth. In other embodiments, the expanded hematopoietic stem/progenitor cell sample, obtained using the methods described herein, is a pool of two or more different expanded hematopoietic stem/progenitor cell samples, each different sample in the pool derived from hematopoietic stem/progenitor cells isolated from a different human at birth. In one embodiment, all the samples in the pool are derived from the hematopoietic stem/progenitor cells of humans of the same race. In another embodiment, all the samples in the pool are derived from the hematopoietic stem/progenitor cells of humans of the same ethnicity. In some embodiments, the expanded hematopoietic stem/progenitor cell sample, obtained using the methods described herein, is frozen prior to administering such sample to the patient, and the method further includes a step of thawing the sample prior to administering it to the patient. In yet other embodiments, the expanded hematopoietic stem/progenitor cell sample, obtained using the methods described herein, has not been frozen prior to administering to the patient. In some embodiments, the expanded hematopoietic stem/progenitor cell sample, obtained using the methods described herein and administered to a patient, is not HLA-matched to the patient. In specific embodiments, the expanded hematopoietic stem/progenitor cell sample is administered to a patient without taking into account the HLA-type of the expanded human cord blood stem cell/progenitor sample or the HLA-type of the patient. Patients that can be treated in accordance with the invention include, but are not limited to, patients with pancytopenia or neutropenia, any of which may be caused by an intensive chemotherapy regimen, a myeloablative regimen for hematopoietic cell transplantation, or exposure to acute ionizing radiation.

Further described herein are kits comprising in one or more containers: (a) a Notch agonist, and (b) an aryl hydrocarbon receptor antagonist. Preferably, the Notch agonist is a human or rodent protein or a fragment or derivative thereof. In one embodiment, the Notch agonist and the aryl hydrocarbon receptor antagonist are in separate containers. In some embodiments, the Notch agonist is an extracellular domain of a Delta, a Jagged, or a Serrate protein. In specific embodiments, an immobilized Notch agonist, e.g., an extracellular domain of a Notch ligand (such as an immobilized extracellular domain of a Delta, a Jagged, or a Serrate protein), is used in the methods of the invention. In particular embodiments, the Notch agonist is an extracellular domain of a Delta protein, e.g., Delta-1, Delta-3 or Delta-4. In other embodiments, the Notch agonist is an extracellular domain of a Jagged protein, e.g., Jagged-1 or Jagged-2. In one specific embodiment, the Notch agonist is Delta$^{ext-IgG}$. In some embodiments, Delta$^{ext-IgG}$ (e.g., Delta1$^{ext-IgG}$) is present in the container at a concentration between about 0.2 and 20 µg/ml, between about 1.25 and 10 µg/ml, or between about 2 and 6 µg/ml. In other embodiments, the Notch agonist is Delta$^{ext-myc}$. In some embodiments, the kits of the invention include a solid phase coated with a Notch agonist (e.g., an extracellular domain of a Notch ligand), which may be fused to a fusion partner. In one embodiment, the kits of the invention include a solid phase coated with Delta$^{ext-IgG}$. In certain embodiments, the solid phase comprises a surface of a cell culture dish (e.g., an inside plastic surface of the cell culture dish). In other embodiments, the solid phase comprises beads (e.g., Sepharose beads). In some embodiments, Delta$^{ext-IgG}$ is (or has been) applied to the solid phase at a concentration between about 0.2 and 20 µg/ml, between about 1.25 and 10 µg/ml, or between about 2 and 6 µg/ml. In certain embodiments, the kits of the invention further include a fibronectin or a fragment thereof (e.g., CH-296), which can be immobilized on a solid phase (e.g., on the solid phase coated with a Notch agonist, e.g., an extracellular domain of a Notch ligand). In some embodiments of the kits described herein, the aryl hydrocarbon receptor antagonist is a compound of Formula I:

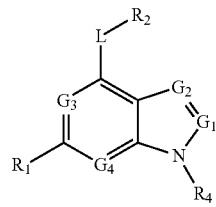

in which:
$G_1$ is selected from N and $CR_3$;
$G_2$, $G_3$ and $G_4$ are independently selected from CH and N; with the proviso that at least 1 of $G_3$ and $G_4$ is N; with the proviso that $G_1$ and $G_2$ are not both N;
L is selected from —NR$_{5a}$(CH$_2$)$_{0-3}$—, —NR$_{5a}$CH(C(O)OCH$_3$)CH$_2$—, —NR$_{5a}$(CH$_2$)$_2$NR$_{5b}$—, —NR$_{5a}$(CH$_2$)$_2$S—, —NR$_{5a}$CH$_2$CH(CH$_3$)CH$_2$—, —NR$_{5a}$CH$_2$CH(OH)— and —NR$_{5a}$CH(CH$_3$)CH$_2$—; wherein R$_{5a}$ and R$_{5b}$ are independently selected from hydrogen and C$_{1-4}$alkyl;

R$_1$ is selected from hydrogen, phenyl, thiophenyl, furanyl, 1H-benzoimidazolyl, isoquinolinyl, 1H-imidazopyridinyl, benzothiophenyl, pyrimidinyl, 1H-pyrazolyl, pyridinyl, 1H-imidazolyl, pyrrolidinyl, pyrazinyl, pyridazinyl, 1H-pyrrolyl and thiazolyl; wherein said phenyl, thiophenyl, furanyl, 1H-benzoimidazolyl, isoquinolinyl, 1H-imidazopyridinyl, benzothiophenyl, pyrimidinyl, 1H-pyrazolyl, pyridinyl, 1H-imidazolyl, pyrrolidinyl, pyrazinyl, pyridazinyl, 1H-pyrrolyl or thiazolyl of R$_1$ can be optionally substituted by 1 to 3 radicals independently selected from cyano, hydroxy, C$_{1-4}$alkyl, C$_{1-4}$alkoxy, halo, halo-substituted-C$_{1-4}$alkyl, halo-substituted-C$_{1-4}$alkoxy, hydroxy, amino, —C(O)R$_{8a}$, —S(O)$_{0-2}$R$_{8a}$, —C(O)OR$_{8a}$ and —C(O)NR$_{8a}$R$_{8b}$; wherein R$_{8a}$ and R$_{8b}$ are independently selected from hydrogen and C$_{1-4}$alkyl; with the proviso that R$_1$ and R$_3$ are not both hydrogen;

R$_2$ is selected from —S(O)$_2$NR$_{6a}$R$_{6b}$, —NR$_{9a}$C(O)R$_{9b}$, —NR$_{6a}$C(O)NR$_{6b}$R$_{6c}$, phenyl, 1H-pyrrolopyridin-3-yl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl and 1H-indazolyl; wherein R$_{6a}$, R$_{6b}$ and R$_{6c}$ are independently selected from hydrogen and C$_{1-4}$alkyl; wherein said phenyl, 1H-pyrrolopyridin-3-yl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl or 1H-indazolyl of R$_2$ is optionally substituted with 1 to 3 radicals independently selected from hydroxy, halo, methyl, methoxy, amino, —O(CH$_2$)$_n$NR$_{7a}$R$_{7b}$, —S(O)$_2$NR$_{7a}$R$_{7b}$, —OS(O)$_2$NR$_{7a}$R$_{7b}$ and —NR$_{7a}$S(O)$_2$R$_{7b}$; wherein R$_{7a}$ and R$_{7b}$ are independently selected from hydrogen and C$_{1-4}$alkyl;

R$_3$ is selected from hydrogen, C$_{1-4}$alkyl and biphenyl; and R$_4$ is selected from C$_{1-10}$alkyl, prop-1-en-2-yl, cyclohexyl, cyclopropyl, 2-(2-oxopyrrolidin-1-yl)ethyl, oxetan-3-yl, benzhydryl, tetrahydro-2H-pyran-3-yl, tetrahydro-2H-pyran-4-yl, phenyl, tetrahydrofuran-3-yl, benzyl, (4-pentylphenyl)(phenyl)methyl and 1-(1-(2-oxo-6,9,12-trioxa-3-azatetradecan-14-yl)-1H-1,2,3-triazol-4-yl)ethyl; wherein said alkyl, cyclopropyl, cyclohexyl, 2-(2-oxopyrrolidin-1-yl)ethyl, oxetan-3-yl, oxetan-2-yl, benzhydryl, tetrahydro-2H-pyran-2-yl, tetrahydro-2H-pyran-3-yl, tetrahydro-2H-pyran-4-yl, phenyl, tetrahydrofuran-3-yl, tetrahydrofuran-2-yl, benzyl, (4-pentylphenyl)(phenyl)methyl or 1-(1-(2-oxo-6,9,12-trioxa-3-azatetradecan-14-yl)-1H-1,2,3-triazol-4-yl) ethyl can be optionally substituted with 1 to 3 radicals independently selected from hydroxy, C$_{1-4}$alkyl and halo-substituted-C$_{1-4}$alkyl; or a salt thereof.

In some embodiments, the kits of the invention include 4-(2-(2-(benzo[b]thiophen-3-yl)-9-isopropyl-9H-purin-6-ylamino)ethyl)phenol (i.e., "SR1"), which is one of the compounds of Formula I.

In certain embodiments, the kits described herein further include one or more growth factors, two or more growth factors, or three or more growth factors (e.g., wherein one or more growth factors are in a container separate from the container(s) comprising the Notch agonist and/or the aryl hydrocarbon receptor antagonist). In specific embodiments, the growth factors are selected from stem cell factor (SCF), Flt-3 ligand (Flt-3), Interleukin-6 (IL-6), Interleukin-3 (IL-3), Interleukin-11 (IL-11), thrombopoietin (TPO), Granulocyte-macrophage colony stimulating factor (GM-CSF), and granulocyte colony stimulating factor (G-CSF). In one embodiment, the kits described herein include IL-6, Flt-3, SCF and TPO. In another embodiment, the kits described herein include IL-6, Flt-3, SCF, TPO and IL-3.

Also described herein is a solid phase comprising a surface on which a Notch agonist is immobilized, wherein the solid phase is in contact with the hematopoietic stem/progenitor cells, and the hematopoietic stem/progenitor cells are in contact with a fluid medium comprising an aryl hydrocarbon receptor antagonist in contact with the cells. In some embodiments, the solid phase is a cell culture container comprising (a) a Notch agonist immobilized on an inside surface of the container, and (b) hematopoietic stem/progenitor cells cultured on the inside surface, wherein the cells are in contact with a fluid comprising an aryl hydrocarbon receptor antagonist. Also described herein are cell culture containers comprising hematopoietic stem/progenitor cells, an immobilized Notch agonist in contact with the cells, and an aryl hydrocarbon receptor antagonist in contact with the cells (e.g., in a fluid medium). For example, described herein are cell culture containers comprising a Notch agonist immobilized on a solid phase surface of the container (e.g., on an inside surface of the container) on which hematopoietic stem/progenitor cells are cultured, which cells are in contact with a fluid medium containing an aryl hydrocarbon receptor antagonist. In some embodiments of the cell culture containers or the solid phase, the Notch agonist comprises an extracellular domain of a Delta, a Jagged, or a Serrate protein. In one embodiment, the Notch agonist is Delta$^{ext-IgG}$. In another embodiment, the Notch agonist is Delta$^{ext-myc}$. In some embodiments of the containers or the solid phase, Delta$^{ext-IgG}$ is (or has been) applied to the solid phase at a concentration between about 0.2 and 20 μg/ml, between about 1.25 and 10 μg/ml, or between about 2 and 6 μg/ml. In some embodiments of the cell culture containers or the solid phase, the aryl hydrocarbon receptor antagonist is a compound of Formula I:

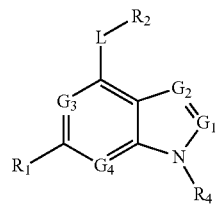

in which:

$G_1$ is selected from N and $CR_3$;

$G_2$, $G_3$ and $G_4$ are independently selected from CH and N; with the proviso that at least 1 of $G_3$ and $G_4$ is N; with the proviso that $G_1$ and $G_2$ are not both N;

L is selected from —$NR_{5a}(CH_2)_{0-3}$—, —$NR_{5a}CH(C(O)OCH_3)CH_2$—, —$NR_{5a}(CH_2)_2NR_{5b}$—, —$NR_{5a}(CH_2)_2S$—, —$NR_{5a}CH_2CH(CH_3)CH_2$—, —$NR_{5a}CH_2CH(OH)$— and —$NR_{5a}CH(CH_3)CH_2$—; wherein $R_{5a}$ and $R_{5b}$ are independently selected from hydrogen and $C_{1-4}$alkyl:

$R_1$ is selected from hydrogen, phenyl, thiophenyl, furanyl, 1H-benzoimidazolyl, isoquinolinyl, 1H-imidazopyridinyl, benzothiophenyl, pyrimidinyl, 1H-pyrazolyl, pyridinyl, 1H-imidazolyl, pyrrolidinyl, pyrazinyl, pyridazinyl, 1H-pyrrolyl and thiazolyl; wherein said phenyl, thiophenyl, furanyl, 1H-benzoimidazolyl, isoquinolinyl, 1H-imidazopyridinyl, benzothiophenyl, pyrimidinyl, 1H-pyrazolyl, pyridinyl, 1H-imidazolyl, pyrrolidinyl, pyrazinyl, pyridazinyl, 1H-pyrrolyl or thiazolyl of $R_1$ can be optionally substituted by 1 to 3 radicals independently selected from cyano, hydroxy, $C_{1-4}$alkyl, $C_{1-4}$alkoxy, halo, halo-substituted-$C_{1-4}$-alkyl, halo-substituted-$C_{1-4}$alkoxy, hydroxy, amino, —$C(O)R_{8a}$, —$S(O)_{0-2}R_{8a}$, —$C(O)OR_{8a}$ and —$C(O)NR_{8a}R_{8b}$; wherein $R_{8a}$ and $R_{8b}$ are independently selected from hydrogen and $C_{1-4}$alkyl; with the proviso that $R_1$ and $R_3$ are not both hydrogen;

$R_2$ is selected from —$S(O)_2NR_{6a}R_{6b}$, —$NR_{9a}C(O)R_{9b}$, —$NR_{6a}C(O)NR_{6b}R_{6c}$, phenyl, 1H-pyrrolopyridin-3-yl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl and 1H-indazolyl; wherein $R_{6a}$, $R_{6b}$ and $R_{6c}$ are independently selected from hydrogen and $C_{1-4}$alkyl; wherein said phenyl, 1H-pyrrolopyridin-3-yl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl or 1H-indazolyl of $R_2$ is optionally substituted with 1 to 3 radicals independently selected from hydroxy, halo, methyl, methoxy, amino, —$O(CH_2)_nNR_{7a}R_{7b}$, —$S(O)_2NR_{7a}R_{7b}$, —$OS(O)_2NR_{7a}R_{7b}$ and —$NR_{7a}S(O)_2R_{7b}$; wherein $R_{7a}$ and $R_{7b}$ are independently selected from hydrogen and $C_{1-4}$alkyl;

$R_3$ is selected from hydrogen, $C_{1-4}$alkyl and biphenyl; and $R_4$ is selected from $C_{1-10}$alkyl, prop-1-en-2-yl, cyclohexyl, cyclopropyl, 2-(2-oxopyrrolidin-1-yl)ethyl, oxetan-3-yl, benzhydryl, tetrahydro-2H-pyran-3-yl, tetrahydro-2H-pyran-4-yl, phenyl, tetrahydrofuran-3-yl, benzyl, (4-pentylphenyl)(phenyl)methyl and 1-(1-(2-oxo-6,9,12-trioxa-3-azatetradecan-14-yl)-1H-1,2,3-triazol-4-yl)ethyl; wherein said alkyl, cyclopropyl, cyclohexyl, 2-(2-oxopyrrolidin-1-yl)ethyl, oxetan-3-yl, oxetan-2-yl, benzhydryl, tetrahydro-2H-pyran-2-yl, tetrahydro-2H-pyran-3-yl, tetrahydro-2H-pyran-4-yl, phenyl, tetrahydrofuran-3-yl, tetrahydrofuran-2-yl, benzyl, (4-pentylphenyl)(phenyl)methyl or 1-(1-(2-oxo-6,9,12-trioxa-3-azatetradecan-14-yl)-1H-1,2,3-triazol-4-yl) ethyl can be optionally substituted with 1 to 3 radicals independently selected from hydroxy, $C_{1-4}$alkyl and halo-substituted-$C_{1-4}$alkyl; or a salt thereof.

In specific embodiments, described herein are cell culture containers or the solid phase, wherein the aryl hydrocarbon receptor antagonist is 4-(2-(2-(benzo[b]thiophen-3-yl)-9-isopropyl-9H-purin-6-ylamino)ethyl)phenol (i.e., SR1).

In certain embodiments, the cell culture containers or the solid phase described herein further comprise one or more growth factors, two or more growth factors, or three or more growth factors (such as any of the growth factors described herein) in contact with the cells (e.g., in a fluid medium). In one embodiment, the cell culture container or the solid phase of the invention contains IL-6, Flt-3, SCF and TPO (e.g., in a fluid medium). In another embodiment, the cell culture container or the solid phase of the invention contains IL-6, Flt-3, SCF, TPO and IL-3 (e.g., in a fluid medium). The cell culture containers or the solid phase described herein, in some embodiments, further comprise a fibronectin or a fragment thereof (e.g., CH-296) immobilized on the solid phase (e.g., on the inside surface of the container).

4. DEFINITIONS

Although any methods and materials similar or equivalent to those described herein can be used in the practice or testing of the present invention, the preferred methods and materials are described. For purposes of the present invention, the following terms are defined below.

As used herein, the terms "hematopoietic stem/progenitor cells" or "HSPC" mean hematopoietic stem cells and/or hematopoietic progenitor cells. The hematopoietic stem/progenitor cells can be positive for a specific marker expressed in increased levels on hematopoietic stem/progenitor cells relative to other types of hematopoietic cells. For example, such markers can be, but are not limited to CD34, CD43, CD45RO, CD45RA, CD59, CD90, CD109, CD117, CD133, CD166, HLA DR, or a combination thereof. Also, the hematopoietic stem/progenitor cells can be negative for an expressed marker relative to other types of hematopoietic cells. For example, such markers can be, but are not limited to Lin, CD38, or a combination thereof. Preferably, the hematopoietic stem/progenitor cells are CD34$^+$ cells. The HSPC are preferably human. The HSPC can be derived from umbilical cord blood and/or placental blood collected at birth, peripheral blood, bone marrow or another source.

As used herein, the term "Enriched HSPC" refers to a cell population enriched in hematopoietic stem/progenitor cells. The Enriched HSPC are preferably human.

As used herein, the term "CB" refers to cord blood.

As used herein, the term "CB Stem Cells" refers to herein interchangeably as "a CB Stem Cell Sample," refers to a cell population enriched in hematopoietic stem/progenitor cells derived from umbilical cord blood and/or placental blood collected at birth. The CB Stem Cells are preferably human.

As used herein, the term "Expanded HSPC" refers to HSPC that have been expanded in cell number by use of a combination of a Notch agonist and an aryl hydrocarbon receptor antagonist according to a method of the invention as disclosed herein. Preferably, such method results in (i) an increase in the number of HSPC in an aliquot of the sample thus expanded, or (ii) an increased number of SCID repopulating cells determined by limiting-dilution analysis as shown by enhanced engraftment in NOD/SCID mice infused with an aliquot of the sample thus expanded; relative to that seen with an aliquot of the sample that is not subjected to the expansion method. In a specific embodiment, the enhanced engraftment in NOD/SCID mice can be detected by detecting an increased percentage of human $CD45^+$ cells in the bone marrow of mice infused with an aliquot of the expanded sample relative to mice infused with an aliquot of the sample prior to expansion, at, e.g., 10 days, 3 weeks or 9 weeks post-infusion (see Delaney et al., 2010, Nature Med. 16(2): 232-236). In a specific embodiment, the expansion method results in an at least 50-, 75-, 100-, 150-, 200-, 250-, 300-, 350-, 400-, 450-, or 500-fold increase in the number of HSPC in an aliquot of the sample expanded, and preferably is at least 100-, 200-, 300- or 500-fold increase.

As used herein, the term "Delta" refers to any of the proteins or genes, as the case may be, of the *Drosophila* Delta family or its mammalian homolog Delta (also known as "Delta-like") family. Proteins or genes of the Delta family, as the case may be, include, but are not limited to, Delta-1 (where mammalian Delta-1 is also known as Delta-like 1), Delta-3 (where mammalian Delta-3 is also known as Delta-like 3), and Delta-4 (where mammalian Delta-4 is also known as Delta-like 4).

As used herein, the term "Serrate" refers to any of the proteins or genes, as the case may be, of the *Drosophila* Serrate family or its mammalian homolog, Jagged, family.

As used herein, the term "Jagged" refers to any of the proteins or genes, as the case may be, of the Jagged family such as, but not limited to, Jagged-1 and Jagged-2.

As used herein, the term "Alkyl" as a group and as a structural element of other groups, for example halo-substituted-alkyl and alkoxy, can be either straight-chained or branched. For example, alkyl includes methyl, ethyl, propyl, isopropyl, butyl, isobutyl, sec-butyl, t-butyl, etc. $C_{1-4}$-alkoxy includes methoxy, ethoxy, and the like. Halo-substituted alkyl includes trifluoromethyl, pentafluoroethyl, and the like.

As used herein, the term "Aryl" refers to a monocyclic or fused bicyclic aromatic ring assembly containing six to ten ring carbon atoms. For example, aryl can be phenyl or naphthyl, preferably phenyl. "Arylene" refers to a divalent radical derived from an aryl group.

As used herein, the term "Heteroaryl" is as defined for aryl where one or more of the ring members are a heteroatom or moiety selected from —O—, —N═, —NR—, —C(O)—, —S—, —S(O)— or —S(O)$_2$—, wherein R is hydrogen, $C_{1-4}$alkyl or a nitrogen protecting group. For example, heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

As used herein, the term "Cycloalkyl" refers to a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc. "Heterocycloalkyl" refers to cycloalkyl, as defined herein, provided that one or more of the ring carbons indicated, are replaced by a moiety selected from —O—, —N—, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, piperazinyl, piperidinyl, piperidinylone, 2-Oxo-pyrrolidin-1-yl, 1,4-dioxa-8-aza-spiro[4.5]dec-8-yl, etc.

As used herein, the term "Halogen" (or halo) preferably refers to chloro or fluoro, but can also be bromo or iodo.

Delta$^{ext-IgG}$ and Delta$^{Ext-IgG}$ are used interchangeably herein.

Delta1$^{ext-IgG}$ and Delta1$^{Ext-IgG}$ are used interchangeably herein.

5. BRIEF DESCRIPTION OF THE DRAWINGS

FIG. 1. Combination of Delta1$^{Ext-IgG}$ and SR-1 expand CB HSPC in vitro compared to control. Cells were cultured in the presence of IgG at 2.5 µg/ml or Delta1$^{Ext-IgG}$ (2 dose densities) and SR1. CD34 fold expansion (CD34 cell number at given time point/CD34 cell number at day 0) calculated at 7, 14, 18, and 21 days in culture. Hatched lines represent combination groups, solid line represents IgG control.

FIG. 2. Combination of Delta1$^{ext-IgG}$ and SR-1 maintain CB HSPC in culture. $CD34^+$ CB HSPC were incubated with Delta1$^{ext-IgG}$, SR1 or the combination for 16 days prior to transplant into immunodeficient mice. Percent (A) $CD34^+$ cells, (B) $CD34^+CD90^+$, or (C) $CD34^-14^+$ cells after 16 days in culture. Results are the mean of 4 combined experiments±SEM. *,** Significantly different from Delta1$^{ext-IgG}$ control, p=0.02 and 0.01. #, ## Significantly different from IgG+SR1 control, p=0.01 and 0.01. All other comparisons did not achieve significant. Non-parametric, two-tailed t-test.

FIG. 3. Maintenance of $CD34^+CD90^+$ cells correlates with engraftment. $CD34^+$ selected CB HSPC were incubated with Delta1$^{ext-IgG}$ at 2.5 µg/ml (circle), SR1 (light squares) or the combination (dark squares) with Delta1$^{ext-IgG}$ densities of 2.5, 5, or 10 µg/ml for 16 days and transplanted into NSG mice. SR1 and combination groups were performed in duplicate. Percent $CD34^+CD90^+$ cells at time of transplant v. (A) total human engraftment at 2 weeks or (B) total myeloid engraftment at 2 weeks. Pearson correlation coefficient and associated p-values displayed on graphs.

Figures 4A, 4B, 4C:
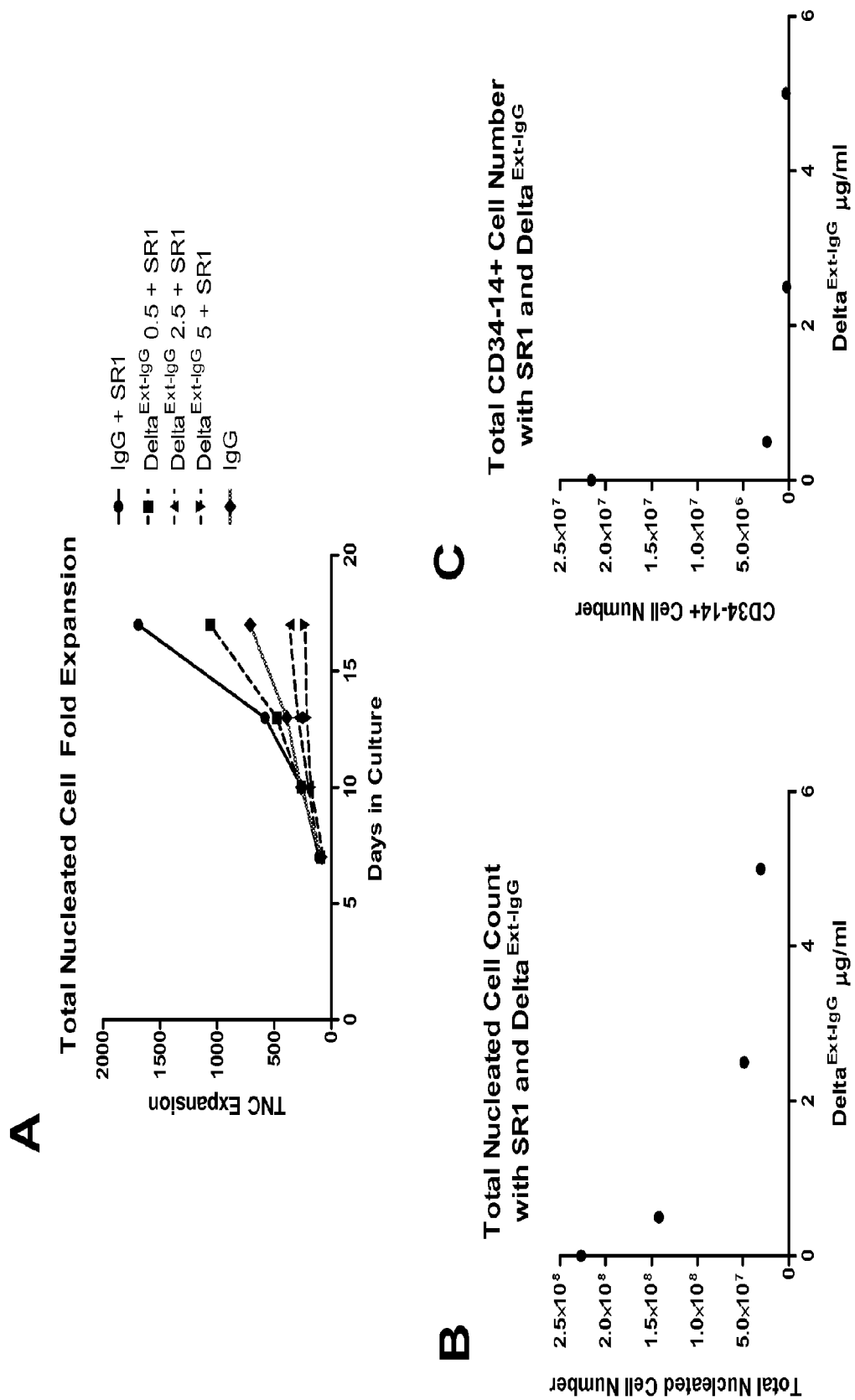
Figure 4D:
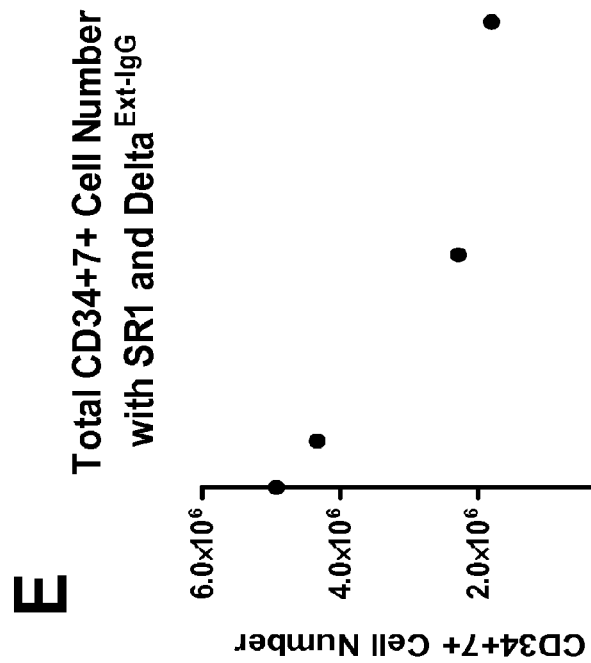
Figure 4E:
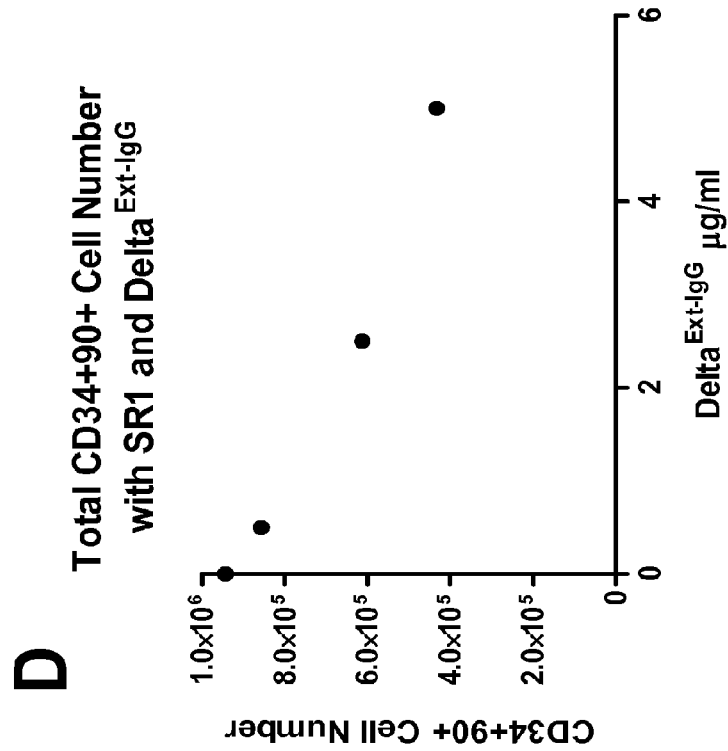

FIG. 4. SR-1 promotes cellular expansion and Delta1$^{Ext-IgG}$ blocks differentiation. $CD34^+$ selected CB HSPC were cultured for 16 days in the presence of SR1 and increasing densities of Delta1$^{Ext-IgG}$ (0, 0.5, 2.5, or 5 µg/ml) or an IgG control. (A) Total nucleated cell (TNC) fold expansion at 7, 10, 13, and 16 days in culture. (B-E) Total nucleated, $CD34^-CD14^+$, $CD34^+CD90^+$, or $CD34^+CD7^+$ cell numbers at day 16 of culture for SR1 with increasing densities of Delta1$^{Ext-IgG}$.

Figure 5A:
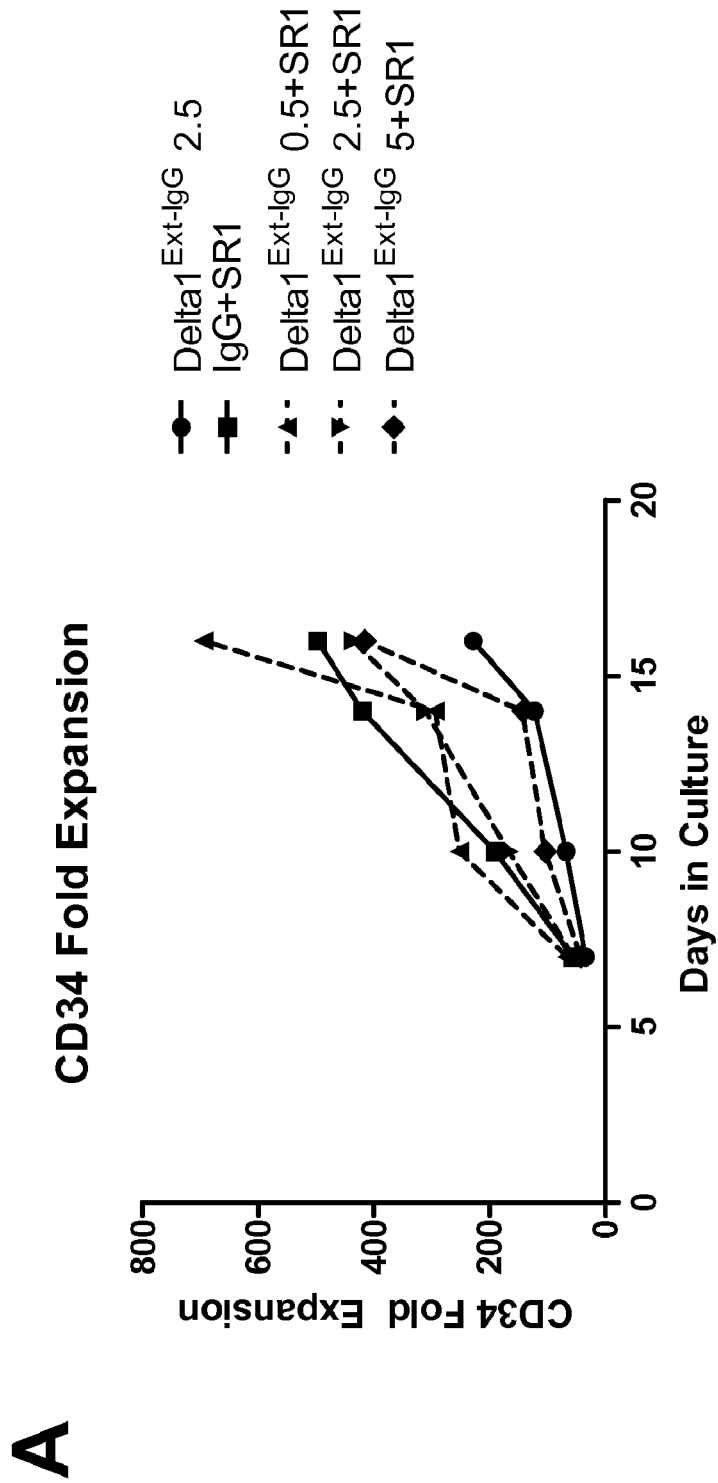
Figure 5B:
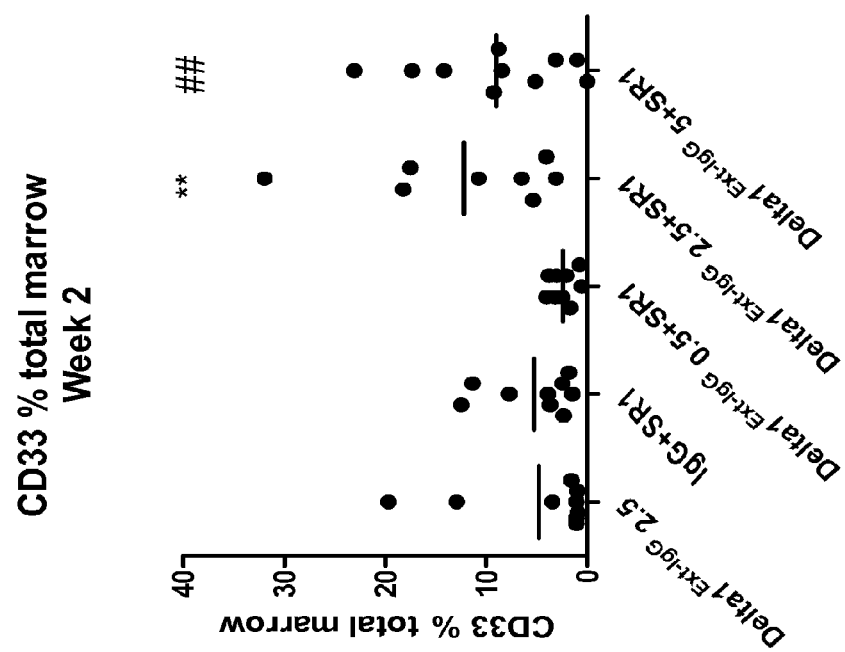
Figure 5C:
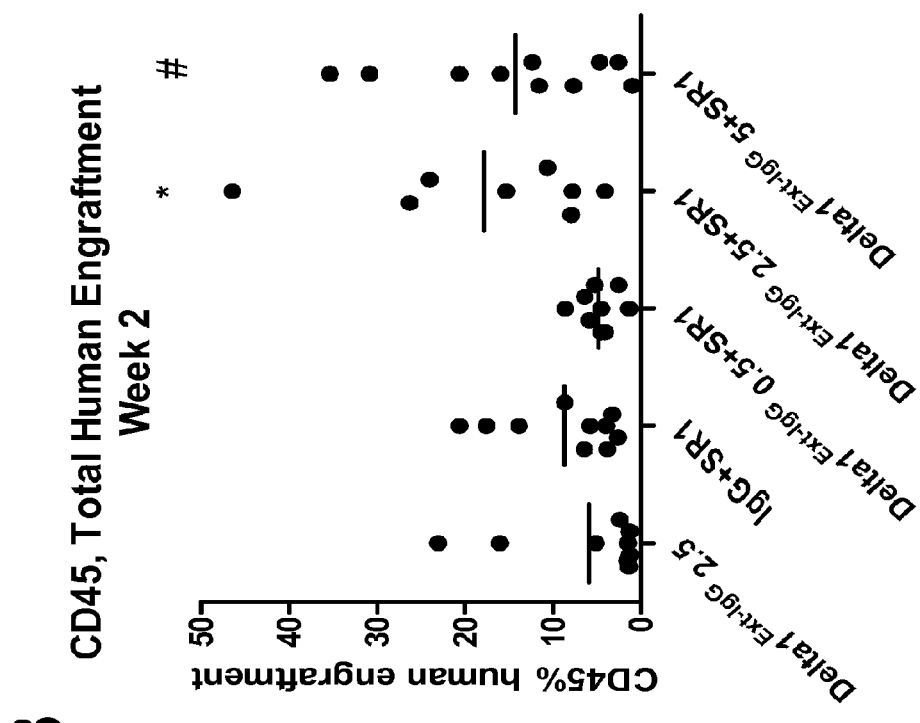

FIG. 5. Higher densities of Delta1$^{ext-IgG}$ result in enhanced generation of CB HSPC. Representative experiment demonstrating (A) ex vivo CD34+ cell expansion and (B,C) in vivo repopulating of these expanded cells in immunodeficient mice. All cultures were initiated with $8.5 \times 10^4$ CD34+ cells from the same pool of CB HSPC. Panels B and C demonstrate total human CD45 engraftment and total marrow CD33 engraftment at 2 weeks post-transplant. (●) represent individual mice with horizontal lines demonstrating means. *,** Significantly different from Delta1$^{Ext-IgG}$ 0.5, p-value=0.0144, 0.0099. #, ## Significantly different from Delta1$^{Ext-IgG}$ 0.5, p-value=0.0284, 0.0165. Non-parametric, two-tailed t-test.

FIG. 6. Delta1$^{ext-IgG}$ and SR-1 combined enhance early myeloid engraftment while maintaining progenitor cells. CD34+ CB HSPC were cultured for 16 days in the presence of Delta1$^{ext-IgG}$, SR1 or the combination and transplanted into NSG mice. Data represent results of 4 independent experiments. (●) represent individual mice with horizontal lines demonstrating means. (A) shows total human engraftment (CD45) at 2 weeks post-transplant. *,** Significantly different from Delta1$^{ext-IgG}$ 2.5 control, p-value=0.0056, 0.0026. #, ##, Not significantly different from IgG+SR1, p-value=0.1624, 0.1699. (B) shows total myeloid engraftment (CD33) at 2 weeks post-transplant. ! Significantly different from Delta1$^{ext-IgG}$ 2.5 control, p-value=0.0196, !! Not significantly different from Delta1$^{ext-IgG}$ 2.5 control, p-value=0.0686. &, && Significantly different from IgG+SR1, p-value=0.008, 0.0338. (C) shows total progenitor cell (CD34) engraftment 2 weeks post-transplant. %, %% Significantly different from Delta1$^{ext-IgG}$ 2.5 control, p-value=0.0012, 0.0002. +,++ Significantly different from IgG+SR1, p-value=0.0.0068, 0.0038. All statistics represent non-parametric, two-tailed t-test.

FIG. 7. Delta1$^{ext-IgG}$ and SR-1 combined demonstrate multi-lineage repopulation of NSG mice. CD34+ CB HSPC were cultured for 16 days in the presence of Delta1$^{ext-IgG}$, IgG+SR-1, or the combination (with two densities of Delta1$^{ext-IgG}$) and the progeny of 10,000 cells transplanted into sublethally irradiated NSG mice. (A) Percent overall human engraftment (CD45), (B) Percent progenitor cell engraftment (CD34), (C) Percent total myeloid engraftment (CD33), (D) Percent total lymphoid engraftment at 2, 8, and 13 weeks post transplant. Data are the results of a single transplant into 10 mice per condition, with mean±SEM.

Figure 8A:
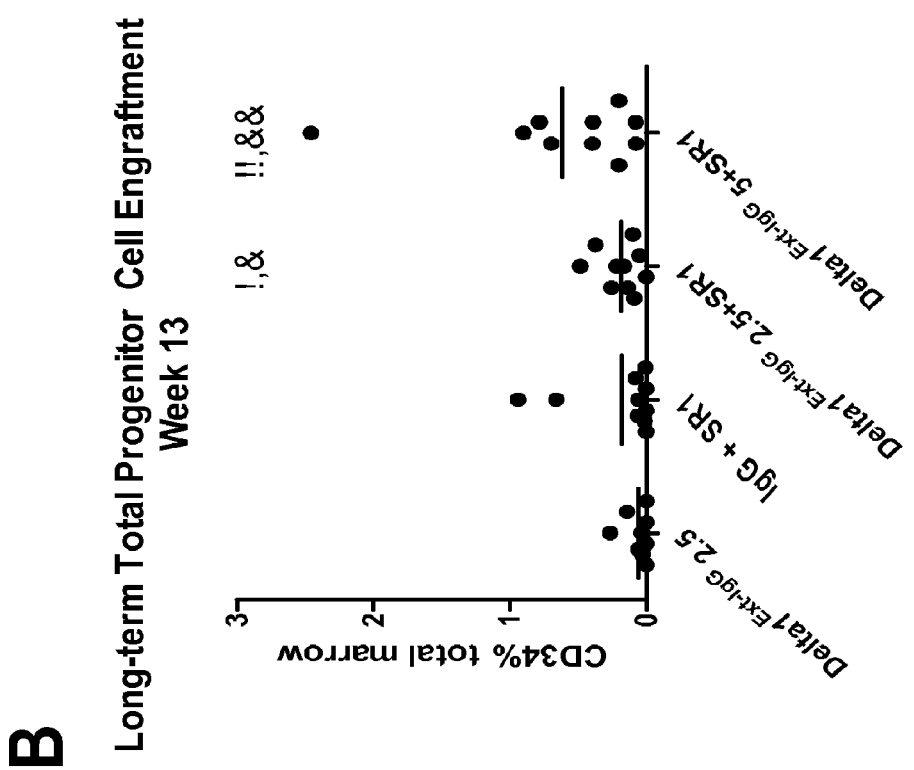
Figure 8B:
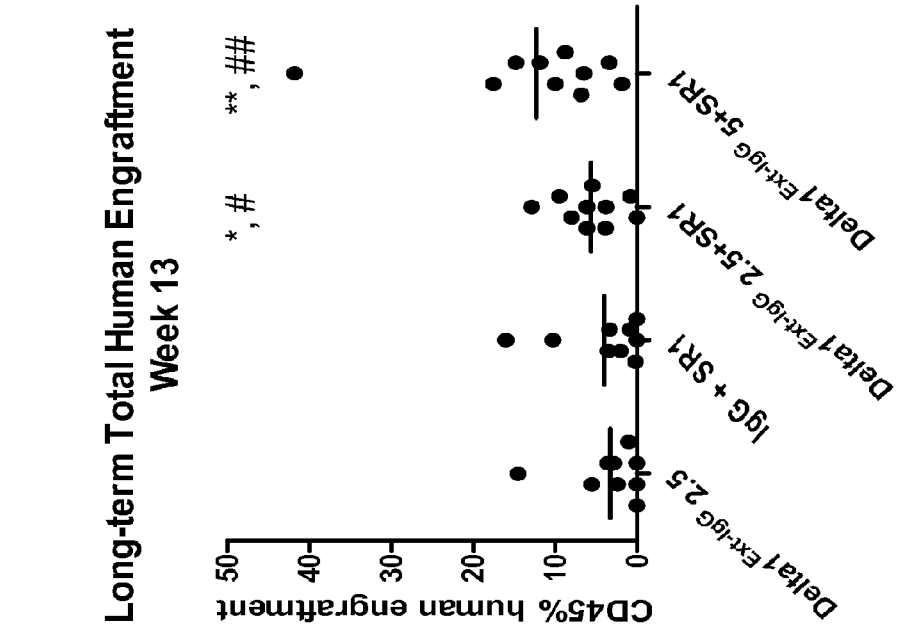

FIG. 8. Delta1$^{ext-IgG}$ and SR-1 in combination may enhance maintenance of long-term repopulating HSPC. CD34+ CB HSPC were cultured for 16 days in the presence of Delta1$^{ext-IgG}$, IgG+SR-1, or the combination (with two densities of Delta1$^{ext-IgG}$) and the progeny of 10,000 cells transplanted into sublethally irradiated NSG mice. (●) represent individual mice with mean engraftment indicated by horizontal line. Long-term total human (A) and progenitor cell (B) engraftment 13 weeks post-transplant are shown. **, !, !! Significantly different from Delta1$^{ext-IgG}$ 2.5 control, p-values=0.0411, 0.0417, 0.0317. * Not significantly different from Delta1$^{ext-IgG}$ 2.5 control, p-value=0.2436. #, ##, &, && Not significantly different from IgG+SR1, p-values=0.4601, 0.0638, 0.9670, 0.0952.

Figure 9A:
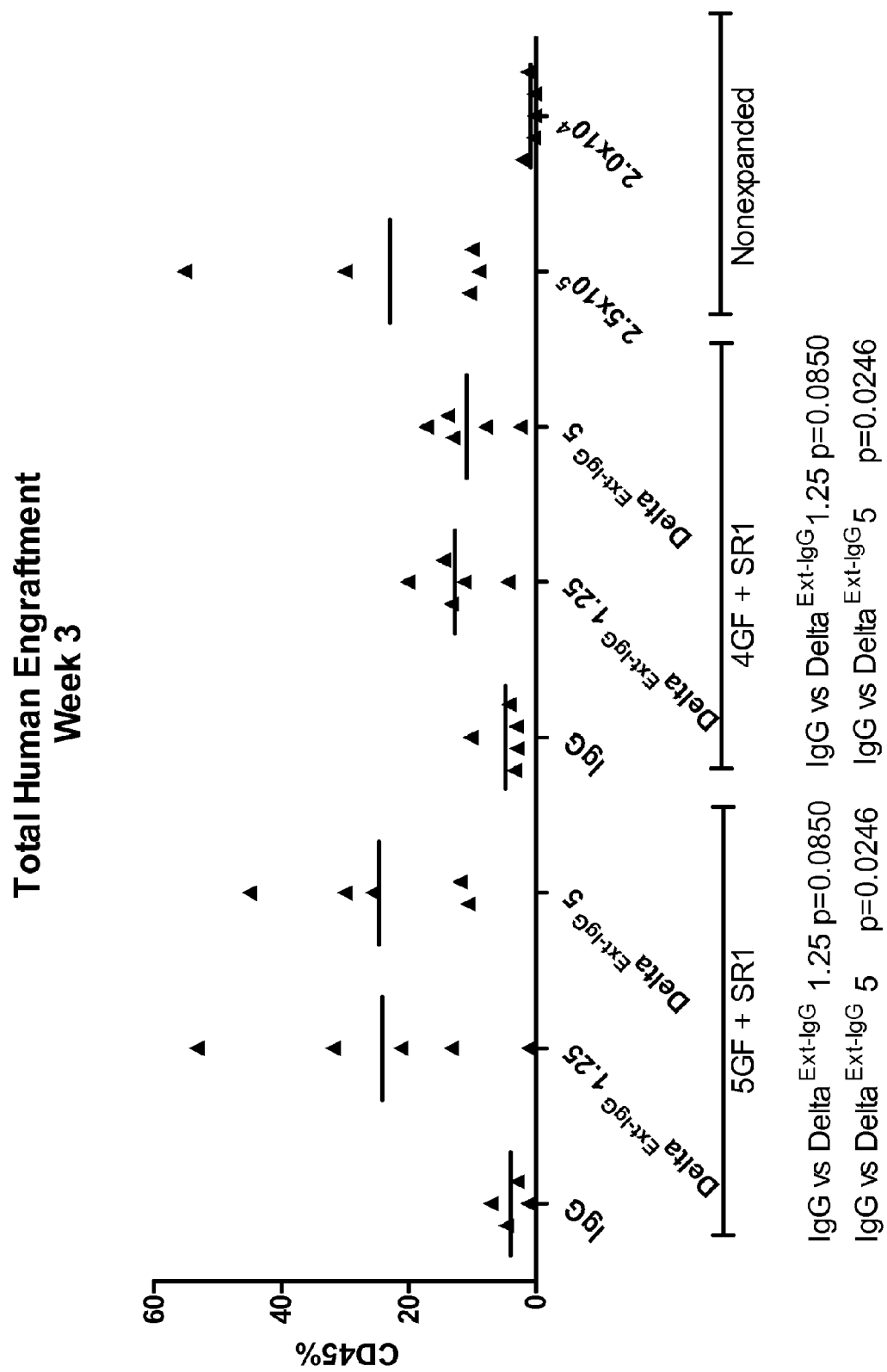
Figure 9B:
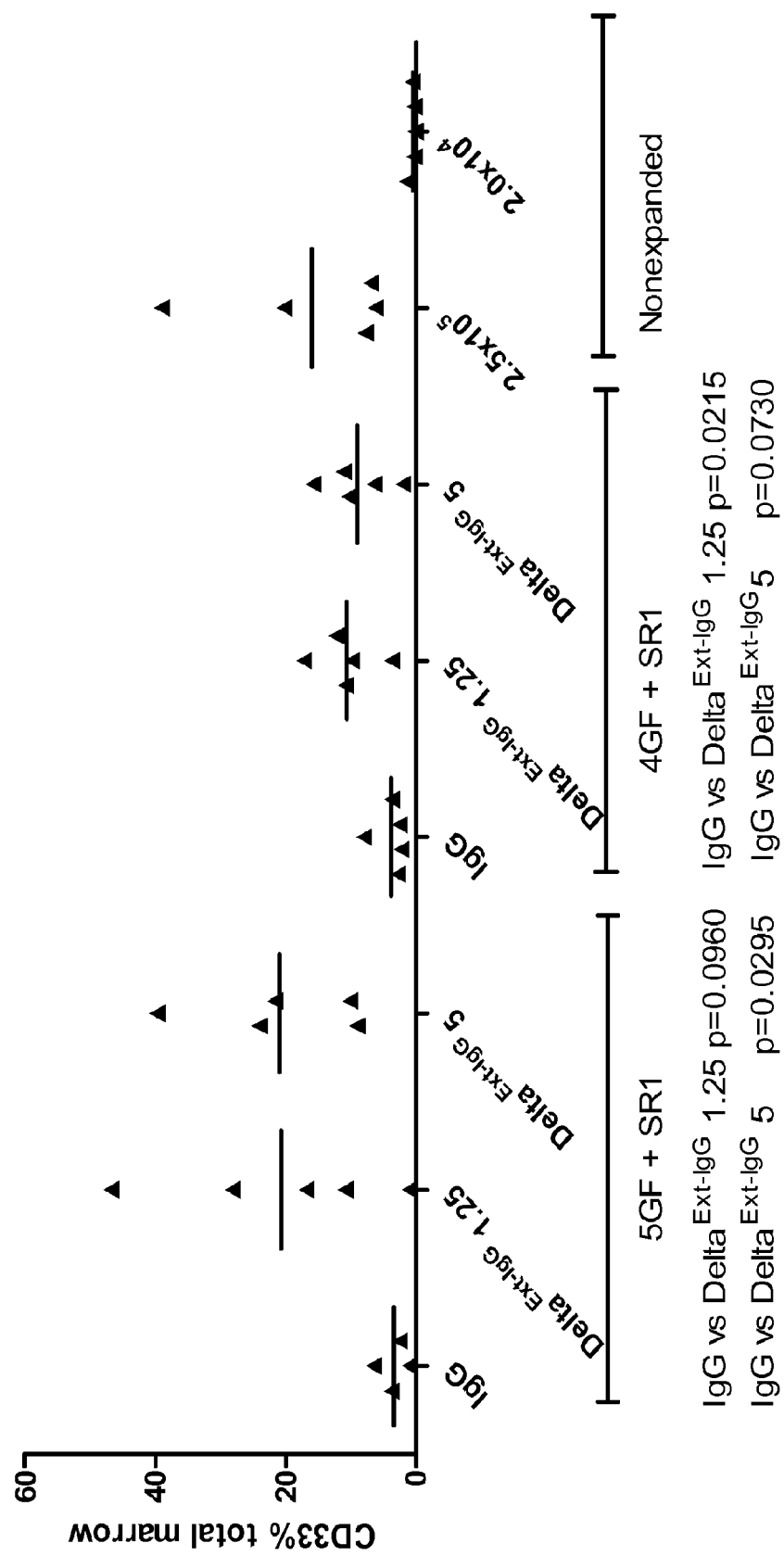

FIG. 9. Delta1$^{Ext-IgG}$ and SR1 in combination enhance generation of mPBSC HSPC. CD34+ mPSBC HSPC were cultured for 16 days in the presence of SR1 or Delta1$^{ext-IgG}$ (1.25 or 5 µg/ml) and the progeny of 20,000 cells transplanted into NSG mice. Week 3 total human and myeloid engraftment is shown here. P-values are shown on the graphs. Non-expanded cells were also transplanted from the same donor. Comparisons between non-expanded cells at the 20,000 cell dose and Delta1$^{ext-IgG}$/SR1 combination groups all achieved significance (p-values <0.05).

FIG. 10. Delta1$^{Ext-IgG}$ delays differentiation of cord blood HSPC cultured with SR1. CD34+ CB HSPC were cultured for 14 days in the presence of Delta1$^{Ext-IgG}$ (2.5 µg/ml), SR1 (750 nM), or the combination of Delta1$^{Ext-IgG}$ and SR1 with increasing doses of Delta1$^{Ext-IgG}$ (0.5, 2.5, or 5 µg/ml). Linear regression analysis models were used to test differences in number of cells generated across culture conditions. Base 2 logarithm transformations were applied to cell numbers to accommodate modeling assumptions. Two-sided P values from regression models were derived from the Wald test. No adjustments were made for multiple comparisons. Analyses were performed using SAS software, version 9.3 (SAS Institute, Cary, N.C.). Total nucleated cell (TNC) number was significantly decreased with Delta1$^{Ext-IgG}$ or the combination with Delta1$^{Ext-IgG}$ at 5 µg/ml as compared to SR1 alone (p<0.001, p=0.04). Significantly fewer TNC and CD34+ cells were generated with increasing Delta1$^{Ext-IgG}$ dose: 0.5, 2.5, and 5 µg/ml (p=0.02, p=0.04). Although not significant, Lin−CD34+CD38−CD45RA−CD90+ numbers tended to increase over Delta1$^{Ext-IgG}$ dose (p=0.07) (A). Similar numbers of common myeloid progenitors (CMP) were generated across all Delta1$^{Ext-IgG}$ doses in combination with SR1 as compared to SR1 alone (p=0.63); however, although not statistically significant, greater percentages of these cells were maintained with higher Delta1$^{Ext-IgG}$ doses (p=0.18) (B). Although not significant, generation of granulocyte-monocyte progenitors (GMP) and megakaryocyte-erythrocyte progenitors (MEP) cells decreased with higher Delta1$^{Ext-IgG}$ doses (C, D). Significantly fewer CD14/15+ mature myeloid cells were generated with increasing Delta1$^{Ext-IgG}$ dose (p=0.005) (C). Megakaryocyte generation was comparable across all groups with suggestion of greater percentage of these cells in Delta1$^{Ext-IgG}$ containing groups (D). Results shown are means±s.e.m. from 5 independent experiments.

FIG. 11. Delta1$^{Ext-IgG}$ and SR1 in combination enhance generation of early progenitor and myeloid repopulating cells. CD34+ selected CB HSPC were cultured for 16 days in the presence of Delta1$^{Ext-IgG}$ 2.5 µg/ml, IgG 2.5 µg/ml with SR1 or the combination of SR1 with Delta1$^{Ext-IgG}$ 5 µg/ml. The cultured progeny of 10,000 starting CD34+ cells were transplanted into NOD-SCID IL-2Rγ-null mice (NSG) and early and late repopulating capability assessed at 2 weeks by bone marrow aspirates and 12-14 weeks by bone marrow harvests. Engraftment was assessed by immunofluorescence analysis for early myeloid repopulation (percent CD45+CD33+) and progenitor repopulation (percent CD45+CD34+) (A, B). Progressive maturation of myeloid precursors was assessed in 3 cell populations: percent CD45+CD34+CD33−, CD45+CD34+CD33+ and CD45+CD34−CD33+ (C). Early monocyte/granulocyte (percent human CD45+CD14+CD15+) (D) and early B-lymphoid repopulation (CD45+CD19+CD33−) were assessed (E). All groups demonstrated multi-lineage engraftment with longer-term primary transplantation (F) with enhanced total human and B-lymphoid engraftment in the combination group (F). All p-values represent non-parametric two-tailed student t-tests, GraphPad software and are displayed on graphs with lines denoting comparisons. Results shown represent 4 independent experiments.

6. DETAILED DESCRIPTION OF THE INVENTION

The present invention provides kits, compositions and methods for expanding precursor cells, such as hematopoietic stem/progenitor cells, and providing hematopoietic function to a human patient in need thereof by administering the expanded hematopoietic stem/progenitor cells to the patient. In particular, the present invention relates to methods, kits and compositions for expanding hematopoietic stem/progenitor cells and providing hematopoietic function to human patients in need thereof, that use a Notch agonist, such as any of the Notch agonists described in U.S. Pat. No. 7,399,633 (which is incorporated herein by reference in its entirety), in combination with an aryl hydrocarbon receptor antagonist, such as any of the aryl hydrocarbon receptor antagonists described in U.S. Patent Publication No. 2010/0183564 (which is incorporated by reference herein in its entirety).

The inventors of the present invention found that combining the compositions and methodology described in U.S. Patent Publication No. 2004/0067583 (now U.S. Pat. No. 7,399,633) with the compositions and methodology described in U.S. Patent Publication No. 2010/0183564 results in an additive and/or synergistic effect. Specifically, the inventors combined a Notch agonist and an aryl hydrocarbon receptor antagonist for use in expansion of HSPC and demonstrated that this combination leads to an additive and/or synergistic effect on HSPC ex vivo expansion and in vivo repopulation/engraftment. The compositions and methodology for HSPC expansion described in U.S. Patent Publication No. 2004/0067583, U.S. Pat. No. 7,399,633 and U.S. Patent Publication No. 2010/0183564 are incorporated by reference herein in their entireties.

Hematopoietic stem/progenitor cells are fundamental for stem cell transplantation and gene therapy uses; however, historically ex vivo expansion attempts of HSPC have been insufficient for appreciable clinical application. Prior to the present invention, it was not appreciated that a combination of a Notch agonist and an aryl hydrocarbon receptor antagonist could be used for HSPC expansion and for subsequent administration of such expanded HSPC to patients in need thereof. In particular, it was not appreciated that the disclosed combination of agents results in synergistic or additive effects on ex vivo expansion and in vivo repopulation. The present invention takes advantage of the prompt short-term and long-term hematopoietic benefit provided by HSPC expanded using a combination of a Notch agonist and an aryl hydrocarbon receptor antagonist.

Specifically, and without being limited by any particular mechanism of action, the inventors of the present invention have discovered that use of a Notch agonist capable of blocking cellular differentiation and use of an aryl hydrocarbon receptor antagonist capable of promoting cellular expansion, at least in part by blocking cellular differentiation, leads to generation of greater numbers of HSPC capable of in vivo repopulation in NOD-SCID IL-2Rγ-null mice (NSG) compared to either approach alone. These findings suggest a novel approach to ex vivo expansion of HSPC by targeting these different aspects of stem cell self-renewal for additive and/or synergistic effect.

A potential model of enhancing HSPC expansion by targeting different pathways in HSPC self-renewal and differentiation, is that Notch2 affects HSPC self-renewal by blocking differentiation into multi-potent progenitors (MPP) and myeloid/monocytic (M) cell lineage, while SR1 promotes HSPC self-renewal likely, at least in part, by preventing cellular differentiation. Notch1 promotes T cell (T) differentiation versus B cell (B) differentiation.

Recent culture strategies have led to ex vivo expansion of CB HSPC with enhanced in vivo short-term repopulating abilities (see Delaney C, Heimfeld S, Brashem-Stein C, Voorhies H, Manger R L, Bernstein I D. Nat. Med. 2010; 16(20): 232-237; and Boitano A E, Wang J, Romeo R, et al. Science. 2010; 329(5997): 1345-1348). However, by combining two culture approaches, Delta$^{ext-IgG}$, a Notch pathway ligand capable of blocking cellular differentiation, and StemRegenin1 (SR1), an aryl hydrocarbon receptor antagonist capable of promoting cellular expansion also, at least in part, by blocking cellular differentiation, the inventors have been able to generate greater numbers of HSPC capable of in vivo short-term repopulation in NOD-SCID IL-2Rγ-null mice (NSG) compared to either approach alone.

Delayed neutrophil engraftment remains a challenge in CB transplantation with time to engraftment of 3 weeks even in the setting of double cord blood transplantation (Barker et al., 2005, Blood. 105 (3): 1343-1347). Recent approaches in phase I trials expanding CB HSPC on the immobilized Notch ligand Delta1$^{Ext-IgG}$ or on a layer of mesenchymal stem cells have demonstrated over one week reduction in time to engraftment when expanded cells are infused with non-manipulated CB units (de Lima et al., 2010, Blood. 116, Abstract 362; Delaney et al., 2010, Nat Med. 16(20): 232-237). The inventors of this invention have observed increased generation of repopulating cells capable of early myeloid repopulation in NSG mice as compared to Delta1$^{Ext-IgG}$ or SR1 alone, suggesting this combination may further enhance generation of short-term repopulating cells. HSPC expanded using the compositions and methods described herein could have clear clinical benefit since they can further reduce time to neutrophil engraftment in transplant recipients.

Further, the inventors have found that culturing of HSPC in the presence of both a Notch agonist and an aryl hydrocarbon receptor antagonist results in greater maintenance of immature hematopoietic precursors both in vitro and in vivo. In particular, the inventors have observed enhanced maintenance of CD34$^+$CD90$^+$ cells when CD34$^+$ CB HSPC were cultured in the presence of Delta$^{Ext-IgG}$ and SR1. This effect was particularly pronounced with higher densities of the Notch agonist, Delta$^{ext-IgG}$, such as 2.5 and 5 µg/ml Delta$^{ext-IgG}$. This is in notable contrast to the results using Delta$^{ext-IgG}$ alone, which showed maximal generation of long-term repopulating cells with lower Delta$^{ext-IgG}$ densities (see Delaney C, Varnum-Finney B, Aoyama K, Brashem-Stein C, Bernstein I D. Blood. 2005; 106(9): 2693-2699). It is possible that induction of more Notch signaling to block differentiation is required in the combination approach given the significant cellular expansion induced by SR1.

Further, the inventors have observed that expansion of HSPC in the presence of both a Notch agonist and an aryl hydrocarbon receptor antagonist results in greater maintenance of immature hematopoietic precursors in vitro, while decreasing total nucleated cell (TNC) and total CD34$^+$ cell generation, relative to the HSPC expanded in the presence of an aryl hydrocarbon antagonist alone. In particular, the inventors have observed that culturing of CB HSPC in the presence of SR1 and increasing concentrations of Delta$^{Ext-IgG}$ (0.5, 2.5 and 5 µg/ml Delta$^{ext-IgG}$) significantly decreases TNC and total CD34$^+$ cell number while maintaining or enhancing Lin$^-$CD34$^+$CD38$^-$CD45RA$^-$CD90$^+$ cell number relative to CB HSPC cultured in the presence of an aryl hydrocarbon antagonist alone. In addition, the inventors have found that culturing of CB HSPC in the presence of SR1 and increasing concentrations of Delta$^{Ext-IgG}$ (0.5, 2.5 and 5 µg/ml Delta$^{ext-IgG}$) leads to decreased generation of more mature myeloid cell populations (CD14$^+$ and CD15$^+$ cells) relative to CB HSPC cultured in the presence of an aryl hydrocarbon antagonist alone.

Unexpectedly, the inventors have found that expansion of HSPC in the presence of both a Notch agonist and an aryl hydrocarbon receptor antagonist results in generation of more cells capable of greater early engraftment (such as cells capable of rapidly repopulating bone marrow with early myeloid and progenitor cells) than expansion of HSPC in the presence of an aryl hydrocarbon receptor antagonist alone, despite the lesser number of total CD34$^+$ cells generated in the presence of both a Notch agonist and an aryl hydrocarbon receptor antagonist relative to the number generated in the presence of an aryl hydrocarbon receptor antagonist alone.

Furthermore, the inventors have found that expansion of HSPC in the presence of the combination of a Notch agonist and an aryl hydrocarbon receptor antagonist results in generation of more cells capable of short-term in vivo repopulation than expansion of HSPC in the presence of a Notch agonist alone or an aryl hydrocarbon receptor antagonist alone. In particular, the inventors have found that expansion of HSPC in the presence of the combination of a Notch agonist (specifically, Delta$^{ext-IgG}$) and an aryl hydrocarbon receptor antagonist (specifically, SR1) results in early generation of a higher percentage of early myeloid cells (CD45$^+$CD33$^+$), early progenitor cell (CD45$^+$CD34$^+$), CD45$^+$CD34$^+$CD33$^-$ cells, CD45$^+$CD34$^+$CD33$^+$ cells, and early monocyte/granulocyte cells (CD45$^+$CD14$^+$CD15$^+$), for short-term in vivo repopulation, than expansion of HSPC in the presence of a Notch agonist alone and/or an aryl hydrocarbon receptor antagonist alone.

Furthermore, the inventors have found that expansion of HSPC in the presence of the combination of a Notch agonist and an aryl hydrocarbon receptor antagonist results in generation of cells with multi-lineage potential capable of long-term in vivo repopulation (in addition to generation of cells capable of short-term in vivo repopulation). As detailed in the examples hereinafter, the inventors have discovered that culturing HSPC in the presence of a combination of a Notch agonist and an aryl hydrocarbon receptor antagonist leads to generation of greater numbers of HSPC capable of in vivo long-term, multi-lineage repopulation in NOD-SCID IL-2Rγ-null mice (NSG) than either approach alone. As described herein, the inventors have found that culturing HSPC in the presence of a combination of a Notch agonist (specifically, Delta$^{ext-IgG}$) and an aryl hydrocarbon receptor antagonist (specifically, SR1) leads to increase in long-term B-lymphocyte engraftment (i.e., engraftment of CD45$^+$CD19$^+$CD33$^-$ cells) in NOD-SCID IL-2Rγ-null mice (NSG) than either approach alone. Thus, the described combination, can be used for both short-term and/or long-term clinical benefits. This is significant because, despite advances in generation of short-term repopulating cells capable of enhanced early myeloid repopulation, significant generation of HSPC capable of sustained long-term in vivo repopulation in immunodeficient mice or humans remained elusive. Current expansion approaches in early clinical trials require administration of non-manipulated CB cells along with the cultured product. While some patients have demonstrated longer-term repopulation with expanded cells, most sustained long-term engraftment in these patients is from the non-manipulated CB unit. The expansion approach described herein, capable of generating both short- and long-term repopulating cells, can provide a significant benefit by allowing administration of a single, expanded HSPC unit (e.g., a single, expanded CB unit) to recipients (e.g., without administration of non-manipulated HSPC such as non-manipulated CB cells). However, administration of the non-manipulated CB cells along with the Expanded HSPC of the invention is also contemplated for additional benefits.

In addition, the inventors of this application have discovered that the combination of a Notch agonist and an aryl hydrocarbon receptor antagonist is effective to expand peripheral blood stem cells (e.g., mobilized peripheral blood stem cells) and to generate cells capable of enhanced in vivo repopulation. This effect was significantly more pronounced when the combination of agents described herein was used than when an aryl hydrocarbon receptor antagonist alone was used. The inventors demonstrated a similar effect on maintenance of immature progenitor cells and enhanced engraftment when mPBSC (i.e., mobilized peripheral blood stem cells) were cultured in the presence of SR1 and Delta$^{Ext-IgG}$, as that obtained in CB HSPC in the presence of SR1 and Delta$^{Ext-IgG}$. This is a significant finding considering that previous attempts to expand mPBSC ex vivo had generated no difference in engraftment. This data show that peripheral blood stem cells can be used as a source of HSPC for ex vivo expansion and subsequent therapeutic use for short-term and long-term in vivo repopulation in patients. It also suggests that not only CB HSPC but multiple sources of stem/progenitor cells can be used for effective expansion and engraftment using the combination of agents described herein.

Infusion of the Expanded HSPC of the invention can provide a therapeutic benefit for patients with immunodeficient and autoimmune diseases, diverse hematopoietic disorders, or those who had undergone chemotherapy. The use of chemotherapeutic agents can be immunosuppressive and/or highly myelosuppressive, leading to prolonged neutropenia, often resulting in frequent infections in treated patients. In some aspects of the invention, the infusion of HSPC expanded in accordance with the methods described herein abrogate or ameliorate neutropenia in a patient. In one aspect, the Expanded HSPC of the invention abrogate or ameliorate neutropenia resulting from chemotherapy, preventing infectious complications, and facilitating host hematopoietic recovery post-chemotherapy.

6.1 HSPC Culture/Expansion

In a preferred embodiment of the present invention, HSPC are expanded by culturing the cells in the presence of an agonist of Notch function and an aryl hydrocarbon receptor antagonist for a given period of time. One of more growth factors or cytokines can also be added during cell culture for a given period of time. Culturing HSPC can take place under any suitable culture medium/conditions described in U.S. Patent Publication No. 2004/0067583, U.S. Pat. No. 7,399,633, or U.S. Patent Publication No. 2010/0183564 (each of which is incorporated by reference herein in their entireties), or known in the art (see, e.g., Freshney Culture of Animal Cells, Wiley-Liss, Inc., New York, N.Y. (1994)). The time in culture is a time sufficient to produce an Expanded HSPC population, as defined herein. For example, HSPC can be cultured in a serum-free medium in the presence of an agonist of Notch function, an aryl hydrocarbon receptor antagonist, and, optionally, one or more growth factors or cytokines for 2, 3, 4, 5, 6, 7, 8, 9, 10, 11, 12, 13, 14, 15, 16, 17, 18, 19, 20, 21, 22, 23, 24, 25, 26, 27, 28, 29, 30, 32, or 35 days; or, preferably, for at least 10 or at least 15 days or at least 16 days. Optionally, at any point during the culturing period, the culture medium can be replaced with fresh medium or fresh medium can be added. In one embodiment, the fresh culture medium is added every 3 or 4 days.

6.2 Notch Agonists

The present invention contemplates use of a Notch agonist. Contemplated for use in the present invention are any of the Notch agonists disclosed in U.S. Pat. No. 7,399,633, incorporated by reference herein in its entirety, or any other Notch agonists known in the art (also, the disclosure of Notch agonists in sec. 5.1 of U.S. Pat. No. 7,399,633 is specifically incorporated herein by reference in its entirety). The description of Notch agonists provided herein is largely found in sec. 5.1 of U.S. Pat. No. 7,399,633.

A Notch agonist is an agent that promotes, i.e., causes or increases, activation of Notch pathway function. As used herein, "Notch pathway function" shall mean a function mediated by the Notch signaling (signal transduction) pathway, including but not limited to nuclear translocation of the intracellular domain of Notch, nuclear translocation of RBP-Jκ or its *Drosophila* homolog Suppressor of Hairless; activation of bHLH genes of the Enhancer of Split complex, e.g., Mastermind; activation of the HES-1 gene or the KBF2 (also called CBF1) gene; inhibition of *Drosophila* neuroblast segregation; and binding of Notch to a Delta protein, a Jagged/Serrate protein, Fringe, Deltex or RBP-Jκ/Suppressor of Hairless, or homologs or analogs thereof. See generally the review article by Kopan et al., 2009, Cell 137:216-233 for a discussion of the Notch signal transduction pathway and its effects upon activation; see also Jarriault et al., 1998, Mol. Cell. Biol. 18:7423-7431.

Notch activation is carried out by exposing a cell to a Notch agonist. The agonist of Notch can be but is not limited to a soluble molecule, a molecule that is recombinantly expressed on a cell-surface, a molecule on a cell monolayer to which the HSPC are exposed, or a molecule immobilized on a solid phase. Exemplary Notch agonists are the extracellular binding ligands Delta and Serrate (e.g., Jagged) which bind to the extracellular domain of Notch and activate Notch signal transduction, or a fragment (e.g., the extracellular domain) of Delta or Serrate (e.g., Jagged) that binds to the extracellular domain of Notch and activates Notch signal transduction. Nucleic acid and amino acid sequences of Delta family members and Serrate family members (e.g., Jagged family members) have been isolated from several species, including human, are known in the art, and are disclosed in International Patent Publication Nos. WO 93/12141, WO 96/27610, WO 97/01571, Gray et al., 1999, Am. J. Path. 154:785-794. Jagged is a mammalian homologue of Serrate. As used in this application, Serrate shall encompass Jagged unless the context indicates otherwise.

In a specific embodiment, the Notch agonist is an extracellular domain of a Delta protein or a Serrate (e.g., Jagged) protein, or a Notch-binding region thereof, fused to a different protein (a fusion partner). The Notch agonist is preferably immobilized on a solid support. In certain embodiments, the Notch agonist is an immobilized fragment of a Delta or a Serrate (e.g., Jagged) protein consisting of the extracellular domain of the protein fused to a myc epitope tag (Delta$^{ext-myc}$ or Serrate$^{ext-myc}$, respectively) or an immobilized fragment of a Delta or a Serrate (e.g., Jagged) protein consisting of the extracellular domain of the protein fused to the Fc portion of IgG (Delta$^{ext-IgG}$ or Serrate$^{ext-IgG}$, respectively). In preferred embodiments, the Notch agonist is an immobilized fragment of a Delta or a Serrate (e.g., Jagged) protein consisting of the extracellular domain of the Delta or Serrate fused to the Fc domain of human IgG1. In preferred embodiments, a Delta protein is a human or rodent Delta protein, and a Serrate or Jagged protein is a human or rodent Jagged protein.

Notch agonists of the present invention include but are not limited to Notch proteins and analogs and derivatives (including fragments) thereof; proteins that are other elements of the Notch pathway and analogs and derivatives (including fragments) thereof; activating antibodies thereto and fragments or other derivatives of such antibodies containing the binding region thereof; nucleic acids encoding the proteins and derivatives or analogs; as well as proteins and derivatives and analogs thereof which bind to or otherwise interact with Notch proteins or other proteins in the Notch pathway such that Notch pathway activity is promoted. Such agonists include but are not limited to Notch proteins and derivatives thereof comprising the intracellular domain, Notch nucleic acids encoding the foregoing, and proteins comprising the Notch-interacting domain of Notch ligands (e.g., the extracellular domain of Delta or Serrate). Other agonists include but are not limited to RBPJκ/Suppressor of Hairless or Deltex. Fringe can be used to enhance Notch activity, for example in conjunction with Delta protein. These proteins, fragments and derivatives thereof can be recombinantly expressed and isolated or can be chemically synthesized.

In another specific embodiment, the Notch agonist is a cell which recombinantly expresses a protein or fragment or derivative thereof, which agonizes Notch. The cell expresses the Notch agonist in such a manner that it is made available to HSPC in which Notch signal transduction is to be activated, e.g., it is secreted, expressed on the cell surface, etc.

In yet another specific embodiment, the agonist of Notch is a peptidomimetic or peptide analog or organic molecule that binds to a member of the Notch signaling pathway. Such an agonist can be identified by binding assays selected from those known in the art, for example the cell aggregation assays described in Rebay et al., 1991, Cell 67:687-699 and in International Patent Publication No. WO 92/19734.

In a preferred embodiment the agonist is a protein consisting of at least a fragment of a protein encoded by a Notch-interacting gene which mediates binding to a Notch protein or a fragment of Notch, which fragment of Notch contains the region of Notch responsible for binding to the agonist protein, e.g., epidermal growth factor-like repeats 11 and 12 of Notch. Notch interacting genes, as used herein, shall mean the genes Notch, Delta, Serrate, Jagged, RBPJκ, Suppressor of Hairless and Deltex, as well as other members of the Delta/Serrate family or Deltex family which may be identified by virtue of sequence homology or genetic interaction and more generally, members of the "Notch cascade" or the "Notch group" of genes, which are identified by molecular interactions (e.g., binding in vitro, or genetic interactions (as depicted phenotypically, e.g., in *Drosophila*). Exemplary fragments of Notch-binding proteins containing the region responsible for binding to Notch are described in U.S. Pat. Nos. 5,648,464; 5,849,869; and 5,856,441.

The Notch agonists utilized by the methods of the invention can be obtained commercially, produced by recombinant expression, or chemically synthesized.

In a specific embodiment, the Notch agonist is a dominant active mutant of a Notch protein (e.g., a Notch receptor lacking the extracellular, ligand binding domain). In another embodiment, the Notch agonist is not a dominant active mutant of a Notch protein.

In some embodiments, the Notch agonist is recombinantly expressed from a nucleic acid introduced into the HSPC. Methods that can be used for recombinantly expressing a Notch agonist are described in sec. 5.3 of U.S. Pat. No. 7,399,633, which is specifically incorporated by reference herein in its entirety. In particular embodiments, the Notch agonist is a Notch protein (e.g., human or murine Notch-1, Notch-2, Notch-3 or Notch-4) consisting essentially of the intracellular domain of the Notch protein expressed recombinantly in HSPC. In specific embodiments, the recombinantly expressed Notch agonist is a chimeric Notch protein which comprises the intracellular domain of Notch receptor and the extracellular domain of another ligand-binding surface receptor (e.g., the EGF receptor). In such embodiments, the Notch pathway can be activated by exposure to a ligand of such another ligand-binding surface receptor (e.g., EGF). The recombinantly expressed Notch agonist can be expressed by HSPC from an inducible promoter. In certain embodiments, the expression of the nucleic acid encoding the Notch agonist is under the control of Cre/Lox system or FLP/FRT system. In one embodiment, the Notch agonist is flanked by Cre sites.

In a specific embodiment, exposure of the cells to a Notch agonist is not done by incubation with other cells recombinantly expressing a Notch ligand on the cell surface (although in other embodiments, this method can be used), but rather is by exposure to a cell-free Notch ligand, e.g., incubation with a cell-free ligand of Notch, which ligand is immobilized on the surface of a solid phase, e.g., immobilized on the surface of a tissue culture dish.

In specific embodiments, Notch activity is promoted by the binding of Notch ligands (e.g., Delta ligands, Serrate ligands) to the extracellular portion of the Notch receptor. Notch signaling appears to be triggered by the physical interaction between the extracellular domains of Notch and its ligands that are either membrane-bound on adjacent cells or immobilized on a solid surface. Full length ligands are agonists of Notch, as their expression on one cell triggers the activation of the pathway in the neighboring cell which expresses the Notch receptor. Soluble truncated Delta or Serrate (e.g., Jagged) molecules, comprising the extracellular domains of the proteins or Notch-binding portions thereof, preferably fused to a different protein, that have been immobilized on a solid surface, such as a tissue culture plate, are particularly preferred Notch pathway agonists. Such soluble proteins can be immobilized on a solid surface by an antibody or interacting protein, for example an antibody directed to an epitope tag with which a Delta or a Serrate is expressed as a fusion protein (e.g., a myc epitope tag, which is recognized by the antibody 9E10) or a protein which interacts with an epitope tag with which a Delta or a Serrate is expressed as a fusion protein (e.g., an immunoglobulin epitope tag, which is bound by Protein A). Immobilization can be by any method known in the art (see, e.g., Section 6.8).

In another specific embodiment, and as described in U.S. Pat. No. 5,780,300 to Artavanis-Tsakonas et al., Notch agonists include reagents that promote or activate cellular processes that mediate the maturation or processing steps required for the activation of Notch or a member of the Notch signaling pathway, such as the furin-like convertase required for Notch processing, Kuzbanian, the metalloprotease-disintegrin (ADAM) thought to be required for the activation of the Notch pathway upstream or parallel to Notch (Schlondorff and Blobel, 1999, J. Cell Sci. 112:3603-3617), or, more generally, cellular trafficking and processing proteins such as the rab family of GTPases required for movement between cellular compartments (for a review on Rab GTPases, see Olkkonen and Stenmark, 1997, Int. Rev. Cytol. 176:1-85). The agonist can be any molecule that increases the activity of one of the above processes, such as a nucleic acid encoding a furin, Kuzbanian or rab protein, or a fragment or derivative or dominant active mutant thereof, or a peptidomimetic or peptide analog or organic molecule that binds to and activates the function of the above proteins.

U.S. Pat. No. 5,780,300 further discloses classes of Notch agonist molecules (and methods of their identification) which can be used to activate the Notch pathway in the practice of the present invention, for example molecules that trigger the dissociation of the Notch ankyrin repeats with RBP-Jκ, thereby promoting the translocation of RBP-Jκ from the cytoplasm to the nucleus.

6.3 Aryl Hydrocarbon Receptor Antagonists

In addition to the Notch agonist, the present invention contemplates use of an aryl hydrocarbon receptor antagonist. Such agent may include any compound capable of down-regulating the activity and/or expression of aryl hydrocarbon receptor and/or a downstream effector of aryl hydrocarbon receptor pathway (e.g., an agent capable of down-regulating the protein expression of aryl hydrocarbon receptor and/or the protein expression of one or more downstream effectors of aryl hydrocarbon receptor). Contemplated for use in the present invention are any of the compounds disclosed in U.S. Patent Application No. 2010/0183564, which is incorporated by reference herein in its entirety (also, the disclosure of compounds at pages 1-9 and 21-67 of U.S. Patent Application No. 2010/0183564 is specifically incorporated by reference herein in its entirety). The description of aryl hydrocarbon receptor antagonists provided herein is largely found in U.S. Patent Publication No. 2010/0183564.

In certain embodiments, an aryl hydrocarbon receptor antagonist is an organic compound, a small interference RNA (siRNA) molecule capable of down-regulating the expression of aryl hydrocarbon receptor, or an antisense oligonucleotide capable of down-regulating the expression of aryl hydrocarbon receptor (see U.S. Patent Publication No. 2010/0183564).

In certain embodiments, an aryl hydrocarbon receptor antagonist is a compound of Formula I:

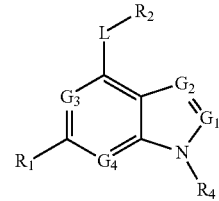

in which:

$G_1$ is selected from N and CR3;

$G_2$, $G_3$ and $G_4$ are independently selected from CH and N; with the proviso that at least 1 of $G_3$ and $G_4$ is N; with the proviso that $G_1$ and $G_2$ are not both N;

L is selected from —$NR_{5a}(CH_2)_{0-3}$— (0-3 herein means 0, 1, 2 or 3), —$NR_{5a}CH(C(O)OCH_3)CH_2$—, —$NR_{5a}(CH_2)_2NR_{5b}$—, —$NR_{5a}(CH_2)_2S$—, —$NR_{5a}CH_2CH(CH_3)CH_2$—, —$NR_{5a}CH_2CH(OH)$— and —$NR_{5a}CH(CH_3)CH_2$—; wherein $R_{5a}$ and $R_{5b}$ are independently selected from hydrogen and C1-4alkyl;

$R_1$ is selected from hydrogen, phenyl, thiophenyl, furanyl, 1H-benzoimidazolyl, isoquinolinyl, 1H-imidazopyridinyl, benzothiophenyl, pyrimidinyl, 1H-pyrazolyl, pyridinyl, 1H-imidazolyl, pyrrolidinyl, pyrazinyl, pyridazinyl, 1H-pyrrolyl and thiazolyl; wherein said phenyl, thiophenyl, furanyl, 1H-benzoimidazolyl, isoquinolinyl, 1H-imidazopyridinyl, benzothiophenyl, pyrimidinyl, 1H-pyrazolyl, pyridinyl, 1H-imidazolyl, pyrrolidinyl, pyrazinyl, pyridazinyl, 1H-pyrrolyl or thiazolyl of $R_1$ can be optionally substituted by 1 to 3 radicals independently selected from cyano, hydroxy, $C_{1-4}$alkyl, $C_{1-4}$alkoxy, halo, halo-substituted-$C_{1-4}$alkyl, halo-substituted-$C_{1-4}$alkoxy, hydroxy, amino, —C(O)$R_{8a}$, —S(O)$_{0-2}R_{8a}$, —C(O)OR$_{8a}$ and —C(O)NR$_{8a}R_{8b}$; wherein $R_{8a}$ and $R_{8b}$ are independently selected from hydrogen and $C_{1-4}$alkyl; with the proviso that $R_1$ and $R_3$ are not both hydrogen;

$R_2$ is selected from —S(O)$_2$NR$_{6a}R_{6b}$, —NR$_{9a}$C(O)R$_{9b}$, —NR$_{6a}$C(O)NR$_{6b}R_{6c}$, phenyl, 1H-pyrrolopyridin-3-yl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl and 1H-indazolyl; wherein $R_{6a}$, $R_{6b}$ and $R_{6c}$ are independently selected from hydrogen and $C_{1-4}$alkyl; wherein said phenyl, 1H-pyrrolopyridin-3-yl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl or 1H-indazolyl of $R_2$ is optionally substituted with 1 to 3 radicals independently selected from hydroxy, halo, methyl, methoxy, amino, —O(CH$_2$)$_n$NR$_{7a}R_{7b}$, —S(O)$_2$NR$_{7a}R_{7b}$, —OS(O)$_2$NR$_{7a}R_{7b}$ and —NR$_{7a}$S(O)$_2$R$_{7b}$; wherein $R_{7a}$ and $R_{7b}$ are independently selected from hydrogen and $C_{1-4}$alkyl;

$R_3$ is selected from hydrogen, $C_{1-4}$alkyl and biphenyl; and $R_4$ is selected from $C_{1-10}$alkyl, prop-1-en-2-yl, cyclohexyl, cyclopropyl, 2-(2-oxopyrrolidin-1-yl)ethyl, oxetan-3-yl, benzhydryl, tetrahydro-2H-pyran-3-yl, tetrahydro-2H-pyran-4-yl, phenyl, tetrahydrofuran-3-yl, benzyl, (4-pentylphenyl)(phenyl)methyl and 1-(1-(2-oxo-6,9,12-trioxa-3-azatetradecan-14-yl)-1H-1,2,3-triazol-4-yl)ethyl;

wherein said alkyl, cyclopropyl, cyclohexyl, 2-(2-oxopyrrolidin-1-yl)ethyl, oxetan-3-yl, oxetan-2-yl, benzhydryl, tetrahydro-2H-pyran-2-yl, tetrahydro-2H-pyran-3-yl, tetrahydro-2H-pyran-4-yl, phenyl, tetrahydrofuran-3-yl, tetrahydrofuran-2-yl, benzyl, (4-pentylphenyl)(phenyl)methyl or 1-(1-(2-oxo-6,9,12-trioxa-3-azatetradecan-14-yl)-1H-1,2,3-triazol-4-yl)ethyl can be optionally substituted with 1 to 3 radicals independently selected from hydroxy, $C_{1-4}$alkyl and halo-substituted-$C_{1-4}$alkyl;

or an N-oxide derivative, prodrug derivative, protected derivative, individual isomer or mixture of isomers thereof; or a salt (preferably a pharmaceutically acceptable salt) or solvate (e.g. hydrate) of such compound.

Examples of the compounds of Formula I are depicted in Tables 1 below.

In a specific embodiment, an aryl hydrocarbon receptor antagonist is a pharmaceutically acceptable salt of a compound of Formula I.

In one embodiment, an aryl hydrocarbon receptor antagonist is 4-2-(2-(benzo[b]thiophen-3-yl)-9-isopropyl-9H-purin-6-ylamino)ethyl)phenol ("SR1"). The structure of SR1 is provided below:

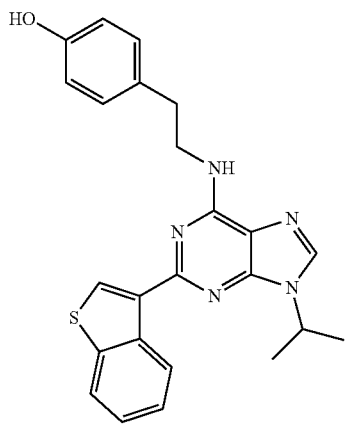 [SMILES: CC(C)n1cnc2c(NCCc3ccc(O)cc3)nc(-c3csc4ccccc34)nc21]

Examples of aryl hydrocarbon receptor antagonists that can be used in the compositions and methods of the present invention include, but are not limited to: SR1, 4-(2-(Pyridin-3-yl)-9-isopropyl-9H-purin-6-ylamino)ethyl)phenol, 4-(2-(9-isopropyl-2-(2-methyl-1H-imidazol-1-yl)-9H-purin-6-ylamino)ethyl)phenol, 4-(2-(2-(5-Chloropyridine-3-yl)-9-isopropyl-9H-purin-6-ylamino)ethyl)phenol, 4-(2-(6-(5-Fluoropyridin-3-yl)-1-isopropyl-1H-pyrazolo[3,4-d]pyrimidin-4-ylamino)ethyl)phenol, 4-(2-(2-(5-Fluoropyridin-3-yl)-7-isopropyl-7H-pyrrolo[2,3-d]pyrimidin-4-ylamino)ethyl)phenol, (R)-4-2-(2-(benzo[b]thiophen-3-yl)-9-tetrahydrofuran-3-yl)-9H-purin-6-ylamino)ethyl)phenol, 2-(6-(2-(1H-indol-3-yl)ethylamino)-2-(5-fluoropyridin-3-yl)-9H-purin-6-ylamino)ethyl)phenol, (R)-2-(6-(2-(1H-indol-3-yl)ethylamino)-2-(5-fluoropyridin-3-yl)-9H-purin-9-yl)propan-1-ol, (S)-2-(6-(2-(1H-indol-3-yl)ethylamino)-2-(5-fluoropyridin-3-yl)-9H-purin-9-yl)propan-1-ol, 4-(2-(6-(5-Fluoropyridin-3-yl)-1-isopropyl-1H-imidazol[4,5-c]pyridin-4-ylamino)ethyl)phenol, 4-(2-(5-(5-Fluoropyridin-3-yl)-3-isopropyl-3H-imidazo[4,5-c]pyridin-7-ylamino)ethyl)phenol, 3-2-(2-(benzo[b]thiophen-3-yl)-9-isopropyl-9H-purin-6-ylamino)ethyl)-1H-indol-5-yl 6-(5-((3aS,4S,6aR)-2-oxohexahydro-1H-thienol{3,4-d}imidazol-4-yl)pentanamido)hexonoate, and 3-2-(2-(benzo[b]thiophen-3-yl)-9-isopropyl-9H-purin-6-ylamino)ethyl)-1H-indol-5-yl 6-(tert-butoxycarbonylamino)hexonoate. U.S. Patent Publication 2010/0183564 describes and exemplifies these and other aryl hydrocarbon receptor antagonists that can be used in the compositions and methods of this invention (see, e.g., "Description of the Preferred Embodiments" section, and in particular, "Examples" section, Table 1 and Table 2, the disclosures of which are specifically incorporated by reference herein in their entireties).

In certain embodiments, an aryl hydrocarbon receptor antagonist is one or more of SR1, 4-(2-(Pyridin-3-yl)-9H-isopropyl-9H-purin-6-ylamino)ethyl)phenol, 4-(2-(9-isopropyl-2-(2-methyl-1H-imidazol-1-yl)-9H-purin-6-ylamino)ethyl)phenol, 4-(2-(2-(5-Chloropyridine-3-yl)-9-isopropyl-9H-purin-6-ylamino)ethyl)phenol, 4-(2-(6-(5-Fluoropyridin-3-yl)-1-isopropyl-1H-pyrazolo[3,4-d]pyrimidin-4-ylamino)ethyl)phenol, 4-(2-(2-(5-Fluoropyridin-3-yl)-7-isopropyl-7H-pyrrolo[2,3-d]pyrimidin-4-ylamino)ethyl)phenol, (R)-4-2-(2-(benzo[b]thiophen-3-yl)-9-tetrahydrofuran-3-yl)-9H-purin-6-ylamino)ethyl)phenol, 2-(6-(2-(1H-indol-3-yl)ethylamino)-2-(5-fluoropyridin-3-yl)-9H-purin-6-ylamino)ethyl)phenol, (R)-2-(6-(2-(1H-indol-3-yl)ethylamino)-2-(5-fluoropyridin-3-yl)-9H-purin-9-yl)propan-1-ol, (S)-2-(6-(2-(1H-indol-3-yl)ethylamino)-2-(5-fluoropyridin-3-yl)-9H-purin-9-yl)propan-1-ol, 4-(2-(6-(5-Fluoropyridin-3-yl)-1-isopropyl-1H-imidazol[4,5-c]pyridin-4-ylamino)ethyl)phenol, 4-(2-(5-(5-Fluoropyridin-3-yl)-3-isopropyl-3H-imidazo[4,5-c]pyridin-7-ylamino)ethyl)phenol, 3-2-(2-(benzo[b]thiophen-3-yl)-9-isopropyl-9H-purin-6-ylamino)ethyl)-1H-indol-5-yl 6-(5-((3aS,4S,6aR)-2-oxohexahydro-1H-thienol{3,4-d}imidazol-4-yl)pentanamido)thexonoate, and 3-2-(2-(benzo[b]thiophen-3-yl)-9-isopropyl-9H-purin-6-ylamino)ethyl)-1H-indol-5-yl 6-(tert-butoxycarbonylamino)thexonoate.

In another embodiment, an aryl hydrocarbon receptor antagonist is a compound of Formula Ia, Ib, Ic, Id or Ie disclosed at pages 2-9 of U.S. Patent Application No. 2010/0183564, described below. In yet another embodiment, an aryl hydrocarbon receptor antagonist is any one or more of the compounds disclosed in Table I of U.S. Patent Application No. 2010/0183564, described below.

In certain embodiments, an aryl hydrocarbon receptor antagonist is a compound of Formula Ia, Ib, Ic, Id or Ie:

Ia
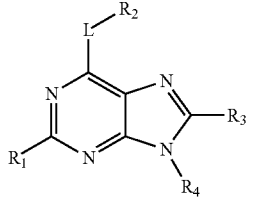

Ib
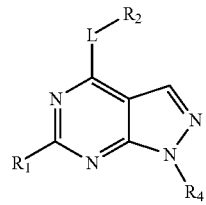

Ic
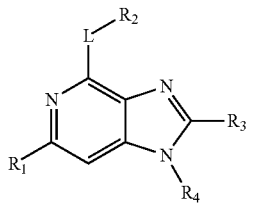

Id
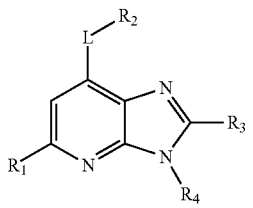

Ie
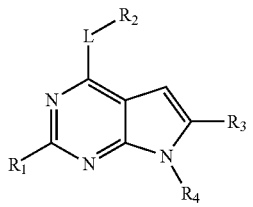

in which:

L is selected from —NR$_{5a}$(CH$_2$)$_{0-3}$—, —NR$_{5a}$CH(C(O)OCH$_3$)CH$_2$—, —NR$_{5a}$(CH$_2$)$_2$NR$_{5b}$—, —NR$_{5a}$(CH$_2$)$_2$S—, —NR$_{5a}$CH$_2$CH(CH$_3$)CH$_2$—, —NR$_{5a}$CH$_2$CH(OH)— and —NR$_{5a}$CH(CH$_3$)CH$_2$—; wherein R$_{5a}$ and R$_{5b}$ are independently selected from hydrogen and C$_{1-4}$alkyl; wherein the right side of the L moiety as shown is attached to R$_2$, for example: —NR$_{5a}$(CH$_2$)$_{0-3}$—R$_2$, —NR$_{5a}$CH(C(O)OCH$_3$)CH$_2$—R$_2$, —NR$_{5a}$(CH$_2$)$_2$NR$_{5b}$—R$_2$, —NR$_{5a}$(CH$_2$)$_2$S—R$_2$, —NR$_{5a}$CH$_2$CH(CH$_3$)CH$_2$—R$_2$, —NR$_{5a}$CH$_2$CH(OH)—R$_2$ and —NR$_{5a}$CH(CH$_3$)CH$_2$—R$_2$.

R$_1$ is selected from hydrogen, phenyl, thiophen-2-yl, thiophen-3-yl, furan-3-yl, 1H-benzo[d]imidazol-1-yl, isoquinolin-4-yl, 1H-imidazo[4,5-b]pyridin-1-yl, benzo[b]thiophen-3-yl, pyrimidin-5-yl, 1H-pyrazol-4-yl, pyridin-2-yl, pyridin-4-yl, 1H-imidazol-1-yl, pyrrolidin-1-yl, pyrazin2-yl, pyridin-3-yl, pyridazin-4-yl, 1H-pyrrol-2-yl and thiazol-5-yl;

wherein said phenyl, thiophen-2-yl, thiophen-3-yl, furan-3-yl, 1H-benzo[d]imidazol-1-yl, isoquinolin-4-yl, 1H-imidazo[4,5-b]pyridin-1-yl, benzo[b]thiophen-3-yl, pyrimidin-5-yl, pyridin-2-yl, pyridin-4-yl, 1H-imidazol-1-yl, pyrrolidin-1-yl, pyrazin-2-yl, pyridin-3-yl, pyridazin-4-yl, 1H-pyrrol-2-yl or thiazol-5-yl of R$_1$ can be optionally substituted by 1 to 3 radicals independently selected from cyano, hydroxy, C$_{1-4}$alkyl, C$_{1-4}$alkoxy, halo, halo-substituted-C$_{1-4}$alkyl, —S(O)$_{0-2}$R$_{8a}$ and —C(O)OR$_{8a}$; wherein R$_{8a}$ and R$_{8b}$ are independently selected from hydrogen and C$_{1-4}$alkyl; with the proviso that R$_1$ and R$_3$ are not both hydrogen;

R$_2$ is selected from —NR$_{6a}$C(O)NR$_{6b}$R$_{6c}$, phenyl, 1H-pyrrolo[2,3-b]pyridin-3-yl, 1H-pyrrolo[2,3-b]pyridin-5-yl, 1H-indol-3-yl, thiophen-3-yl, pyridin-2-yl, pyridin-3-yl, pyridin-4-yl, 1H-1,2,4-triazol-5-yl, 2-oxoimidazolidin-1-yl, 1H-pyrazol-3-yl, 1H-pyrazol-4-yl, 2-oxo-2,3-dihydro-1H-benzo[d]imidazol-5-yl and 1H-indazol-3-yl; wherein R$_{6a}$, R$_{6b}$ and R$_{6c}$ are independently selected from hydrogen and C$_{1-4}$alkyl; wherein said phenyl, 1H-pyrrolo[2,3-b]pyridin-3-yl, 1H-pyrrolo[2,3-b]pyridin-5-yl, 1H-indol-3-yl, thiophen-3-yl pyridin-2-yl, pyridin-3-yl, pyridin-4-yl, 1H-1,2,4-triazol-5-yl, 2-oxoimidazolidin-1-yl, 1H-pyrazol-3-yl, 1H-pyrazol-4-yl, 2-oxo-2,3-dihydro-1H-benzo[d]imidazol-5-yl or 1H-indazol-3-yl of R$_2$ is optionally substituted with 1 to 3 radicals independently selected from hydroxy, halo, methoxy, amino, —OS(O)$_2$NR$_{7a}$R$_{7b}$ and —NR$_{7a}$S(O)$_2$R$_{7b}$; wherein R$_{7a}$ and R$_{7b}$ are independently selected from hydrogen and C$_{1-4}$alkyl;

R$_3$ is selected from hydrogen, C$_{1-4}$alkyl and biphenyl; and

R$_4$ is selected from isopropyl, methyl, ethyl, prop-1-en-2-yl, isobutyl, cyclohexyl, sec-butyl, (S)-sec-butyl, (R-sec-butyl, 1-hydroxypropan-2-yl, (S)-1-hydroxypropan-2-yl, (R)-1-hydroxypropan-2-yl, nonan-2-yl, 2-(2-oxopyrrolidin-1-yl)ethyl, oxetan-3-yl, oxetan-2-yl, benzhydryl, tetrahydro-2H-pyran-2-yl, phenyl, tetrahydrofuran-3-yl and benzyl; wherein said cyclohexyl, 2-(2-oxopyrrolidin-1-yl)ethyl, oxetan-3-yl, oxetan-2-yl, benzhydryl, tet-rahydro-2H-pyran-4-yl, phenyl, tetrahydrofuran-3-yl or benzyl can be optionally substituted with 1 to 3 radicals independently selected from C$_{1-4}$alkyl and halo-substituted C$_{1-4}$alkyl.

In another embodiment, L is selected from —NR$_{5a}$(CH$_2$)$_{0-3}$—, —NR$_{5a}$CH(C(O)OCH$_3$)CH$_2$—, —NR$_{5a}$(CH$_2$)$_2$NR$_{5b}$—, —NR$_{5a}$(CH$_2$)$_2$S—, —NR$_{5a}$CH$_2$CH(CH$_3$)CH$_2$—, —NR$_{5a}$CH(CH$_3$)CH$_2$— and —NR$_{5a}$CH$_2$CH(OH)—; wherein R$_{5a}$ and R$_{5b}$ are independently selected from hydrogen and methyl; and R$_1$ is selected from hydrogen, phenyl, thiophen-2-yl, thiophen-3-yl, furan-3-yl, 1H-benzo[d]imidazol-1-yl, isoquinolin-4-yl, 1-imidazo[4,5-b]pyridin-1-yl benzo[b]thiophen-3-yl, pyrimidin-5-yl, 1H-pyrazol-4-yl, pyridin-2-yl, pyridin-4-yl, 1H-imidazol-1-yl, pyrrolidin-1-yl, pyrazin-2-yl, pyridin-3-yl, pyridazin-4-yl, 1H-pyrrol-2-yl and thiazol-5-yl; wherein said phenyl, thiophen-2-yl, thiophen-3-yl, furan-3-yl, 1H-benzo[d]imidazol-1-yl, isoquinolin-4-yl, 1H-imidazo[4,5-b]pyridin-1-yl, benzo[b]thiophen-3-yl, pyrimidin-5-yl, pyridin-2-yl, pyridin-4-yl, 1H-imidazol-1-yl, pyrrolidin-1-yl, pyrazin-2-yl, pyridin-3-yl, pyridazin-4-yl, 1H-pyrrol-2-yl orthiazol-5-yl of R$_1$ can be optionally substituted by 1 to 3 radicals independently selected from cyano, hydroxy, C$_{1-4}$alkyl, C$_{1-4}$alkoxy, halo, halo-substituted-C$_{1-4}$alkyl, —S(O)$_{0-2}$R$_{8a}$ and —C(O)OR$_{8a}$; wherein R$_{8a}$ and R$_{8b}$ are independently selected from hydrogen and C$_{1-4}$alkyl; with the proviso that R$_1$ and R$_3$ are not both hydrogen.

In another embodiment, when L is —NR$_{5a}$(CH$_2$)$_{0-3}$, it is preferably —NR$_{5a}$(CH$_2$)$_{1-3}$ (where 1-3 herein 1, 2 or 3).

In another embodiment, R$_2$ is selected from urea, phenyl, 1H-indol-2-yl, 1H-indol-3-yl, thiophen-3-yl, piperi-din-1-yl, pyridin-2-yl, pyridin-3-yl, pyridin-4-yl, 1H-1,2,4-triazol- 3-yl, 1H-1,2,4-triazol-5-yl, 2-oxoimidazolidin-1-yl, 1H-pyrazol-3-yl, 1H-pyrazol-4-yl, 2-oxo-2,3-dihydro-1H-benzo[d]imidazol-5-yl, 1H-benzo[d]imidazol-5-yl and 1H-imidazol-4-yl; wherein said phenyl, 1H-indol-3-yl, 1H-indol-3-yl, thiophen-3-yl, piperidin-1-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, 2-oxo-2,3-dihydro-1H-benzo[d]imidazol-5-yl or 1H-benzo[d]imidazol-5-yl of R2 is optionally substituted with hydroxy, methoxy, methyl, halo, amino and aminosulfonyl.

In another embodiment, $R_3$ is selected from hydrogen, methyl and biphenyl; and $R_4$ is selected from isopropyl, methyl, ethyl, prop-1-en-2-yl, isobutyl, cyclohexyl, sec-butyl, (S)-sec-butyl, (R)-sec-butyl, 1-hydroxypropan-2-yl, (S)-1-hydroxypropan-2-yl, (R)-1-hydroxypropan-2-yl, nonan-2-yl, 2-(2-oxopyrrolidin-1-yl)ethyl, oxetan-3-yl, oxetan-2-yl, benzhydryl, tetrahydro-2H-pyran-2-yl, phenyl, tetrahydrofuran-3-yl and benzyl; wherein said cyclohexyl, 2-(2-oxopyrrolidin-1-yl)ethyl, oxetan-3-yl, oxetan-2-yl, benzhydryl, tetrahydro-2H-pyran-4-yl, phenyl, tetrahydrofuran-3-yl or benzyl can be optionally substituted with 1 to 3 radicals independently selected from methyl and trifluoromethyl.

In another embodiment are compounds selected from: 4-(2-(2-(benzo[b]thiophen-3-yl)-9-isopropyl-9H-purin-6-ylamino)ethyl)phenol; 4-(2-(2-(benzo[b]thiophen-3-yl)-9-sec-butyl-9H-purin-6-ylamino)ethyl)phenol; 4-(2-(9-benzhydryl-2-(benzo[b]thiophen-3-yl)-9H-purin-6-ylamino)ethyl)phenol; 4-(2-(2-(benzo[b]thiophen-3-yl)-9-(tetrahydro-2H-pyran-3-yl)-9H-purin-6-ylamino)ethyl)phenol; 4-(2-(9-isopropyl-2-(thiophen-2-yl)-9H-purin-6-ylamino)ethyl)phenol; 4-(2-(2-(benzo[b]thiophen-3-yl)-9-(4-(trifluoromethyl)benzyl)-9H-purin-6-ylamino)ethyl)phenol; 4-(2-(2-(benzo[b]thiophen-3-yl)-9-isobutyl-9H-purin-6-ylamino)ethyl)phenol; 4-(2-(2-(benzo[b]thiophen-3-yl)-9-methyl-9H-purin-6-ylamino)ethyl)phenol; 4-(2-(2-(benzo[b]thiophen-3-yl)-9-(4-methylbenzyl)-9H-purin-6-ylamino)ethyl)phenol; N-(2-(1H-indol-3-yl)ethyl)-2-(benzo[b]thiophen-3-yl)-9-isopropyl-9H-purin-6-amine; 2-(benzo[b]thiophen-3-yl)-9-isopropyl-N-(2-(thiophen-3-yl)ethyl)-9H-purin-6-amine; 3-(2-(2-(benzo[b]thiophen-3-yl)-9-isopropyl-9H-purin-6-ylamino)ethyl)phenol; 2-(benzo[b]thiophen-3-yl)-N-(4-fluorophenethyl)-9-isopropyl-9H-purin-6-amine; N-(4-aminophenethyl)-2-(benzo[b]thiophen-3-yl)-9-isopropyl-98-purin-6-amine; 4-(2-(9-isopropyl-2-(pyrimidin-5-yl)-9H-purin-6-ylamino)ethyl)phenol; 4-(2-(9-isopropyl-2-(pyridin-3-yl)-9H-purin-6-ylamino)ethyl)phenol; 4-(2-(9-isopropyl-2-phenyl-9H-purin-6-ylamino)ethyl)phenol; 4-(2-(9-isopropyl-2-(thiophen-3-yl)-9H-purin-6-ylamino)ethyl)phenol; 4-(2-(2-(furan-3-yl)-9-isopropyl-9H-purin-6-ylamino)ethyl)phenol; 2-(benzo[b]thiophen-3-yl)-N-(4-fluorophenethyl)-9-phenyl-9H-purin-6-amine; N-benzyl-8-(biphenyl-4-yl)-9-isopropyl-9H-purin-6-amine; 4-(2-(2-(benzo[b]thiophen-3-yl)-9-(nonan-2-yl)-9H-purin-6-ylamino)ethyl)phenol; N-(2-(1-Hindol-3-yl)ethyl)-2-(benzo[b]thiophen-3-yl)-9-sec-butyl-9H-purin-6-amine; 3-(2-(2-(benzo[b]thiophen-3-yl)-9-isopropyl-9H-purin-6-ylamino)ethyl)-1H-indol-5-yl, 5-((3aS,4S,6aR)-2-oxohexahydro-1H-thieno[3,4-d]imidazol-4-yl)pentanoate; N-(2-(2-(2-(2-(4-(1-(2-(benzo[b]thiophen-3-yl)-6-(4-hydroxyphenethylamino)-9H-purin-9-yl)ethyl)-1H-1,2,3-triazol-1-yl)ethoxy)ethoxy)ethoxy)ethyl)acetamide; 4-(2-(9-isopropyl-2-(pyridin-4-yl)-9H-purin-6-ylamino)ethyl)phenol; ethyl5-(6-(4-hydroxyphenethylamino)-9-isopropyl-9H-purin-2-yl)nicotinate; ethyl5-(6-(4-hydroxyphenethylamino)-9-isopropyl-9H-purin-2-yl)nicotinate; 4-(2-(2-(6-fluoropyridin-3-yl)-9-isopropyl-9H-purin-6-ylamino)ethyl)phenol; 4-(2-(9-isopropyl-2-(4-methylpyridin-3-yl)-9H-purin-6-ylamino)ethyl)phenol; 5-(6-(4-hydroxyphenethylamino)-9-isopropyl-9H-purin-2-yl)nicotinonitrile; 4-(2-(9-isopropyl-2-(pyrrolidin-1-yl)-9H-purin-6-ylamino)ethyl)phenol; 4-(2-(2-(1H-imidazol-1-yl)-9-isopropyl-9H-purin-6-ylamino)ethyl)phenol; 4-(2-(9-isopropyl-2-(pyridazin-4-yl)-9H-purin-6-ylamino)ethyl)phenol; 4-(2-(9-isopropyl-2-(pyrazin-2-yl)-9H-purin-6-ylamino)ethyl)phenol; 4-(2-(9-isopropyl-2-(pyridin-2-yl)-9H-purin-6-ylamino)ethyl)phenol; 4-(2-(9-isopropyl-2-(5-(methylsulfonyl)pyridin-3-yl)-9H-purin-6-ylamino)ethyl)phenol; 4-(2-(9-isopropyl-2-(5-methylpyridin-3-yl)-9H-purin-6-ylamino)ethyl)phenol; 4-(2-(2-(4-chloropyridin-3-yl)-9-isopropyl-9H-purin-6-ylamino)ethyl)phenol; 4-(2-(2-(5-fluoropyridin-3-yl)-9-isopropyl-9H-purin-6-ylamino)ethyl)phenol; 4-(2-(9-isopropyl-2-(1-methyl-1H-pyrazol-4-yl)-9H-purin-6-ylamino)ethyl)phenol; 4-(2-(9-isopropyl-2-(pyridin-3-yl)-9H-purin-6-ylamino)ethyl)-2-methoxyphenol; 4-(2-(9-isopropyl-2-(pyridin-3-yl)-9H-purin-6-ylamino)ethyl)-2-methoxyphenol; N-[2-(6-methoxy-1H-indol-3-yl)ethyl]-9-(propan-2-yl)-2-(pyridin-3-yl)-9H-purin-6-amine; N-[2-(5-methyl-1H-indol-3-yl)ethyl]-9-(propan-2-yl)-2-(pyridin-3-yl)-9H-purin-6-amine; 1-(2-{[9-(propan-2-yl)-2-(pyridin-3-yl)-9H-purin-6-yl]amino}ethyl)imidazolidin-2-one; N-(2-{[9-(propan-2-yl)-2-(pyridin-3-yl)-9H-purin-6-yl]amino}ethyl)pyridin-2-amine; 9-(propan-2-yl)-N-[3-(1H-pyrazol-4-yl)propyl]-2-(pyridin-3-yl)-9H-purin-6-amine; N-{2-[(3-methyl-1H-1,2,4-triazol-5-yl)sulfanyl]ethyl}-9-(propan-2-yl)-2-(pyridin-3-yl)-9H-purin-6-amine; 1-(2-{[2-(1-benzothiophen-3-yl)-9-(propan-2-yl)-9H-purin-6-yl]amino}ethyl)imidazolidin-2-one; N-[2-(5-amino-1H-1,2,4-triazol-3-yl)ethyl]-2-(1-benzothiophen-3-yl)-9-(propan-2-yl)-9H-purin-6-amine; N-(2-{[2-(1-benzothiophen-3-yl)-9-(propan-2-yl)-9H-purin-6-yl]amino}ethyl)pyridin-2-amine; 2-(1-benzothiophen-3-yl)-9-(propan-2-yl)-N-[3-(1H-pyrazol-4-yl)propyl]-9H-purin-6-amine; 2-(1-benzothiophen-3-yl)-N-[3-(3,5-dimethyl-1H-pyrazol-4-yl)propyl]-9-(propan-2-yl)-9H-purin-6-amine; (2-{[2-(1-benzothiophen-3-yl)-9-(propan-2-yl)-9H-purin-6-yl]amino}ethyl)urea; 5-({[2-(1-benzothiophen-3-yl)-9-(propan-2-yl)-9H-purin-6-yl]amino}methyl)-2,3-dihydro-1H-1,3-benzodiazol-2-one; N-[2-(1H-indol-3-yl)ethyl]-9-(propan-2-yl)-2-(pyridin-3-yl)-9H-purin-6-amine; N-(4-(2-(9-isopropyl-2-(pyridin-3-yl)-9H-purin-6-ylamino)ethyl)phenyl)methane-sulfonamide; 4-(2-(2-(pyridin-3-yl)-9-(tetrahydrofuran-3-yl)-9H-purin-6-ylamino)ethyl)phenol; 4-(2-(9-isopropyl-2-(pyridin-3-yl)-9H-purin-6-ylamino)propyl)phenol; 4-(2-(9-(oxetan-3-yl)-2-(pyridin-3-yl)-9H-purin-6-ylamino)ethyl)phenol; 5-(6-(4-hydroxyphenethylamino)-9-isopropyl-9H-purin-2-yl)-N-methylnicotinamide; 4-(2-(9-(1-hydroxypropan-2-yl)-2-(pyridin-3-yl)-9H-purin-6-ylamino)ethyl)phenol; 4-(2-(9-isopropyl-2-(pyridin-3-yl)-9H-purin-6-ylamino)ethyl)phenylsulfamate; 4-(2-(2-(2-fluoropyridin-3-yl)-9-isopropyl-9H-purin-6-ylamino)ethyl)phenol; 4-(2-(9-isopropyl-2-(1-methyl-1H-pyrrol-2-yl)-9H-purin-6-ylamino)ethyl)phenol; 4-(2-(9-isopropyl-2-(thiazol-5-yl)-9H-purin-6-ylamino)ethyl)phenol; 4-(2-(2-(1H-benzo[d]imidazol-1-yl)-9-isopropyl-9H-purin-6-ylamino)ethyl)phenol; 4-(2-(2-(2,4-dimethyl-1H-imidazol-1-yl)-9-isopropyl-9H-purin-6-ylamino)ethyl)phenol; 4-(2-(9-isopropyl-2-(2-methyl-1H-imidazol-1-yl)-9H-purin-6-ylamino)ethyl)phenol; 5-(9-sec-butyl-6-(4-hydroxy-3-methylphenethylamino)-9H-purin-2-yl)nicotinonitrile; N-(2-(1H-pyrrolo[2,3-b]pyridin-5-yl)ethyl)-9-isopropyl-2-(pyridin-3-yl)-9H-purin-6-amine; 9-isopropyl-N-(2-(5- methyl-1H-pyrazol-3-yl)ethyl)-2-(pyridin-3-yl)-9H-purin-6-amine; 4-(2-(2-(5-fluoropyridin-3-yl)-9-(oxetan-3-yl)-9H-purin-6-ylamino)ethyl)phenol; 4-(2-(2-(5-chloropyridin-3-yl)-9-isopropyl-9H-purin-6-ylamino)ethyl) phenol; 4-(2-(9-isopropyl-2-(5-(trifluoromethyl)pyridin-3-yl)-9H-purin-6-ylamino)ethyl)phenol; 5-(6-(2-(1H-indol-3-yl)ethylamino)-9-sec-butyl-9H-purin-2-yl)nicotinonitrile; N-(2-(1H-indol-3-yl)ethyl)-9-sec-butyl-2-(5-methylpyridin-3-yl)-9H-purin-6-amine; (R)—N-(2-(1H-indol-3-yl)ethyl)-9-sec-butyl-2-(5-fluoropyridin-3-yl)-9H-purin-6-amine; (S)—N-(2-(1H-indol-3-yl)ethyl)-9-sec-butyl-2-(5-fluoropyridin-3-yl)-9H-purin-6-amine; N-(2-(1H-indol-3-yl)ethyl)-9-sec-butyl-2-(5-fluoropyridin-3-yl)-9H-purin-6-amine; (R)—N-(2-(1H-indol-3-yl)ethyl)-9-sec-butyl-2-(5-methylpyridin-3-yl)-9H-purin-6-amine; (S)—N-(2-(1H-indol-3-yl)ethyl)-9-secbutyl-2-(5-methylpyridin-3-yl)-9H-purin-6-amine; 5-(6-(4-hydroxyphenethylamino)-9-(oxetan-3-yl)-9H-purin-2-yl)nicotinonitrile; 4-(2-(6-(5-fluoropyridin-3-yl)-1-isopropyl-1H-pyrazolo[3,4-d]pyrimidin-4-ylamino)ethyl)phenol; 4-(2-(6-(benzo[b]thiophen-3-yl)-1-isopropyl-1H-pyrazolo[3,4-d]pyrimidin-4-ylamino)ethyl)phenol; (R)-4-(2-(2-(5-fluoropyridin-3-yl)-9-(tetrahydrofuran-3-yl)-9H-purin-6-ylamino)ethyl)phenol; 4-(2-(9-isopropyl-2-(pyridin-3-yl)-9H-purin-6-ylamino) ethyl)-3-methylphenol; 5-(6-(4-hydroxyphenethylamino)-9-isopropyl-9H-purin-2-yl)picolinonitrile; 3-(6-(4-hydroxyphenethylamino)-9-isopropyl-9H-purin-2-yl) isonicotinonitrile; 4-(2-(2-(5-fluoropyridin-3-yl)-7-isopropyl-7H-pyrrolo[2,3-d]pyrimidin-4-ylamino)ethyl) phenol; 3-(6-(4-hydroxyphenethylamino)-9-isopropyl-9H-purin-2-yl)picolinonitrile; 4-(2-(9-isopropyl-2-(6-methylpyridin-3-yl)-9H-purin-6-ylamino)ethyl)phenol; 4-(2-(9-isopropyl-2-(isoquinolin-4-yl)-9H-purin-6-ylamino) ethyl)phenol; 2-chloro-4-(2-(9-isopropyl-2-(pyridin-3-yl)-9H-purin-6-ylamino)ethyl)phenol; 3-fluoro-4-(2-(9-isopropyl-2-(pyridin-3-yl)-9H-purin-6-ylamino)ethyl)phenol; N-(2-(5-chloro-1H-indol-3-yl)ethyl)-9-isopropyl-2-(pyridin-3-yl)-9H-purin-6-amine; N-(2-(5-fluoro-1H-indol-3-yl) ethyl)-9-isopropyl-2-(pyridin-3-yl)-9H-purin-6-amine; 4-(2-(9-isopropyl-2-(pyridin-3-yl)-9H-purin-6-ylamino) ethyl)-2-methylphenol; 4-(2-(2-(benzo[b]thiophen-3-yl)-9-(oxetan-3-yl)-9H-purin-6-ylamino)ethyl)phenol; (S)-4-(2-(2-(benzo[b]thiophen-3-yl)-9-(tetrahydrofuran-3-yl)-9H-purin-6-ylamino)ethyl)phenol; (R)-4-(2-(2-(benzo[b]thiophen-3-yl)-9-(tetrahydrofuran-3-yl)-9H-purin-6-ylamino)ethyl)phenol; 2-(6-(2-(1H-indol-3-yl)ethylamino)-2-(5-fluoropyridin-3-yl)-9H-purin-9-yl)propan-1-ol; (R)-2-(6-(2-(1H-indol-3-yl)ethylamino)-2-(5-fluoropyridin-3-yl)-9H-purin-9-yl)pro-pan-1-ol; (S)-2-(6-(2-(1H-indol-3-yl)ethylamino)-2-(5-fluoropyridin-3-yl)-9H-purin-9-yl) propan-1-ol; (R)—N-(2-(1H-indol-3-yl)ethyl)-2-(5-fluoropyridin-3-yl)-9-(tetrahydrofuran-3-yl)-9H-purin-6-amine; 4-(2-(2-(3H-imidazo[4,5-b]pyridin-3-yl)-9-isopropyl-9H-purin-6-ylamino)ethyl)phenol; 4-(2-(2-(1H-imidazo[4,5-b]pyridine-1-yl)-9-isopropyl-9H-purin-6-ylamino)ethyl)phenol; 4-(2-(6-(5-fluoropyridin-3-yl)-1-isopropyl-1H-imidazo[4,5-c]pyridin-4-ylamino)ethyl) phenol; 4-(2-(2-(4,5-dimethyl-1H-imidazol-1-yl)-9-isopropyl-9H-purin-6-ylamino)ethyl)phenol; 2-(5-fluoropyridin-3-yl)-9-isopropyl-N-(2-(pyridin-3-yl)ethyl)-9H-purin-6-amine; 4-(2-(2-(5-fluoropyridin-3-yl)-9-isopropyl-9H-purin-6-ylamino)-1-hydroxyethyl)phenol; 2-(5-fluoropyridin-3-yl)-9-isopropyl-N-(2-(6-methoxy-1H-indol-3-yl)ethyl)-9H-purin-6-amine; N-(2-(1H-indol-3-yl) ethyl)-2-(5-fluoropyridin-3-yl)-9-isopropyl-9H-purin-6-amine; 2-(5-fluoropyridin-3-yl)-9-isopropyl-N-(2-(5-methoxy-1H-indol-3-yl)ethyl)-9H-purin-6-amine; N-(2-(1H-indol-3-yl)ethyl)-2-(5-fluoropyridin-3-yl)-9-(prop-1-en-2-yl)-9H-purin-6-amine; 5-(2-(2-(5-fluoropyri-din-3-yl)-9-isopropyl-9H-purin-6-ylamino)ethyl)pyridin-2-ol; N-(2-(1H-pyrrolo[2,3-b]pyridin-3-yl)ethyl)-2-(5-fluoropyridin-3-yl)-9-isopropyl-9H-purin-6-amine; N-(2-(6-(2-(diethylamino)ethoxy)-1H-indol-3-yl)ethyl)-2-(5-fluoropyridin-3-yl)-9-isopropyl-9H-purin-6-amine; 4-(2-(5-t5-fluoropyridin-3-yl)-3-isopropyl-3H-imidazo[4,5-b]pyridin-7-ylamino)ethyl)phenol; N-(2-(1H-indol-3-yl) ethyl)-9-sec-butyl-2-(2-methyl-1H-imidazol-1-yl)-9H-purin-6-amine; 4-(2-(2-(2-ethyl-1H-imidazol-1-yl)-9-isopropyl-9H-purin-6-ylamino)ethyl)phenol; 4-(2-(9-isopropyl-2-(2-propyl-1H-imidazol-1-yl)-9H-purin-6-ylamino)ethyl)phenol; 3-(2-(2-(5-fluoropyridin-3-yl)-9-isopropyl-9H-purin-6-ylamino)ethyl)-1H-indol-6-ol; N-(2-(1H-indol-3-yl)ethyl)-9-isopropyl-2-(5-methylpyridin-3-yl)-9H-purin-6-amine; N-(2-(1H-indol-3-yl)ethyl)-9-isopropyl-2-(2-methyl-1H-imidazol-1-yl)-9H-purin-6-amine; 2-(5-fluoropyridin-3-yl)-9-isopropyl-N-(2-(7-methyl-1H-indol-3-yl)ethyl)-9H-purin-6-amine N-(2-(1H-indol-3-yl)ethyl)-2-(5-fluoropyridin-3-yl)-9-(oxetan-3-yl)-9H-purin-6-amine; N-(2-(1H-indol-3-yl)ethyl)-2-(5-methylpyridin-3-yl)-9-(oxetan-3-yl)-9H-purin-6-amine; N-(2-(6-fluoro-1H-indol-3-yl)ethyl)-2-(5-fluoropyridin-3-yl)-9-isopropyl-9H-purin-6-amine; 2-(5-fluoropyridin-3-yl)-9-isopropyl-N-(2-(6-methyl-1H-indol-3-yl)ethyl)-9H-purin-6-amine; 2-(5-fluoropyridin-3-yl)-9-isopropyl-N-(2-(2-methyl-1H-indol-3-yl)ethyl)-9H-purin-6-amine; N-(2-(4-fluoro-1H-indol-3-yl)ethyl)-2-(5-fluoropyridin-3-yl)-9-isopropyl-9H-purin-6-amine; N-(2-(7-fluoro-1H-indol-3-yl)ethyl)-2-(5-fluoropyridin-3-yl)-9-isopropyl-9H-purin-6-amine; 2-(5-fluoropyridin-3-yl)-9-isopropyl-N-(2-(4-methyl-1H-indol-3-yl)ethyl)-9H-purin-6-amine; 4-(2-(2-(benzo[b]thiophen-3-yl)-7-isopropyl-7H-pyrrolo[2,3-d] pyrimidin-4-ylamino)ethyl)phenol; 9-isopropyl-2-(pyridin-3-yl)-N-(2-(pyridin-4-yl)ethyl)-9H-purin-6-amine; N-(2-(1H-pyrrolo[2,3-b]pyridin-5-yl)ethyl)-9-isopropyl-2-(pyridin-3-yl)-9H-purin-6-amine; 4-(2-(2-(5-fluoropyridin-3-yl)-9-(1-hydroxypropan-2-yl)-9H-purin-6-ylamino) ethyl)-2-methylphenol; 4-(2-(2-(benzo[b]thiophen-3-yl)-9-cyclohexyl-9H-purin-6-ylamino)ethyl)phenol; 4-(2-(9-isopropyl-2-(thiophen-3-yl)-9H-purin-6-ylamino)ethyl) phenol; and 1-(2-(2-(benzo[b]thiophen-3-yl)-6-(4-hydroxyphenethylamino)-9H-purin-9-yl)ethyl)pyrrolidin-2-one.

In another embodiment, an aryl hydrocarbon receptor antagonist is a compound of Formula Ia:

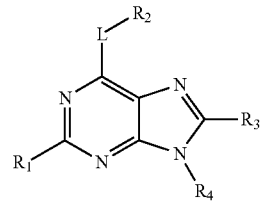

in which:

L is selected from —NR$_{5a}$(CH$_2$)$_{0-3}$—, —NR$_{5a}$CH(C(O)OCH$_3$)CH$_2$—, —NR$_{5a}$(CH$_2$)$_2$NR$_{5b}$—, —NR$_{5a}$(CH$_2$)$_2$S—, —NR$_{5a}$CH$_2$CH(CH$_3$)(CH$_2$—, —NR$_{5a}$ CH(CH$_3$) CH$_2$—, —(CH$_2$)$_3$—, —CH$_2$OCH$_2$—, —CH$_2$NR$_{5a}$CH$_2$—, —NR$_{5a}$C(O)CH$_2$— and —NR$_{5a}$Y—; wherein R$_{5a}$ and R$_{5b}$ are independently selected from hydrogen and C$_{1-4}$alkyl; and Y is a 5 member heteroaryl ring containing up to 3 heteroatoms selected from O, N and S;

R₁ is selected from hydrogen, phenyl, thiophen-2-yl, thiophen-3-yl, furan-2-yl, furan-3-yl, benzo[b]thiophen-2-yl, benzo[b]thiophen-3-yl, benzofuran-2-yl, benzofuran-3-yl, pyrimidin-4-yl, pyrimidin-5-yl, 1H-pyrazol-4-yl, 1H-pyrazol-3-yl, pyridin-2-yl, pyridazin-3-yl, pyridin-4-yl, 1H-imidazol-1-yl, pyrrolidin-1-yl, pyrazin-2-yl, pyridin-3-yl, 1H-pyrazol-1-yl, pyridazin-4-yl, 1H-indol-2-yl, thiazol-4-yl, 1H-indol-3-yl, 1H-pyrrol-2-yl and thiazol-5-yl; wherein said phenyl, thiophen-2-yl, thiophen-3-yl, furan-2-yl, furan-3-yl, benzo[b]thiophen-2-yl, benzo[b]thiophen-3-yl, benzofuran-2-yl, benzofuran-3-yl, pyrimidin-4-yl, pyrimidin-5-yl, 1H-pyrazol-4-yl, 1H-pyrazol-3-yl, pyridin-2-yl, pyridazin-3-yl, pyridin-4-yl, 1H-imidazol-1-yl, pyrrolidin-1-yl, pyrazin-2-yl, pyridin-3-yl, 1H-pyrazol-1-yl, pyridazin-4-yl, 1H-indol-2-yl, thiazol-4-yl, 1H-indol-3-yl, 1H-pyrrol-2-yl or thiazol-5-yl of R₁ can be optionally substituted by 1 to 3 radicals independently selected from cyano, hydroxy, $C_{1-4}$alkyl, $C_{1-4}$alkoxy, halo, halo-substituted-$C_{1-4}$alkyl, halo-substituted-$C_{1-4}$alkoxy, hydroxy, amino, —C(O)R$_{8a}$, —S(O)$_{0-2}$R$_{8a}$, —C(O)OR$_{8a}$ and —C(O)NR$_{8a}$R$_{8b}$; wherein R$_{8a}$ and R$_{8b}$ are independently selected from hydrogen and $C_{1-4}$alkyl; with the proviso that R₁ and R₃ are not both hydrogen;

R₂ is selected from —S(O)₂NR$_{6a}$R$_{6b}$, —NR$_{9a}$C(O)R$_{9b}$, —NR$_{6a}$C(O)NR$_{6b}$R$_{6c}$, phenyl, 1H-indol-2-yl, 1H-indol-3-yl, benzo[b]thiophen-2-yl, benzo[b]thiophen-3-yl, benzofuran-2-yl, benzofuran-3-yl, thiophen-2-yl, thiophen-3-yl, furan-2-yl, furan-3-yl, piperidin-4-yl, piperidin-3-yl, piperidin-2-yl, piperidin-1-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, 3-oxopiperazin-1-yl, 2-oxo-2,3-dihydro-1H-benzo[d]imidazol-5-yl, 1,2,3,4-tetrahydronaphthalen-2-yl, indolin-5-yl, 2-oxoindolin-5-yl, 1H-benzo[d]imidazol-5-yl, 1H-indazol-5-yl and 1H-imidazol-4-yl; wherein R$_{6a}$, R$_{6b}$ and R$_{6c}$ are independently selected from hydrogen and $C_{1-4}$alkyl; wherein said phenyl, 1H-indol-2-yl, 1H-indol-3-yl, benzo[b]thiophen-2-yl, benzo[b]thiophen-3-yl, benzofuran-2-yl, benzofuran-3-yl, thiophen-2-yl, thiophen-3-yl or furan-2-yl, furan-3-yl, piperidin-4-yl, piperidin-3-yl, piperidin-2-yl, piperidin-1-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 3-oxopiperazin-1-yl, 2-oxo-2,3-dihydro-1H-benzo[d]imidazol-5-yl, 1,2,3,4-tetrahydronaphthalen-2-yl, indolin-5-yl, 2-oxoindolin-5-yl, 1H-benzo[d]imidazol-5-yl, 1H-indazol-5-yl or 1H-imidazol-4-yl of R₂ is optionally substituted with 1 to 3 radicals independently selected from hydroxy, halo, methyl, methoxy, amino, —S(O)₂NR$_{7a}$R$_{7b}$, —OS(O)₂NR$_{7a}$R$_{7b}$ and —NR$_{7a}$S(O)₂R$_{7b}$; wherein R$_{7a}$ and R$_{7b}$ are independently selected from hydrogen and $C_{1-4}$alkyl; or a single radical selected from 5-((3aS,4S,6aR)-2-oxohexahydro-1H-thieno[3,4-d]imidazol-4-yl)pentanoyloxy, 2-(2-(5-((3aS,4S,6aR-2-oxohexahydro-1H-thieno[3,4-d]imidazol-4-yl)penta-namido)ethoxy)ethoxy and 2-(4-(4-hex-5-ynamidobenzoyl)phenylamino)-2-oxoethoxy;

R₃ is selected from hydrogen, $C_{1-4}$alkyl and biphenyl; and

R₄ is selected from isopropyl, isobutyl, sec-butyl, 1-hydroxypropan-2-yl, cyclopropyl, oxetan-3-yl, oxetan-2-yl, benzhydryl, piperidin-4-yl, piperidin-3-yl, piperidin-2-yl, tetrahydro-2H-pyran-2-yl, tetrahydro-2H-pyran-3-yl, tetrahydro-2H-pyran-4-yl, phenyl, tetrahydrofuran-3-yl, tetrahydrofuran-2-yl, benzyl, (4-pentylphenyl)(phenyl)methyl and 1-(1-(2-oxo-6,9,12-trioxa-3-azatetradecan-14-yl)-1H-1,2,3-triazol-4-yl)ethyl; wherein said cyclopropyl, oxetan-3-yl, oxetan-2-yl, benzhydryl, piperidin-4-yl, piperidin-3-yl, piperidin-2-yl, tetrahydro-2H-pyran-2-yl, tetrahydro-2H-pyran-3-yl, tetrahydro-2H-pyran-4-yl, phenyl, tetrahydrofuran-3-yl, tetrahydrofuran-2-yl, benzyl, (4-pentylphenyl)(phenyl)methyl or 1-(1-(2-oxo-6,9,12-trioxa-3-azatetradecan-14-yl)-1H-1,2,3-triazol-4-yl)ethyl can be optionally substituted with 1 to 3 radicals independently selected from $C_{1-4}$alkyl and halo-substituted-$C_{1-4}$alkyl;

or an N-oxide derivative, prodrug derivative, protected derivative, individual isomer or mixture of isomers thereof; or a pharmaceutically acceptable salt or solvate (e.g. hydrate) of such compound.

In another embodiment, with reference to compounds of Formula Ia, L is selected from —NR$_{5a}$(CH₂)$_{0-3}$—, —NR$_{5a}$CH(C(O)OCH₃)CH₂—, —NR$_{5a}$(CH₂)₂NR$_{5b}$, —NR$_{5a}$(CH₂)₂S—, —NR$_{5a}$CH₂CH(CH₃)CH₂—, —NR$_{5a}$CH(CH₃)CH₂—, —(CH₂)₃—, —CH₂OCH₂—, —CH₂NR$_{5a}$CH₂—, —NR$_{5a}$C(O)CH₂— and —NR$_{5a}$Y—; wherein R$_{5a}$ and R$_{5b}$ are independently selected from hydrogen and methyl; Y is selected from isoxazole and 1,3,4-oxadiazole.

In another embodiment, when L is —NR$_{5a}$(CH₂)$_{0-3}$, it is preferably —NR$_{5a}$(CH₂)$_{1-3}$ (where 1-3 herein means 1, 2 or 3).

In another embodiment, R₁ is selected from hydrogen, phenyl, thiophen-3-yl, thiophen-2-yl, furan-3-yl, furan-2-yl, benzo[b]thiophen-3-yl, pyrimidin-5-yl, pyridin-4-yl, pyridin-2-yl, pyrrolidin-1-yl, 1H-pyrazol-4-yl, pyrazin-2-yl, pyridazin-3-yl, pyridazin-4-yl, 1H-pyrazol-1-yl, 1H-pyrazol-3-yl, 1H-imidazol-1-yl, thiazol-4-yl, 1H-pyrrol-2-yl, thiazol-5-yl, and pyridin-3-yl; wherein said phenyl, thiophen-3-yl, thiophen-2-yl, furan-3-yl, furan-2-yl, benzo[b]thiophen-3-yl, pyrimidin-5-yl, pyridin-4-yl, pyridin-2-yl, pyrrolidin-1-yl, 1H-pyrazol-4-yl, pyrazin-2-yl, pyridazin-3-yl, pyridazin-4-yl, 1H-pyrazol-1-yl, 1H-pyrazol-3-yl, 1H-imidazol-1-yl, thiazol-4-yl, 1H-pyrrol-2-yl, thiazol-5-yl or pyridin-3-yl of R₁ is optionally substituted with 1 to 3 radicals independently selected from cyano, methyl, methylsulfonyl, methoxy, halo, hydroxy, carboxyl, ethoxy-carbonyl, methyl-amino-carbonyl and amino; with the proviso that R₁ and R₃ are not both hydrogen.

In another embodiment, R₂ is selected from amino-sulfonyl, methyl-carbonyl-amino, methyl-sulfonyl-amino, amino-sulfonyl-oxy, urea, phenyl, 1H-indol-2-yl, 1H-indol-3-yl, benzo[b]thiophen-2-yl, benzo[b]thiophen-3-yl, benzofuran-2-yl, benzofuran-3-yl, thiophen-2-yl, thiophen-3-yl, furan-2-yl, furan-3-yl, piperidin-4-yl, piperidin-3-yl, piperidin-2-yl, piperidin-1-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, 3-oxopiperazin-1-yl, 2-oxo-2,3-dihydro-1H-benzo[d]imidazol-5-yl, 1,2,3,4-tetrahydronaphthalen-2-yl, indolin-5-yl, 2-oxoindolin-5-yl, 1H-benzo[d]imidazol-5-yl, 1H-indazol-5-yl and 1H-imidazol-4-yl; wherein said phenyl, 1H-indol-2-yl, 1H-indol-3-yl, benzo[b]thiophen-2-yl, benzo[b]thiophen-3-yl, benzofuran-2-yl, benzofuran-3-yl, thiophen-2-yl, thiophen-3-yl, furan-2-yl, furan-3-yl, piperidin-4-yl, piperidin-3-yl, piperidin-2-yl, piperidin-1-yl, pyridin-2-yl, pyridin-3-yl, pyridin-4-yl, 1H-1,2,4-triazol-3-yl, 1H-1,2,4-triazol-5-yl, 2-oxoimidazolidin-1-yl, 1H-pyrazol-3-yl, 1H-pyrazol-4-yl, 3-oxopiperazin-1-yl, 2-oxo-2,3-dihydro-1H-benzo[d]imidazol-5-yl, 1,2,3,4-tetrahydronaphthalen-2-yl, indolin-5-yl, 2-oxoindolin-5-yl, 1H-benzo[d]imidazol-5-yl, 1H-indazol-5-yl and 1H-imidazol-4-yl of R₂ is optionally substituted with hydroxy, methoxy, methyl, halo, amino, amino-sulfonyl, 5-((3aS,4S,6aR)-2-oxohexahydro-1H-thieno[3,4-d]imidazol-4-yl)pentanoyloxy, 2-(2-(5-((3aS,4S,6aR)-2-oxohexahydro-1H-thieno[3,4-d]imidazol-4-yl)pentanamido)ethoxy)ethoxy and 2-(4-(4-hex-5-ynamidobenzoyl)phenylamino)-2-oxoethoxy.

In another embodiment, $R_3$ is selected from hydrogen, methyl, and biphenyl; and $R_4$ is selected from isopropyl, isobutyl, sec-butyl, 1-hydroxypropan-2-yl, cyclopropyl, oxetan-3-yl, oxetan-2-yl, benzhydryl, piperidin-4-yl, piperidin-3-yl, piperidin-2-yl, tetrahydro-2H-pyran-2-yl, tetrahydro-2H-pyran-3-yl, tetrahydro-2H-pyran-4-yl, phenyl, tetrahydrofuran-3-yl, tetrahydrofuran-2-yl, benzyl, (4-pentylphenyl)(phenyl)methyl and 1-(1-(2-oxo-6,9,12-trioxa-3-azatetradecan-14-yl)-1H-1,2,3-triazol-4-yl)ethyl; wherein said cyclopropyl, oxetan-3-yl, oxetan-2-yl, benzhydryl, piperidin-4-yl, piperidin-3-yl, piperidin-2-yl, tetrahydro-2H-pyran-2-yl, tetrahydro-2H-pyran-3-yl, tetrahydro-2H-pyran-4-yl, phenyl, tetrahydrofuran-3-yl, tetrahydrofuran-2-yl, benzyl, (4-pentylphenyl)(phenyl)methyl or 1-(1-(2-oxo-6,9,12-trioxa-3-azatetradecan-14-yl)-1H-1,2,3-triazol-4-yl) ethyl can be optionally substituted with 1 to 3 radicals independently selected from methyl and trifluoromethyl.

In another embodiment are compounds selected from: 4-(2-(2-(benzo[b]thiophen-3-yl)-9-isopropyl-9H-purin-6-ylamino)ethyl)phen; 4-(2-(2-(benzo[b]thiophen-3-yl)-9-sec-butyl-9H-purin-6-ylamino)ethyl)phenol; 4-(2-(9-benzhydryl-2-(benzo[b]thiophen-3-yl)-9H-purin-6-ylamino)eth-yl) phenol; 4-(2-(2-(benzo[b]thiophen-3-yl)-9-(tetrahydro-2H-pyran-3-yl)-9H-purin-6-ylamino)ethyl)phenol; 4-(2-(2-(benzo[b]thiophen-3-yl)-9-(4-(trifluoromethyl)benzyl)-9H-purin-6-ylamino)ethyl)phenol; 4-(2-(2-(benzo[b]thiophen-3-yl)-9-isobutyl-9H-purin-6-ylamino)ethyl)phenol; 4-(2-(2-(benzo[b]thiophen-3-yl)-9-methyl-9H-purin-6-ylamino) ethyl)phenol; 4-(2-(2-(benzo[b]thiophen-3-yl)-9-(4-methylbenzyl)-9H-purin-6-ylamino)ethyl)phenol; N-(2-(1H-indol-3-yl)ethyl)-2-(benzo[b]thiophen-3-yl)-9-isopropyl-9H-purin-6-amine; 2-(benzo[b]thiophen-3-yl)-9-isopropyl-N-(2-(thiophen-3-yl)ethyl)-9H-purin-6-amine; 3-(2-(2-(benzo[b]thiophen-3-yl)-9-isopropyl-9H-purin-6-ylamino)ethyl)phenol; 2-(benzo[b]thiophen-3-yl)-N-(4-fluorophenethyl)-9-isopropyl-9H-purin-6-amine; N-(4-aminophenethyl)-2-(benzo[b]thiophen-3-yl)-9-isopropyl-9H-purin-6-amine; 4-(2-(9-isopropyl-2-(pyrimidin-5-yl)-9H-purin-6-ylamino)ethyl)phenol; 4-(2-(9-isopropyl-2-(pyridin-3-yl)-9H-purin-6-ylamino)ethyl)phenol; 4-(2-(9-isopropyl-2-phenyl-9H-purin-6-ylamino)ethyl)phenol; 4-(2-(9-isopropyl-2-(thiophen-3-yl)-9H-purin-6-ylamino)ethyl) phenol; 4-(2-(2-(furan-3-yl)-9-isopropyl-9H-purin-6-ylamino)ethyl)phenol; 2-(benzo[b]thiophen-3-yl)-N-(4-fluorophenethyl)-9-phenyl-9H-purin-6-amine; N-benzyl-8-(biphenyl-4-yl)-9-isopropyl-9H-purin-6-amine; 4-(2-(2-(benzo[b]thiophen-3-yl)-9-(nonan-2-yl)-9H-purin-6-ylamino)ethyl)phenol; 4-(2-(2-(benzo[b]thiophen-3-yl)-9-((4-pentylphenyl)(phenyl)methyl)-9H-purin-6-ylamino) ethyl)phenol; N-(2-(1H-indol-3-yl)ethyl)-2-(benzo[b] thiophen-3-yl)-9-sec-butyl-9H-purin-6-amine; 4-(2-(2-(benzo[b]thiophen-3-yl)-9-sec-butyl-9H-purin-6-ylamino) ethyl)phenol; 3-(2-(2-(benzo[b]thiophen-3-yl)-9-isopropyl-9H-purin-6-ylamino)ethyl)-1H-indol-5-ol; 3-(2-(2-(benzo [b]thiophen-3-yl)-9-isopropyl-9H-purin-6-ylamino)ethyl)-1H-indol-5-yl, 5-((3aS,4S,6aR)-2-oxohexahydro-1H-thieno [3,4-d]imidazol-4-yl)pentanoate; N-(2-(2-(3-(2-(2-(benzo [b]thiophen-3-yl)-9-isopropyl-9H-purin-6-ylamino)ethyl)-1H-indol-5-yloxy)ethoxy)ethyl)-5-((3aS,4S,6aR)-2-oxohexahydro-1H-thieno[3,4-d]imidazol-4-yl) pentanamide; N-(4-(4-(2-(3-(2-(2-(benzo[b]thiophen-3-yl)-9-isopropyl-9H-purin-6-ylamino)ethyl)-1H-indol-5-yloxy) acetamido)benzoyl)phenyl)hex-5-ynamide; N-(2-(2-(2-(2-(4-(1-(2-(benzo[b]thiophen-3-yl)-6-(4-hydroxyphenethylamino-)-9H-purin-9-yl)ethyl)-1H-1,2,3-triazol-1-yl)ethoxy)ethoxy)ethoxy)ethyl)acetamide; 4-(2-(9-isopropyl-2-(pyridin-4-yl)-9H-purin-6-ylamino)ethyl) phenol; ethyl 5-(6-(4-hydroxyphenethylamino)-9-isopropyl-9H-purin-2-yl)nicotinate; ethyl 5-(6-(4-hydroxyphenethylamino)-9-isopropyl-9H-purin-2-yl) nicotinate; 4-(2-(2-(6-fluoropyridin-3-yl)-9-isopropyl-9H-purin-6-ylamino)ethyl)phenol; 4-(2-(9-isopropyl-2-(4-methylpyridin-3-yl)-9H-purin-6-ylamino)ethyl)phenol; 4-(2-(9-isopropyl-2-(2-methoxypyridin-3-yl)-9H-purin-6-ylamino)ethyl)phenol; 5-(6-(4-hydroxyphenethylamino)-9-isopropyl-9H-purin-2-yl)nicotinonitrile; 4-(2-(9-isopropyl-2-(pyrrolidin-1-yl)-9H-purin-6-ylamino)ethyl)phenol; 4-(2-(9-isopropyl-2-(1H-pyrazol-1-yl)-9H-purin-6-ylamino) ethyl)phenol; 4-(2-(2-(1H-imidazol-1-yl)-9-isopropyl-9H-purin-6-ylamino)ethyl)phenol; 4-(2-(9-isopropyl-2-(pyridazin-3-yl)-9H-purin-6-ylamino)ethyl)phenol; 4-(2-(9-isopropyl-2-(pyridazin-4-yl)-9H-purin-6-ylamino)ethyl) phenol; 4-(2-(9-isopropyl-2-(pyrazin-2-yl)-9H-purin-6-ylamino)ethyl)phenol; 4-(2-(9-isopropyl-2-(pyridin-2-yl)-9H-purin-6-ylamino)ethyl)phenol; 4-(2-(9-isopropyl-2-(5-(methylsulfonyl)pyridin-3-yl)-9H-purin-6-ylamino)ethyl) phenol; 4-(2-(9-isopropyl-2-(5-methylpyridin-3-yl)-9H-purin-6-ylamino)ethyl)phenol; 4-(2-(2-(2-chloropyridin-3-yl)-6-isopropyl-2,6-dihydroimidazo[4,5-c]pyrazol-3-ylamino)ethyl)phenol; 4-(2-(2-(4-chloropyridin-3-yl)-9-isopropyl-9H-purin-6-ylamino)ethyl)phenol; 4-(2-(9-isopropyl-2-(4-methoxypyridin-3-yl)-9H-purin-6-ylamino) ethyl)phenol; 4-(2-(2-(5-fluoropyridin-3-yl)-9-isopropyl-9H-purin-6-ylamino)ethyl)phenol; 4-(2-(9-isopropyl-2-(thiazol-4-yl)-9H-purin-6-ylamino)ethyl)phenol; 4-(2-(9-isopropyl-2-(1-methyl-1H-pyrazol-4-yl)-9H-purin-6-ylamino)ethyl)phenol; 4-(2-(9-isopropyl-2-(1H-pyrazol-3-yl)-9H-purin-6-ylamino)ethyl)phe-nol; 4-(2-(9-isopropyl-2-(1H-pyrazol-4-yl)-9H-purin-6-ylamino)ethyl)phenol; 4-(2-(9-isopropyl-2-(thiophen-2-yl)-9H-purin-6-ylamino)ethyl) phenol; 4-(6-(4-hydroxyphenethylamino)-9-isopropyl-9H-purin-2-yl)thiophene-2-carboxylic acid; 4-(2-(2-(furan-2-yl)-9-isopropyl-9H-purin-6-ylamino)ethyl)phenol; 4-(2-(9-isopropyl-2-(4-methylthiophen-3-yl)-9H-purin-6-ylamino) ethyl)phenol; 4-(2-(9-isopropyl-2-(pyridin-3-yl)-9H-purin-6-ylamino)ethyl)-2-methoxyphenol; 4-(2-(9-isopropyl-2-(pyridin-3-yl)-9H-purin-6-ylamino)ethyl)-2-methoxyphenol; N-[2-(6-methoxy-1H-indol-3-yl)ethyl]-9-(propan-2-yl)-2-(pyridin-3-yl)-9H-purin-6-amine; N-[2-(5-methyl-1H-indol-3-yl)ethyl]-9-(propan-2-yl)-2-(pyridin-3-yl)-9H-purin-6-amine; N-[2-(piperidin-4-yl)ethyl]-9-(propan-2-yl)-2-(pyridin-3-yl)-9H-purin-6-amine; 1-(2-{[9-(propan-2-yl)-2-(pyridin-3-yl)-9H-purin-6-yl]amino}ethyl) piperidin-4-ol; methyl (2S)-3-(4-hydroxyphenyl)-2-{[9-(propan-2-yl)-2-(pyridin-3-yl)-9H-purin-6-yl] amino}propanoate; 4-(2-{[9-(propan-2-yl)-2-(pyridin-3-yl)-9H-purin-6-yl]amino}ethyl)benzene-1-sulfonamide; 2-{[2-(1-benzothiophen-3-yl)-9-(propan-2-yl)-9H-purin-6-yl] amino}ethane-1-sulfonamide; 4-(2-{[9-(propan-2-yl)-2-(pyridin-3-yl)-9H-purin-6-yl]amino}ethyl)benzene-1,2-diol; N-[2-(1H-imidazol-4-yl)ethyl]-9-(propan-2-yl)-2-(pyridin-3-yl)-9H-purin-6-amine; 1-(2-{[9-(propan-2-yl)-2-(pyridin-3-yl)-9H-purin-6-yl]amino}ethyl)imidazolidin-2-one; N-[2-(5-amino-1H-1,2,4-triazol-3-yl)ethyl]-9-(propan-2-yl)-2-(pyridin-3-yl)-9H-purin-6-amine; N-(2-{[9-(propan-2-yl)-2-(pyridin-3-yl)-9H-purin-6-yl]amino}ethyl)pyridin-2-amine; 9-(propan-2-yl)-N-[3-(1H-pyrazol-4-yl)propyl]-2-(pyridin-3-yl)-9H-purin-6-amine; N-[2-({[9-(propan-2-yl)-2-(pyridin-3-yl)-9H-purin-6-yl]amino}methyl)propyl] acetamide; 4-(2-{[9-(propan-2-yl)-2-(pyridin-3-yl)-9H-purin-6-yl]amino}ethyl)piperazin-2-one; N-{2-[(3-methyl-1H-1,2,4-triazol-5-yl)sulfanyl]ethyl}-9-(propan-2-yl)-2-

(pyridin-3-yl)-9H-purin-6-amine; N-[3-(3,5-dimethyl-1H-pyrazol-4-yl)propyl]-9-(propan-2-yl)-2-(pyridin-3-yl)-9H-purin-6-amine; (2-{[9-(propan-2-yl)-2-(pyridin-3-yl)-9H-purin-6-yl]amino}ethyl)urea; 5-({[9-(propan-2-yl)-2-(pyridin-3-yl)-9H-purin-6-yl]amino}methyl)-2,3-dihydro-1H-1,3-benzodiazol-2-one; 2-(1-benzothiophen-3-yl)-N-[2-(1H-imidazol-4-yl)ethyl]-9-(propan-2-yl)-9H-purin-6-amine; 1-(2-{[2-(1-benzothiophen-3-yl)-9-(propan-2-yl)-9H-purin-6-yl]amino}ethyl)imidazolidin-2-one; N-[2-(5-amino-1H-1,2,4-triazol-3-yl)ethyl]-2-(1-benzothiophen-3-yl)-9-(propan-2-yl)-9H-purin-6-amine; N-(2-{[2-(1-benzothiophen-3-yl)-9-(propan-2-yl)-9H-purin-6-yl]amino}ethyl)pyridin-2-amine; 2-(1-benzothiophen-3-yl)-9-(propan-2-yl)-N-[3-(1H-pyrazol-4-yl)propyl]-9H-purin-6-amine; N-[2-({[2-(1-benzothiophen-3-yl)-9-(propan-2-yl)-9H-purin-6-yl]amino}methyl)propyl]acetamide; 4-(2-{[2-(1-benzothiophen-3-yl)-9-(propan-2-yl)-9H-purin-6-yl]amino}ethyl)piperazin-2-one; 2-(1-benzothiophen-3-yl)-N-{2-[(3-methyl-1H-1,2,4-triazol-5-yl)sulfanyl]e-thyl}-9-(propan-2-yl)-9H-purin-6-amine; 2-(1-benzothiophen-3-yl)-N-[3-(3,5-dimethyl-1H-pyrazol-4-yl)propyl]-9-(propan-2-yl)-9H-purin-6-amine; (2-{[2-(1-benzothiophen-3-yl)-9-(propan-2-yl)-9H-purin-6-yl]amino}ethyl)urea; 5-({[2-(1-benzothiophen-3-yl)-9-(propan-2-yl)-9H-purin-6-yl]amino}methyl)-2,3-dihydro-1H-1,3-benzodiazol-2-one; N-[2-(1H-indol-3-yl)ethyl]-9-(propan-2-yl)-2-(pyridin-3-yl)-9H-purin-6-amine; N-(4-(2-(9-isopropyl-2-(pyridin-3-yl)-9H-purin-6-ylamino)ethyl)phenyl)methanesulfonamide; 4-(2-(2-(pyridin-3-yl)-9-(tetrahydrofuran-3-yl)-9H-purin-6-ylamino)ethyl)phenol; 4-(2-(9-isopropyl-2-(pyridin-3-yl)-9H-purin-6-ylamino)propyl)phenol; 4-(2-(9-(oxetan-3-yl)-2-(pyridin-3-yl)-9H-purin-6-ylamino)ethyl)phenol; 5-(6-(4-hydroxyphenethylamino)-9-isopropyl-9H-purin-2-yl)-N-methylnicotinamide; 6-(9-isopropyl-2-(pyridin-3-yl)-9H-purin-6-ylamino)-5,6,7,8-tetrahydronaphthalen-2-ol; N-(2-(1H-indazol-3-yl)ethyl)-9-isopropyl-2-(pyridin-3-yl)-9H-purin-6-amine; 4-(2-((9-isopropyl-2-(pyridin-3-yl)-9H-purin-6-yl)(methyl)amino)ethyl)phenol; 4-(2-(9-isopropyl-8-methyl-2-(pyridin-3-yl)-9H-purin-6-ylamino)ethyl)phenol; 1-(2-(9-isopropyl-2-(pyridin-3-yl)-9H-purin-6-ylamino)ethyl)-1H-benzo[d]imidazol-2(3H)-one; 4-(3-(9-isopropyl-2-(pyridin-3-yl)-9H-purin-6-yl)propyl)phenol; 4-((((9-isopropyl-2-(pyridin-3-yl)-9H-purin-6-yl)methyl)(methyl)amino)methyl)phenol; 4-(((9-isopropyl-2-(pyridin-3-yl)-9H-purin-6-yl)methylamino)methyl)phenol; 4-(((9-isopropyl-2-(pyridin-3-yl)-9H-purin-6-yl)methoxy)methyl)phenol; N-(2-(indolin-5-yl)ethyl)-9-isopropyl-2-(pyridin-3-yl)-9H-purin-6-amine; 4-(2-(9-(1-methylpiperidin-4-yl)-2-(pyridin-3-yl)-9H-purin-6-ylamino)ethyl-1)phenol; 4-(2-(9-(piperidin-4-yl)-2-(pyridin-3-yl)-9H-purin-6-ylamino)ethyl)phenol; N-(2-(1H-indazol-5-yl)ethyl)-9-isopropyl-2-(pyridin-3-yl)-9H-purin-6-amine; N-(2-(1H-benzo[d]imidazol-5-yl)ethyl)-9-isopropyl-2-(pyridin-3-yl)-9H-purin-6-amine; 5-(2-(9-isopropyl-2-(pyridin-3-yl)-9H-purin-6-ylamino)ethyl)indolin-2-one; 4-(2-(9-cyclopropyl-2-(pyridin-3-yl)-9H-purin-6-ylamino)ethyl)phenol; 4-(2-(9-(1-hydroxypropan-2-yl)-2-(pyridin-3-yl)-9H-purin-6-ylamino)ethyl)phenol; 4-(2-(9-isopropyl-2-(pyridin-3-yl)-9H-purin-6-ylamino)ethyl)phenyl sulfamate; 2-(4-hydroxyphenyl)-N-(9-isopropyl-2-(pyridin-3-yl)-9H-purin-6-yl)acetamide; 4-(5-(9-isopropyl-2-(pyridin-3-yl)-9H-purin-6-ylamino)isoxazol-3-yl)phenol; 4-(5-(9-isopropyl-2-(pyridin-3-yl)-9H-purin-6-ylamino)-1,3,4-oxadiazol-2-yl)phenol; 4-(2-(2-(2-fluoropyridin-3-yl)-9-isopropyl-9H-purin-6-ylamino)ethyl)phenol; 4-(2-(9-isopropyl-2-(1-methyl-1H-pyrrol-2-yl)-9H-purin-6-ylamino)ethyl)phenol; and 4-(2-(9-isopropyl-2-(thiazol-5-yl)-9H-purin-6-ylamino)ethyl)phenol.

In another embodiment, an aryl hydrocarbon receptor antagonist is a compound of Formula If:

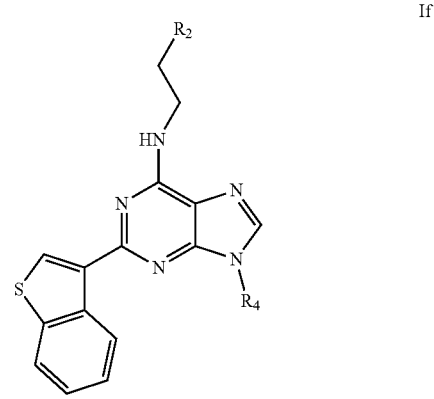

in which: $R_2$ is selected from 1H-indol-3-yl and phenyl optionally substituted with hydroxy; and $R_4$ is selected from isopropyl, sec-butyl, benzhydryl, nonan-2-yl, oxetan-3-yl and tetrahydrofuran-3-yl.

In a further embodiment are compounds selected from: 4-(2-(2-(benzo[b]thiophen-3-yl)-9-isopropyl-9H-purin-6-ylamino)ethyl)phenol; 4-(2-(2-(benzo[b]thiophen-3-yl)-9-sec-butyl-9H-purin-6-ylamino)ethyl)phenol; 4-(2-(9-benzhydryl-2-(benzo[b]thiophen-3-yl)-9H-purin-6-ylamino)ethyl)phenol; N-(2-(1H-indol-3-yl)ethyl)-2-(benzo[b]thiophen-3-yl)-9-isopropyl-9H-purin-6-amine; 4-(2-(2-(benzo[b]thiophen-3-yl)-9-(nonan-2-yl)-9H-purin-6-ylamino)ethyl)phenol; N-(2-(1H-indol-3-yl)ethyl)-2-(benzo[b]thiophen-3-yl)-9-sec-butyl-9H-purin-6-amine; 4-(2-(2-(benzo[b]thiophen-3-yl)-9-(oxetan-3-yl)-9H-purin-6-ylamino)ethyl)-phenol; (S)-4-(2-(2-(benzo[b]thiophen-3-yl)-9-(tetrahydrofuran-3-yl)-9H-purin-6-ylamino)ethyl) phenol; and (R)-4-(2-(2-(benzo[b]thiophen-3-yl)-9-(tetrahydrofuran-3-yl)-9H-purin-6-ylamino)ethyl)phenol.

In another embodiment, an aryl hydrocarbon receptor antagonist is a compound of Formula Ig:

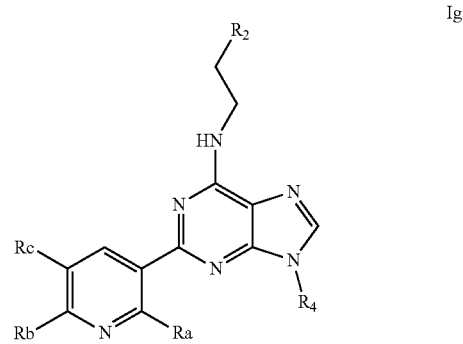

in which: $R_2$ is selected from: 1H-pyrrolo[2,3-b]pyridin-3-yl; 1H-indol-3-yl optionally substituted with 1 to 2 radicals independently selected from halo, methyl and methoxy; and phenyl optionally substituted with 1 to 2 radicals independently selected from methyl, halo and hydroxy; $R_4$ is selected from isopropyl, sec-butyl, 1-hydroxypropan-2-yl, prop-1-en-2-yl, benzhydryl, nonan-2-yl, oxetan-3-yl and tetrahydrofuran-3-yl; and Ra, Rb and Rc are independently selected from hydrogen, cyano, methyl, halo, —SO$_2$CH$_3$ and trifluoromethyl.

In a further embodiment are compounds selected from: 4-(2-(9-isopropyl-2-(pyridin-3-yl)-9H-purin-6-ylamino)ethyl)phenol; 4-(2-(2-(6-fluoropyridin-3-yl)-9-isopropyl-9H-purin-6-ylamino)ethyl)phenol; 4-(2-(9-isopropyl-2-(4-methylpyridin-3-yl)-9H-purin-6-ylamino)ethyl)phenol; 5-(6-(4-hydroxyphenethylamino)-9-isopropyl-9H-purin-2-yl)nicotinonitrile; 4-(2-(9-isopropyl-2-(5-methylpyridin-3-yl)-9H-purin-6-ylamino)ethyl)phenol; 4-(2-(9-isopropyl-2-(5-(methylsulfonyl)pyridin-3-yl)-9H-purin-6-ylamino)ethyl)phenol; 4-(2-(2-(4-chloropyridin-3-yl)-9-isopropyl-9H-purin-6-ylamino)ethyl)phenol; 4-(2-(2-(5-fluoropyridin-3-yl)-9-isopropyl-9H-purin-6-ylamino)ethyl)phenol; 9-isopropyl-N-(2-(6-methoxy-1H-indol-3-yl)ethyl)-2-(pyridin-3-yl)-9H-purin-6-amine; 9-isopropyl-N-(2-(5-methyl-1H-indol-3-yl)ethyl)-2-(pyridin-3-yl)-9H-purin-6-amine; N-(2-(1H-indol-3-yl)ethyl)-9-isopropyl-2-(pyridin-3-yl)-9H-purin-6-amine; 4-(2-(9-(oxetan-3-yl)-2-(pyridin-3-yl)-9H-purin-6-ylamino)ethyl)phenol; 4-(2-(9-(1-hydroxypropan-2-yl)-2-(pyridin-3-yl)-9H-purin-6-ylamino)ethyl)phenol; 4-(2-(2-(2-fluoropyridin-3-yl)-9-isopropyl-9H-purin-6-ylamino)ethyl)phenol; 5-(9-sec-butyl-6-(4-hydroxy-3-methylphenethylamino)-9H-purin-2-yl)nicotinonitrile; 4-(2-(2-(5-fluoropyridin-3-yl)-9-(oxetan-3-yl)-9H-purin-6-ylamino)ethyl)phenol; 4-(2-(2-(5-chloropyridin-3-yl)-9-isopropyl-9H-purin-6-ylamino)ethyl)phenol; 4-(2-(9-isopropyl-2-(5-(trifluoromethyl)pyridin-3-yl)-9H-purin-6-ylamino)ethyl)phenol; 5-(6-(2-(1H-indol-3-yl)ethylamino)-9-sec-butyl-9H-purin-2-yl)nicotinonitrile; N-(2-(1H-indol-3-yl)ethyl)-9-sec-butyl-2-(5-methylpyridin-3-yl)-9H-purin-6-amine; (R)—N-(2-(1H-indol-3-yl)ethyl)-9-sec-butyl-2-(5-fluoropyridin-3-yl)-9H-purin-6-amine; (S)—N-(2-(1H-indol-3-yl)ethyl)-9-sec-butyl-2-(5-fluoropyridin-3-yl)-9H-purin-6-amine; N-(2-(1H-indol-3-yl)ethyl)-9-sec-butyl-2-(5-fluoropyridin-3-yl)-9H-purin-6-amine; (R)—N-(2-(1H-indol-3-yl)ethyl)-9-sec-butyl-2-(5-methylpyridin-3-yl)-9H-purin-6-amine; (S)—N-(2-(1H-indol-3-yl)ethyl)-9-sec-butyl-2-(5-methylpyridin-3-yl)-9H-purin-6-amine; 5-(6-(4-hydroxyphenethylamino)-9-(oxetan-3-yl)-9H-purin-2-yl)nicotinonitrile; 4-(2-(6-(5-fluoropyridin-3-yl)-1-isopropyl-1H-pyrazolo[3,4-d]pyrimidin-4-ylamino)ethyl)phenol; 3-(6-(4-hydroxyphenethylamino)-9-isopropyl-9H-purin-2-yl)isonicotinonitrile; 4-(2-(2-(5-fluoropyridin-3-yl)-7-isopropyl-7H-pyrrolo[2,3-d]pyrimidin-4-ylamino)ethyl)phenol; 4-(2-(9-isopropyl-2-(6-methylpyridin-3-yl)-9H-purin-6-ylamino)ethyl)phenol; 2-chloro-4-(2-(9-isopropyl-2-(pyridin-3-yl)-9H-purin-6-ylamino)ethyl)phenol; 3-fluoro-4-(2-(9-isopropyl-2-(pyridin-3-yl)-9H-purin-6-ylamino)ethyl)phenol; N-(2-(5-fluoro-1H-indol-3-yl)ethyl)-9-isopropyl-2-(pyridin-3-yl)-9H-purin-6-amine; N-(2-(5-chloro-1H-indol-3-yl)ethyl)-9-isopropyl-2-(pyridin-3-yl)-9H-purin-6-amine; 4-(2-(9-isopropyl-2-(pyridin-3-yl)-9H-purin-6-ylamino)ethyl)-2-methylphenol; 2-(6-(2-(1H-indol-3-yl)ethylamino)-2-(5-fluoropyridin-3-yl)-9H-purin-9-yl)propan-1-ol; (R)-2-(6-(2-(1H-indol-3-yl)ethylamino)-2-(5-fluoropyridin-3-yl)-9H-purin-9-yl)propan-1-ol; (S)-2-(6-(2-(1H-indol-3-yl)ethylamino)-2-(5-fluoropyridin-3-yl)-9H-purin-9-yl)propan-1-ol; (R)—N-(2-(1H-indol-3-yl)ethyl)-2-(5-fluoropyridin-3-yl)-9-(tetrahydrofuran-3-yl)-9H-purin-6-amine; 4-(2-(6-(5-fluoropyridin-3-yl)-1-isopropyl-1H-imidazo[4,5-c]pyridin-4-ylamino)ethyl)phenol; N-(2-(1H-indol-3-yl)ethyl)-2-(5-fluoropyridin-3-yl)-9-isopropyl-9H-purin-6-amine; 2-(5-fluoropyridin-3-yl)-9-isopropyl-N-(2-(6-methoxy-1H-indol-3-yl)ethyl)-9H-purin-6-amine; 2-(5-fluoropyridin-3-yl)-9-isopropyl-N-(2-(5-methoxy-1H-indol-3-yl)ethyl)-9H-purin-6-amine; N-(2-(1H-indol-3-yl)ethyl)-2-(5-fluoropyridin-3-yl)-9-(prop-1-en-2-yl)-9H-purin-6-amine; N-(2-(1H-pyrrolo[2,3-b]pyridin-3-yl)ethyl)-2-(5-fluoropyridin-3-yl)-9-isopropyl-9H-purin-6-amine; 4-(2-(5-(5-fluoropyridin-3-yl)-3-isopropyl-3H-imidazo[4,5-b]pyridin-7-ylamino)ethyl)phenol; N-(2-(1H-indol-3-yl)ethyl)-9-isopropyl-2-(5-methylpyridin-3-yl)-9H-purin-6-amine; 2-(5-fluoropyridin-3-yl)-9-isopropyl-N-(2-(7-methyl-1H-indol-3-yl)ethyl)-9H-purin-6-amine; N-(2-(1H-indol-3-yl)ethyl)-2-(5-fluoropyridin-3-yl)-9-(oxetan-3-yl)-9H-purin-6-amine; N-(2-(1H-indol-3-yl)ethyl)-2-(5-methylpyridin-3-yl)-9-(oxetan-3-yl)-9H-purin-6-amine; N-(2-(6-fluoro-1H-indol-3-yl)ethyl)-2-(5-fluoropyridin-3-yl)-9-isopropyl-9H-purin-6-amine; 2-(5-fluoropyridin-3-yl)-9-isopropyl-N-(2-(2-methyl-1H-indol-3-yl)ethyl)-9H-purin-6-amine; 2-(5-fluoropyridin-3-yl)-9-isopropyl-N-(2-(6-methyl-1H-indol-3-yl)ethyl)-9H-purin-6-amine; N-(2-(4-fluoro-1H-indol-3-yl)ethyl)-2-(5-fluoropyridin-3-yl)-9-isopropyl-9H-purin-6-amine; 2-(5-fluoropyridin-3-yl)-9-isopropyl-N-(2-(4-methyl-1H-indol-3-yl)ethyl)-9H-purin-6-amine; N-(2-(7-fluoro-1H-indol-3-yl)ethyl)-2-(5-fluoropyridin-3-yl)-9-isopropyl-9H-purin-6-amine; and 4-(2-(2-(5-fluoropyridin-3-yl)-9-(1-hydroxypropan-2-yl)-9H-purin-6-ylamino)ethyl)-2-methylphenol.

In specific embodiments, an aryl hydrocarbon receptor antagonist is salt (e.g., a pharmaceutically acceptable salt) of a compound of Formula Ia, Ib, Ic, Id, Ie, If or Ig.

In specific embodiments, an aryl hydrocarbon receptor antagonist is one of the following compounds (the methods of making of which are described at pages 21-27 of U.S. Patent Publication No. 2010/0183564, which are specifically incorporated by reference herein):

4-(2-(2-(benzo[b]thiophen-3-yl)-9-isopropyl-9H-purin-6-ylamino)ethyl)phenol

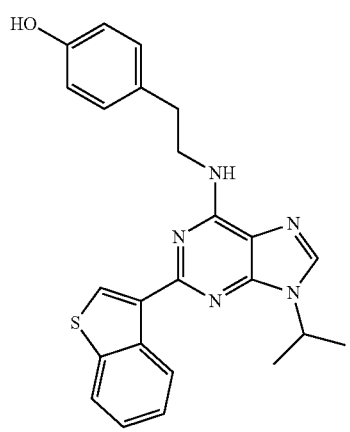

45

4-(2-(Pyridin-3-yl)-9-isopropyl-9H-purin-6-ylamino)ethyl)phenol

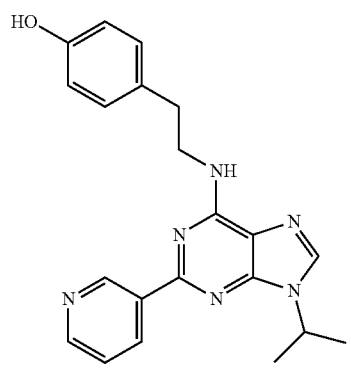 [SMILES: CC(C)n1cnc2c(NCCc3ccc(O)cc3)nc(-c3cccnc3)nc21]

4-(2-(9-isopropyl-2-(2-methyl-1H-imidazol-1-yl)-9H-purin-6-ylamino)ethyl)phenol

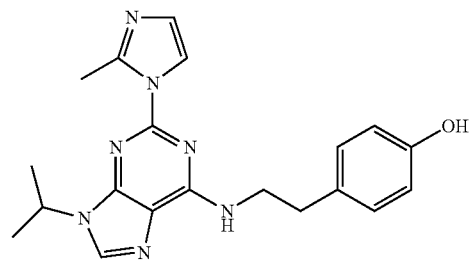 [SMILES: Cc1nccn1-c1nc(NCCc2ccc(O)cc2)c2ncn(C(C)C)c2n1]

4-(2-(2-(5-Chloropyridin-3-yl)-9-isopropyl-9H-purin-6-ylamino)ethyl)phenol

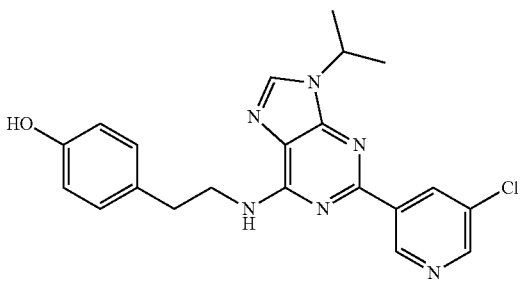 [SMILES: CC(C)n1cnc2c(NCCc3ccc(O)cc3)nc(-c3cncc(Cl)c3)nc21]

4-(2-(6-(5-Fluoropyridin-3-yl)-1-isopropyl-1H-pyrazolo[3,4-d]pyrimidin-4-ylamino)ethyl)phenol

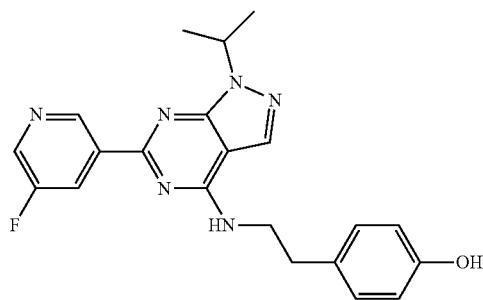 [SMILES: CC(C)n1ncc2c(NCCc3ccc(O)cc3)nc(-c3cncc(F)c3)nc21]

46

4-(2-(2-(5-Fluoropyridin-3-yl)-7-isopropyl-7H-pyrrolo[2,3-d]pyrimidin-4-ylamino)ethyl)phenol

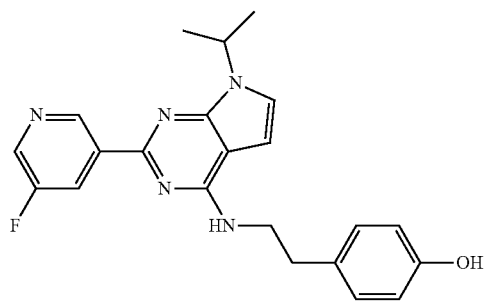 [SMILES: CC(C)n1ccc2c(NCCc3ccc(O)cc3)nc(-c3cncc(F)c3)nc21]

(R)-4-(2-(2-(benzo[b]thiophen-3-yl)-9-(tetrahydrofuran-3-yl)-9H-purin-6-ylamino)ethyl)phenol

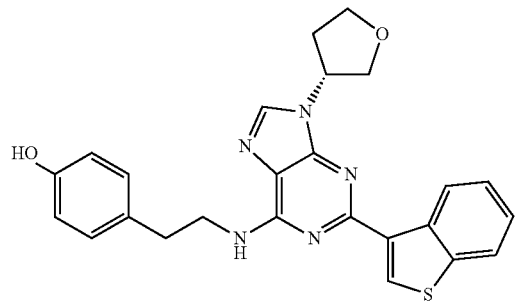 [SMILES: Oc1ccc(CCNc2nc(-c3csc4ccccc34)nc3c2ncn3[C@@H]2CCOC2)cc1]

2-(6-(2-(1H-indol-3-yl)ethylamino)-2-(5-fluoropyridin-3-yl)-9H-purin-9-yl)propan-1-ol

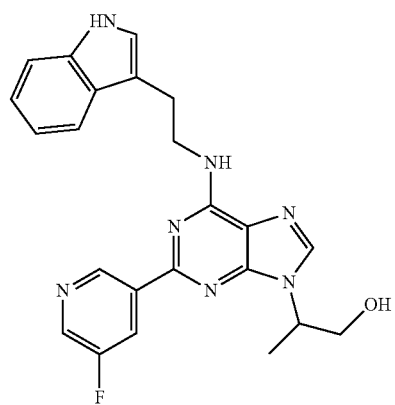 [SMILES: CC(CO)n1cnc2c(NCCc3c[nH]c4ccccc34)nc(-c3cncc(F)c3)nc21]

| 47 | 48 |
|---|---|
| (R)-2-(6-(2-(1H-indol-3-yl)ethylamino)-2-(5-fluoropyridine-3-yl)-9H-purin-9-yl)propan-1-ol & (S)-2-(6-(2-(1H-indol-3-yl)ethylamino)-2-(5-fluoropyridin-3-yl)-9H-purin-9-yl)propan-1-ol | (S)-2-(6-(2-(1H-indol-3-yl)ethylamino)-2-(5-fluoropyridin-3-yl)-9H-purin-9-yl)propan-1-ol |

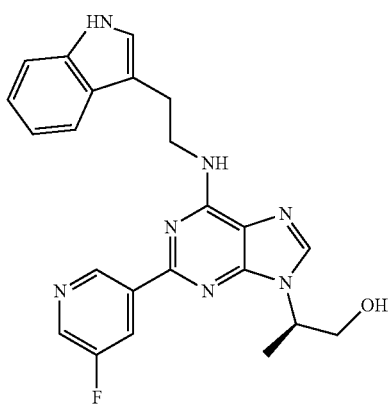 [SMILES: C[C@H](CO)n1cnc2c(NCCc3c[nH]c4ccccc34)nc(-c3cncc(F)c3)nc21]

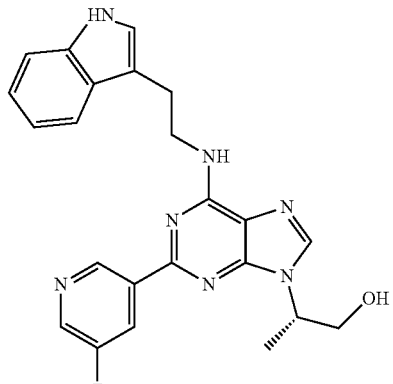

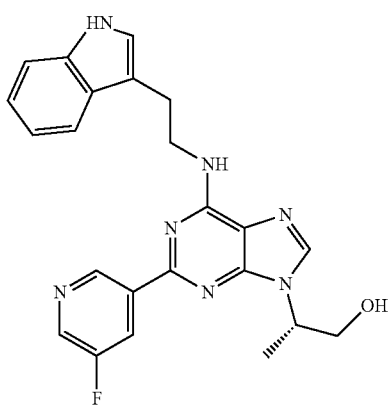 [SMILES: C[C@@H](CO)n1cnc2c(NCCc3c[nH]c4ccccc34)nc(-c3cncc(F)c3)nc21]

(R)-2-(6-(2-(1H-indol-3-yl)ethylamino)-2-(5-fluoropyridin-3-yl)-9H-purin-9-yl)propan-1-ol 4-(2-(6-(5-Fluoropyridin-3-yl)-1-isopropyl-1H-imidazo[4,5-c]pyridin-4-ylamino)ethyl)phenol

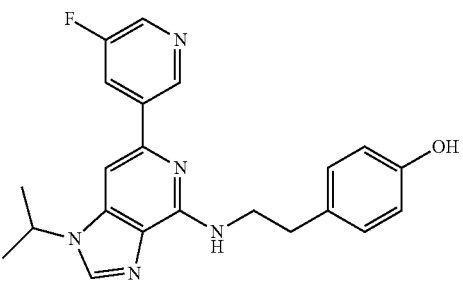

4-(2-(5-(5-Fluoropyridin-3-yl)-3-isopropyl-3H-imidazo[4,5-b]pyridin-7-ylamino)ethyl)phenol

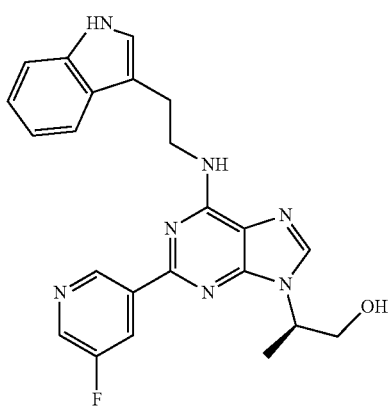 [SMILES: C[C@H](CO)n1cnc2c(NCCc3c[nH]c4ccccc34)nc(-c3cncc(F)c3)nc21]

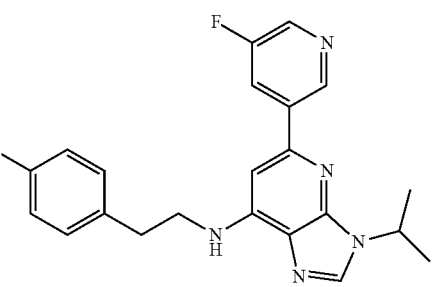

In certain embodiments, an aryl hydrocarbon receptor antagonist is one of the compounds depicted in Table 1 (corresponding to Table 1 of U.S. Patent Publication No. 2010/0183564).

TABLE 1

| Example Number | Structure | Physical Data ¹H NMR and/or MS | EC$_{50}$ (% CD34+) µM |
|---|---|---|---|
| 1 | 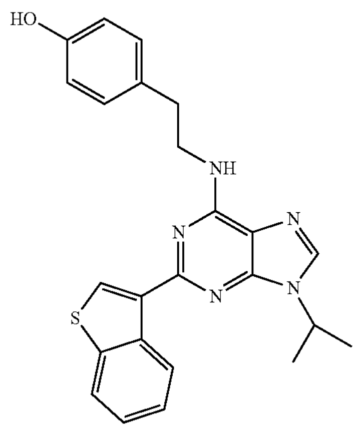 [SMILES: CC(C)n1cnc2c(NCCc3ccc(O)cc3)nc(-c3csc4ccccc34)nc21] | ¹H NMR (500 MHz, CDCl$_3$): δ = 9.20 (d, 1H), 8.58 (s, 1H), 8.00-7.80 (m, 2H), 7.55-7.38 (m, 3H), 7.11 (d, 2H), 6.72 (d, 2H), 6.18 (br, 1H), 5.01-4.68 (m, 1H), 4.02 (br, 2H), 3.00 (t, 2H), 1.68 (d, 6H); HRMS (EI) m/z 430.1698 (M + 1) | 0.12 |
| 2 | 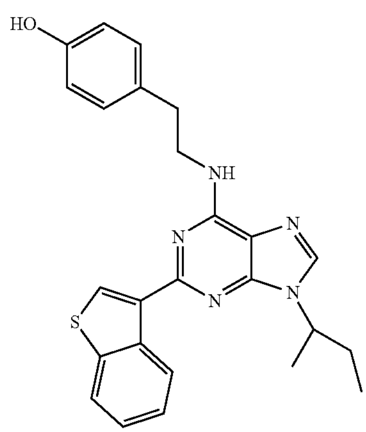 [SMILES: CCC(C)n1cnc2c(NCCc3ccc(O)cc3)nc(-c3csc4ccccc34)nc21] | ¹H NMR (500 MHz, CDCl$_3$): δ = 9.22 (d, 1H), 8.53 (s, 1H), 7.92 (d, 1H), 7.80 (s, 1H), 7.52-7.33 (m, 3H), 7.13 (d, 2H), 6.74 (d, 2H), 6.08 (br, 1H), 4.80-4.62 (m, 1H), 4.02 (br, 2H), 3.01 (t, 2H), 2.20-1.90 (m, 2H), 1.77 (d, 3H), 0.92 (t, 3H); HRMS (EI) m/z 444.1857 (M + 1) | 0.03 |
| 3 | 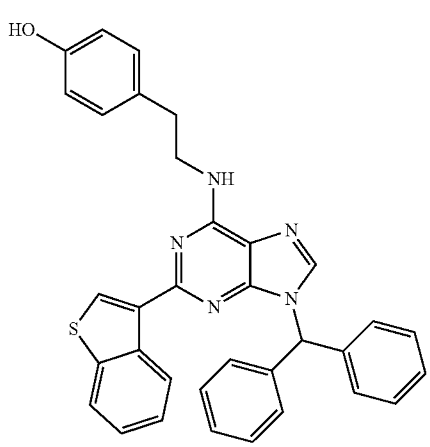 [SMILES: Oc1ccc(CCNc2nc(-c3csc4ccccc34)nc3c2ncn3C(c2ccccc2)c2ccccc2)cc1] | HRMS (EI) m/z 554.2005 (M + 1) | 0.15 |

TABLE 1-continued
| Example Number | Structure | Physical Data ¹H NMR and/or MS | EC$_{50}$ (% CD34+) μM |
|---|---|---|---|
| 4 | 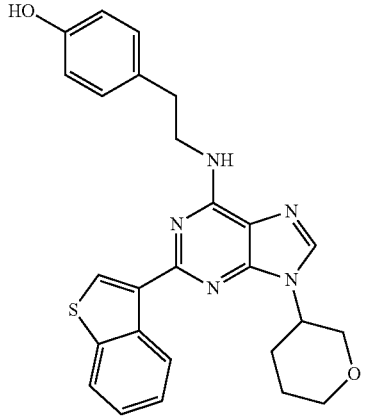 [SMILES: Oc1ccc(CCNc2nc(-c3csc4ccccc34)nc3c2ncn3C2CCCOC2)cc1] | HRMS (EI) m/z 472.1807 (M + 1) | 1.49 |
| 5 | 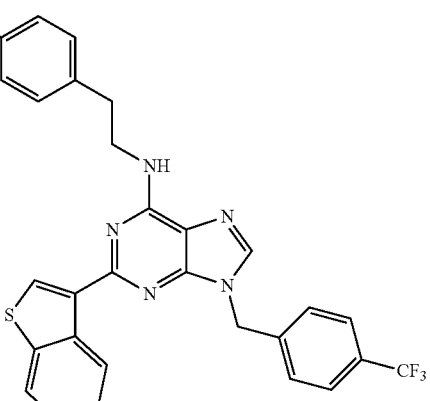 | HRMS (EI) m/z 546.1571 (M + 1) | 2.08 |
| 6 | 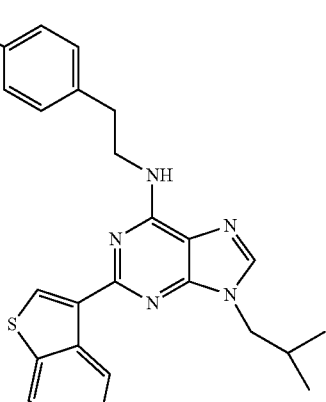 | HRMS (EI) m/z 444.1857 (M + 1) | 2.53 |

TABLE 1-continued

| Example Number | Structure | Physical Data $^1$H NMR and/or MS | EC$_{50}$ (% CD34+) μM |
|---|---|---|---|
| 7 | (structure) | HRMS (EI) m/z 402.1385 (M + 1) | 7.2 |
| 8 | (structure) | HRMS (EI) m/z 492.1856 (M + 1) | 6.03 |
| 9 | (structure) | $^1$H NMR (500 MHz, CDCl$_3$): δ = 9.21 (d, 1H), 8.48 (s, 1H), 8.02 (br, 1H), 7.89 (d, 1H), 7.79 (s, 1H), 7.70 (d, 1H), 7.50-7.07 (m, 6H), 5.82 (br, 1H), 5.00-4.88 (m, 1H), 4.13 (br, 2H), 3.22 (t, 2H), 1.69 (d, 6H); HRMS (EI) m/z 453.1857 (M + 1) | 0.02 |

TABLE 1-continued

| Example Number | Structure | Physical Data ¹H NMR and/or MS | EC$_{50}$ (% CD34+) μM |
|---|---|---|---|
| 10 | 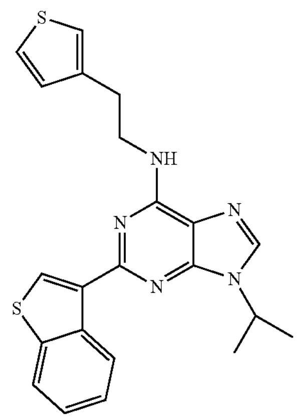 [SMILES: CC(C)n1cnc2c(NCCc3ccsc3)nc(-c3csc4ccccc34)nc21] | HRMS (EI) m/z 420.1315 (M + 1) | 1.38 |
| 11 | 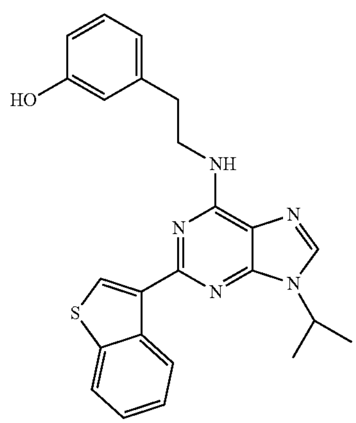 [SMILES: CC(C)n1cnc2c(NCCc3cccc(O)c3)nc(-c3csc4ccccc34)nc21] | HRMS (EI) m/z 430.1697 (M + 1) | 1.45 |
| 12 | 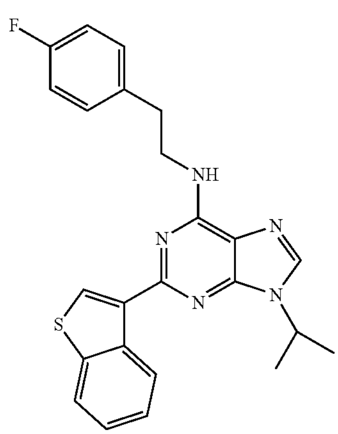 [SMILES: CC(C)n1cnc2c(NCCc3ccc(F)cc3)nc(-c3csc4ccccc34)nc21] | HRMS (EI) m/z 432.1655 (M + 1) | 1.76 |

TABLE 1-continued

| Example Number | Structure | Physical Data $^1$H NMR and/or MS | EC$_{50}$ (% CD34+) μM |
|---|---|---|---|
| 13 | (structure: 6-[2-(4-aminophenyl)ethylamino]-2-(benzothiophen-3-yl)-9-isopropylpurine) | HRMS (EI) m/z 429.1853 (M + 1) | 5.75 |
| 14 | (structure: 6-[2-(4-hydroxyphenyl)ethylamino]-2-(pyrimidin-5-yl)-9-isopropylpurine) | HRMS (EI) m/z 376.1881 (M + 1) | 0.17 |
| 15 | (structure: 6-[2-(4-hydroxyphenyl)ethylamino]-2-(pyridin-3-yl)-9-isopropylpurine) | $^1$H NMR (400 MHz, CD$_3$OD) δ 9.57 (d, 1H), 8.85-8.83 (m, 1H), 8.59 (q, 1H), 8.16 (s, 1H), 7.57 (q, 1H), 7.13 (d, 2H), 6.72 (d, 2H), 4.98-4.91 (m, 1H), 3.91 (bs, 2H), 2.98 (t, 2H), 1.68 (d, 6H); HRMS (EI) m/z 375.1928 (M + 1) | 0.19 |
| 16 | (structure: 6-[2-(4-hydroxyphenyl)ethylamino]-2-phenyl-9-isopropylpurine) | HRMS (EI) m/z 374.1976 (M + 1) | 0.46 |

TABLE 1-continued

| Example Number | Structure | Physical Data $^1$H NMR and/or MS | EC$_{50}$ (% CD34+) μM |
|---|---|---|---|
| 17 | (4-hydroxyphenethyl)-NH-purine with 3-thienyl and 9-isopropyl | HRMS (EI) m/z 380.1544 (M + 1) | 0.97 |
| 18 | (4-hydroxyphenethyl)-NH-purine with 3-furyl and 9-isopropyl | HRMS (EI) m/z 364.1769 (M + 1) | 3.9 |
| 19 | (4-fluorophenethyl)-NH-purine with benzothien-3-yl and 9-phenyl | HRMS (EI) m/z 466.1493 (M + 1) | 1.1 |
| 20 | N-benzyl purine with 8-(4-biphenyl) substituent | HRMS (EI) m/z 420.2184 (M + 1) | 7.8 |

TABLE 1-continued

| Example Number | Structure | Physical Data $^1$H NMR and/or MS | EC$_{50}$ (% CD34+) μM |
|---|---|---|---|
| 21 | 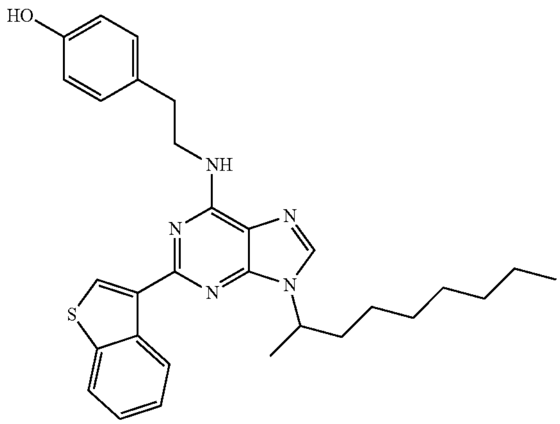 [SMILES: CCCCCCCC(C)n1cnc2c(NCCc3ccc(O)cc3)nc(-c3csc4ccccc34)nc21] | HRMS (EI) m/z 514.2638 (M + 1) | 0.13 |
| 23 | 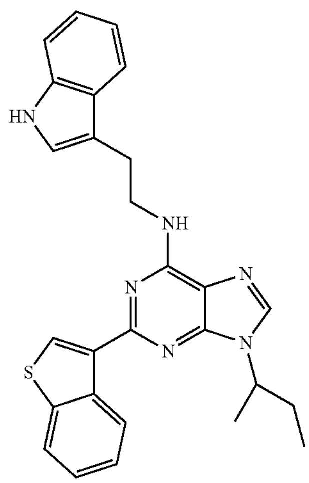 [SMILES: CCC(C)n1cnc2c(NCCc3c[nH]c4ccccc34)nc(-c3csc4ccccc34)nc21] | HRMS (EI) m/z 467.2013 (M + 1) | 0.019 |
| 31 | 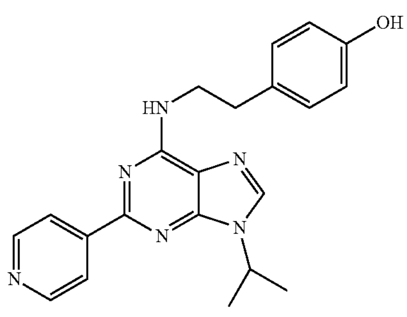 [SMILES: CC(C)n1cnc2c(NCCc3ccc(O)cc3)nc(-c3ccncc3)nc21] | MS m/z 375.2 (M + 1) | 0.66 |
| 32 | 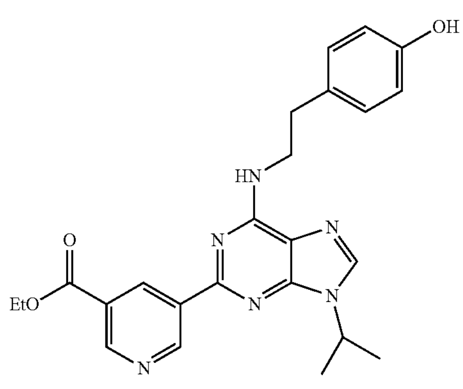 [SMILES: CCOC(=O)c1cncc(-c2nc(NCCc3ccc(O)cc3)c3ncn(C(C)C)c3n2)c1] | MS m/z 447.2 (M + 1) | 5.6 |

TABLE 1-continued

| Example Number | Structure | Physical Data ¹H NMR and/or MS | EC$_{50}$ (% CD34+) μM |
|---|---|---|---|
| 33 | 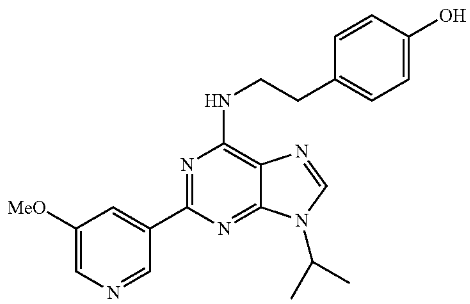 [SMILES: COc1cncc(-c2nc(NCCc3ccc(O)cc3)c3ncn(C(C)C)c3n2)c1] | MS m/z 405.2 (M + 1) | 0.27 |
| 34 | 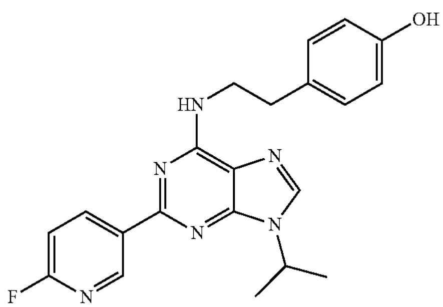 [SMILES: CC(C)n1cnc2c(NCCc3ccc(O)cc3)nc(-c3ccc(F)nc3)nc21] | MS m/z 393.2 (M + 1) | 0.16 |
| 35 | 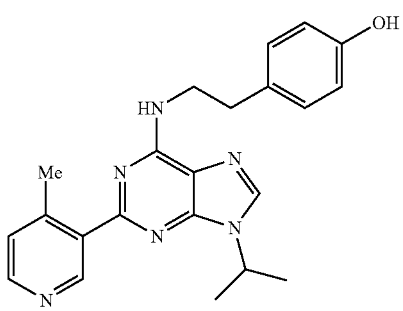 [SMILES: Cc1ccncc1-c1nc(NCCc2ccc(O)cc2)c2ncn(C(C)C)c2n1] | MS m/z 389.2 (M + 1) | 0.34 |
| 37 | 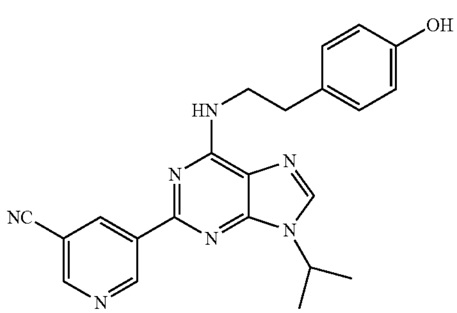 [SMILES: CC(C)n1cnc2c(NCCc3ccc(O)cc3)nc(-c3cncc(C#N)c3)nc21] | MS m/z 400.2 (M + 1) | 0.024 |
| 38 | 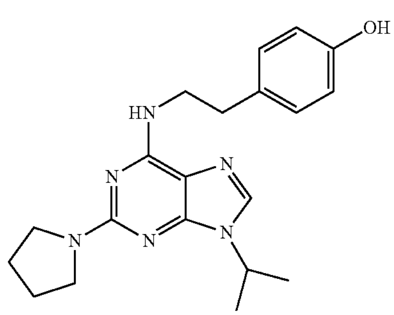 [SMILES: CC(C)n1cnc2c(NCCc3ccc(O)cc3)nc(N3CCCC3)nc21] | MS m/z 367.2 (M + 1) | 1.6 |

TABLE 1-continued

| Example Number | Structure | Physical Data $^1$H NMR and/or MS | EC$_{50}$ (% CD34+) μM |
|---|---|---|---|
| 40 | 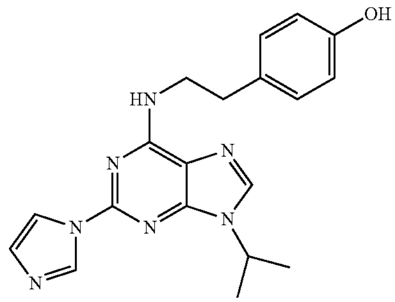 [SMILES: CC(C)n1cnc2c(NCCc3ccc(O)cc3)nc(-n3ccnc3)nc21] | MS m/z 364.2 (M + 1) | 0.26 |
| 42 | 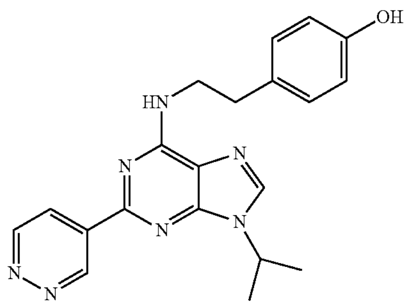 [SMILES: CC(C)n1cnc2c(NCCc3ccc(O)cc3)nc(-c3ccnnc3)nc21] | MS m/z 376.2 (M + 1) | 0.64 |
| 43 | 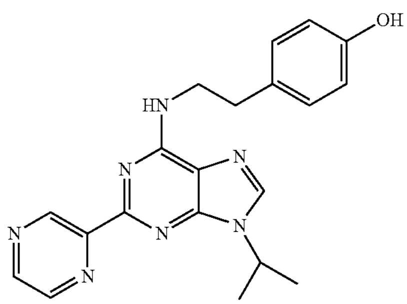 [SMILES: CC(C)n1cnc2c(NCCc3ccc(O)cc3)nc(-c3cnccn3)nc21] | MS m/z 376.2 (M + 1) | 2.4 |
| 44 | 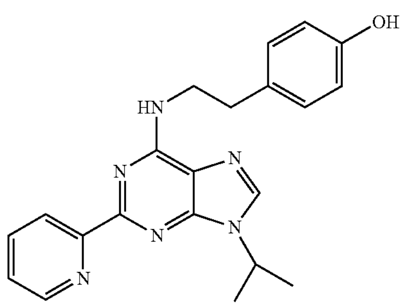 [SMILES: CC(C)n1cnc2c(NCCc3ccc(O)cc3)nc(-c3ccccn3)nc21] | MS m/z 375.2 (M + 1) | 1.7 |
| 45 | 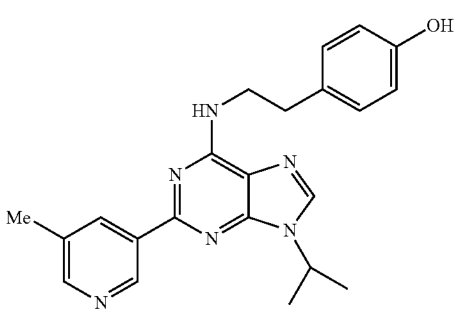 [SMILES: Cc1cncc(-c2nc(NCCc3ccc(O)cc3)c3ncn(C(C)C)c3n2)c1] | MS m/z 389.2 (M + 1) | 0.063 |

TABLE 1-continued

| Example Number | Structure | Physical Data ¹H NMR and/or MS | EC$_{50}$ (% CD34+) μM |
|---|---|---|---|
| 46 | 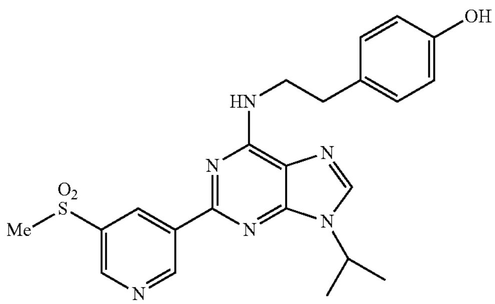 [SMILES: CC(C)n1cnc2c(NCCc3ccc(O)cc3)nc(-c3cncc(S(C)(=O)=O)c3)nc21] | MS m/z 453.2 (M + 1) | 0.65 |
| 48 | 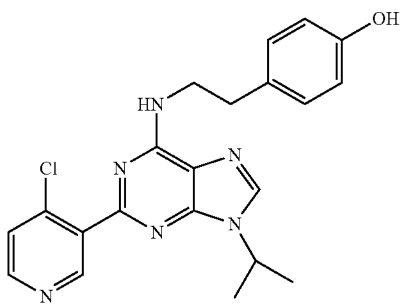 [SMILES: CC(C)n1cnc2c(NCCc3ccc(O)cc3)nc(-c3cnccc3Cl)nc21] | MS m/z 409.2 (M + 1) | 0.51 |
| 50 | 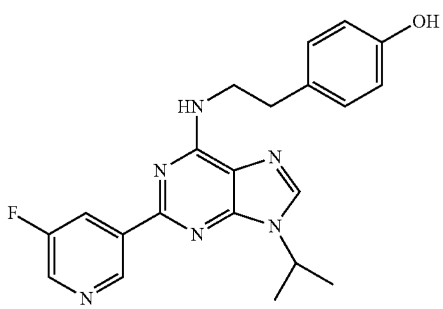 [SMILES: CC(C)n1cnc2c(NCCc3ccc(O)cc3)nc(-c3cncc(F)c3)nc21] | MS m/z 393.2 (M + 1) | 0.034 |
| 52 | 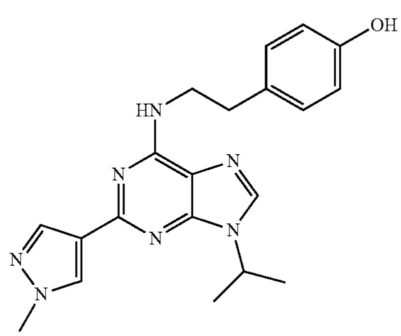 [SMILES: CC(C)n1cnc2c(NCCc3ccc(O)cc3)nc(-c3cnn(C)c3)nc21] | MS m/z 378.2 (M + 1) | |
| 55 | 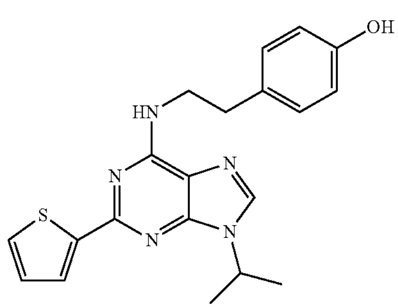 [SMILES: CC(C)n1cnc2c(NCCc3ccc(O)cc3)nc(-c3cccs3)nc21] | MS m/z 380.2 (M + 1) | 1.3 |

TABLE 1-continued

| Example Number | Structure | Physical Data $^1$H NMR and/or MS | EC$_{50}$ (% CD34+) μM |
|---|---|---|---|
| 58 | 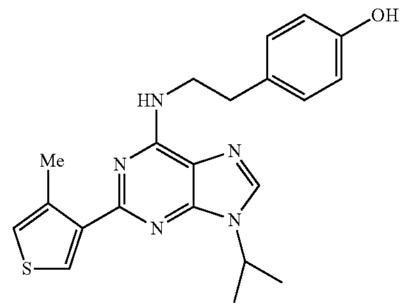 [SMILES: Cc1cscc1-c1nc(NCCc2ccc(O)cc2)c2ncn(C(C)C)c2n1] | MS m/z 394.2 (M + 1) | 0.24 |
| 60 | 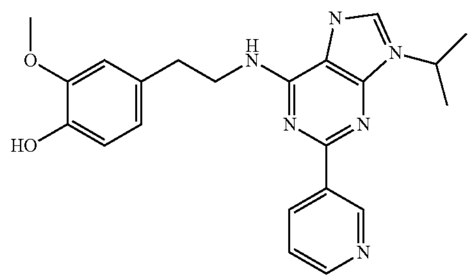 | MS m/z 405.1 (M + 1) | 3.2 |
| 61 | 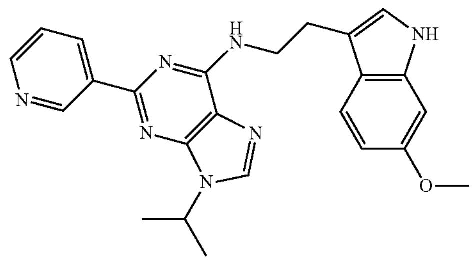 [SMILES: COc1ccc2c(CCNc3nc(-c4cccnc4)nc4c3ncn4C(C)C)c[nH]c2c1] | MS m/z 428.1 (M + 1) | 0.13 |
| 62 | 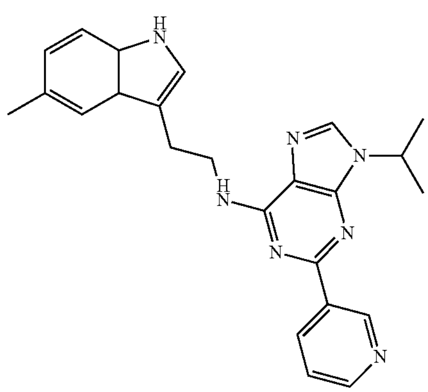 [SMILES: CC1=CC2C(CCNc3nc(-c4cccnc4)nc4c3ncn4C(C)C)=CNC2C=C1] | MS m/z 412.1 (M + 1) | 0.72 |
| 70 | 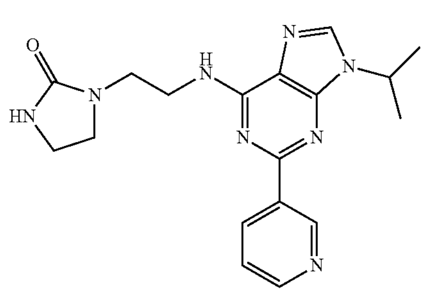 [SMILES: CC(C)n1cnc2c(NCCN3CCNC3=O)nc(-c3cccnc3)nc21] | MS m/z 367.2 (M + 1) | 2.7 |

TABLE 1-continued

| Example Number | Structure | Physical Data $^1$H NMR and/or MS | EC$_{50}$ (% CD34+) μM |
|---|---|---|---|
| 72 | 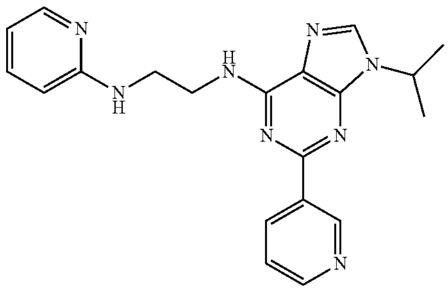 [SMILES: CC(C)n1cnc2c(NCCNc3ccccn3)nc(-c3cccnc3)nc21] | MS m/z 375.2 (M + 1) | 6.3 |
| 73 | 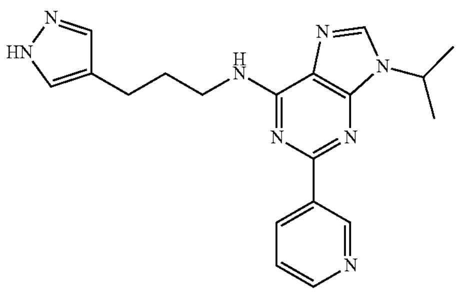 [SMILES: CC(C)n1cnc2c(NCCCc3cn[nH]c3)nc(-c3cccnc3)nc21] | MS m/z 363.2 (M + 1) | 8.2 |
| 76 | 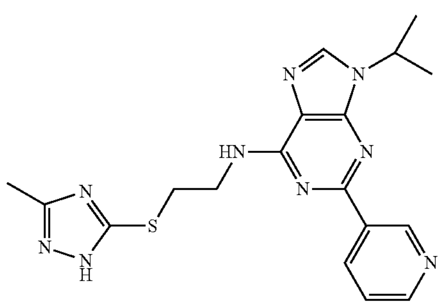 [SMILES: Cc1n[nH]c(SCCNc2nc(-c3cccnc3)nc3c2ncn3C(C)C)n1] | MS m/z 396.2 (M + 1) | 6.0 |
| 81 | 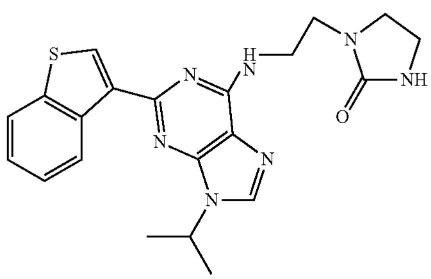 [SMILES: CC(C)n1cnc2c(NCCN3CCNC3=O)nc(-c3csc4ccccc34)nc21] | MS m/z 422.1 (M + 1) | 2.7 |
| 82 | 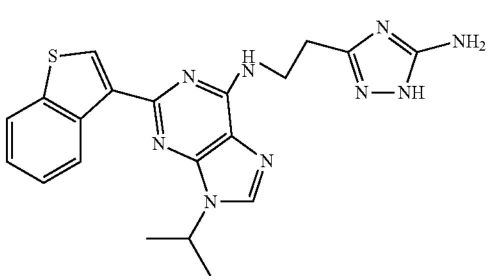 [SMILES: CC(C)n1cnc2c(NCCc3n[nH]c(N)n3)nc(-c3csc4ccccc34)nc21] | MS m/z 420.1 (M + 1) | 7.9 |

TABLE 1-continued
| Example Number | Structure | Physical Data $^1$H NMR and/or MS | $EC_{50}$ (% CD34+) μM |
|---|---|---|---|
| 83 | 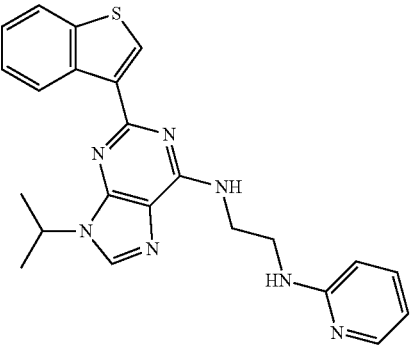 [SMILES: CC(C)n1cnc2c(NCCNc3ccccn3)nc(-c3csc4ccccc34)nc21] | MS m/z 430.1 (M + 1) | 7.1 |
| 84 | 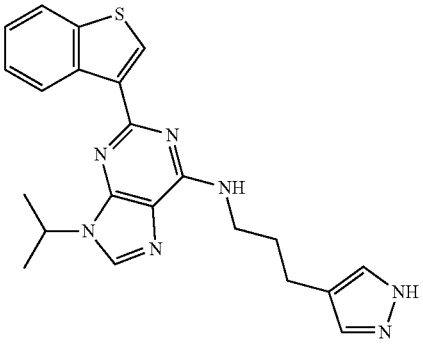 [SMILES: CC(C)n1cnc2c(NCCCc3cn[nH]c3)nc(-c3csc4ccccc34)nc21] | MS m/z 418.1 (M + 1) | 5.4 |
| 88 | 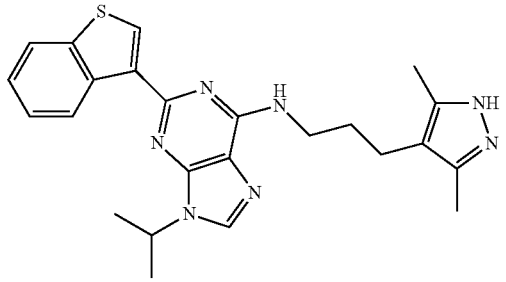 [SMILES: Cc1n[nH]c(C)c1CCCNc1nc(-c2csc3ccccc23)nc2c1ncn2C(C)C] | MS m/z 446.10 (M + 1) | 2.6 |
| 89 | 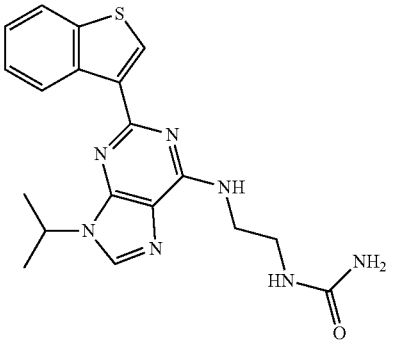 [SMILES: CC(C)n1cnc2c(NCCNC(N)=O)nc(-c3csc4ccccc34)nc21] | MS m/z 396.10 (M + 1) | 1.4 |

TABLE 1-continued

| Example Number | Structure | Physical Data $^1$H NMR and/or MS | EC$_{50}$ (% CD34+) μM |
|---|---|---|---|
| 90 | 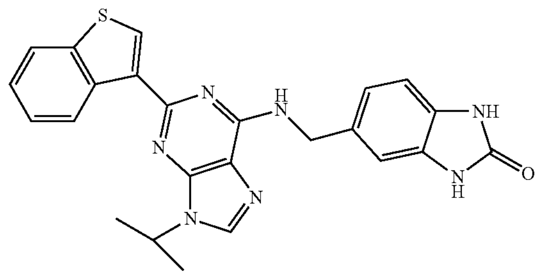 [SMILES: CC(C)n1cnc2c(NCc3ccc4[nH]c(=O)[nH]c4c3)nc(-c3csc4ccccc34)nc21] | MS m/z 456.2 (M + 1) | 3.3 |
| 91 | 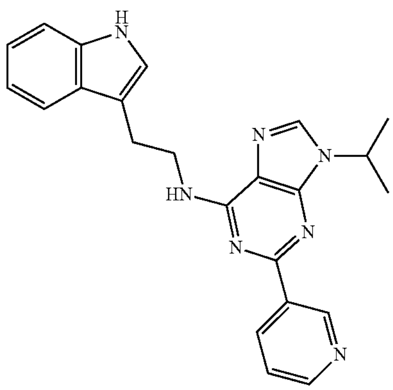 [SMILES: CC(C)n1cnc2c(NCCc3c[nH]c4ccccc34)nc(-c3cccnc3)nc21] | MS m/z 398.1 (M + 1) | 0.029 |
| 92 | 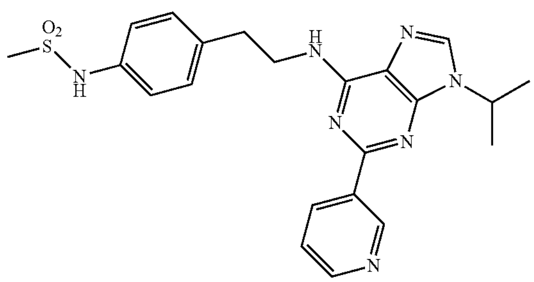 [SMILES: CC(C)n1cnc2c(NCCc3ccc(NS(C)(=O)=O)cc3)nc(-c3cccnc3)nc21] | MS m/z 452.2 (M + 1) | 7.1 |
| 93S | 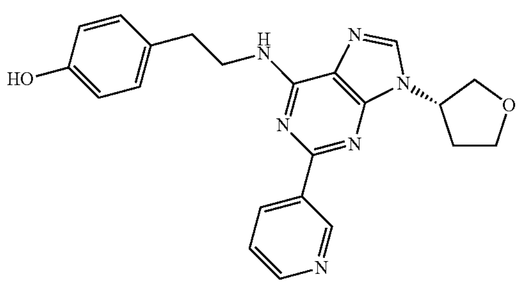 [SMILES: Oc1ccc(CCNc2nc(-c3cccnc3)nc3c2ncn3[C@H]2CCOC2)cc1] | MS m/z 403.1 (M + 1) | 1.1 |
| 93R | 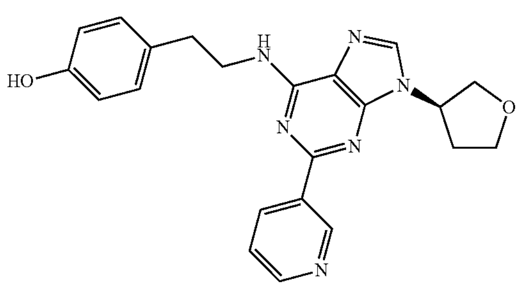 [SMILES: Oc1ccc(CCNc2nc(-c3cccnc3)nc3c2ncn3[C@@H]2CCOC2)cc1] | MS m/z 403.1 (M + 1) | 0.52 |

TABLE 1-continued

| Example Number | Structure | Physical Data $^1$H NMR and/or MS | EC$_{50}$ (% CD34+) μM |
|---|---|---|---|
| 94 | 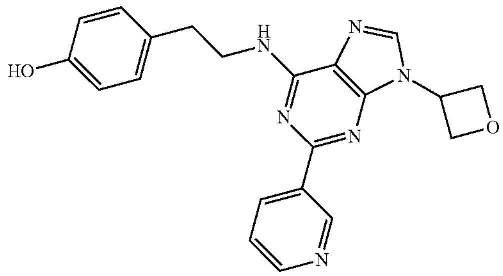 [SMILES: Oc1ccc(CCNc2nc(-c3cccnc3)nc3c2ncn3C2COC2)cc1] | MS m/z 389.1 (M + 1) | 0.97 |
| 95 | 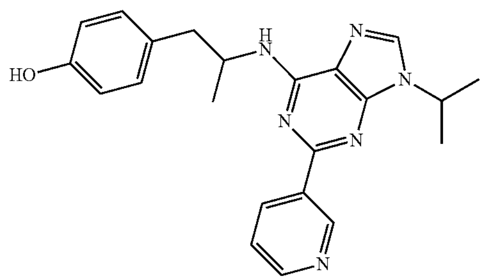 [SMILES: CC(Cc1ccc(O)cc1)Nc1nc(-c2cccnc2)nc2c1ncn2C(C)C] | MS m/z 389.1 (M + 1) | 2.3 |
| 98 | 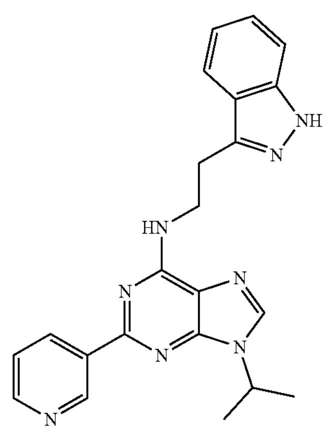 [SMILES: CC(C)n1cnc2c(NCCc3n[nH]c4ccccc34)nc(-c3cccnc3)nc21] | MS m/z 399.2 (M + 1) | 8.2 |
| 99 | 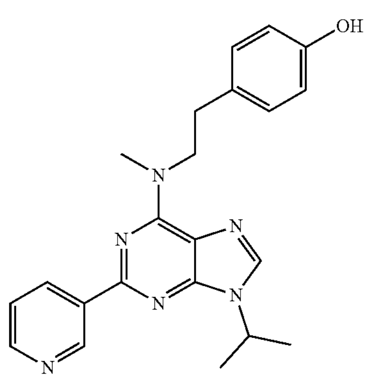 [SMILES: CC(C)n1cnc2c(N(C)CCc3ccc(O)cc3)nc(-c3cccnc3)nc21] | MS m/z 389.2 (M + 1) | 7.5 |

TABLE 1-continued

| Example Number | Structure | Physical Data $^1$H NMR and/or MS | EC$_{50}$ (% CD34+) μM |
|---|---|---|---|
| 113 | 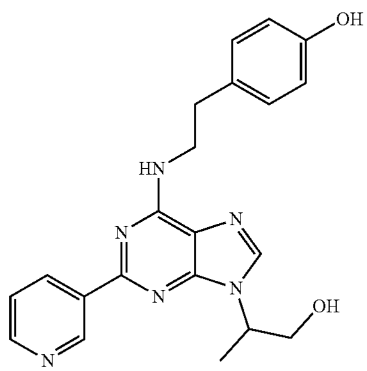 [SMILES: CC(CO)n1cnc2c(NCCc3ccc(O)cc3)nc(-c3cccnc3)nc21] | MS m/z 391.2 (M + 1) | 0.54 |
| 114 | 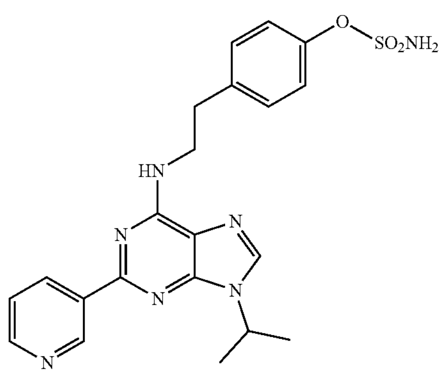 [SMILES: CC(C)n1cnc2c(NCCc3ccc(OS(N)(=O)=O)cc3)nc(-c3cccnc3)nc21] | MS m/z 454.1 (M + 1) | 1.1 |
| 118 | 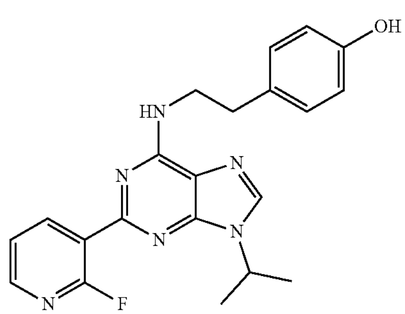 [SMILES: CC(C)n1cnc2c(NCCc3ccc(O)cc3)nc(-c3cccnc3F)nc21] | MS m/z 393.2 (M + 1) | 0.45 |
| 119 | 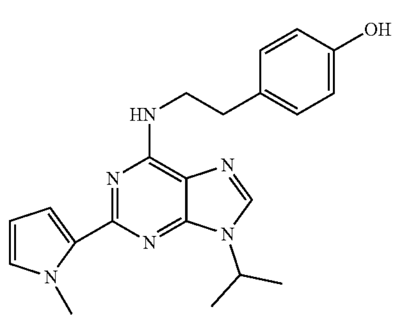 [SMILES: CC(C)n1cnc2c(NCCc3ccc(O)cc3)nc(-c3cccn3C)nc21] | MS m/z 377.2 (M + 1) | 1.4 |

TABLE 1-continued

| Example Number | Structure | Physical Data $^1$H NMR and/or MS | EC$_{50}$ (% CD34+) μM |
|---|---|---|---|
| 120 | 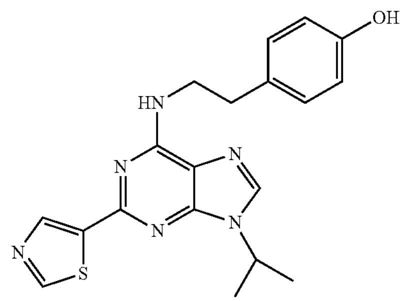 [SMILES: CC(C)n1cnc2c(NCCc3ccc(O)cc3)nc(-c3cncs3)nc21] | MS m/z 381.2 (M + 1) | 1.4 |
| 121 | 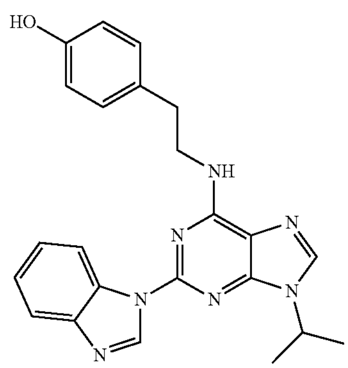 [SMILES: CC(C)n1cnc2c(NCCc3ccc(O)cc3)nc(-n3cnc4ccccc43)nc21] | MS m/z 414.2 (M + 1) | 0.086 |
| 122 | 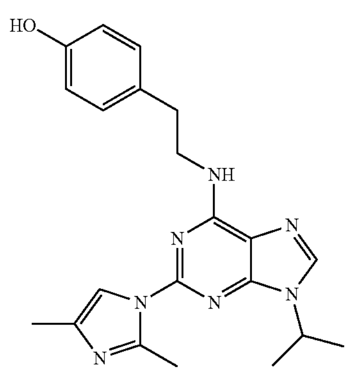 [SMILES: Cc1cn(-c2nc(NCCc3ccc(O)cc3)c3ncn(C(C)C)c3n2)c(C)n1] | MS m/z 414.2 (M + 1) | 0.42 |
| 123 | 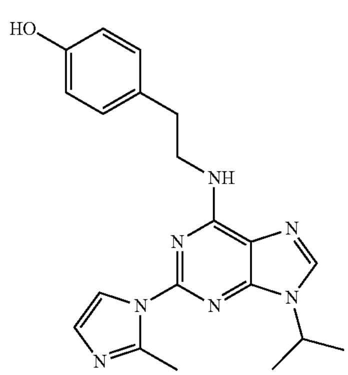 [SMILES: Cc1nccn1-c1nc(NCCc2ccc(O)cc2)c2ncn(C(C)C)c2n1] | $^1$H NMR (400 MHz, DMSO): δ = 9.21 (br, 1H), 8.57 (t, 1H), 8.36 (s, 1H), 8.23 (d, 1H), 7.70 (d, 1H), 7.04 (d, 2H), 6.66 (d, 2H), 4.84-4.72 (m, 1H), 3.67 (q, 2H), 2.99 (s, 3H), 2.83 (t, 2H), 1.56 (d, 6H); MS m/z 378.2 (M + 1) | 0.066 |

TABLE 1-continued

| Example Number | Structure | Physical Data <br> ¹H NMR and/or MS | EC$_{50}$ <br> (% CD34+) <br> μM |
|---|---|---|---|
| 124 | 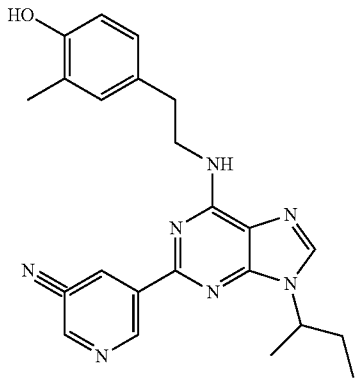 | MS m/z 428.2 (M + 1) | 0.003 |
| 125 | 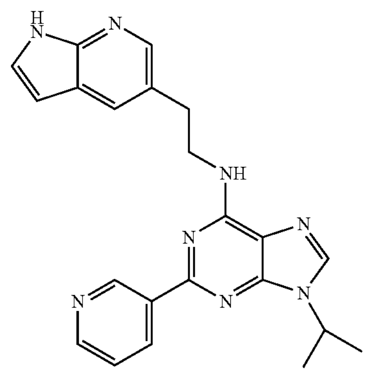 [SMILES: CC(C)n1cnc2c(NCCc3cnc4[nH]ccc4c3)nc(-c3cccnc3)nc21] | MS m/z 399.2 (M + 1) | |
| 126 | 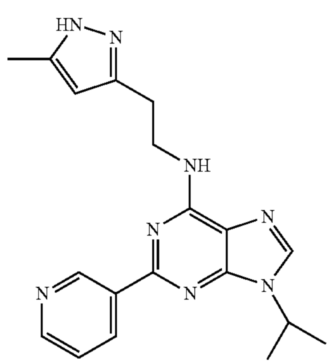 [SMILES: Cc1cc(CCNc2nc(-c3cccnc3)nc3c2ncn3C(C)C)n[nH]1] | MS m/z 363.2 (M + 1) | 5.0 |
| 127 | 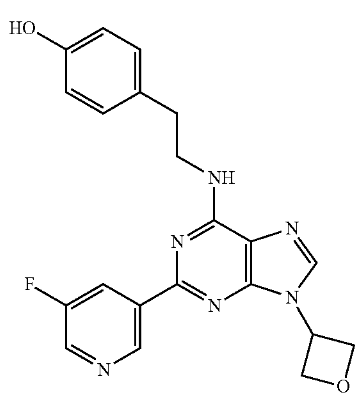 [SMILES: Oc1ccc(CCNc2nc(-c3cncc(F)c3)nc3c2ncn3C2COC2)cc1] | MS m/z 407.3 (M + 1) | 0.47 |

TABLE 1-continued

| Example Number | Structure | Physical Data ¹H NMR and/or MS | EC$_{50}$ (% CD34+) μM |
|---|---|---|---|
| 128 | 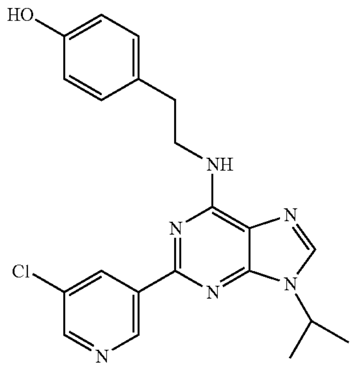 [SMILES: CC(C)n1cnc2c(NCCc3ccc(O)cc3)nc(-c3cncc(Cl)c3)nc21] | ¹H NMR (400 MHz, DMSO): δ = 9.47 (s, 1H), 8.71 (s, 1H), 8.67 (s, 1H), 8.32 (s, 1H), 8.04 (t, 1H), 7.10 (d, 2H), 6.69 (d, 2H), 4.91-4.81 (m, 1H), 3.80-3.70 (m, 2H), 2.86 (t, 2H), 1.58 (d, 6H); MS m/z 409.2 (M + 1) | 0.019 |
| 129 | 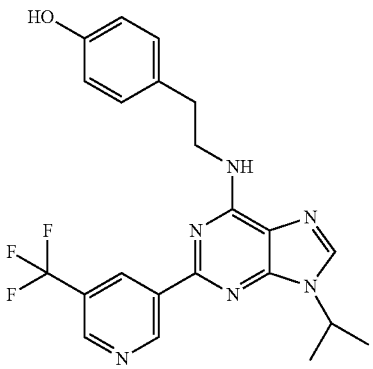 [SMILES: CC(C)n1cnc2c(NCCc3ccc(O)cc3)nc(-c3cncc(C(F)(F)F)c3)nc21] | MS m/z 443.2 (M + 1) | 0.12 |
| 130 | 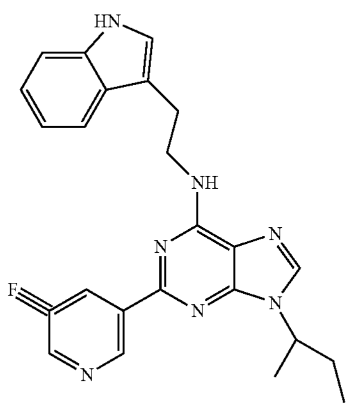 | ¹H NMR (400 MHz, DMSO): δ = 10.82 (s, 1H), 9.74 (s, 1H), 9.10 (s, 1H), 8.99 (s, 1H), 8.32 (s, 1H), 8.13 (t, 1H), 7.65 (d, 1H), 7.32 (d, 1H), 7.22 (s, 1H), 7.06 (t, 1H), 6.99 (t, 1H), 4.72-4.60 (m, 1H), 3.96-3.85 (m, 2H), 3.08 (t, 2H), 2.08-1.88 (m, 2H), 1.58 (d, 3H), 0.77 (t, 3H); MS m/z 437.2 (M + 1) | 0.001 |
| 131 | 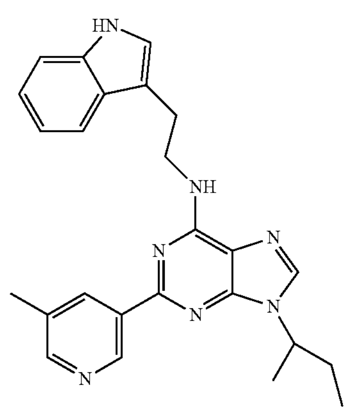 [SMILES: CCC(C)n1cnc2c(NCCc3c[nH]c4ccccc34)nc(-c3cncc(C)c3)nc21] | ¹H NMR (400 MHz, DMSO): δ = 10.83 (s, 1H), 9.40 (s, 1H), 8.97 (s, 1H), 8.76 (s, 1H), 8.35 (s, 1H), 8.18 (t, 1H), 7.62 (d, 1H), 7.33 (d, 1H), 7.23 (s, 1H), 7.06 (t, 1H), 6.97 (t, 1H), 4.72-4.60 (m, 1H), 3.96-3.82 (m, 2H), 3.10 (t, 2H), 2.53 (s, 3H), 2.09-1.89 (m, 2H), 1.58 (d, 3H), 0.77 (t, 3H); MS m/z 426.2 (M + 1) | 0.004 |

TABLE 1-continued

| Example Number | Structure | Physical Data <br> ¹H NMR and/or MS | EC$_{50}$ <br> (% CD34+) <br> μM |
|---|---|---|---|
| 131R | 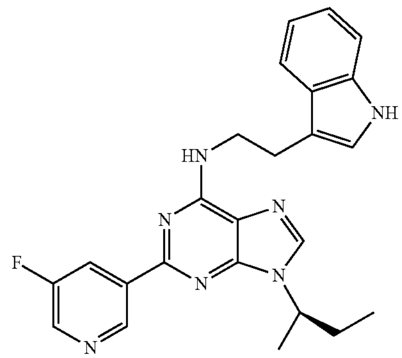 [SMILES: CC[C@@H](C)n1cnc2c(NCCc3c[nH]c4ccccc34)nc(-c3cncc(F)c3)nc21] | MS m/z 430.2 (M + 1) | 0.001 |
| 131S | 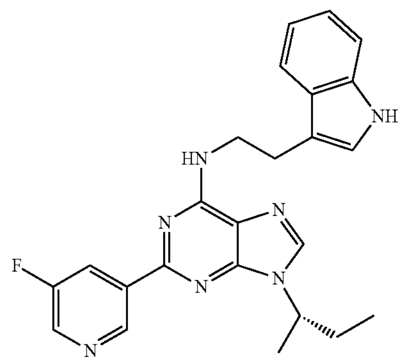 [SMILES: CC[C@H](C)n1cnc2c(NCCc3c[nH]c4ccccc34)nc(-c3cncc(F)c3)nc21] | MS m/z 430.2 (M + 1) | 0.002 |
| 132 | 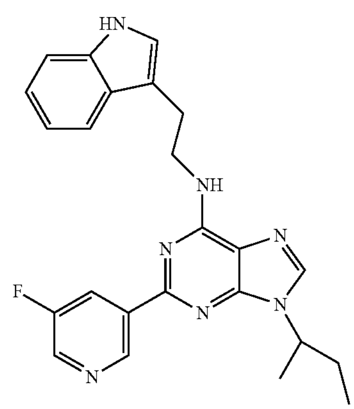 [SMILES: CCC(C)n1cnc2c(NCCc3c[nH]c4ccccc34)nc(-c3cncc(F)c3)nc21] | ¹H NMR (400 MHz, DMSO): δ = 10.83 (s, 1H), 9.42 (s, 1H), 8.66 (s, 1H), 8.41 (d, 1H), 8.31 (s, 1H), 8.09 (t, 1H), 7.64 (d, 1H), 7.34 (d, 1H), 7.22 (s, 1H), 7.07 (t, 1H), 6.97 (t, 1H), 4.68-4.60 (m, 1H), 3.92-3.84 (m, 2H), 3.08 (t, 2H), 2.08-1.90 (m, 2H), 1.58 (d, 3H), 0.77 (t, 3H); MS m/z 430.2 (M + 1) | 0.003 |
| 132R | 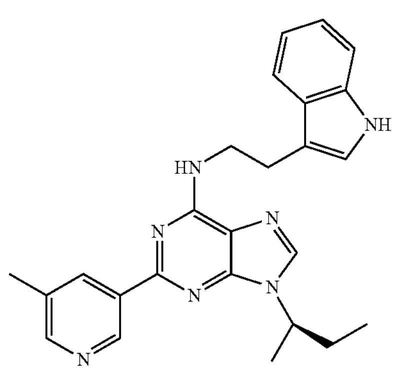 [SMILES: CC[C@@H](C)n1cnc2c(NCCc3c[nH]c4ccccc34)nc(-c3cncc(C)c3)nc21] | MS m/z 426.2 (M + 1) | 0.003 |

TABLE 1-continued

| Example Number | Structure | Physical Data $^1$H NMR and/or MS | EC$_{50}$ (% CD34+) μM |
|---|---|---|---|
| 132S | 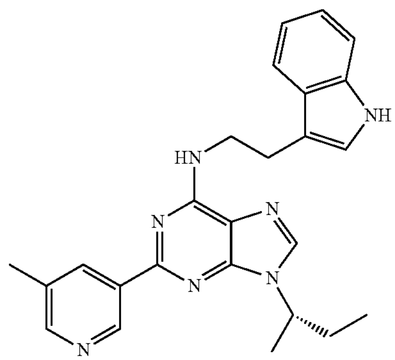 [SMILES: CC[C@H](C)n1cnc2c(NCCc3c[nH]c4ccccc34)nc(-c3cncc(C)c3)nc21] | MS m/z 426.2 (M + 1) | 0.003 |
| 133 | 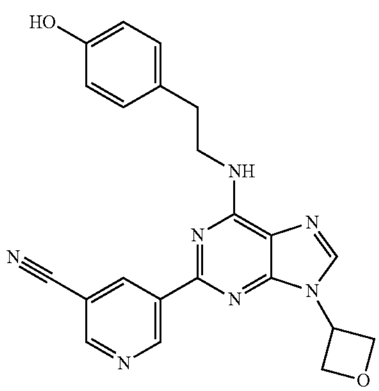 [SMILES: N#Cc1cncc(-c2nc(NCCc3ccc(O)cc3)c3ncn(C4COC4)c3n2)c1] | MS m/z 414.2 (M + 1) | 0.18 |
| 134 | 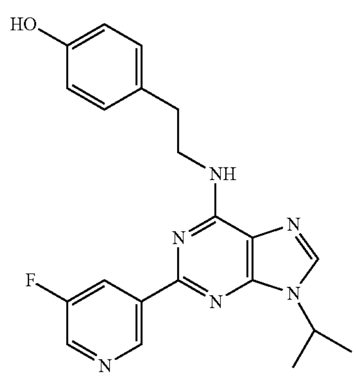 [SMILES: CC(C)n1cnc2c(NCCc3ccc(O)cc3)nc(-c3cncc(F)c3)nc21] | $^1$H NMR (400 MHz, DMSO): δ = 9.44 (s, 1H), 9.21 (s, 1H), 8.69 (d, 1H), 8.56 (t, 1H), 8.47 (d, 1H), 8.14 (s, 1H), 7.09 (d, 2H), 6.69 (d, 2H), 5.17-5.09 (m, 1H), 3.80-3.75 (m, 2H), 2.87 (t, 2H), 1.48 (d, 6H); MS m/z 393.2 (M + 1) | 0.20 |
| 135 | 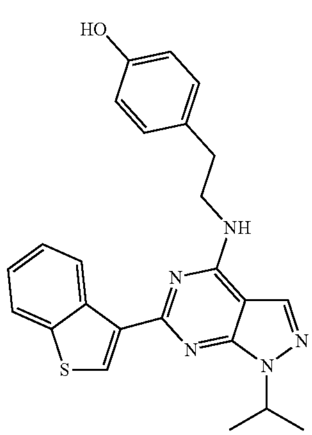 [SMILES: CC(C)n1ncc2c(NCCc3ccc(O)cc3)nc(-c3csc4ccccc34)nc21] | MS m/z 430.2 (M + 1) | 0.38 |

TABLE 1-continued

| Example Number | Structure | Physical Data $^1$H NMR and/or MS | EC$_{50}$ (% CD34+) μM |
|---|---|---|---|
| 137 | 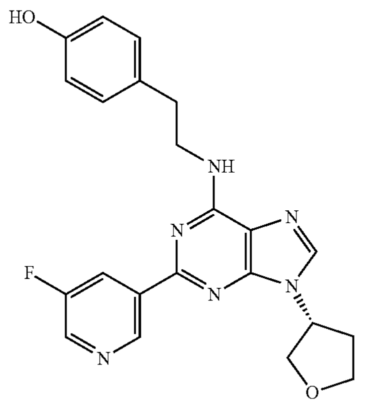 [SMILES: Oc1ccc(CCNc2nc(-c3cncc(F)c3)nc3c2ncn3[C@@H]2CCOC2)cc1] | MS m/z 421.1 (M + 1) | |
| 138 | 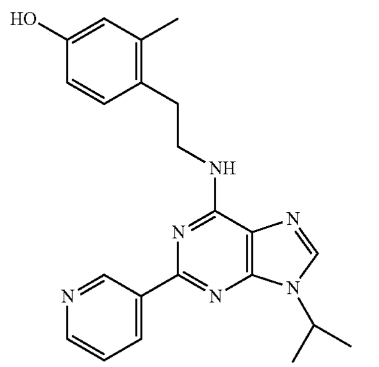 [SMILES: Cc1cc(O)ccc1CCNc1nc(-c2cccnc2)nc2c1ncn2C(C)C] | MS m/z 389.2 (M + 1) | 0.40 |
| 139 | 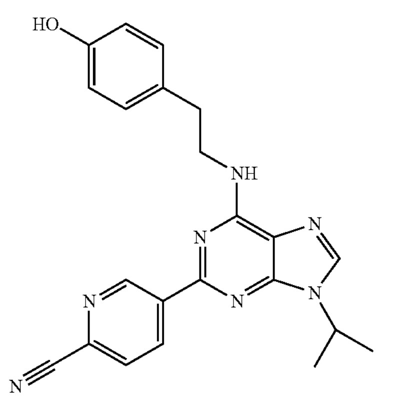 [SMILES: CC(C)n1cnc2c(NCCc3ccc(O)cc3)nc(-c3ccc(C#N)nc3)nc21] | MS m/z 400.2 (M + 1) | 1.3 |
| 140 | 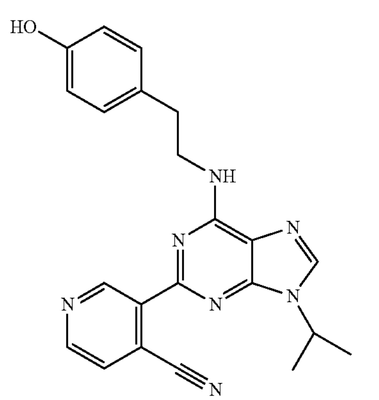 [SMILES: CC(C)n1cnc2c(NCCc3ccc(O)cc3)nc(-c3cnccc3C#N)nc21] | MS m/z 400.2 (M + 1) | 0.091 |

TABLE 1-continued

| Example Number | Structure | Physical Data $^1$H NMR and/or MS | EC$_{50}$ (% CD34+) μM |
|---|---|---|---|
| 141 | 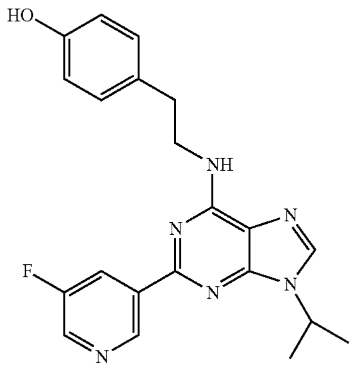 [SMILES: CC(C)n1cnc2c(NCCc3ccc(O)cc3)nc(-c3cncc(F)c3)nc21] | $^1$H NMR (400 MHz, DMSO): δ = 9.42 (s, 1H), 8.63 (d, 1H), 8.42 (d, 1H), 7.79 (t, 1H), 7.35 (d, 1H), 7.09 (d, 2H), 6.70 (d, 2H), 6.61 (d, 1H), 5.08-5.00 (m, 1H), 3.76-3.70 (m, 2H), 2.87 (t, 2H), 1.47 (d, 6H); MS m/z 392.2 (M + 1) | 0.16 |
| 143 | 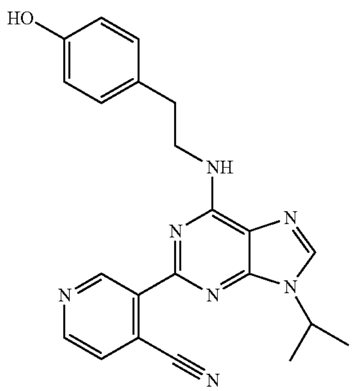 [SMILES: CC(C)n1cnc2c(NCCc3ccc(O)cc3)nc(-c3cnccc3C#N)nc21] | MS m/z 400.2 (M + 1) | 4.3 |
| 144 | 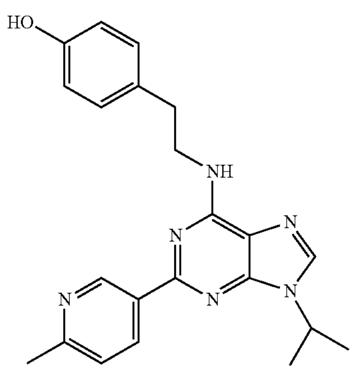 [SMILES: Cc1ccc(-c2nc(NCCc3ccc(O)cc3)c3ncn(C(C)C)c3n2)cn1] | MS m/z 389.2 (M + 1) | 0.16 |
| 145 | 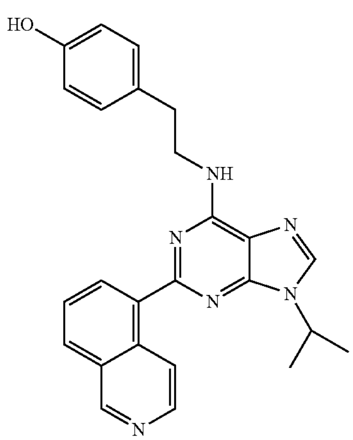 [SMILES: CC(C)n1cnc2c(NCCc3ccc(O)cc3)nc(-c3cccc4cnccc34)nc21] | MS m/z 425.2 (M + 1) | 5.4 |

TABLE 1-continued
| Example Number | Structure | Physical Data $^1$H NMR and/or MS | EC$_{50}$ (% CD34+) μM |
|---|---|---|---|
| 146 | 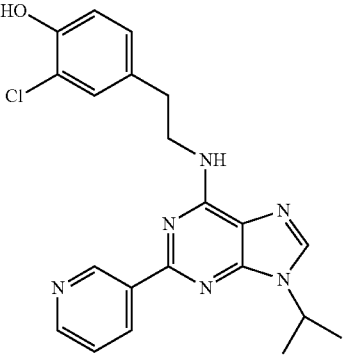 [SMILES: CC(C)n1cnc2c(NCCc3ccc(O)c(Cl)c3)nc(-c3cccnc3)nc21] | MS m/z 409.1 (M + 1) | 0.24 |
| 147 | 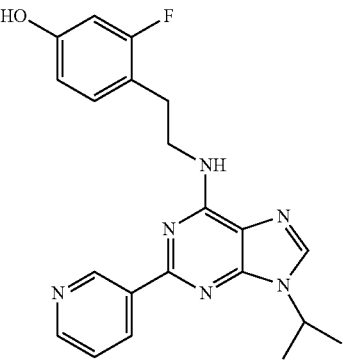 [SMILES: CC(C)n1cnc2c(NCCc3ccc(O)cc3F)nc(-c3cccnc3)nc21] | MS m/z 393.2 (M + 1) | 0.092 |
| 148 | 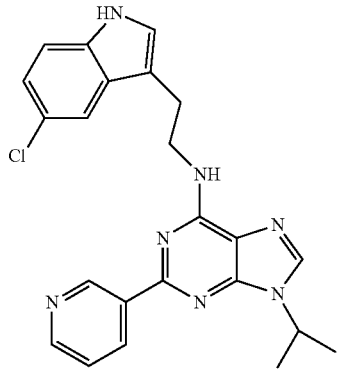 [SMILES: CC(C)n1cnc2c(NCCc3c[nH]c4ccc(Cl)cc34)nc(-c3cccnc3)nc21] | MS m/z 432.2 (M + 1) | 0.75 |
| 149 | 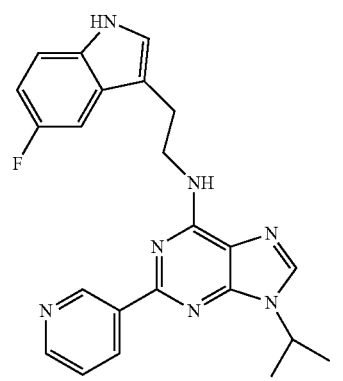 [SMILES: CC(C)n1cnc2c(NCCc3c[nH]c4ccc(F)cc34)nc(-c3cccnc3)nc21] | MS m/z 416.2 (M + 1) | 0.52 |

TABLE 1-continued
| Example Number | Structure | Physical Data $^1$H NMR and/or MS | EC$_{50}$ (% CD34+) μM |
|---|---|---|---|
| 150 | 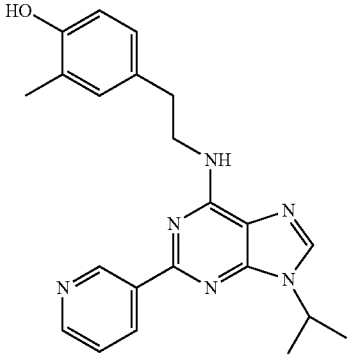 [SMILES: Cc1cc(CCNc2nc(-c3cccnc3)nc3c2ncn3C(C)C)ccc1O] | MS m/z 389.2 (M + 1) | 0.057 |
| 151 | 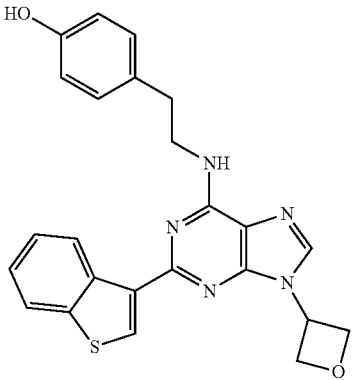 [SMILES: Oc1ccc(CCNc2nc(-c3csc4ccccc34)nc3c2ncn3C2COC2)cc1] | MS m/z 444.1 (M + 1) | 0.17 |
| 152 | 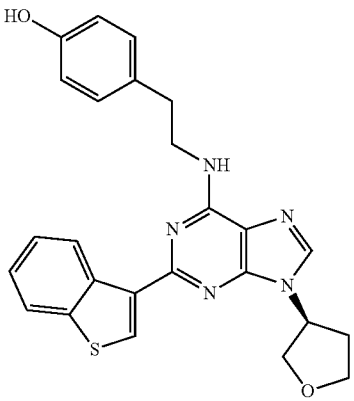 [SMILES: Oc1ccc(CCNc2nc(-c3csc4ccccc34)nc3c2ncn3[C@H]2CCOC2)cc1] | MS m/z 458.2 (M + 1) | 0.35 |
| 153 | 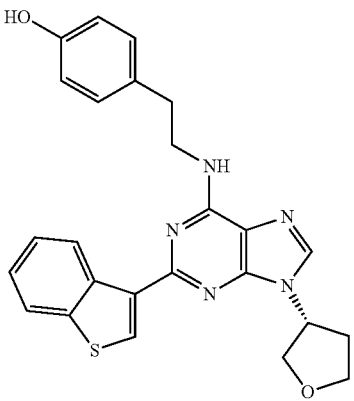 [SMILES: Oc1ccc(CCNc2nc(-c3csc4ccccc34)nc3c2ncn3[C@@H]2CCOC2)cc1] | 1H NMR (400 MHz, CD3OD): δ = 9.14 (s, 1H), 8.55 (s, 1H), 8.33 (s, 1H), 7.96 (d, 1H), 7.14 (t, 1H), 7.15 (d, 2H), 6.73 (d, 2H), 5.46-5.43 (m, 1H), 4.27-3.94 (m, 6H), 2.98 (t, 2H), 2.73-2.64 (m, 1H), 2.46-2.39 (m, 1H); MS m/z 458.2 (M + 1) | 0.22 |

TABLE 1-continued

| Example Number | Structure | Physical Data ¹H NMR and/or MS | EC$_{50}$ (% CD34+) μM |
|---|---|---|---|
| 157 | 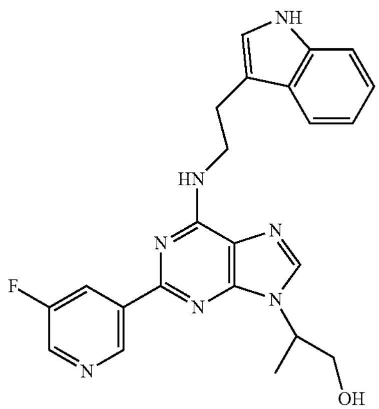 [SMILES: CC(CO)n1cnc2c(NCCc3c[nH]c4ccccc34)nc(-c3cncc(F)c3)nc21] | ¹H NMR (400 MHz, CD$_3$OD): δ = 9.40 (s, 1H), 8.53-8.48 (m, 2H), 8.23 (s, 1H), 7.65 (d, 1H), 7.31 (d, 1H), 7.11 (s, 1H), 7.08-7.04 (m, 1H), 7.01-6.97 (m, 1H), 4.08-4.03 (m, 3H), 3.94 (dd, 1H), 3.35-3.30 (m, 1H), 3.19 (t, 2H), 1.68 (d, 3H); MS m/z 432.2 (M + 1) | 0.005 |
| 157R | 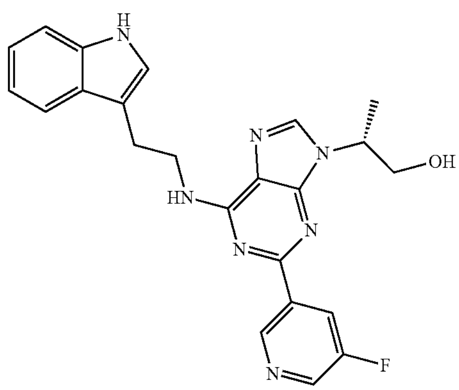 [SMILES: C[C@H](CO)n1cnc2c(NCCc3c[nH]c4ccccc34)nc(-c3cncc(F)c3)nc21] | MS m/z 432.2 (M + 1). | 0.008 |
| 157S | 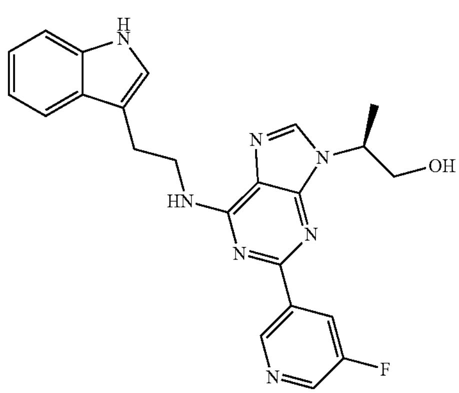 [SMILES: C[C@@H](CO)n1cnc2c(NCCc3c[nH]c4ccccc34)nc(-c3cncc(F)c3)nc21] | MS m/z 432.2 (M + 1) | 0.003 |

TABLE 1-continued

| Example Number | Structure | Physical Data ¹H NMR and/or MS | EC$_{50}$ (% CD34+) μM |
|---|---|---|---|
| 158 | 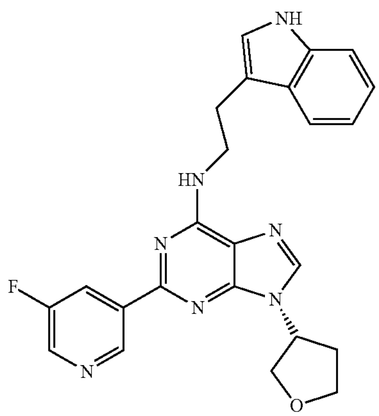 | MS m/z 444.2 (M + 1) | 0.012 |
| 159 | 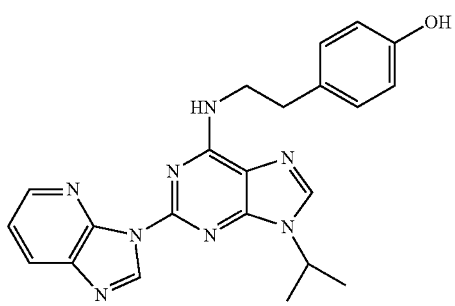 [SMILES: CC(C)n1cnc2c(NCCc3ccc(O)cc3)nc(-n3cnc4cccnc43)nc21] | MS m/z 415.2 (M + 1) | 0.59 |
| 160 | 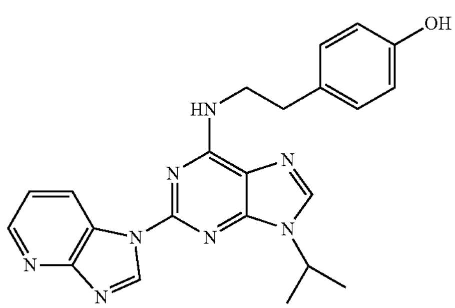 | MS m/z 415.2 (M + 1) | 1.9 |
| 161 | 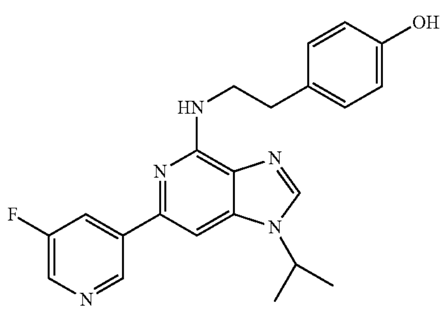 [SMILES: CC(C)n1cnc2c(NCCc3ccc(O)cc3)nc(-c3cncc(F)c3)cc21] | ¹H NMR (400 MHz, DMSO): δ = 9.11 (s, 1H), 8.64 (s, 1H), 8.51 (s, 1H), 8.30 (d, 1H), 7.74 (s, 1H), 7.09 (d, 2H), 6.69 (d, 2H), 4.88-4.76 (m, 1H), 3.88-3.78 (m, 2H), 2.88 (t, 2H), 1.56 (d, 6H); MS m/z 392.2 (M + 1) | 0.17 |

TABLE 1-continued

| Example Number | Structure | Physical Data $^1$H NMR and/or MS | EC$_{50}$ (% CD34+) μM |
|---|---|---|---|
| 162 | 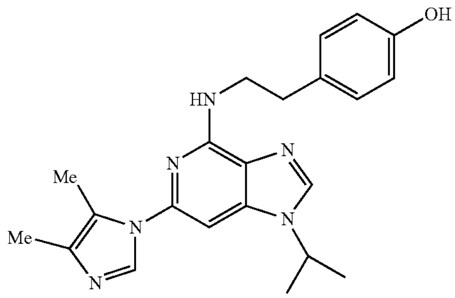 [SMILES: Cc1ncn(-c2cc3c(ncn3C(C)C)c(NCCc3ccc(O)cc3)n2)c1C] | MS m/z 392.2 (M + 1) | 0.14 |
| 166 | 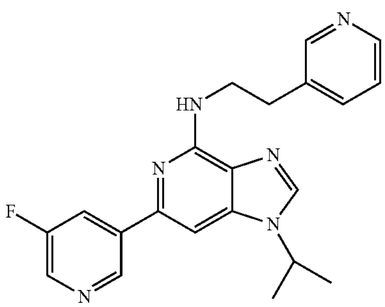 [SMILES: CC(C)n1cnc2c(NCCc3cccnc3)nc(-c3cncc(F)c3)cc21] | MS m/z 378.1 (M + 1) | 7.5 |
| 167 | 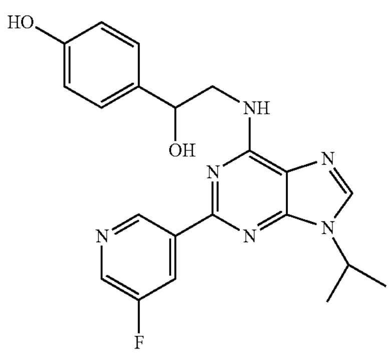 [SMILES: CC(C)n1cnc2c(NCC(O)c3ccc(O)cc3)nc(-c3cncc(F)c3)nc21] | MS m/z 409.2 (M + 1) | 0.29 |
| 169 | 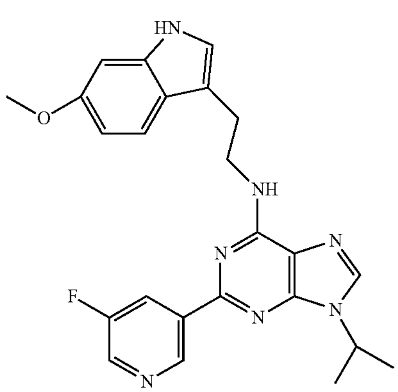 [SMILES: COc1ccc2c(CCNc3nc(-c4cncc(F)c4)nc4c3ncn4C(C)C)c[nH]c2c1] | MS m/z 446.2 (M + 1) | 0.044 |

TABLE 1-continued

| Example Number | Structure | Physical Data $^1$H NMR and/or MS | EC$_{50}$ (% CD34+) μM |
|---|---|---|---|
| 170 | 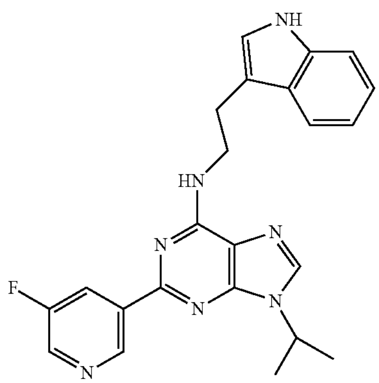 [SMILES: CC(C)n1cnc2c(NCCc3c[nH]c4ccccc34)nc(-c3cncc(F)c3)nc21] | MS m/z 416.2 (M + 1) | 0.006 |
| 172 | 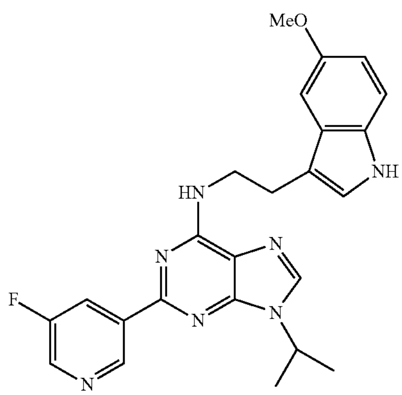 [SMILES: COc1ccc2[nH]cc(CCNc3nc(-c4cncc(F)c4)nc4c3ncn4C(C)C)c2c1] | MS m/z 446.2 (M + 1) | 0.42 |
| 173 | 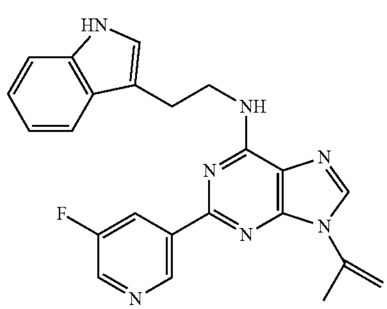 [SMILES: C=C(C)n1cnc2c(NCCc3c[nH]c4ccccc34)nc(-c3cncc(F)c3)nc21] | MS m/z 414.1 (M + 1) | 0.012 |
| 174 | 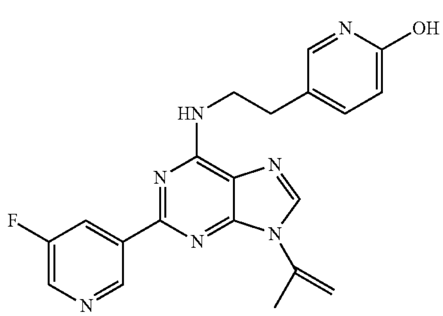 [SMILES: C=C(C)n1cnc2c(NCCc3ccc(O)nc3)nc(-c3cncc(F)c3)nc21] | MS m/z 394.2 (M + 1) | 2.2 |

TABLE 1-continued

| Example Number | Structure | Physical Data $^1$H NMR and/or MS | EC$_{50}$ (% CD34+) μM |
|---|---|---|---|
| 175 | 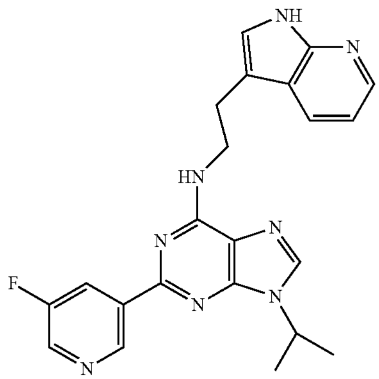 [SMILES: CC(C)n1cnc2c(NCCc3c[nH]c4ncccc34)nc(-c3cncc(F)c3)nc21] | MS m/z 417.2 (M + 1) | 0.42 |
| 176 | 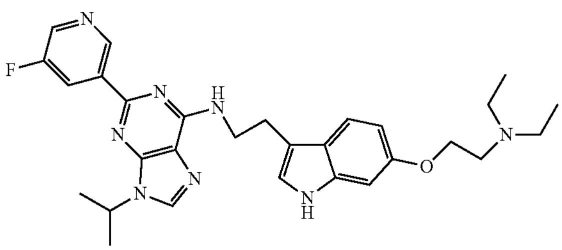 [SMILES: CCN(CC)CCOc1ccc2c(CCNc3nc(-c4cncc(F)c4)nc4c3ncn4C(C)C)c[nH]c2c1] | MS m/z 513.3 (M + 1) | 1.1 |
| 177 | 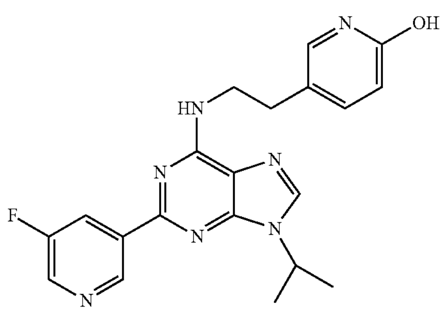 [SMILES: CC(C)n1cnc2c(NCCc3ccc(O)nc3)nc(-c3cncc(F)c3)nc21] | $^1$H NMR (400 MHz, DMSO): δ = 9.18 (s, 1H), 9.15 (s, 1H), 8.57 (d, 1H), 8.29 (d, 1H), 8.26 (s, 1H), 7.11 (d, 2H), 7.01 (s, 1H), 6.79 (t, 1H), 6.95 (d, 2H), 4.92-4.84 (m, 1H), 3.72-3.62 (m, 2H), 2.83 (t, 2H), 1.56 (d, 6H); MS m/z 392.2 (M + 1) | 0.14 |
| 178 | 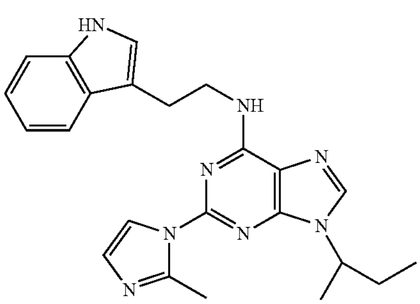 [SMILES: CCC(C)n1cnc2c(NCCc3c[nH]c4ccccc34)nc(-n3ccnc3C)nc21] | $^1$H NMR (400 MHz, DMSO): δ = 10.83 (s, 1H), 8.67 (t, 1H), 8.37 (s, 1H), 8.15 (d, 1H), 7.71 (d, 1H), 7.57 (d, 1H), 7.33 (d, 1H), 7.20 (s, 1H), 7.06 (t, 1H), 6.96 (t, 1H), 4.60-4.48 (m, 1H), 3.86-3.76 (m, 2H), 3.06 (t, 2H), 2.96 (s, 3H), 2.05-1.85 (m, 2H), 1.56 (d, 3H), 0.76 (t, 3H); MS m/z 415.2 (M + 1) | 0.003 |
| 180 | 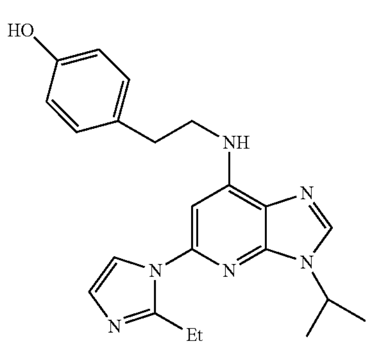 [SMILES: CCc1nccn1-c1cc(NCCc2ccc(O)cc2)c2ncn(C(C)C)c2n1] | MS m/z 392.2 (M + 1) | 0.13 |

TABLE 1-continued

| Example Number | Structure | Physical Data ¹H NMR and/or MS | EC$_{50}$ (% CD34+) μM |
|---|---|---|---|
| 181 | 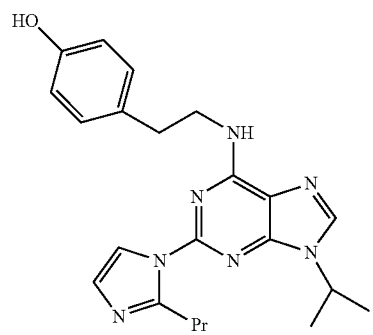 | MS m/z 406.2 (M + 1) | 2.5 |
| 182 | 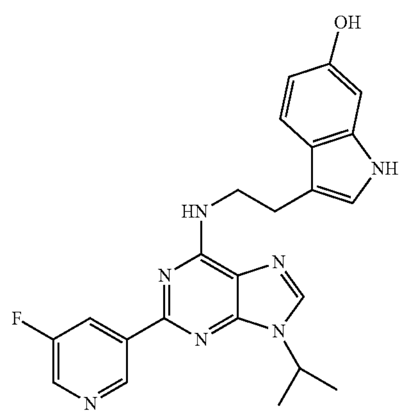 [SMILES: CC(C)n1cnc2c(NCCc3c[nH]c4cc(O)ccc34)nc(-c3cncc(F)c3)nc21] | MS m/z 432.2 (M + 1) | 5.1 |
| 183 | 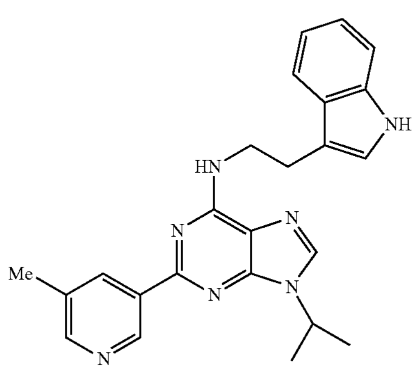 [SMILES: Cc1cncc(-c2nc(NCCc3c[nH]c4ccccc34)c3ncn(C(C)C)c3n2)c1] | ¹H NMR (400 MHz, DMSO): δ = 10.84 (s, 1H), 9.37 (s, 1H), 8.52 (s, 1H), 8.50 (s, 1H), 8.29 (s, 1H), 8.01 (t, 1H), 7.66 (d, 1H), 7.34 (d, 1H), 7.23 (m, 1H), 7.07 (t, 1H), 6.98 (t, 1H), 4.89-4.83 (m, 1H), 3.95-3.85 (m, 2H), 3.09 (t, 2H), 2.41 (s, 3H), 1.58 (d, 6H); MS m/z 412.2 (M + 1) | 0.01 |
| 184 | 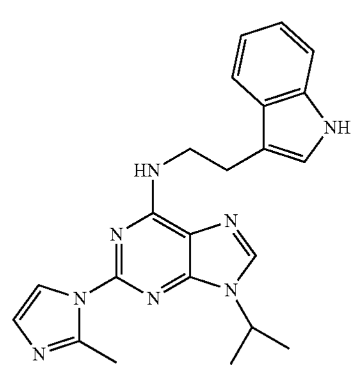 [SMILES: Cc1nccn1-c1nc(NCCc2c[nH]c3ccccc23)c2ncn(C(C)C)c2n1] | MS m/z 401.2 (M + 1) | 0.008 |

TABLE 1-continued
| Example Number | Structure | Physical Data $^1$H NMR and/or MS | EC$_{50}$ (% CD34+) μM |
|---|---|---|---|
| 185 | 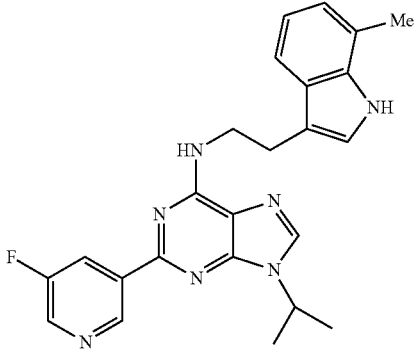 [SMILES: Cc1cccc2c(CCNc3nc(-c4cncc(F)c4)nc4c3ncn4C(C)C)c[nH]c12] | MS m/z 430.2 (M + 1) | 0.024 |
| 186 | 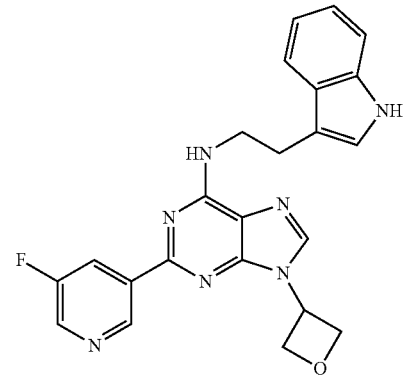 [SMILES: Fc1cncc(-c2nc(NCCc3c[nH]c4ccccc34)c3ncn(C4COC4)c3n2)c1] | MS m/z 430.2 (M + 1) | 0.007 |
| 187 | 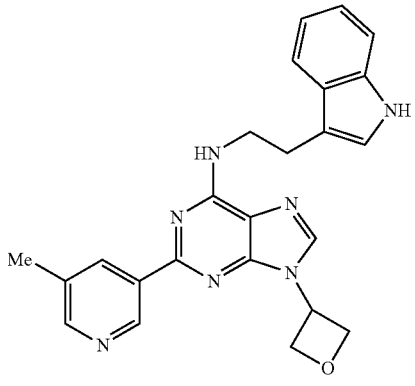 [SMILES: Cc1cncc(-c2nc(NCCc3c[nH]c4ccccc34)c3ncn(C4COC4)c3n2)c1] | $^1$H NMR (400 MHz, DMSO): δ = 10.84 (s, 1H), 9.38 (s, 1H), 8.49 (m, 1H), 8.47 (s, 1H), 8.10 (t, 1H), 7.67 (d, 1H), 7.35 (d, 1H), 7.22 (m, 1H), 7.07 (t, 1H), 6.98 (t, 1H), 5.85-5.78 (m, 1H), 5.17 (t, 2H), 5.03 (t, 2H), 3.84-3.84 (m, 2H), 3.09 (t, 2H), 2.40 (s, 3H); MS m/z 426.2 (M + 1) | 0.034 |
| 188 | 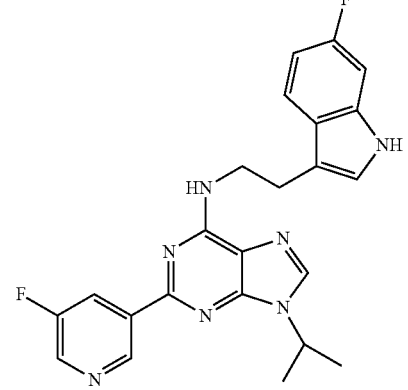 | MS m/z 434.2 (M + 1) | 0.005 |

TABLE 1-continued

| Example Number | Structure | Physical Data <sup>1</sup>H NMR and/or MS | EC<sub>50</sub> (% CD34+) μM |
|---|---|---|---|
| 189 | 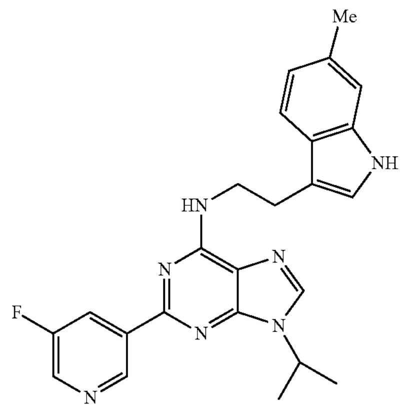 [SMILES: Cc1ccc2c(CCNc3nc(-c4cncc(F)c4)nc4c3ncn4C(C)C)c[nH]c2c1] | $^1$H NMR (400 MHz, DMSO): δ = 10.65 (s, 1H), 9.42 (s, 1H), 8.68 (m, 1H), 8.41 (d, 1H), 8.34 (s, 1H), 8.08 (t, 1H), 7.53 (d, 1H), 7.12 (m, 2H), 6.81 (d, 1H), 4.90-4.81 (m, 1H), 3.93-3.80 (m, 2H), 3.05 (t, 2H), 2.38 (s, 3H), 1.58 (d, 6H); MS m/z 432.0 (M + 1) | 0.026 |
| 190 | 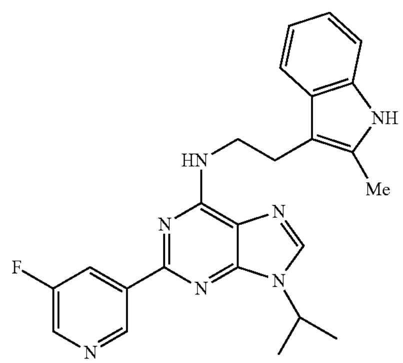 [SMILES: Cc1[nH]c2ccccc2c1CCNc1nc(-c2cncc(F)c2)nc2c1ncn2C(C)C] | $^1$H NMR (400 MHz, DMSO): δ = 10.71 (s, 1H), 9.42 (s, 1H), 8.67 (d, 1H), 8.38 (dd, 1H), 8.32 (s, 1H), 8.05 (t, 1H), 7.55 (d, 1H), 7.21 (d, 1H), 6.98 (t, 1H), 6.93 (t, 1H), 4.92-4.83 (m, 1H), 3.78-3.71 (m, 2H), 2.99 (t, 2H), 2.33 (s, 3H), 1.59 (d, 6H); MS m/z 430.2 (M + 1) | 0.005 |
| 195 | 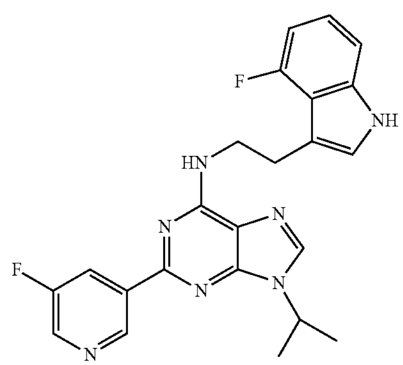 [SMILES: CC(C)n1cnc2c(NCCc3c[nH]c4cccc(F)c34)nc(-c3cncc(F)c3)nc21] | HPLC-MS calculated MS m/z 434.2 (M + 1) | 0.003 |
| 196 | 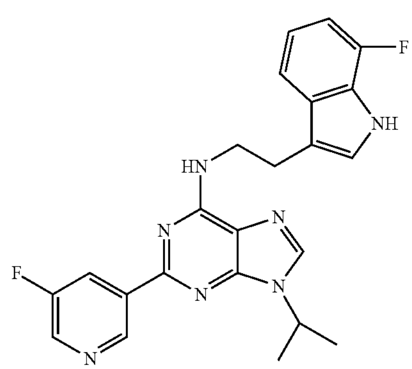 [SMILES: CC(C)n1cnc2c(NCCc3c[nH]c4c(F)cccc34)nc(-c3cncc(F)c3)nc21] | MS m/z 434.2 (M + 1) | 0.002 |

| Example Number | Structure | Physical Data $^1$H NMR and/or MS | EC$_{50}$ (% CD34+) μM |
|---|---|---|---|
| 197 | 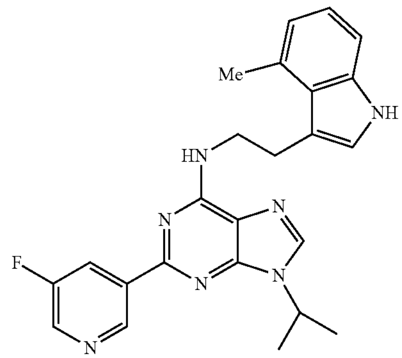 [SMILES: Cc1cccc2[nH]cc(CCNc3nc(-c4cncc(F)c4)nc4c3ncn4C(C)C)c12] | $^1$H NMR (400 MHz, DMSO): δ = 10.79 (s, 1H), 9.37 (s, 1H), 8.64 (d, 1H), 8.39 (d, 1H), 8.31 (s, 1H), 8.06 (t, 1H), 7.15 (s, 1H), 7.13 (d, 1H), 6.90 (t, 1H), 6.69 (d, 1H), 4.90-4.83 (m, 1H), 3.83-3.87 (m, 2H), 3.24 (t, 2H), 2.65 (s, 3H), 1.57 (d, 6H); MS m/z 430.2 (M + 1) | 0.011 |
| 198 | 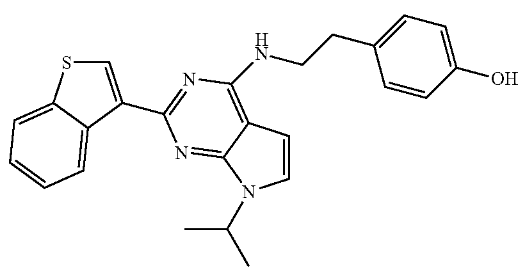 [SMILES: CC(C)n1ccc2c(NCCc3ccc(O)cc3)nc(-c3csc4ccccc34)nc21] | MS m/z 429.1 (M + 1) | 1.1 |
| 199 | 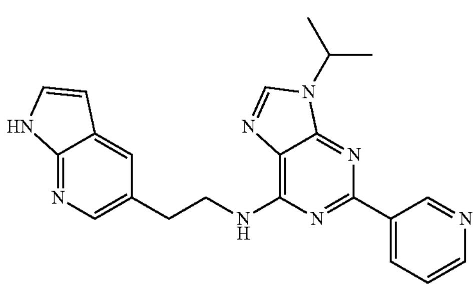 [SMILES: CC(C)n1cnc2c(NCCc3cnc4[nH]ccc4c3)nc(-c3cccnc3)nc21] | MS m/z 399.2 (M + 1) | 1.6 |
| 200 | 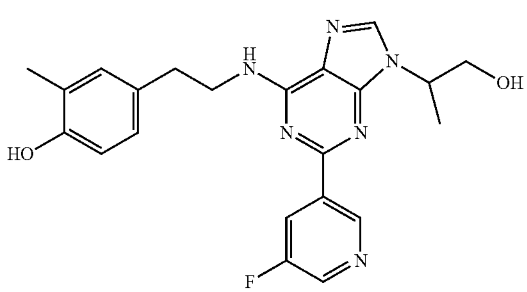 [SMILES: Cc1cc(CCNc2nc(-c3cncc(F)c3)nc3c2ncn3C(C)CO)ccc1O] | MS m/z 423.2 (M + 1) | 0.001 |

TABLE 1-continued

| Example Number | Structure | Physical Data $^1$H NMR and/or MS | $EC_{50}$ (% CD34+) μM |
|---|---|---|---|
| 201 | 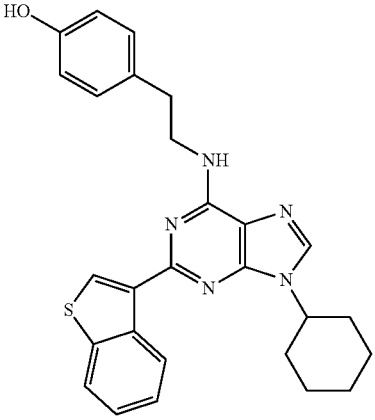 [SMILES: Oc1ccc(CCNc2nc(-c3csc4ccccc34)nc3c2ncn3C2CCCCC2)cc1] | | |
| 202 | 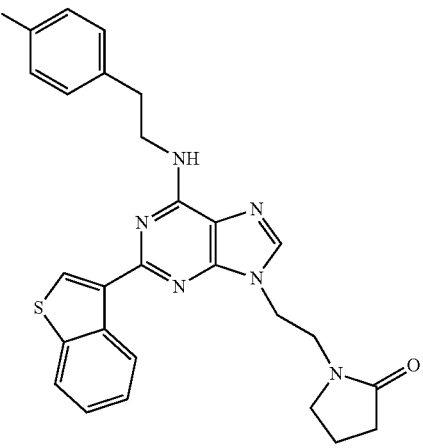 | | |
| 203 | 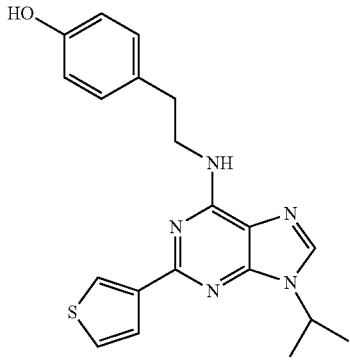 | | |

In specific embodiments, any salt of an aryl hydrocarbon receptor antagonist, disclosed in U.S. Patent Application No. 2010/0183564 or known in the art, can be used in the methods described herein. An aryl hydrocarbon receptor antagonist or a salt thereof for use in the methods described herein can be formulated in DMSO or some other suitable carrier, as described in U.S. Patent Application No. 2010/0183564 (see e.g., page 10, [0086], specifically incorporated by reference herein in its entirety) or known in the art.

In one specific embodiment, an aryl hydrocarbon receptor antagonist is not alpha-napthoflavone or 3'-methoxy-4'-nitroflavone.

In some embodiments, an aryl hydrocarbon receptor antagonist is an organic compound, for example, 2-methyl-2H-pyrazole-3-carboxylic acid (2-methyl-4-o-tolylazophenyl)amide (CH223191), alpha napthoflavone, resveratrol (Nutr. Metab. Cardiovasc. Dis., 2003 April; 13(2):104-13), 3'-methoxy-4'-nitroflavone (Biochem. Pharmacol., 2007 May 15; 73(10):1622-34, Epub 2007 Jan. 30), or 6-methyl-1,3,8-trichlorodibenzofuran (Cancer Res., 2004, April 15; 64(8):2889-97) (see pages 11-12 of U.S. Patent Publication No. 2010/0183564).

In some embodiments, an aryl hydrocarbon receptor antagonist is a compound that decreases aryl hydrocarbon receptor activity to at least 10%, 20%, 30%, 50%, 60%, 70%, 80% or at least 90% the transcriptional activity of aryl hydrocarbon receptor as observed under activated conditions. Any assay known in the art can be used to measure aryl hydrocarbon receptor inhibitory activity, e.g., the dioxin-induced aryl hydrocarbon receptor dependent luciferase reporter gene assay as described at page 12 and in the Examples of U.S. Patent Publication No. 2010/0183564. In one embodiment, an aryl hydrocarbon receptor antagonist is a compound that has an EC50 of less than 10 µM, preferably less than 5 µM (e.g., as measured in the dioxin-induced aryl hydrocarbon receptor dependent luciferase reporter gene assay).

In one embodiment, the downstream effector of an aryl hydrocarbon receptor pathway is one or more of: Cyp1B1, Cyp1A1, AHRR, β-catenin, STATS, STAT1, HES-1, c-Myc, C/EBP, PU.1, p21, P27, pRb, deoxynucleotidyl transferase, CXCR4, and CXCL12 (SDF-1). In other embodiments, the downstream effector of aryl hydrocarbon receptor pathway is one or more of: genes coding for phase I xenobiotic-metabolizing enzymes (e.g., cytochromes P450 CYP1A1, CYP1A2, CYP1B1 and CYP2S1), or genes coding for the phase II enzymes (e.g., UDP-glucuronosyltransferase UGT1A6, NAD(P)H-dependent quinone oxidoreductase-1 (NQO1), the aldehyde dehydrogenase ALDH3A1, and several glutathione-5-transferase).

In the embodiments wherein an aryl receptor antagonist is an antisense oligonucleotide capable of down-regulating the expression of aryl hydrocarbon receptor, the design of such oligonucleotides must enable specific binding of the target mRNA within cells in a way which inhibits translation, thus, inhibiting aryl hydrocarbon receptor protein expression. As described at page 12 of U.S. Patent Publication No. 2010/0183564, sequence suitable for use in design and synthesis of such antisense oligonucleotides which specifically bind to aryl hydrocarbon receptor mRNA, genomic DNA and/or its promoter or other control sequences are available, and algorithms for identifying sequences with the highest predicted binding affinity are also known.

In the embodiments wherein an aryl receptor antagonist is an siRNA molecule capable of downregulating the expression of aryl hydrocarbon receptor, synthesis of RNAi molecules can be affected as described at page 12, [0101] of U.S. Patent Publication No. 2010/0183564. Examples of siRNA molecules which are capable of down-regulating the expression of aryl hydrocarbon receptor are: AHR 111S, 5' GCG GCA TAG AGA CCG ACT TAA TTT CAA GAG AAT TAA GTC GGT CTC TAT GCC GCT TTT TTG G 3' (SEQ ID NO:1); AHR 111AS, 5' CGC GCC AAA AAA GCG GCA TAG AGA CCG ACT TAA TTC TCT TGA AAT TAA GTC GGT CTC TAT GCC GC 3' (SEQ ID NO:2); AHR 242S, 5' GGC TTC TTT GAT GTT GCA TTA ATT CAA GAG ATT AAT GCA ACA TCA AAG AAG CCT TTT TTG G 3' (SEQ ID NO:3); AHR 242AS, 5' CGC GCC AAA AAA GGC TTC TTT GAT GTT GCA TTA ATC TCT TGA ATT AAT GCA ACA TCA AAG AAG CC 3' (SEQ ID NO:4).

In some embodiments, also contemplated herein is the use of pharmaceutically acceptable acid salts and derivatives of the compounds of Formula I, i.e., salts and derivatives that retain the biological effectiveness and properties as described. Pharmaceutically acceptable salts can be formed, for example, with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

In specific embodiments, the chemical stability of a composition comprising a compound of Formula I, or a pharmaceutically acceptable salt or ester thereof, can be enhanced by any method known in the art, e.g., by addition of an alkanoic acid ester of a polyethoxylated sorbitol (a polysorbate) in an amount effective to enhance the chemical stability of the compound.

The dose of an aryl hydrocarbon receptor antagonist for use in the methods described herein can be estimated using one or more of cell culture assays described at pages 67-69 of U.S. Patent Publication No. 2010/0183564.

An aryl hydrocarbon receptor antagonist can be made using any of the methods known in the art. For example, U.S. Patent Publication No. 2010/0183564 describes processes for making the compounds of Formula I (see, e.g., pages 16-27, which are specifically incorporated by reference herein in their entireties).

Exposing HSPC to an aryl hydrocarbon receptor antagonist can be done prior to, concurrently with, or following exposure of the cells to a Notch agonist. In one embodiment, HSPC are exposed to both a Notch agonist and an aryl receptor antagonist for the entire period of ex vivo expansion of HSPC. In some embodiments, HSPC are exposed to both a Notch agonist and an aryl receptor antagonist for more than 80%, 85%, 90%, 95%, 98%, or 99% of the period of ex vivo expansion of HSPC. In another embodiment, HSPC are exposed to a Notch agonist and/or an aryl receptor antagonist for less than the entire period of ex vivo expansion of HSPC. In yet another embodiment, HSPC are exposed to a Notch agonist for the entire period of ex vivo expansion of HSPC, but are exposed to an aryl receptor antagonist for less than the entire period of ex vivo expansion (e.g., for less than 100%, 99%, 98%, 95%, 90%, 85%, 80%, 75%, 70%, 60%, or 50% of the ex vivo expansion period).

6.4 Growth Factors/Cytokines

In a preferred embodiment of the present invention, HSPC are expanded by culturing the cells in the presence of an agonist of Notch function, an aryl hydrocarbon receptor antagonist, discussed supra, and one of more growth factors or cytokines for a given period of time. In some embodiments, HSPC are cultured in the presence of two or more growth factors. In yet another embodiment, HSPC are cultured in the presence of three or more growth factors, four or more growth factors, or five or more growth factors. When expansion of HSPC without differentiation is to be achieved, HSPC are cultured in the presence of growth factors that support growth but not differentiation. The growth factor can be any type of molecule, such as a protein or a chemical compound, that promotes cellular proliferation and/or survival.

The description of growth factors provided herein is at least in part found in sec. 5.2 of U.S. Pat. No. 7,399,633, and at least in part found in U.S. Patent Publication No. U.S. 2010/0183564 (e.g., pages 13-14).

Exposing HSPC to one or more growth factors can be done prior to, concurrently with, or following exposure of the cells to a Notch agonist and/or an aryl hydrocarbon receptor antagonist. In some embodiments, HSPC are exposed to one or more growth factors for at least a portion of the time or the minimal culture time, most preferably the majority or all of the time, that HSPC are exposed to a Notch agonist and/or an aryl hydrocarbon receptor antagonist. The minimal culture time is the amount of time at which the cell would die or stop proliferating in the absence of the Notch agonist, the aryl hydrocarbon receptor antagonist and the growth factors (e.g., 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, or 25 weeks). In specific embodiments, the minimal culture time is from 3 to 4 weeks.

In specific exemplary embodiments, the growth factors present in the expansion medium include one or more of the following growth factors: stem cell factor (SCF), also known as the c-kit ligand or mast cell growth factor, Flt-3 ligand (Flt-3L), interleukin-6 (IL-6), interleukin-3 (IL-3), interleukin-7 (IL-7), interleukin-11 (IL-11), thrombopoietin (TPO), granulocyte-macrophage colony stimulating factor (GM-CSF), granulocyte colony stimulating factor (G-CSF), angiopoietin-like proteins (Angptls) (Angptl2, Angptl3, Angptl5, Angptl7, and Mfap4), insulin growth factor-2 (IFG-2), and fibroblast growth factor-1 (FGF-1).

In some embodiments, the growth factors present in the expansion medium include one or more of the following growth factors: IL-1, IL-3, IL-6, IL-11, G-CSF, GM-CSF, SCF, FlT3-L, TPO, erythropoietin and analogs thereof (wherein the analogs include any structural variants of the growth factors having the biological activity of the naturally occurring growth factor and cytokine receptor agonists, e.g., agonist antibody against the TPO receptor such as VB22B sc(Fv)2 described in WO 2007/145227) (see page 13 of U.S. Patent Publication No. 2010/0183564). In one embodiment, SCF, Flt3-L and TPO are used in the expansion methods provided herein. In another embodiment, IL-6, SCF, Flt3-L and TPO are used in the expansion methods provided herein. In some embodiments, one or more growth factors (e.g., TPO) are used in a serum-free medium.

The amount of SCF, Flt-3L, IL-6, or TPO can be in the range of 5-1000 ng/ml, more preferably about 25-250 ng/ml or about 25-100 ng/ml, most preferably about 50-100 ng/ml. In certain specific embodiments, the amount of SCF, Flt-3L, IL-6, or TPO is 25, 30, 50, 100, 125, 150, 175, 200, 225, 250, 275, 300, 325, 350, 375, 400, 425 or 450 ng/ml. The amount of IL-3, IL-11, G-CSF, or GM-CSF can be in the range of 2-100 ng/ml, more preferably about 5-50 ng/ml, more preferably about 7.5-25 ng/ml or about 5-15 ng/ml, most preferably about 10-15 ng/ml. In certain specific embodiments, the amount of 11-3, IL-11, G-CSF, or GM-CSF is 5, 6, 7, 8, 9, 10, 12.5, or 15 ng/ml. In one embodiment, one or more growth factors are added to HSPC in serum free medium.

The amount or concentration of growth factors suitable for expanding HSPC of the present invention will depend on the activity of the growth factor preparation, and the species correspondence between the growth factors and HSPC, etc. Generally, when the growth factor(s) and HSPC are of the same species, the total amount of growth factor in the culture medium ranges from 1 ng/ml to 5 µg/ml, more preferably from 5 ng/ml to 1 µg/ml, and most preferably from about 5 ng/ml to 250 ng/ml. In one embodiment, HSPC are expanded by exposing HSPC to a Notch agonist, an aryl hydrocarbon receptor antagonist, and 50 ng/ml or 100 ng/ml of SCF. In another embodiment, HSPC are expanded by exposing the HSPC to a Notch agonist, an aryl hydrocarbon receptor antagonist, and 50 ng/ml or 100 ng/ml of each of Flt-3L, IL-6, TPO and SCF. In yet another embodiment, HSPC are expanded by exposing the HSPC to a Notch agonist, an aryl hydrocarbon receptor antagonist, 50 ng/ml or 100 ng/ml of each of Flt-3L, IL-6, TPO and SCF, and 10 ng/ml of IL-11 or IL-3.

In some embodiments, the amount or concentration of growth factors suitable for expanding HSPC of the present invention is the amount or concentration effective to promote proliferation of HSPC but substantially no differentiation of HSPC.

In a preferred embodiment for expanding HSPC, the cells are cultured in a tissue culture dish onto which an extracellular matrix protein is bound. In a preferred mode of the embodiment, the extracellular matrix protein is fibronectin (FN), or a fragment thereof. Such a fragment can be but is not limited to CH-296 (Dao et al., 1998, Blood 92(12):4612-21) or RetroNectin® (a recombinant human fibronectin fragment) (Clontech Laboratories, Inc., Madison, Wis.). In certain embodiments to the foregoing culture conditions, fibronectin is excluded from the tissue culture dishes or is replaced by another extracellular matrix protein. See also U.S. Pat. No. 7,399,633 to Bernstein et al. for additional exemplary culture conditions for HSPC expansion.

In a specific embodiment for expanding HSPC of the present invention, the cells are cultured on a plastic tissue culture dish containing immobilized Delta ligand, e.g., the extracellular domain of Delta, and fibronectin in the presence of an aryl hydrocarbon receptor antagonist, and about 25 ng/ml or about 100 ng/ml (or any range in between these values), and preferably about 50 ng/ml, of each of SCF and TPO. In another specific embodiment for expanding HSPC of the present invention, the cells are cultured on a plastic tissue culture dish containing immobilized Delta ligand and fibronectin in the presence of an aryl hydrocarbon receptor antagonist, and about 25 ng/ml or about 100 ng/ml (or any range in between these values), and preferably about 50 ng/ml of each of SCF and Flt-3L. In another specific embodiment for expanding HSPC, the cells are cultured on a plastic tissue culture dish containing immobilized Delta ligand and fibronectin in the presence of an aryl hydrocarbon receptor antagonist, and about 25 ng/ml or about 100 ng/ml (or any range in between these values), and preferably about 50 ng/ml, of each of SCF, Flt-3L and TPO. In another specific embodiment for expanding HSPC, the cells are cultured on a plastic tissue culture dish containing immobilized Delta ligand and fibronectin in the presence of an aryl hydrocarbon receptor antagonist, and about 25 ng/ml or about 100 ng/ml (or any range in between these values), and preferably about 50 ng/ml, of each of SCF, Flt-3L, TPO and IL-6. In some of these embodiments, the HSPC are cultured further in the presence of about 5 to 15 ng/ml, and preferably about 10 ng/ml of IL-3. While in other embodiments, the HSPC are cultured further in the presence of about 5 to 15 ng/ml, and preferably about 10 ng/ml, GM-CSF. In some embodiments, the one or more growth factors used in compositions and methods described herein is not GM-SCF or IL-7. In some alternative embodiments, fibronectin is excluded from the tissue culture dishes or is replaced by another extracellular matrix protein.

Where differentiation of HSPC is desired, HSPC (e.g., enriched HSPC or expanded HSPC) can be exposed to one or more growth factors that promote differentiation. The growth factors and cell culture conditions that promote differentiation are known in the art (see, e.g., U.S. Pat. No. 7,399,633 at Section 5.2 and Section 5.5, the disclosures of which are specifically incorporated by reference herein in their entireties). For example, SCF can be used in combination with GM-SCF or IL-7 to differentiate HSPC (e.g., expanded HSPC) into myeloid stem/progenitor cells or lymphoid stem/progenitor cells, respectively. In specific embodiments, HSPC can be differentiated into a lymphoid stem/progenitor cell by exposing HSPC to about 100 ng/ml of each of SCF and IL-7. In other embodiments, HSPC can be differentiated into a myeloid stem/progenitor cell by exposing HSPC to about 100 ng/ml of each of SCF and GM-SCF. In some embodiments, a retinoic acid receptor (RAR) agonist, or preferably all trans retinoic acid (ATRA) is used to promote the differentiation of HSPC (e.g., expanded HSPC). In certain embodiments, HSPC (e.g., expanded HSPC) are differentiated before engraftment/in vivo repopulation (i.e., before administration of Expanded HSPC to the patient).

The growth factors utilized by the methods of the invention can be obtained commercially, produced by recombinant expression, or chemically synthesized. For example, Flt-3L (human), IGF-1 (human), IL-6 (human and mouse), IL-11 (human), SCF (human), TPO (human and murine) can be purchased from Sigma (St. Louis, Mo.). IL-6 (human and murine), IL-7 (human and murine), and SCF (human) can be purchased from Life Technologies, Inc. (Rockville, Md.).

In other embodiments, the growth factors are produced by recombinant expression or by chemical peptide synthesis (e.g. by a peptide synthesizer). Methods that can be used for recombinantly expressing the growth factors are described in, e.g., sec. 5.3 of U.S. Pat. No. 7,399,633, which is specifically incorporated herein by reference in its entirety. Growth factor nucleic acid and peptide sequences are generally available from GenBank.

Preferably, but not necessarily, the growth factor(s) used to expand HSPC in the presence of a Notch agonist and an aryl hydrocarbon receptor antagonist by the methods of the invention is derived from the same species as HSPC.

6.5 Hematopoietic Stem/Progenitor Cells

U.S. Pat. No. 7,399,633 describes hematopoietic stem/progenitor cells (HSPC) that can be used in the methods described herein (see sections 5.4 and 5.4.1, specifically incorporated by reference herein in their entireties). U.S. Pat. No. 7,399,633 also describes hematopoietic cell markers (see section 5.4.1.1, specifically incorporated by reference herein in its entirety). The above-identified sections of U.S. Pat. No. 7,399,633 also describe isolation, separation and enrichment of HSPC (and, thus, specifically incorporated herein to supply such disclosures). Contemplated herein are compositions and methods for isolation, separation and enrichment of HSPC in accordance with the teachings of U.S. Pat. No. 7,399,633 and/or using other methods known in the art. Further, U.S. Patent Publication No. 2010/0183564 describes hematopoietic stem/progenitor cells (HSPC) that can be used in the methods described herein and their isolation, separation, enrichment and expansion (see section "Utility" and "Methods for Expanding Hematopoietic Cells" at pages 10-13, specifically incorporated by reference herein in their entireties). Compositions and methods that can be used for isolation, separation and enrichment of HSPC are also described hereinbelow.

Sources of HSPC include but are not limited to: umbilical cord blood, placental blood, peripheral blood (e.g., mobilized peripheral blood), bone marrow (e.g., from femurs, hips, ribs, sternum and other bones), embryonic cells (including embryonic stem cells), aortal-gonadal-mesonephros derived cells, lymph, liver (e.g., fetal liver), thymus, and spleen. Sources of HSPC further include fetal blood, neonatal blood (from an infant in the first 28 days after birth), blood from an infant under 12 months of age, blood from a toddler between 1 year and 3 years of age, blood form a child between 3 and 18 years of age, and adult blood (i.e., derived from a subject who is older than 18 years of age).

HSPC can be collected from any species, including without limitation, any vertebrate, preferably any mammal (such as a human, a primate, a mouse, a rat, a rabbit, a guinea pig, a dog, a cat, a horse, a cow, a pig, a sheep, a goat, etc.). In a preferred embodiment, HSPC are collected from one or more humans. In one embodiment, HSPC are obtained from a tissue of a patient to whom they are to be administered after expansion (and, optionally, differentiation). Collection of cord blood is described in further detail in the section below. Methods that can be used for collection of HSPC from bone marrow, peripheral blood and/or other sources can be any of the methods known in the art.

HSPC from bone marrow can be obtained, e.g., directly from bone marrow from the posterior iliac crest by needle aspiration (see, e.g., Kodo et al., 1984, J. Clin Invest. 73:1377-1384), or from the blood following pre-treatment with cytokines (such as G-CSF) that induce cells to be released from the bone marrow compartment.

HSPC from peripheral blood can be collected from the blood through a syringe or catheter inserted into a patient's vein. For example, the peripheral blood can be collected using an apheresis machine. Blood flows from the vein through the catheter into an apheresis machine, which separates the stem cells from the rest of the blood and then returns the blood to the patient's body. Apheresis can be performed for several days (e.g., 1 to 5 days) until enough stem cells have been collected.

Peripheral blood is preferably mobilized prior to its collection. Peripheral blood can be mobilized by any method known in the art. Peripheral blood can be mobilized by treating the subject from whom HSPC are to be collected with any agent(s), described herein or known in the art, that increase the number of HSPC circulating in the peripheral blood of a subject. For example, in some embodiments, peripheral blood is mobilized by treating the subject from whom HSPC are to be collected with one or more cytokines or growth factors (e.g., G-CSF, kit ligand (KL), IL-1, IL-7, IL-8, IL-11, Flt3 ligand, SCF, thrombopoietin, or GM-CSF (such as sargramostim)). Different types of G-CSF that can be used in the methods for mobilization of peripheral blood include, without limitation, filgrastim and longer acting G-CSF-pegfilgrastim. In certain embodiments, peripheral blood is mobilized by treating the subject from whom HSPC are to be collected with one or more chemokines (e.g., macrophage inflammatory protein-1α (MIP1α/CCL3)), chemokine receptor ligands (e.g., chemokine receptor 2 ligands GROβ and GROβ$_{A4}$), chemokine receptor analogs (e.g., stromal cell derived factor-1α (SDF-1α) peptide analogs such as CTCE-0021 and CTCE-0214, or SDF-1α analog such as Met-SDF-1β), or chemokine receptor antagonists (e.g., chemokine (C—X—C motif) receptor 4 (CXCR4) antagonists such as AMD3100). In some embodiments, peripheral blood is mobilized by treating the subject from whom HSPC are to be collected with one or more anti-integrin signaling agents (e.g., function blocking anti-very late antigen 4 (VLA-4) antibody, or anti-vascular cell adhesion molecule 1 (VCAM-1)). In other embodiments, peripheral blood is mobilized by treating the subject from whom HSPC are to be collected with one or more cytotoxic drugs such as cyclophosphamid, etoposide or paclitaxel. In particular, peripheral blood can be mobilized by administering to a subject one or more of the agents listed above for a certain period of time. For example, the subject can be treated with one or more agents (e.g., G-CSF) via injection (e.g., subcutaneous, intravenous or intraperitoneal), once daily or twice daily, for 1, 2, 3, 4, 5, 6, 7, 8, 9, 10, 11, 12, 13 or 14 days prior to collection of HSPC. In specific embodiments, HSPC are collected within 1, 2, 3, 4, 5, 6, 7, 8, 12, 14, 16, 18, 20 or 24 hours after the last dose of an agent used for mobilization of peripheral blood. In some embodiments, peripheral blood is mobilized by treating the subject from whom HSPC are to be collected with two or more different types of agents described above or known in the art, such as a growth factor (e.g., G-CSF) and a chemokine receptor antagonist (e.g., CXCR4 receptor antagonist such as AMD3100), or a growth factor (e.g., G-CSF or KL) and an anti-integrin agent (e.g., function blocking VLA-4 antibody). In particular embodiments, different types of mobilizing agents are administered concurrently or sequentially. Methods of mobilization of peripheral blood are known in the art (see, e.g., Craddock et al., 1997, Blood 90(12):4779-4788; Jin et al., 2008, Journal of Translational Medicine 6:39; Pelus, 2008, Curr. Opin. Hematol. 15(4):285-292; Papayannopoulou et al., 1998, Blood 91(7): 2231-2239; Tricot et al., 2008, Haematologica 93(11):1739-1742; Weaver et al., 2001, Bone Marrow Transplantation 27(2):S23-S29).

In one aspect, HSPC used in the methods described herein can be collected from a single human. In another aspect, HSPC used in the methods described herein can be collected from two or more humans. In some aspects, HSPC used in the methods described herein are collected from a single human at birth or not more than two humans at birth. In one embodiment, one or more HSPC samples (from one, two or more humans) can be pooled prior to enriching for HSPC, prior to expansion of HSPC, and/or prior to engraftment of the expanded HSPC. In another embodiment, individual HSPC samples (from one, two or more humans) can be pooled after enriching for HSPC, and/or after expansion of such HSPC. In specific embodiments, the number of HSPC samples that are pooled is 2, 3, 4, 5, 6, 7, 8, 9, 10, 15, 20, 25, 30, 35, or 40, or at least any of the foregoing numbers, or no more than 2, 3, 4, 5, 10, 15 or 20 HSPC samples, respectively. In some embodiments, the HSPC samples are pooled without regard to the HLA type of the HSPC. In some embodiments, the HSPC samples (e.g., one or more HSPC samples from one, two or more humans) are for administration to a patient without regard to the HLA type of the HSPC or without HLA matching. In a specific embodiment, the Expanded HSPC are administered to a patient without regard to the HLA type of the HSPC or without HLA matching. In certain embodiments, the samples in the pool are derived from HSPC from individuals of the same race, e.g., African-American, Caucasian, Asian, Hispanic, Native-American, Australian Aboriginal, Inuit, Pacific Islander, or derived from HSPC from individuals of the same ethnicity, e.g., Irish, Italian, Indian, Japanese, Chinese, Russian, etc.

6.6 Collecting Umbilical Cord Blood or Placental Blood

Sources of HSPC include human umbilical cord blood and/or human placental blood. Such blood can be obtained by any method known in the art. The use of cord or placental blood as a source of CB Stem Cells provides numerous advantages, including that the cord and placental blood can be obtained easily and without trauma to the donor. See, e.g., U.S. Pat. No. 5,004,681 for a discussion of collecting cord and placental blood at the birth of a human. In one embodiment, cord blood collection is performed by the method disclosed in U.S. Pat. No. 7,147,626 to Goodman et al.

Collections should be made under sterile conditions. Immediately upon collection, cord or placental blood should be mixed with an anticoagulant. Such an anticoagulant can be any known in the art, including but not limited to CPD (citrate-phosphate-dextrose), ACD (acid citrate-dextrose), Alsever's solution (Alsever et al., 1941, N.Y. St. J. Med. 41:126), De Gowin's Solution (De Gowin, et al., 1940, J. Am. Med. Ass. 114:850), Edglugate-Mg (Smith, et al., 1959, J. Thorac. Cardiovasc. Surg. 38:573), Rous-Turner Solution (Rous and Turner, 1916, J. Exp. Med. 23:219), other glucose mixtures, heparin, ethyl biscoumacetate, etc. See, generally, Hurn, 1968, Storage of Blood, Academic Press, New York pp. 26-160) In one embodiment, ACD can be used.

The cord blood can preferably be obtained by direct drainage from the cord and/or by needle aspiration from the delivered placenta at the root and at distended veins. See, generally, U.S. Pat. No. 5,004,681. Preferably, the collected human cord blood and/or placental blood is free of contamination.

In certain embodiments, HSPC are obtained from the fetal blood from the fetal circulation at the placental root with the use of needle guided ultrasound, by placentocentisis, or by fetoscopy as described in sec. 5.4.5 of U.S. Pat. No. 7,399,633. In specific embodiments, HSPC are obtained from Wharton's jelly as described in sec. 5.4.5 of U.S. Pat. No. 7,399,633.

In certain embodiments, the following tests on the collected blood sample can be performed either routinely, or where clinically indicated:

(i) Bacterial culture: To ensure the absence of microbial contamination, established assays can be performed, such as routine hospital cultures for bacteria under aerobic and anaerobic conditions.

(ii) Diagnostic screening for pathogenic microorganisms: To ensure the absence of specific pathogenic microorganisms, various diagnostic tests can be employed. Diagnostic screening for any of the numerous pathogens transmissible through blood can be done by standard procedures. As one example, the collected blood sample (or a maternal blood sample) can be subjected to diagnostic screening for the presence of Human Immunodeficiency Virus-1 or 2 (HIV-1 or HIV-2). Any of numerous assay systems can be used, based on the detection of virions, viral-encoded proteins, HIV-specific nucleic acids, antibodies to HIV proteins, etc. The collected blood can also be tested for other infectious diseases, including but not limited to human T-Cell lymphotropic virus I and II (HTLV-I and HTLV-II), Hepatitis B, Hepatitis C, Cytomegalovirus, Syphilis, West Nile Virus.

Preferably, prior to collection of the cord blood, maternal health history is determined in order to identify risks that the cord blood cells might pose in transmitting genetic or infectious diseases, such as cancer, leukemia (e.g., acute myeloid leukemia), immune disorders, neurological disorders, hepatitis or AIDS. The collected cord blood samples can undergo testing for one or more of cell viability, HLA typing, ABO/Rh typing, CD34$^+$ cell count, and total nucleated cell count.

In one aspect, umbilical cord blood or placental blood for use in the methods described herein can be collected from a single human at birth. In another aspect, umbilical cord blood or placental blood for use in the methods described herein can be collected from two or more humans. In one embodiment, one or more umbilical cord blood and/or placental blood samples can be pooled prior to enriching for CB HSPC, prior to expansion of such samples, and/or prior to engraftment of expanded samples of umbilical cord blood and/or placental blood. In another embodiment, individual umbilical cord blood and/or placental blood samples can be pooled after enriching for HSPC, and/or after expansion of such cells. In specific embodiments, the number of umbilical cord blood and/or placental blood samples, or CB Stem Cell samples, that are pooled is 2, 3, 4, 5, 6, 7, 8, 9, 10, 15, 20, 25, 30, 35, or 40, or at least any of the foregoing numbers, or no more than 3, 5, 10, 20 or 25, umbilical cord blood and/or placental blood samples, or CB Stem Cell samples, respectively. In one embodiment, the umbilical cord blood and/or placental blood samples or CB Stem Cell samples are pooled without regard to the HLA type of the hematopoietic stem/progenitor cells. In some embodiments, the umbilical cord blood and/or placental blood samples or CB Stem Cell samples (e.g., one or more samples from one, two or more humans) are for administration to a patient without regard to the HLA type of the HSPC or without HLA matching. In a specific embodiment, the Expanded HSPC, obtained from umbilical cord blood or placental blood using the methods described herein, are administered to a patient without regard to the HLA type of the HSPC or without HLA matching. In certain embodiments, the samples in the pool are derived from the umbilical cord blood and/or placental blood of individuals of the same race, e.g., African-American, Caucasian, Asian, Hispanic, Native-American, Australian Aboriginal, Inuit, Pacific Islander, or derived from umbilical cord blood and/or placental blood of individuals of the same ethnicity, e.g., Irish, Italian, Indian, Japanese, Chinese, Russian, etc.

6.7 Enrichment of HSPC

Once HSPC are isolated or collected, the blood is processed to produce an enriched hematopoietic stem and progenitor cell population. Enriched HSPC produced from umbilical cord blood or placental blood form a population of CB Stem Cells.

The hematopoietic stem/progenitor cells can be positive for a specific marker expressed in increased levels on the hematopoietic stem/progenitor cells relative to other types of hematopoietic cells. For example, such markers can be, but are not limited to, CD34, CD43, CD45RO, CD45RA, CD59, CD90, CD109, CD117, CD133, CD166, HLA DR, or a combination thereof. The hematopoietic stem/progenitor cells also can be negative for a specific marker relative to other types of hematopoietic cells. For example, such markers can be, but are not limited to, Lin, CD38, or a combination thereof. Preferably, the hematopoietic stem/progenitor cells are $CD34^+$ cells. Preferably, the Enriched HSPC are enriched in $CD34^+$ stem/progenitor cells (and, thus, T cell depleted). Enrichment thus refers to a process wherein the percentage of hematopoietic stem/progenitor cells in the sample is increased (relative to the percentage in the sample before the enrichment procedure). Purification is one example of enrichment. In certain embodiments, the increase in the number of $CD34^+$ cells (or other suitable antigen-positive cells) as a percentage of cells in the enriched sample, relative to the sample prior to the enrichment procedure, is at least 25-, 50-, 75-, 100-, 150-, 200-, 250-, 300-, 350-fold, and preferably is 100-200 fold. In a preferred embodiment, the $CD34^+$ cells are enriched using a monoclonal antibody to CD34, which antibody is conjugated to a magnetic bead, and a magnetic cell separation device to separate out the $CD34^+$ cells. In some embodiments, using anti-CD34 antibodies, HSPC are enriched from 1-2% of a normal bone marrow cell population to approximately 50-80% of the population, as described in sec. 5.4.1.1 of U.S. Pat. No. 7,399,633.

In certain embodiment, prior to processing for enrichment, the collected HSPC sample (derived, e.g., from peripheral blood, bone marrow, umbilical cord blood, or placental blood) is fresh and has not been previously cryopreserved. In one embodiment, prior to processing for enrichment, the collected cord and/or placental blood is fresh and has not been previously cryopreserved. In other embodiments, prior to processing for enrichment, the collected HSPC sample has been cryopreserved and thawed.

Any technique known in the art for cell separation/selection can be used to carry out the enrichment for hematopoietic stem/progenitor cells. For example, methods which rely on differential expression of cell surface markers can be used. For example, cells expressing the cell surface marker CD34 can be positively selected using a monoclonal antibody to CD34, such that cells expressing CD34 are retained, and cells not expressing CD34 are not retained. Moreover, the separation techniques employed should maximize the viability of the cell to be selected. The particular technique employed will depend upon efficiency of separation, cytotoxicity of the methodology, ease and speed of performance, and necessity for sophisticated equipment and/or technical skill.

Procedures for separation may include magnetic separation, using antibody-coated magnetic beads; fluorescence activated cell sorting (FACS); affinity chromatography; cytotoxic agents joined to a monoclonal antibody or used in conjunction with a monoclonal antibody, e.g., complement and cytotoxins; and "panning" with antibody attached to a solid matrix, e.g., plate, or other convenient technique. Techniques providing accurate separation/selection include fluorescence activated cell sorters, which can have varying degrees of sophistication, e.g., a plurality of color channels, low angle and obtuse light scattering detecting channels, impedance channels, etc.

The antibodies may be conjugated with markers, such as magnetic beads, which allow for direct separation, biotin, which can be removed with avidin or streptavidin bound to a support, fluorochromes, which can be used with a fluorescence activated cell sorter, or the like, to allow for ease of separation of the particular cell type. Any technique may be employed which is not unduly detrimental to the viability of the remaining cells.

In one embodiment, the enrichment of HSPC is affected by contacting an HSPC sample with a solid substrate (e.g., beads, flask, magnetic particles) to which antibodies are bound, and by removing any unbound cells, wherein the Enriched HSPC can be found either in the cells bound to the solid substrate or in the unbound cells depending on the antibodies used.

In one embodiment of the present invention, an HSPC sample (e.g., a fresh cord blood unit) is processed to select for, i.e., enrich for, $CD34^+$ cells using anti-CD34 antibodies directly or indirectly conjugated to magnetic particles in connection with a magnetic cell separator, for example, the CliniMACS® Cell Separation System (Miltenyi Biotec, Bergisch Gladbach, Germany), which employs nano-sized super-paramagnetic particles composed of iron oxide and dextran coupled to specific monoclonal antibodies. The CliniMACS® Cell Separator is a closed sterile system, outfitted with a single-use disposable tubing set. The disposable set can be used for and discarded after processing a single unit of collected cord and/or placental blood to enrich for $CD34^+$ cells. Similarly, $CD133^+$ cells can be enriched using anti-CD133 antibodies. In a specific embodiment, $CD34^+CD90^+$ cells are enriched for. Similarly, cells expressing CD43, CD45RO, CD45RA, CD59, CD90, CD109, CD117, CD166, HLA DR, or a combination of the foregoing, can be enriched for using antibodies against the antigen.

In one embodiment, HSPC express CD34 ($CD34^+$) and lack CD38 expression ($CD38^-$). In some embodiments, HSPC are selected and/or enriched for $CD34^+CD38$ cells. In specific embodiments, HSPC are $CD34^+$ and $CD33^-$, $CD38^-$, HLA $DR^-$ and/or $Thy-1^{lo}$. In some embodiments, HSPC are selected and/or enriched for $CD34^+$ and $CD33^-$, $CD38^-$, HLA $DR^-$ and/or $Thy-1^{lo}$ cells. In particular embodiments, human HSPC are CD45Ra$^-$, CD19$^-$ and/or c-kit$^+$. In some embodiments, HSPC are selected and/or enriched for CD45Ra$^-$, CD19$^-$ and/or c-kit$^+$ cells. In one embodiment, HSPC express vascular endothelial growth factor receptor 2 (VEGFR2). In some embodiments, HSPC are selected and/or enriched for VEGFR2, which can be used as a marker for HSPC.

HSPC can also be enriched as described in sec. 5.4.1.1 of U.S. Pat. No. 7,399,633. In particular, human HSPC can be enriched by incubating a sample with antibodies that recognize one or more of glycophorin A, CD3, CD24, CD16, CD14, CD45Ra, CD36, CD56, CD2, CD19, CD20, CD66a and CD66b, and separating the antibody-bound cells from non-antibody bound cells. In some of these embodiments, the non-antibody bound cell population would be enriched for HSPC. In some embodiments My10 and HLA-DR are used to obtain enriched HSPC. In some embodiments, T lymphocyte depletion is used to enrich for HSPC, e.g., by pretreating cells with a monoclonal antibody that recognizes a T cell antigen plus complement. In one embodiment, glycophorin A antibody is used to select for or against erythrocytes. In other embodiments, antibodies against CD14, CD16, CD66a and CD66b are used to select for or against monocytes. In other embodiments, antibodies against CD24, CD3, CD19, CD20, CD56, CD2 are used to select for or against B and T lymphocytes and NK cells. In yet another embodiment, antibodies against CD45RA and CD36 are used to select for or against T-cells, B-cells, granulocytes, platelets, monocytes, differentiated erythroid precursors, and some committed mature progenitors. T-cell markers for use in the subject invention include CD7, CD5, TCD-2, and either CD4 or CD8. CD7 and terminal deoxyribonucleotidyl transferase (Tdt), which are markers of pre-T progenitor cells. Markers of pre-B progenitor cells can be MHC class II antigens. CD21 is a marker of mature B cells. In specific embodiments, antibodies which can be used for enrichment of HSPC include My-10 and 3C5 (which recognize CD34), or RFB-1 (which recognizes CD99 and identifies populations of BFU-E cells). Other antibodies against the above-mentioned hematopoietic antigens are disclosed in U.S. Pat. No. 5,877,299.

The above-mentioned antibodies can be used alone or in combination with procedures such as "panning" (Broxmeyer et al., 1984, J. Clin. Invest. 73:939-953) or fluorescence activated cell-sorting (FACS) (Williams et al., 1985, J. Immunol. 135:1004; Lu et al., 1986, Blood 68(1):126-133) to isolate the cells containing surface determinants recognized by these antibodies, as described in sec. 5.4.1.1 of U.S. Pat. No. 7,399,633. HSPC can also be separated and/or enriched using selective agglutination using a lectin such as soybean (Reisner et al., 1980, Proc. Natl. Acad. Sci. U.S.A. 77:1164).

In particular embodiments, HSPC separated and/or enriched as described herein still contain accessory or helper cells (non-stem/progenitor cells that influence the growth of stem/progenitor cells). In other embodiments, HSPC separated and/or enriched as described herein do not contain accessory or helper cells.

Optionally, prior to enrichment for HSPC, the red blood cells and white blood cells of the HSPC sample can be separated. Once the separation of the red blood cells and the white blood cells has taken place, the red blood cell fraction can be discarded, and the white blood cell fraction can be processed in the magnetic cell separator as above. Separation of the white and red blood cell fractions can be performed by any method known in the art, including centrifugation techniques. Other separation methods that can be used include the use of commercially available products FICOLL™ or FICOLL-PAQUE™ or PERCOLL™ (GE Healthcare, Piscataway, N.J.). FICOLL-PAQUE™ is normally placed at the bottom of a conical tube, and the whole blood is layered above. After being centrifuged, the following layers will be visible in the conical tube, from top to bottom: plasma and other constituents, a layer of mononuclear cells called buffy coat containing the peripheral blood mononuclear cells (white blood cells), FICOLL-PAQUE™, and erythrocytes and granulocytes, which should be present in pellet form. This separation technique allows easy harvest of the peripheral blood mononuclear cells.

Optionally, prior to CD34$^+$ cell selection, an aliquot of the HSPC sample (e.g., a fresh cord blood unit) can be checked for total nucleated cell count and/or CD34$^+$ content. In a specific embodiment, after the CD34$^+$ cell selection, both CD34$^+$ and CD34– cell fractions are recovered. Optionally, DNA can be extracted from a sample of the CD34– cell fraction for initial HLA typing and future chimerism studies. The CD34$^+$ enriched stem cell fraction can be subsequently processed prior to expansion, for example, the HSPC can be suspended in an appropriate cell culture medium for transport or storage. In a specific embodiment, the cell culture medium consists of STEMSPAN™ Serum Free Expansion Medium (StemCell Technologies, Vancouver, British Columbia) supplemented with 10 ng/ml recombinant human Interleukin-3 (rhIL-3), 50 ng/ml recombinant human Interleukin-6 (rhIL-6), 50 ng/ml recombinant human Thrombopoietin (rhTPO), 50 ng/ml recombinant human Flt-3 Ligand (rhFlt-3L), 50 ng/ml and recombinant human stem cell factor (rhSCF).

In a specific embodiment, the HSPC (e.g., from umbilical cord blood and/or placental blood) sample are red cell depleted, and the number of CD34$^+$ cells in the red cell depleted fraction is calculated. Preferably, the HSPC (e.g. umbilical cord blood and/or placental blood) samples containing more than 3.5 million CD34$^+$ cells are enriched by the enrichment methods described above.

6.8 Methods of HSPC Expansion

After HSPC have been isolated according to the enrichment methods described above or other methods known in the art, the Enriched HSPC can be expanded in order to increase the number of hematopoietic stem/progenitor cells, e.g., CD34$^+$ cells. In less preferred embodiments, the methods described herein can be applied to HSPC without prior enrichment, or prior to enrichment.

In some embodiments, HSPC that are subjected to expansion using the methods described herein are fresh, i.e., they have not been previously cryopreserved and thawed. In other embodiments, HSPC that are subjected to expansion using the methods described herein have been cryopreserved and thawed. The HSPC can be derived, e.g., from peripheral blood (such as mobilized peripheral blood), bone marrow, umbilical cord blood, or placental blood.

In certain embodiments, described herein are methods for expansion of HSPC (e.g., the Enriched HSPC) using a composition comprising a Notch agonist and an aryl hydrocarbon receptor antagonist. In one embodiment, a Notch agonist as described herein is immobilized (e.g., immobilized on a solid phase surface to which the cells are exposed during cell culturing), while the aryl hydrocarbon receptor antagonist is present in the cell culture medium. In specific embodiments, the Notch agonist (e.g., an extracellular domain of a Notch ligand) is fused to a fusion partner before immobilization. The fusion partners can be, but are not limited to, an Fc domain of IgG or tags that contain antigenic determinants such as a myc tag. The fusion partner can be any protein or peptide preferably of at least six amino acids in length.

The solid phase surface on which a Notch agonist is immobilized can be any surface known in the art, e.g., the inside surface of a cell culture dish, flask, or container, or the surface of a bead, etc. The immobilization of a Notch agonist on the solid surface can be by any method known in the art, and can be covalent or noncovalent, by adsorption or cross-linking, etc. In a specific embodiment, an antibody to the fusion partner of an extracellular domain of a Notch ligand (e.g., a Delta or a Serrate protein, or a Notch-binding portion thereof) can be bound (e.g., covalently) to the solid phase surface, and then immunospecifically bound to the fusion partner. In one embodiment, the solid phase surface (e.g., an inside surface of a cell culture dish, flask, or container, or the surface of a bead) is pre-coated with an antibody to a fusion partner protein (e.g., an anti-myc where the fusion partner is a myc tag, or an anti-IgG Fc domain antibody where the fusion partner is an Fc domain of an IgG) before addition of an extracellular domain of a Notch ligand fused to the fusion partner.

Preferably, the Notch agonist (e.g., an extracellular domain of a Notch ligand) is immobilized on the inside surface of a cell culture dish, flask or another container. In specific embodiments, $Delta^{ext-IgG}$ (e.g., $Delta1^{ext-IgG}$) or $Delta^{ext-myc}$ (e.g., $Delta1^{ext-myc}$) is immobilized on the inside surface of a cell culture dish, flask or another container. In some embodiments, to present $Delta^{ext-IgG}$ (e.g., $Delta1^{ext-IgG}$) or $Delta^{ext-myc}$ (e.g., $Delta1^{ext-myc}$) in immobilized form, $Delta^{ext-IgG}$ or $Delta^{ext-myc}$ is attached to the surface of the cell culture dish by binding to an anti-myc tag antibody (e.g., 9E10), or anti-human IgG Fc domain antibody, respectively, that had previously been adsorbed to the surface of the cell culture dish.

In a specific embodiment, a Notch agonist (e.g., an extracellular domain of a Notch ligand) is immobilized on beads (e.g., Sepharose beads, agarose beads, or another type of bead known in the art). A Notch agonist can be attached to the beads utilizing any methodology known in the art including, but not limited to, cross-linking, binding via antibody, or sticking. For example, an extracellular domain of a Notch ligand can be fused to a myc tag and bound to Sepharose beads crosslinked to an anti-myc tag antibody (e.g., 9E10) (see, e.g., methodology described in Varnum Finney et al., 1998, Blood 91(11):4084-4091).

In certain embodiments, a Notch agonist is any one of the compounds described in Section 6.2 above. In some embodiments, a Notch agonist is a Notch-interacting domain of a Delta (e.g., Delta-1, Delta-3 or Delta-4), a Jagged (e.g., Jagged-1 or Jagged-2), or a Serrate protein. In some embodiments, a Notch agonist comprises an extracellular domain of a Delta protein or a Serrate (e.g., Jagged) protein. In preferred embodiments, a Notch agonist comprises a human or rodent Delta protein or a human or rodent Jagged protein (e.g., an extracellular domain of a human Delta protein or a human Jagged protein). Any ligand immobilization technique known in the art can be used in the methods of the invention to immobilize the Notch agonist. In specific embodiments, a Notch agonist (e.g., an extracellular domain of a Notch ligand) is fused to a fusion partner protein. Any fusion partner protein known in the art can be used in the methods, kits and compositions of the invention. For example, a tag (with an antigenic determinant) or an intracellular domain of a receptor can be used as the fusion partner protein. Fusion partner proteins include, but are not limited to, an Fc domain of an IgG, a myc tag, and a his tag.

In one embodiment, the Notch agonist is the extracellular domain of a Delta protein or a Serrate (e.g., Jagged) protein fused to the Fc domain of human IgG (e.g., $Delta1^{ext-IgG}$). In another embodiment, the Notch agonist is the extracellular domain of a Delta protein or a Serrate (e.g., Jagged) protein fused to a myc epitope tag (e.g., $Delta1^{ext-myc}$). Preferably, a Notch agonist (e.g., $Delta1^{ext-IgG}$) is immobilized on the surface of the tissue culture dish during HSPC expansion. In specific embodiments, a Notch agonist (e.g., $Delta1^{ext-IgG}$) is immobilized on beads (e.g., Sepharose beads, agarose beads, or other types of beads known in the art).

In preferred embodiments, an aryl hydrocarbon receptor antagonist is any one of the compounds described in Section 6.3 above. In one embodiment, an aryl hydrocarbon receptor antagonist is SR1.

In some embodiments, described herein are methods for expansion of HSPC (e.g., the Enriched HSPC) using a composition comprising a Notch agonist, an aryl hydrocarbon receptor antagonist, and one or more growth factors. Growth factors that can be used in the methods for expansion of HSPC (e.g., the Enriched HSPC) are described in Section 6.4 above. In certain embodiments, the one or more growth factors can be selected from the following human growth factors: stem cell factor, Flt-3-ligand, thrombopoietin, interleukin-6, and interleukin-3. In some embodiments, HSPC (e.g., the Enriched HSPC) are expanded in the presence of two or more, or three or more growth factors. In one embodiment, the following four human growth factors are present during HSPC expansion: stem cell factor, Flt-3-ligand, thrombopoietin and interleukin-6. In one embodiment, the following five human growth factors are present during HSPC expansion: stem cell factor, Flt-3-ligand, thrombopoietin, interleukin-6 and interleukin-3.

In specific embodiments, described herein are methods for expansion of HSPC (e.g., the Enriched HSPC) using a composition comprising a Notch agonist, an aryl hydrocarbon receptor antagonist, one or more growth factors, and an immobilized fibronectin or a fragment thereof. In one embodiment, an immobilized fibronectin or a fragment thereof is CH-296 or RetroNectin® (a recombinant human fibronectin fragment).

Preferably, HSPC (e.g., the Enriched HSPC) are cultured under cell growth conditions (e.g., promoting mitosis) such that the HSPC grow and divide (proliferate) to obtain a population of Expanded HSPC. In some embodiments, HSPC (e.g., the Enriched HSPC) used for ex vivo expansion are derived from a single human (e.g., CB Stem Cells derived from a single human at birth). In another embodiment, HSPC (e.g., the Enriched HSPC) used for ex vivo expansion are derived from two or more humans and pooled prior to the expansion methods described herein. In some embodiments, the Expanded HSPC are pooled after the expansion methods described herein. In one embodiment, individual populations of CB Stem Cells each derived from the umbilical cord blood and/or placental blood of a single human at birth can be pooled prior to or after the expansion technique. In another embodiment, the sample that is expanded is not a pool of samples but is obtained from a single individual at birth.

In one embodiment, the HSPC sample that is expanded as described herein is derived from only one cord blood unit. In one embodiment, the HSPC sample that is expanded as described herein is derived from one or two cord blood units. In one embodiment, the HSPC sample that is expanded as described herein is derived from mobilized peripheral blood from only one patient (e.g., human).

In one specific embodiment where the HSPC sample essentially consists of CD34⁺ enriched cells from one or two cord blood units, described herein are methods for expansion wherein HSPC are cultured from about 3 days to about 90 days, e.g., between 7 and 2 days, and/or until the fold expansion or the characteristic cell populations described herein are obtained. In one embodiment, described herein are methods for expansion wherein HSPC are cultured not more than 21 days, 16 days, 14 days or 7 days.

In particular embodiments, the HSPC sample that is expanded as described herein contains at least 50% CD34⁺ cells or more than 90% of CD34⁺ cells. In one embodiment, the HSPC sample that is expanded as described herein contains between $10^5$ and $10^9$ nucleated cells. In specific embodiments, the sample that is expanded as described herein is derived from mobilized peripheral blood (e.g., human) which have been enriched in CD34⁺ cells.

In specific embodiments, wherein the HSPC sample that is expanded as described herein is derived from not more than one or two cord blood units, the Expanded HSPC contain a total amount of cells of at least $10^5$, $10^6$, $10^7$, $10^8$ or $10^9$ cells, with between 20-100%, e.g., between 40-80%, of total cells being CD34⁺ cells. In one embodiment, the Expanded HSPC contain a total amount of cells between 0.1-40%, e.g., between 0.1-10%, of total cells being CD34⁺Thy1⁺ and 20-80% of cells being CD34⁺CD45RA⁺. In some embodiments, the Expanded HSPC contain between 10-95% of cells being CD38⁺ and between 5-70% of cells being CD133⁺.

In one embodiment, described herein are methods for expansion wherein HSPC are cultured for a period of time sufficient to reach an absolute number of CD34⁺ cells of at least $10^5$, $10^6$, $10^7$, $10^8$ or $10^9$ cells. In another embodiment described herein are methods for expansion wherein HSPC are cultured for a period of time sufficient to achieve a 10 to 50000 fold expansion of CD34⁺ cells, e.g., between 100 and 10000 fold expansion.

Preferably, the technique used for expansion is one that has been shown to (i) result in an increase in the number of hematopoietic stem/progenitor cells, e.g., CD34⁺ cells, in the expanded sample relative to the unexpanded HSPC sample, or (ii) results in an increased number of SCID repopulating cells in the expanded sample determined by limiting-dilution analysis as shown by enhanced engraftment in NOD/SCID mice infused with the expanded sample, relative to that seen with the unexpanded sample, where the unexpanded sample and expanded sample are from different aliquots of the same sample, wherein the expanded sample but not the unexpanded sample is subjected to the expansion technique.

In certain embodiments, the technique results in (or more than) a 50-, 75-, 100-, 150-200-, 250-, 300-, 350-, 400-, 450-, 500-, 1000-, 2000-, 3000-, 4000-, 5000-fold increase in the number of hematopoietic stem/progenitor cells in the expanded sample, relative to the unexpanded sample. The hematopoietic stem/progenitor cells can be positive for one or more of CD34, CD43, CD45RO, CD45RA, CD59, CD90, CD109, CD117, CD133, CD166, and HLA DR and/or negative for Lin and/or CD38. In a specific embodiment, the enhanced engraftment can be detected by detecting an increased percentage of human CD45⁺ cells in the bone marrow of mice infused with an aliquot of the expanded sample relative to mice infused with an aliquot of the unexpanded sample at, e.g., 10 days, 3 weeks or 9 weeks post-infusion (see Delaney et al., 2010, Nature Med. 16(2): 232-236). In some embodiments, the technique results in (or more than) a 50-, 75-, 100-, 150-, 200-, 250-, 300-, 350-, 400-, 450-, 500-, 1000-, 2000-, 3000-, 4000-, 5000-fold increase in the number of CD34+ hematopoietic stem/progenitor cells in the expanded sample, relative to the unexpanded sample.

Such expansion techniques include, but are not limited to those described in U.S. Pat. No. 7,399,633; Delaney et al., 2010, Nature Med. 16(2): 232-236; Zhang et al., 2008, Blood 111:3415-3423; and Himburg et al., 2010, Nature Medicine doi:10.1038/nm.2119 (advanced online publication), as well as those described below.

In one embodiment of the invention, HSPC (e.g., the Enriched HSPC) are cultured with a Notch agonist, an aryl hydrocarbon receptor antagonist, and growth factors, and are exposed to cell growth conditions (e.g., promoting mitosis) such that the HSPC proliferate to obtain an Expanded HSPC population according to the present invention. In certain embodiments of the invention, HSPC (e.g., the Enriched HSPC) are cultured with an amount of an agonist of Notch function and an amount of an aryl hydrocarbon receptor antagonist, where the amounts of both of these agents together are effective to expand HSPC. In particular, in certain embodiments of the invention, HSPC (e.g., the Enriched HSPC) are cultured with an amount of an agonist of Notch function and an amount of an aryl hydrocarbon receptor antagonist, where the amounts of both of these agents together are effective to expand HSPC, and are exposed to cell growth conditions (e.g., promoting mitosis) such that the HSPC proliferate to obtain an Expanded HSPC population according to the present invention (optionally, HSPC are cultured in the presence of one or more growth factors). In one embodiment of the invention, HSPC (e.g., the Enriched HSPC) are cultured with an amount of an agonist of Notch function effective to inhibit differentiation, and an amount of an aryl hydrocarbon receptor antagonist effective to promote cell proliferation or block cell differentiation, and are exposed to cell growth conditions (e.g., promoting mitosis) such that the HSPC proliferate to obtain an Expanded HSPC population according to the present invention. In another embodiment, HSPC (e.g., the Enriched HSPC) are cultured with an amount of an agonist of Notch function effective to inhibit differentiation, an amount of an aryl hydrocarbon receptor antagonist effective to promote cell proliferation or block cell differentiation, and in the presence of one or more growth factors, and are exposed to cell growth conditions (e.g., promoting mitosis) such that the HSPC proliferate to obtain an Expanded HSPC population according to the present invention. The Expanded HSPC population so obtained can be frozen and stored for later use, for example, to provide hematopoietic function to an immunodeficient human patient. Optionally, the Notch pathway agonist and/or an aryl hydrocarbon receptor antagonist is/are inactivated or removed from the Expanded HSPC population prior to transplantation into the patient (e.g., by separation, dilution).

In one embodiment, one or more agents used in the expansion methods described herein, in addition to the Notch agonist and the aryl hydrocarbon receptor antagonist, are: an agonist antibody against the TPO receptor (e.g., VB22B sc(Fv)2 as described in WO 2007/145227), SCF, IL-6, Flt-3 ligand, TPO or aTPO mimetic (e.g., such as described in WO/2007/022269; WO/2007/009120; WO/2004/054515; WO/2003/103686; WO/2002/085343; WO/2002/049413; WO/2001/089457; WO/2001/039773; WO/2001/034585; WO/2001/021180; WO/2001/021180; WO/2001/017349; WO/2000/066112; WO/2000/035446; WO/2000/028987; WO/2008/028645), granulocyte colony stimulating factor (G-CSF), granulocyte macrophage colony stimulating factor (GM-CSF), a prostaglandin or a prostaglandin receptor agonist (e.g., prostaglandin E2 receptor-1 (EP-I) agonist, prostaglandin E2 receptor-2 (EP-2) agonist, prostaglandin E2 receptor-3 (EP-3) agonist and prostaglandin E2 receptor-4 (EP-4) agonists, as described in WO/2008/073748), tetraethylenepentamine (TEPA), and/or a WNT agonist (see U.S. Patent Publication No. 2010/0183564). In particular embodiments, HSPC are cultured in the presence of mesenchymal stem cells (MSCs).

In specific embodiments, HSPC (e.g., the Enriched HSPC) are cultured for 2, 3, 4, 5, 6, 7, 8, 9, 10, 11, 12, 13, 14, 15, 16, 17, 18, 19, 20, 21, 22, 23, 24, 25, or 30 days or more; or, preferably, the HSPC are cultured for at least 10 days or at least 16 days (in the presence of the combination of a Notch agonist and an aryl hydrocarbon receptor antagonist, and, optionally, one or more growth factors). In other embodiments, HSPC (e.g., the Enriched HSPC) are cultured for 1 week, 2 weeks, 3 weeks, 4 weeks, 5 weeks, 6 weeks, 7 weeks, 8 weeks, 9 weeks or 10 weeks; or, preferably, the HSPC are cultured for at least 3 or 4 weeks (in the presence of the combination of a Notch agonist and an aryl hydrocarbon receptor antagonist, and, optionally, one or more growth factors). In yet other embodiments, HSPC (e.g., the Enriched HSPC) are cultured for less than 4 weeks (in the presence of the combination of a Notch agonist and an aryl hydrocarbon receptor antagonist, and, optionally, one or more growth factors). In yet other embodiments, HSPC (e.g., the Enriched HSPC) are cultured for more than 10 weeks, e.g., 12, 15, 18, 20 or 25 weeks (in the presence of the combination of a Notch agonist and an aryl hydrocarbon receptor antagonist, and, optionally, one or more growth factors).

Exemplary culture conditions for expanding HSPC (e.g., the Enriched HSPC) comprise, as set forth in Section 7 infra, culturing the HSPC for about 16 days or about 16-21 days in the presence of fibronectin fragments and the extracellular domain of a Delta protein fused to the Fc domain of human IgG (e.g., Delta1$^{ext\text{-}IgG}$) in a serum free medium supplemented with the following our human growth factors: stem cell factor, Flt-3 receptor ligand, thrombopoietin and interleukin-6, or in the presence of the following five human growth factors: stem cell factor, Flt-3 receptor ligand, thrombopoietin, interleukin-6 and interleukin-3. In some embodiments, the cell culture dishes are coated overnight at 4° C. (or for a minimum of 2 hours at 37° C.) with 0.2 to 10 µg/ml Delta1$^{ext\text{-}IgG}$ (e.g., 0.5, 1, 1.25, 1.5, 2, 2.5, 5, 7.5, or 10 µg/ml Delta1$^{ext\text{-}IgG}$) and 5 µg/ml RetroNectin® (a recombinant human fibronectin fragment) in phosphate buffered saline, before adding HSPC (e.g., the Enriched HSPC) and an aryl hydrocarbon receptor antagonist.

In certain embodiments, HSPC (e.g., the Enriched HSPC) are expanded in the presence of a Notch agonist, and in particular Delta$^{ext\text{-}IgG}$ (e.g., Delta1$^{ext\text{-}IgG}$, at a concentration that is equal to or more than 0.5, 1, 1.25, 1.5, 2, 2.5, 5, 7.5 or 10 µg/ml, e.g., in a fluid applied to a solid phase surface. In some embodiments, HSPC (e.g., the Enriched HSPC) are expanded in the presence of a Notch agonist, and in particular Delta$^{ext\text{-}IgG}$ (e.g., Delta1$^{ext\text{-}IgG}$), at a concentration that is below 25, 20, 17.5, 15, 12.5, 10, 9, 8, 7.5, 7, 6, 5, 4, 3, 2.5, 2, 1.5 or 1.25 µg/ml, e.g., in a fluid applied to a solid phase surface. In yet other embodiments, HSPC (e.g., the Enriched HSPC) are expanded in the presence of a Notch agonist, and in particular Delta1$^{ext\text{-}IgG}$, at a concentration between 0.5 and 10 µg/ml, between 1 and 15 µg/ml, between 1.25 and 15 µg/ml, between 1.5 and 15 µg/ml, between 1 and 10 µg/ml, between 1.25 and 10 µg/ml, between 1.5 and 10 µg/ml, between 2 and 10 µg/ml, between 1 and 7.5 µg/ml, between 1.25 and 7.5 µg/ml, between 1.5 and 7.5 µg/ml, between 2 and 7.5 µg/ml, between 1 and 5 µg/ml, between 1.25 and 5 µg/ml, between 1.5 and 6 µg/ml, between 2 and 6 µg/ml, between 2.5 and 6 µg/ml, or between 2.5 and 5 µg/ml, e.g., in a fluid applied to a solid phase surface. In a specific embodiment, a Notch agonist, and in particular Delta$^{ext\text{-}IgG}$ (e.g., Delta1$^{ext\text{-}IgG}$), is used for HSPC expansion at a concentration of 0.5, 1, 1.25, 1.5, 2, 2.5, 5 or 7.5 µg/ml, e.g., in a fluid applied to a solid phase surface.

In certain embodiments, an aryl hydrocarbon receptor antagonist (e.g., SR1) is added to the medium in which HSPC (e.g., the Enriched HSPC) are cultured. In some embodiments, an aryl hydrocarbon receptor antagonist is added to the medium in which HSPC (e.g., the Enriched HSPC) are cultured during all of the feedings of the cells. In these embodiments, an aryl hydrocarbon receptor antagonist is present in the HSPC cell culture at all times during the HSPC expansion. In yet other embodiments, an aryl hydrocarbon receptor antagonist is not present in the HSPC cell culture at all times during the HSPC expansion. In a specific embodiment, an aryl hydrocarbon receptor antagonist compound is made fresh before addition of such compound to HSPC (e.g., the Enriched HSPC) or the medium in which HSPC (e.g., the Enriched HSPC) are cultured. In certain embodiment, an aryl hydrocarbon compound (e.g., SR1) is added to the culture medium so as to be present at a concentration between about 100 nM and 1500 nM, 100 nM and 1000 nM, 250 nM and 1500 nM, 250 nM and 1000 nM, 500 nM and 1500 nM, 500 nM and 1000 nM, 600 nM and 1000 nM, 600 nM and 900 nM, 700 nM and 900 nM, or 700 nM and 800 nM. In certain embodiments, an aryl hydrocarbon compound (e.g., SR1) is added to the culture medium so as to be present at a concentration of 500 nM, 550 nM, 600 nM, 650 nM, 700 nM, 750 nM, 800 nM, 850 nM, 900 nM, 950 nM or 1000 nM. In some embodiments, an aryl hydrocarbon compound (e.g., SR1) is added to the culture medium so as to be present at a concentration of no more than 1000 nM. In specific embodiments, an aryl hydrocarbon compound (e.g., SR1) is added to the culture medium so as to be present at a concentration in the range of 200 nM to 1000 nM. In particular embodiments, an aryl hydrocarbon receptor antagonist is added to the culture medium in which HSPC are expanded at a concentration between 1 pM and 100 µM, between 10 pM and 10 µM, or between 100 pM and 1 µM. In some embodiments, an aryl hydrocarbon receptor antagonist is formulated in DMSO or another suitable carrier (e.g., the DMSO formulation can contain 0.3 mg/ml of the aryl hydrocarbon receptor antagonist in 60% DMSO/40% water solution) for use in the expansion technique provided herein.

In certain embodiments, the foregoing growth factors are present in the culture condition for expanding HSPC (e.g., the Enriched HSPC) at the following concentrations: 25-300 ng/ml stem cell factor, 25-300 ng/ml Flt-3 receptor ligand, 25-100 ng/ml thrombopoietin, 25-100 ng/ml interleukin-6 and 10 ng/ml interleukin-3. In more specific embodiments, 50, 100 or 200 ng/ml stem cell factor, 50, 100 or 200 ng/ml of Flt-3 receptor ligand, 50 or 100 ng/ml thrombopoietin, 50 or 100 ng/ml interleukin-6 and about 10 ng/ml interleukin-3 are used.

Other exemplary culture condition for expanding HSPC (e.g., the Enriched HSPC) are set forth in Zhang et al., 2008, Blood 111:3415-3423. In a specific embodiment, HSPC (e.g., the Enriched HSPC) can be cultured in serum free medium supplemented with heparin, stem cell factor, thrombopoietin, insulin-like growth factor-2 (IGF-2), fibroblast growth factor-1 (FGF-1), and Angptl3 or Angptl5. In a specific embodiment, the medium is supplemented with 10 µg/ml heparin, 10 ng/ml stem cell factor, 20 ng/ml thrombopoietin, 20 ng/ml IGF-2, and 10 ng/ml FGF-1, and 100 ng/ml Angptl3 or Angptl5 and the cells are cultured for 19-23 days. In another specific embodiment, the HSPC can be expanded by culturing the HSPC in serum free medium supplemented with 10 µg/ml heparin, 10 ng/ml stem cell factor, 20 ng/ml thrombopoietin, 10 ng/ml FGF-1, and 100 ng/ml Angptl5 for 11-19 days. In another specific embodiment, HSPC (e.g., the Enriched HSPC) can be expanded by culturing the HSPC in serum free medium supplemented with 50 ng/ml stem cell factor, 10 ng/ml thrombopoietin, 50 ng/ml Flt-3 receptor ligand, and 100 ng/ml insulin-like growth factor binding protein-2 (IGFBP2) or 500 ng/ml Angptl5 for 10 days. In yet another embodiment, HSPC (e.g., the Enriched HSPC) can be expanded by culturing HSPC (e.g., the Enriched HSPC) in serum free medium supplemented with 10 µg/ml heparin, 10 ng/ml stem cell factor, 20 ng/ml thrombopoietin, 10 ng/ml FGF-1, 500 ng/ml Angptl5, and 500 ng/ml IGFBP2 for 11 days. See Zhang et al., 2008, Blood 111:3415-3423.

Another exemplary culture condition for expanding HSPC (e.g., the Enriched HSPC) is set forth in Himburg et al., 2010, Nature Medicine doi:10.1038/nm.2119 (advanced online publication). In a specific embodiment, the HSPC can be cultured in liquid suspension culture supplemented with thrombopoietin, stem cell factor, Flt-3 receptor ligand, and pleiotrophin. In a specific embodiment, the liquid suspension culture is supplemented with 20 ng/ml thrombopoietin, 125 ng/ml stem cell factor, 50 ng/ml Flt-3 receptor ligand, and 10, 100, 500, or 1000 ng/ml pleiotrophin and the HSPC are cultured for 7 days.

In specific embodiments, HSPC (e.g., the Enriched HSPC) are expanded in a basal medium, which can be supplemented with one or more growth factors described herein. A basal medium can comprise amino acids, carbon sources, vitamins, serum proteins (e.g. albumin), inorganic salts, divalent cations, buffers or any other element suitable for use in expansion of HSPC as described at page 13 of U.S. Patent Publication No. 2010/0183564. Examples of such basal medium appropriate include, without limitation, StemSpan® SFEM—Serum-Free Expansion Medium (StemCell Technologies, Vancouver, Canada), StemSpan® H3000-defined Medium (StemCell Technologies, Vancouver, Canada), CellGro® SCGM (CellGenix, Freiburg Germany), and StemPro®-34 SFM (Invitrogen).

It is further contemplated herein that HSPC (e.g., the Enriched HSPC) are expanded in the presence of a composition comprising a Notch agonist and an aryl hydrocarbon receptor antagonist, and further comprising any additional component disclosed in U.S. Pat. No. 7,399,633 and U.S. Patent Publication No. 2010/0183564, which are incorporated by reference herein in their entireties.

In a preferred embodiment of the invention, after expansion of the HSPC, the total number of cells, viable $CD34^+$, and/or viable $CD34^+CD90^+$, cells are determined to measure the potency of the sample to provide hematopoietic function. Numerous clinical studies have shown that the total nucleated cell dose and the $CD34^+$ cell dose in stem cell grafts are highly correlated with neutrophil and platelet engraftment as well as the incidence of graft failure and early transplant-related complications (primarily lethal infections) following stem cell transplantation. Further, $CD34^+CD90^+$ cells have been shown to represent a subpopulation of $CD34^+$ cells capable of generating long-term engraftment. For example, at day 5-16 post culture initiation during expansion, a sample can be taken for determination of the total viable nucleated cell count. In addition, the total number of $CD34^+$ cells and/or $CD34^+CD90^+$ cells can be determined by multi-parameter flow cytometry, as well as the percentage of such cells in the sample. Preferably, cultures that have not resulted in at least a 10-fold increase in the absolute number of $CD34^+$ cells at this time are discontinued. Similarly, prior to cryopreservation or after thawing, an aliquot of the Expanded HSPC sample can be taken for determination of total nucleated cells and percentage of viable $CD34^+$ cells and/or viable $CD34^+CD90^+$ cells in order to calculate the total viable $CD34^+$ and/or $CD34^+CD90^+$ cell number in the Expanded HSPC sample. In a preferred embodiment, those Expanded HSPC samples containing less than 75 million $CD34^+$ viable cells can be discarded.

In some specific embodiments, the Expanded HSPC contain at least $10^5$ cells, at least $10^6$ cells, at least $10^7$ cells, at least $10^8$ cells or at least $10^9$ cells, wherein between 20% to 100% of total cells are $CD34^+$, e.g., between 40% to 80%, of total cells are $CD34^+$. In particular embodiments, the Expanded HSPC have at least 100%, 20% 30%, 40% or 50% or more cells relative to the number of cells prior to expansion or relative to the number of cells in the control cell population not subjected to the expansion technique. In particular embodiments, the Expanded HSPC have at least 10%, 20%, 30%, 40% or 50% or more $CD34^+$ cells relative to the number of $CD34^+$ cells prior to expansion or relative to the number of cells in the control cell population not subjected to the expansion technique. Differentiation properties of the $CD34^+$ cells can be assessed by analyzing the colony forming units (CFU) as described in U.S. Patent Publication No. 2010/0183564.

In a specific embodiment, total viable $CD34^+$, $CD34^+CD90^+$ cells (or other antigen-positive) cell numbers can be considered the potency assay for release of the final product for therapeutic use. Viability can be determined by any method known in the art, for example, by trypan blue exclusion or 7-AAD exclusion. Preferably, the total nucleated cell count (TNC) and other data are used to calculate the potency of the product. The percentage of viable $CD34^+$ cells and/or viable $CD34^+CD90^+$ cells can be assessed by flow cytometry and use of a stain that is excluded by viable cells. The percentage of viable $CD34^+$ cells=the number of $CD34^+$ cells that exclude 7-AAD (or other appropriate stain) in an aliquot of the sample divided by the TNC (both viable and non-viable) of the aliquot. Viable $CD34^+$ cells in the sample can be calculated as follows: Viable $CD34^+$ cells=TNC of sample x % viable $CD34^+$ cells in the sample. The proportional increase during enrichment or expansion in viable $CD34^+$ cells can be calculated as follows: Total Viable $CD34^+$ cells Post-culture/Total Viable $CD34^+$ cells Pre-culture. As will be apparent, antigens other than or in addition to CD34 can be used.

In certain embodiments, after expansion of the HSPC in the presence of an amount of a Notch agonist and an amount of an aryl hydrocarbon receptor antagonist (e.g., after culturing HSPC (e.g., the Enriched HSPC) for 5, 6, 7, 8, 9, 10, 11, 12, 13, 14, 15, 16, 17, 18, 19, 20 or more days, or 1, 2, 3, 4, 5, 6, 7, or 8 or more weeks), the percentage of $CD34^+$ and/or $CD34^+CD90^+$ cells increases relative to the percentage of $CD34^+$ and/or $CD34^+CD90^+$ cells cultured in the presence of the same amount of a Notch agonist alone and/or the same amount of an aryl hydrocarbon receptor antagonist alone. In other embodiments, after expansion of the HSPC in the presence of an amount of a Notch agonist and an amount of an aryl hydrocarbon receptor antagonist (e.g., after culturing HSPC (e.g., the Enriched HSPC) for 5, 6, 7, 8, 9, 10, 11, 12, 13, 14, 15, 16, 17, 18, 19, 20 or more days, or 1, 2, 3, 4, 5, 6, 7, 8 or more weeks), the percentage of $CD34^+$ and/or $CD34^+CD90^+$ cells increases relative to the percentage of $CD34^+$ and/or $CD34^+CD90^+$ cells before the expansion (at day 0), or relative to the percentage of $CD34^+$ and/or $CD34^+CD90^+$ cells in the HSPC expanded under conditions lacking either a Notch agonist and/or without an aryl hydrocarbon receptor antagonist.

In some embodiments, after expansion of the HSPC in the presence of an amount of a Notch agonist and an amount of an aryl hydrocarbon receptor antagonist (e.g., after culturing HSPC (e.g., the Enriched HSPC) for 5, 6, 7, 8, 9, 10, 11, 12, 13, 14, 15, 16, 17, 18, 19, 20 or more days, or 1, 2, 3, 4, 5, 6, 7, 8, or more weeks), the percentage of $CD34^-CD14^+$ cells decreases relative to the percentage of $CD34^-CD14^+$ cells cultured in the presence of the same amount of a Notch agonist alone and/or the same amount of an aryl hydrocarbon receptor antagonist alone. In other embodiments, after expansion of the HSPC in the presence of an amount of a Notch agonist and an amount of an aryl hydrocarbon receptor antagonist (e.g., after culturing HSPC (e.g., the Enriched HSPC) for 5, 6, 7, 8, 9, 10, 11, 12, 13, 14, 15, 16, 17, 18, 19, 20 or more days, or 1, 2, 3, 4, 5, 6, 7, 8 or more weeks), the percentage of $CD34^-CD14^+$ cells decreases relative to the percentage of $CD34^-CD14^+$ cells in the HSPC expanded under conditions lacking either a Notch agonist and/or without an aryl hydrocarbon receptor antagonist.

The Expanded HSPC can be used without further purification or selection, or can be subject to further purification or selection. Once the Expanded HSPC are obtained, the Expanded HSPC may then be washed to remove the aryl hydrocarbon receptor antagonist (and, optionally, one or more other agents used during the expansion procedure). Upon washing, the Expanded HSPC can be resuspended in an appropriate cell suspension medium for short term use or in a long-term storage medium, for example, a medium suitable for cryopreservation.

The cell sample containing isolated HSPC, the Enriched HSPC and/or the Expanded HSPC can also contain supporting cells as described, e.g., at pages 10-11 of U.S. Patent Publication No. 2010/0183564. Supporting cells can be cells that are naturally found in the vicinity of HSPC. Supporting cells secrete or express on their cell surface the factors necessary for the maintenance, growth or differentiation of HPSC. Supporting cells include, but are not limited to, lymphoreticular stromal cells. Lymphoreticular stromal cells include, but are not limited to, all cell types present in a lymphoid tissue which are not lymphocytes or lymphocyte precursors or progenitors (e.g., osteoblasts, epithelial cells, endothelial cells, mesothelial cells, dendritic cells, splenocytes and macrophages). Lymphoreticular stromal cells may also include fibroblasts which have been genetically altered to secrete or express on their cell surface the factors necessary for the maintenance, growth or differentiation of HSPC. Lymphoreticular stromal cells can be derived from the lymphoid tissue (e.g., bone marrow, peripheral blood (e.g., mobilized peripheral blood), umbilical cord blood, placental blood, fetal liver, embryonic cells (e.g., embryonic stem cells), aortal-gonadal-mesonephros derived cells, or lymphoid soft tissue such as thymus, spleen, liver, lymph node, skin, tonsil, adenoids and Peyer's patch). Lymphoreticular stromal cells can be autologous (self) or non-autologous (non-self, e.g., heterologous, allogeneic, syngeneic or xenogeneic) with respect to HSPC. Lymphoid tissue (e.g., lymphoreticular stroma cells) can be obtained from a subject (e.g., human) at any time after such tissue has developed to a stage at which it can support the maintenance, growth or differentiation of HSPC. HSPC can be cultured with supporting cells as described in U.S. Patent Publication No. 2010/0183564 (see, e.g., page 11). In an alternative embodiment, the cell sample containing isolated HSPC, the Enriched HSPC and/or the Expanded HSPC does not contain supporting cells.

6.9 Cryopreservation and Thawing 6.9.1 Cryopreservation

Once the isolated HSPC, the Enriched HSPC or the Expanded HSPC are obtained, such isolated HSPC, Enriched HSPC or Expanded HSPC can be cryopreserved in accordance with the methods described below or known in the art.

In one embodiment, an Expanded HSPC population can be divided and frozen in one or more bags (or units). In another embodiment, two or more Expanded HSPC populations can be pooled, divided into separate aliquots, and each aliquot is frozen. In a preferred embodiment, a maximum of approximately 4 billion nucleated cells is frozen in a single bag. In a preferred embodiment, the Expanded HSPC are fresh, i.e., they have not been previously frozen prior to expansion or cryopreservation. The terms "frozen/freezing" and "cryopreserved/cryopreserving" are used interchangeably in the present application. Cryopreservation can be by any method in known in the art that freezes cells in viable form. The freezing of cells is ordinarily destructive. On cooling, water within the cell freezes. Injury then occurs by osmotic effects on the cell membrane, cell dehydration, solute concentration, and ice crystal formation. As ice forms outside the cell, available water is removed from solution and withdrawn from the cell, causing osmotic dehydration and raised solute concentration which eventually destroy the cell. For a discussion, see Mazur, P., 1977, Cryobiology 14:251-272.

These injurious effects can be circumvented by (a) use of a cryoprotective agent, (b) control of the freezing rate, and (c) storage at a temperature sufficiently low to minimize degradative reactions.

Cryoprotective agents which can be used include but are not limited to dimethyl sulfoxide (DMSO) (Lovelock and Bishop, 1959, Nature 183:1394-1395; Ashwood-Smith, 1961, Nature 190:1204-1205), glycerol, polyvinylpyrrolidine (Rinfret, 1960, Ann. N.Y. Acad. Sci. 85:576), polyethylene glycol (Sloviter and Ravdin, 1962, Nature 196:548), albumin, dextran, sucrose, ethylene glycol, i-erythritol, D-ribitol, D-mannitol (Rowe et al., 1962, Fed. Proc. 21:157), D-sorbitol, i-inositol, D-lactose, choline chloride (Bender et al., 1960, J. Appl. Physiol. 15:520), amino acids (Phan The Tran and Bender, 1960, Exp. Cell Res. 20:651), methanol, acetamide, glycerol monoacetate (Lovelock, 1954, Biochem. J. 56:265), and inorganic salts (Phan The Tran and Bender, 1960, Proc. Soc. Exp. Biol. Med. 104:388; Phan The Tran and Bender, 1961, in Radiobiology, Proceedings of the Third Australian Conference on Radiobiology, Ilbery ed., Butterworth, London, p. 59). In a preferred embodiment, DMSO is used, a liquid which is nontoxic to cells in low concentration. Being a small molecule, DMSO freely permeates the cell and protects intracellular organelles by combining with water to modify its freezability and prevent damage from ice formation. Addition of plasma (e.g., to a concentration of 20-25%) can augment the protective effect of DMSO. After addition of DMSO, cells should be kept at 0° C. until freezing, since DMSO concentrations of about 1% are toxic at temperatures above 4° C.

A controlled slow cooling rate can be critical. Different cryoprotective agents (Rapatz et al., 1968, Cryobiology 5(1): 18-25) and different cell types have different optimal cooling rates (see e.g., Rowe and Rinfret, 1962, Blood 20:636; Rowe, 1966, Cryobiology 3(1):12-18; Lewis, et al., 1967, Transfusion 7(1):17-32; and Mazur, 1970, Science 168:939-949 for effects of cooling velocity on survival of marrow-stem cells and on their transplantation potential). The heat of fusion phase where water turns to ice should be minimal. The cooling procedure can be carried out by use of, e.g., a programmable freezing device or a methanol bath procedure.

Programmable freezing apparatuses allow determination of optimal cooling rates and facilitate standard reproducible cooling. Programmable controlled-rate freezers such as Cryomed or Planar permit tuning of the freezing regimen to the desired cooling rate curve. For example, for marrow cells in 10% DMSO and 20% plasma, the optimal rate is 1° to 3° C./minute from 0° C. to −80° C. In a preferred embodiment, this cooling rate can be used for CB cells. The container holding the cells must be stable at cryogenic temperatures and allow for rapid heat transfer for effective control of both freezing and thawing. Sealed plastic vials (e.g., Nunc, Wheaton cryules) or glass ampules can be used for multiple small amounts (1-2 ml), while larger volumes (100-200 ml) can be frozen in polyolefin bags (e.g., Delmed) held between metal plates for better heat transfer during cooling. Bags of bone marrow cells have been successfully frozen by placing them in −80° C. freezers which, fortuitously, gives a cooling rate of approximately 3° C./minute).

In an alternative embodiment, the methanol bath method of cooling can be used. The methanol bath method is well-suited to routine cryopreservation of multiple small items on a large scale. The method does not require manual control of the freezing rate nor a recorder to monitor the rate. In a preferred embodiment, DMSO-treated cells are pre-cooled on ice and transferred to a tray containing chilled methanol which is placed, in turn, in a mechanical refrigerator (e.g., Harris or Revco) at −80° C. Thermocouple measurements of the methanol bath and the samples indicate the desired cooling rate of 1° to 3° C./minute. After at least two hours, the specimens have reached a temperature of −80° C. and can be placed directly into liquid nitrogen (−196° C.) for permanent storage.

After thorough freezing, the Expanded HSPC can be rapidly transferred to a long-term cryogenic storage vessel. In a preferred embodiment, samples can be cryogenically stored in liquid nitrogen (−196° C.) or its vapor (−165° C.). Such storage is greatly facilitated by the availability of highly efficient liquid nitrogen refrigerators, which resemble large Thermos containers with an extremely low vacuum and internal super insulation, such that heat leakage and nitrogen losses are kept to an absolute minimum.

Suitable racking systems are commercially available and can be used for cataloguing, storage, and retrieval of individual specimens.

Considerations and procedures for the manipulation, cryopreservation, and long-term storage of the hematopoietic stem cells, particularly from bone marrow or peripheral blood (e.g., mobilized peripheral blood), which are also largely applicable to the Expanded HSPC can be found, for example, in the following references, incorporated by reference herein: Gorin, 1986, Clinics In Haematology 15(1): 19-48; Bone-Marrow Conservation, Culture and Transplantation, Proceedings of a Panel, Moscow, Jul. 22-26, 1968, International Atomic Energy Agency, Vienna, pp. 107-186.

Other methods of cryopreservation of viable cells, or modifications thereof, are available and envisioned for use (e.g., cold metal-mirror techniques; Livesey and Linner, 1987, Nature 327:255; Linner et al., 1986, J. Histochem. Cytochem. 34(9):1123-1135; see also U.S. Pat. No. 4,199, 022 by Senkan et al., U.S. Pat. No. 3,753,357 by Schwartz, U.S. Pat. No. 4,559,298 by Fahy).

In other embodiments, isolated HSPC, the Enriched HSPC or the Expanded HSPC are preserved by freeze-drying (see Simione, 1992, J. Parenter. Sci. Technol. 46(6): 226-32).

6.9.2 Thawing

Following cryopreservation, frozen isolated HSPC, frozen Enriched HSPC or frozen Expanded HSPC can be thawed in accordance with the methods described below or known in the art.

Frozen cells are preferably thawed quickly (e.g., in a water bath maintained at 37°-41° C.) and chilled immediately upon thawing. In a specific embodiment, the vial containing the frozen cells can be immersed up to its neck in a warm water bath; gentle rotation will ensure mixing of the cell suspension as it thaws and increase heat transfer from the warm water to the internal ice mass. As soon as the ice has completely melted, the vial can be immediately placed in ice.

In an embodiment of the invention, the Expanded HSPC sample as thawed, or a portion thereof, can be infused for providing hematopoietic function in a human patient in need thereof. Several procedures, relating to processing of the thawed cells are available, and can be employed if deemed desirable.

It may be desirable to treat the cells in order to prevent cellular clumping upon thawing. To prevent clumping, various procedures can be used, including but not limited to, the addition before and/or after freezing of DNase (Spitzer et al., 1980, Cancer 45:3075-3085), low molecular weight dextran and citrate, hydroxyethyl starch (Stiff et al., 1983, Cryobiology 20:17-24), etc.

The cryoprotective agent, if toxic in humans, should be removed prior to therapeutic use of the thawed Expanded HSPC. In an embodiment employing DMSO as the cryopreservative, it is preferable to omit this step in order to avoid cell loss, since DMSO has no serious toxicity. However, where removal of the cryoprotective agent is desired, the removal is preferably accomplished upon thawing.

One way in which to remove the cryoprotective agent is by dilution to an insignificant concentration. This can be accomplished by addition of medium, followed by, if necessary, one or more cycles of centrifugation to pellet cells, removal of the supernatant, and resuspension of the cells. For example, intracellular DMSO in the thawed cells can be reduced to a level (less than 1%) that will not adversely affect the recovered cells. This is preferably done slowly to minimize potentially damaging osmotic gradients that occur during DMSO removal.

After removal of the cryoprotective agent, cell count (e.g., by use of a hemocytometer) and viability testing (e.g., by trypan blue exclusion; Kuchler, 1977, Biochemical Methods in Cell Culture and Virology, Dowden, Hutchinson & Ross, Stroudsburg, Pa., pp. 18-19; 1964, Methods in Medical Research, Eisen et al., eds., Vol. 10, Year Book Medical Publishers, Inc., Chicago, pp. 39-47) can be done to confirm cell survival. The percentage of viable antigen (e.g., CD34) positive cells in a sample can be determined by calculating the number of antigen positive cells that exclude 7-AAD (or other suitable dye excluded by viable cells) in an aliquot of the sample, divided by the total number of nucleated cells (TN) (both viable and non-viable) in the aliquot of the sample. The number of viable antigen positive cells in the sample can be then determined by multiplying the percentage of viable antigen positive cells by TNC of the sample.

Prior to cryopreservation and/or after thawing, the total number of nucleated cells, or in a specific embodiment, the total number of $CD34^+$ or $CD133^+$ cells can be determined. For example, total nucleated cell count can be performed by using a hemocytometer and exclusion of trypan blue dye. Specimens that are of high cellularity can be diluted to a concentration range appropriate for manual counting. Final cell counts for products are corrected for any dilution factors. Total nucleated cell count=viable nucleated cells per mL×volume of product in mL. The number of $CD34^+$ or $CD133^+$ positive cells in the sample can be determined, e.g., by the use of flow cytometry using anti-CD34 or anti-CD133 monoclonal antibodies conjugated to a fluorochrome.

Optionally, the Expanded HSPC sample can undergo HLA typing either prior to cryopreservation and/or after cryopreservation and thawing. HLA typing can be performed using serological methods with antibodies specific for identified HLA antigens, or using DNA-based methods for detecting polymophisms in the HLA antigen-encoding genes for typing HLA alleles. In a specific embodiment, HLA typing can be performed at intermediate resolution using a sequence specific oligonucleotide probe method for HLA-A and HLA-B or at high resolution using a sequence based typing method (allele typing) for HLA-DRB1.

In certain embodiments, the identity and purity of the starting HSPC, the enriched HSPC, and the Expanded HSPC prior to cryopreservation, or the Expanded HSPC after thawing can be subjected to multi-parameter flow cytometric immunophenotyping, which provides the percentage of viable antigen positive cells present in a sample. Each sample can be tested for one or more of the following cell phenotypes using a panel of monoclonal antibodies directly conjugated to fluorochromes:

1. $CD34^+$ HPC
2. T cells ($CD3^+$, including both $CD4^+$ and $CD8^+$ subsets)
3. B cells ($CD19^+$ or $CD20^+$)
4. NK cells ($CD56^+$)
5. Monocytes ($CD14^+$)
6. Myelomonocytes ($CD15^+$)
7. Megakaryocytes ($CD41^+$)
8. Dendritic Cells (lineage negative/HLA-DRbright and CD123bright, or lineage negative/HLA-DRbright and CD11cbright).

6.10 Genetically Engineered HSPC

In a preferred embodiment, the Expanded HSPC administered to the patient are non-recombinant. However, in a different embodiment, the isolated HSPC, the Enriched HSPC prior to expansion or the Expanded HSPC can be genetically engineered to produce gene products beneficial upon transplantation of the genetically engineered cells to a subject. Such gene products include but are not limited to anti-inflammatory factors, e.g., anti-TNF, anti-IL-1, anti-IL-2, etc. In some embodiments, HSPC can be genetically engineered to "knock out" expression of MHC. The HSPC can be genetically engineered for use in gene therapy to adjust the level of gene activity in a subject to assist or improve the results of transplantation or to treat a disease caused by, for example, a deficiency in the recombinant gene. The HSPC are made recombinant by the introduction of a recombinant nucleic acid into the isolated HSPC, the Enriched HSPC or into the Expanded HSPC. The description of genetically engineered HSPC provided herein is largely found in sec. 5.1 of U.S. Pat. No. 7,399,633.

In its broadest sense, gene therapy refers to therapy performed by the administration of a nucleic acid to a subject. The nucleic acid, either directly or indirectly via its encoded protein, mediates a therapeutic effect in the subject. The present invention provides methods of gene therapy wherein a nucleic acid encoding a protein of therapeutic value (preferably to humans) is introduced into the HSPC, before or after expansion, such that the nucleic acid is expressible by the HSPC and/or their progeny, followed by administration of the recombinant Expanded HSPC to a subject.

The recombinant HSPC of the present invention can be used in any of the methods for gene therapy available in the art. Thus, the nucleic acid introduced into the cells may encode any desired protein, e.g., a protein missing or dysfunctional in a disease or disorder. The descriptions below are meant to be illustrative of such methods. It will be readily understood by those of skill in the art that the methods illustrated represent only a sample of all available methods of gene therapy.

For general reviews of the methods of gene therapy, see Gardlik et al., 2005, Med. Sci. Monit. 11:RA110-121; Lundstrom, 1999, J. Recept. Signal Transduct. Res. 19:673-686; Robbins and Ghivizzani, 1998, Pharmacol. Ther. 80:35-47; Pelegrin et al., 1998, Hum. Gene Ther. 9:2165-2175; Harvey and Caskey, 1998, Curr. Opin. Chem. Biol. 2:512-518; Guntaka and Swamynathan, 1998, Indian J. Exp. Biol. 36:539-535; Desnick and Schuchman, 1998, Acta Paediatr. Jpn. 40:191-203; Vos, 1998, Curr. Opin. Genet. Dev. 8:351-359; Tarahovsky and Ivanitsky, 1998, Biochemistry (Mosc) 63:607-618; Morishita et al., 1998, Circ. Res. 2:1023-1028; Vile et al., 1998, Mol. Med. Today 4:84-92; Branch and Klotman, 1998, Exp. Nephrol. 6:78-83; Ascenzioni et al., 1997, Cancer Lett. 118:135-142; Chan and Glazer, 1997, J. Mol. Med. 75:267-282. Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In an embodiment in which recombinant HSPC are used in gene therapy, a gene whose expression is desired in a subject is introduced into the HSPC such that it is expressible by the cells and/or their progeny, and the recombinant cells are then administered in vivo for therapeutic effect.

Recombinant Expanded HSPC can be used in any appropriate method of gene therapy, as would be recognized by those in the art upon considering this disclosure. The resulting action of recombinant cell populations administered to a subject can, for example, lead to the activation or inhibition of a pre-selected gene in the subject, thus leading to improvement of the diseased condition afflicting the subject.

In this embodiment, the desired gene is introduced into the HSPC or its progeny prior to administration in vivo of the resulting recombinant cell. Such introduction can be carried out by any method known in the art, including but not limited to transfection, electroporation, microinjection, lipofection, calcium phosphate mediated transfection, infection with a viral or bacteriophage vector containing the gene sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217:599-618; Cohen et al., 1993, Meth. Enzymol. 217:618-644; Cline, 1985, Pharmac. Ther. 29:69-92) and may be used in accordance with the present invention, provided that the necessary developmental and physiological functions of the recipient cells are not disrupted. The technique should provide for the stable transfer of the gene to the cell, so that the gene is expressible by the cell and preferably heritable and expressible by its cell progeny. Usually, the method of transfer includes the transfer of a selectable marker to the cells. The cells are then placed under selection to isolate those cells that have taken up and are expressing the transferred gene. Those cells are then delivered to a subject.

Retroviral vectors (see Miller et al., 1993, Meth. Enzymol. 217:581-599) can be used in gene therapy. In such embodiments, the gene to be used in gene therapy is cloned into the retroviral vector for its delivery into HSPC. In particular embodiments, a retroviral vector for use in gene therapy contains all of the cis-acting sequences necessary for the packaging and integration of the viral genome, i.e., (a) a long terminal repeat (LTR), or portions thereof, at each end of the vector; (b) primer binding sites for negative and positive strand DNA synthesis; and (c) a packaging signal, necessary for the incorporation of genomic RNA into virions.

More detail about retroviral vectors can be found in Boesen et al., 1994, Biotherapy 6:291-302, Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are also of use in gene therapy. See Kozarsky and Wilson, 1993, Current Opinion in Genetics and Development 3:499-503, Rosenfeld et al., 1991, Science 252:431-434; Rosenfeld et al., 1992, Cell 68:143-155; and Mastrangeli et al., 1993, J. Clin. Invest. 91:225-234.

It has been proposed that adeno-associated virus (AAV) be used in gene therapy (Walsh et al., 1993, Proc. Soc. Exp. Biol. Med. 204:289-300). It has also been proposed that alphaviruses be used in gene therapy (Lundstrom, 1999, J. Recept. Signal Transduct. Res. 19:673-686).

Other methods of gene delivery in gene therapy include the use of mammalian artificial chromosomes (Vos, 1998, Curr. Op. Genet. Dev. 8:351-359); liposomes (Tarahovsky and Ivanitsky, 1998, Biochemistry (Mosc) 63:607-618); ribozymes (Branch and Klotman, 1998, Exp. Nephrol. 6:78-83); and triplex DNA (Chan and Glazer, 1997, J. Mol. Med. 75:267-282).

A desired gene can be introduced intracellularly and incorporated within HSPC DNA for expression, by homologous recombination (Koller and Smithies, 1989, Proc. Natl. Acad. Sci. USA 86:8932-8935; Zijlstra et al., 1989, Nature 342:435-438).

In a specific embodiment, isolated HSPC or the Enriched HSPC or the Expanded HSPC are genetically engineered to express a gene that is deficient in the patient to whom such HSPC are to be administered.

In a specific embodiment, the desired gene recombinantly expressed in the HSPC or their progeny after expansion to be introduced for purposes of gene therapy comprises an inducible promoter operably linked to the coding region, such that expression of the recombinant gene is controllable by controlling the presence or absence of the appropriate inducer of transcription.

6.11 Therapeutic Methods

The ideal therapeutic product for treatment of chemotherapy or radiation induced pancytopenia is one that, when infused, would give rise to rapid hematopoietic reconstitution, especially of granulocytes, and also facilitate autologous recovery of hematopoiesis.

The Expanded HSPC populations, whether recombinantly expressing a desired gene or not, can be administered into a human patient in need thereof for hematopoietic function for the treatment of disease or injury or for gene therapy by any method known in the art which is appropriate for the Expanded HSPC and the transplant site. Preferably, the Expanded HSPC are transplanted (infused) intravenously. In one embodiment, the Expanded HSPC differentiate into cells of the myeloid lineage in the patient. In another embodiment, the Expanded HSPC differentiate into cells of the lymphoid lineage in the patient.

In one embodiment, the transplantation of the Expanded HSPC is autologous. In such embodiments, before expansion, the HSPC are isolated from tissues of a subject to whom the Expanded HSPC are to be administered. In other embodiments, the transplantation of the Expanded HSPC is non-autologous. In some of these embodiments, the transplantation of the Expanded HSPC is allogeneic. For non-autologous transplantation, the recipient can be given an immunosuppressive drug to reduce the risk of rejection of the transplanted cells. In some embodiments, the transplantation of the Expanded HSPC is syngeneic.

In specific embodiments, HSPC are isolated from a subject for expansion prior to the subject's exposure to chemotherapy, and the Expanded HSPC obtained using the methods described herein from the isolated HSPC of the subject are administered to the subject following exposure to chemotherapy.

In specific embodiments, the Expanded HSPC are not administered to the patient within 12 hours of administration of a myeloid progenitor cell population as defined in International Patent Publication Nos. WO 2006/047569 A2 and/or WO 2007/095594 A2. In other specific embodiments, the Expanded HSPC are not administered to the patient within 18 or 24 or 36 or 48 or 72 or 96 hours or within 7, 10, 14, 21, 30 days of administration of such a myeloid progenitor cell population to the patient.

In a specific embodiment, the Expanded HSPC sample that is administered to the patient is not a pooled sample, i.e., it is derived from one individual (e.g., the umbilical cord blood and/or placental blood of one individual). In other embodiments, the Expanded HSPC sample that is administered to the patient is a pooled sample, i.e., it is derived from two or more individuals.

In some embodiments, the Expanded HSPC sample that is administered to the patient has been cryopreserved and thawed prior to administration. In other embodiments, the Expanded HSPC sample that is administered to the patient is fresh, i.e., it has not been cryopreserved prior to administration.

In a specific embodiment, the methods of the invention described herein further comprise administering one or more umbilical cord blood/placental blood samples (hereinafter called "Grafts" or "cord blood transplants") Such Grafts are umbilical cord blood and/or placental blood samples from humans that are whole blood samples, except that red blood cells have been removed from the whole blood samples, but which samples have not been further fractionated and have not been expanded. In a specific embodiment, the Grafts have been cryopreserved and are thawed prior to administration. The Grafts can be administered concurrently with, sequentially with respect to, before, or after the Expanded HSPC sample is administered to the patient. In a specific embodiment, the Expanded HSPC sample that is administered to the patient is administered within 1, 2, 3, 4, 5, 6, 7, 8, 9 or 10 days of administering the one or more Grafts. In a specific embodiment, the Expanded HSPC sample is administered before administering the one or more Grafts. In another specific embodiment, the Expanded HSPC sample is administered after administering the one or more Grafts. In a specific embodiment, the Expanded HSPC sample is administered 1 to 24 hours, 2 to 12 hours, 3 to 8 hours, or 3 to 5 hours before or after administering the one or more Grafts. In other specific embodiments, the Expanded HSPC sample is administered about 1, 2, 3, 4, 5, 6, 7, 8, 9, 10, 11, 12, 18, or 24 hours before or after administering the one or more Grafts. In a preferred embodiment, the Expanded HSPC sample is administered about 4 hours after administering the one or more Grafts. In a specific embodiment, a single Graft is administered that is derived from the cord and/or placental blood of a single human individual. In a specific embodiment, two Grafts are administered, each derived from the cord and/or placental blood of a different human individual. In another specific embodiment, a single Graft is administered that is a combination of cord and/or placental blood derived from two or more different human individuals. In the foregoing embodiments, the Graft is intended to provide long-term engraftment.

In certain embodiments, the Expanded HSPC are intended to provide short-term engraftment. Short-term engraftment usually refers to engraftment that lasts for up to a few days to few weeks, preferably 4 weeks, post-transplantation of the Expanded HSPC. In some embodiments, the Expanded HSPC are effective to provide engraftment 1, 2, 3, 4, 5, 6, 7, 8, 9, 10 days; or 1, 2, 3, 4 weeks after administration of the Expanded HSPC to a patient (e.g., a human patient). In other embodiments, the Expanded HSPC are intended to provide long-term engraftment. Long-term engraftment usually refers to engraftment that is present months to years post-transplantation of the Expanded HSPC. In some embodiments, the Expanded HSPC are effective to provide engraftment when assayed at 8, 9, 10 weeks; 2, 3, 4, 5, 6, 7, 8, 9, 10, 11, 12 months (or more than 2, 3, 4, 5, 6, 7, 8, 9, 10, 11, 12 months); or 1, 2, 3, 4, 5 years (or more than 1, 2, 3, 4, 5 years) after administration of the Expanded HSPC to a patient. In some embodiments, the Expanded HSPC are intended to provide both short-term and long-term engraftment. In certain embodiments, the Expanded HSPC provide short-term and/or long-term engraftment in a patient, preferably, a human.

In some embodiments, the Expanded HSPC are effective to provide engraftment when assayed at 1, 2, 3, 4, 5, 6, 7, 8, 9, 10 days (or more than 1, 2, 3, 4, 5, 6, 7, 8, 9, 10 days); 1, 2, 3, 4, 5, 6, 7, 8, 9, 10 weeks (or more than 1, 2, 3, 4, 5, 6, 7, 8, 9, 10 weeks); 1; 2, 3, 4, 5, 6, 7, 8, 9, 10, 11, 12 months (or more than 1, 2, 3, 4, 5, 6, 7, 8, 9, 10, 11, 12 months); or 1, 2, 3, 4, 5 years (or more than 1, 2, 3, 4, 5 years) after administration of the Expanded HSPC to a patient (e.g., a human patient). In other embodiments, the Expanded HSPC are effective to provide engraftment when assayed within 1, 2, 3, 4, 5, 6, 7, 8, 9, 10 days (or less than 1, 2, 3, 4, 5, 6, 7, 8, 9, 10 days); 1, 2, 3, 4, 5, 6, 7, 8, 9, 10 weeks (or less than 1, 2, 3, 4, 5, 6, 7, 8, 9, 10 weeks); or 1; 2, 3, 4, 5, 6, 7, 8, 9, 10, 11, 12 months (or less than 1, 2, 3, 4, 5, 6, 7, 8, 9, 10, 11, 12 months) after administration of the Expanded HSPC to a patient (e.g., a human patient). In specific embodiments, the Expanded HSPC are effective to provide engraftment when assayed within 10 days, 2 weeks, 3 weeks, 4 weeks, 6 weeks, 6 weeks, or 13 weeks after administration of the Expanded HSPC to a patient (e.g., a human patient).

The HSPC expanded using the methods described herein have been shown to provide short-term and/or long-term engraftment when infused into sublethally irradiated immunodeficient mice (e.g., NOD-SCID mice). The HSPC expanded using the methods described herein have been shown to provide short-term and/or long-term engraftment that is superior to the short-term and/or long-term engraftment obtained using cells expanded with a Notch agonist alone (i.e., without an aryl hydrocarbon receptor antagonist) or with an aryl hydrocarbon receptor antagonist (i.e., without a Notch agonist), e.g., in an animal model (NOD-SCID mice).

The inventors of the present invention observed that expansion of HSPC cells under conditions described herein, in the presence of a Notch agonist (e.g., Delta1$^{Ext-IgG}$) and an aryl hydrocarbon receptor antagonist (e.g., SR1), increases generation of repopulating cells capable of early myeloid repopulation in NSG mice as compared to a Notch agonist alone and an aryl hydrocarbon receptor antagonist alone, suggesting this combination may further enhance generation of short-term repopulating cells. This could have clear clinical benefit if these expanded cells were able to further reduce time to neutrophil engraftment in transplant recipients. Thus, the Expanded HSPC can be used for short-term in vivo repopulation/engraftment.

In addition, while significant generation of HSPC capable of sustained long-term repopulation in immunodeficient mice or humans remained elusive, the inventors of the present invention observed that expansion of HSPC cells under conditions described herein, in the presence of a Notch agonist (e.g., Delta1$^{Ext-IgG}$) and an aryl hydrocarbon receptor antagonist (e.g., SR1), increased generation of cells capable of long-term repopulation in NSG mice. Thus, the Expanded HSPC can be used for long-term in vivo repopulation/engraftment. Furthermore, the inventors found that expansion of HSPC cells under conditions described herein, in the presence of a Notch agonist (e.g., Delta1$^{Ext-IgG}$) and an aryl hydrocarbon receptor antagonist (e.g., SR1), increased in vivo generation of cells with multi-lineage potential that may give rise to cells of, e.g., myeloid, lymphoid and progenitor lineage. In addition, the inventors found that expansion of HSPC cells under conditions described herein, in the presence of a Notch agonist (e.g., Delta1$^{Ext-IgG}$) and an aryl hydrocarbon receptor antagonist (e.g., SR1), are capable of long-term maintenance of progenitor cells upon in vivo repopulation. In certain embodiments, the described effects of the Expanded HSPC are superior to the effects observed with HSPC expanded in the presence of a Notch agonist alone, an aryl hydrocarbon receptor antagonist alone, or the effects observed with non-manipulated HSPC.

Suitable methods of administration of the Expanded HSPC are encompassed by the present invention. The Expanded HSPC populations can be administered by any convenient route, for example by infusion or bolus injection, and may be administered together with other biologically active agents. Administration can be systemic or local.

The titer of Expanded HSPC administered which will be effective in the treatment of a particular disorder or condition will depend on the nature of the disorder or condition, and can be determined by standard clinical techniques. In addition, in vitro and in vivo assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. In specific embodiments, suitable dosages of Expanded HSPC for administration are generally about at least $5 \times 10^6$, $10^7$, $5 \times 10^7$, $75 \times 10^6$, $10^7$, $5 \times 10^7$, $10^8$, $5 \times 10^8$, $1 \times 10^9$, $5 \times 10^9$, $1 \times 10^{10}$, $5 \times 10^{10}$, $1 \times 10^{11}$, $5 \times 10^{11}$ or $10^{12}$ CD34$^+$ cells per kilogram patient weight, and most preferably about $10^7$ to about $10^{12}$ CD34$^+$ cells per kilogram patient weight, and can be administered to a patient once, twice, three or more times with intervals as often as needed. In a specific embodiment, a single Expanded HSPC sample provides one or more doses for a single patient. In one specific embodiment, a single Expanded HSPC sample provides four doses for a single patient.

In certain embodiments, the patient is a human patient, preferably an immunodeficient human patient.

In a specific embodiment, the Expanded HSPC population administered to a human patient in need thereof can be a pool of at least two individual Expanded HSPC samples, each sample derived from a single human (e.g., the umbilical cord blood and/or placental blood of a single human). For example, an aliquot of a frozen, thawed, expanded sample that is a pool of samples (i.e., a pooled sample) can be administered. In one embodiment, the individual samples in the pool are all derived from HSPC (e.g., umbilical cord blood and/or placental blood) of individuals of the same race, e.g., African-American, Caucasian, Asian, Hispanic, Native-American, Australian Aboriginal, Inuit, Pacific Islander, or are all derived from HSPC (e.g., umbilical cord blood and/or placental blood) of individuals of the same ethnicity, e.g., Irish, Italian, Indian, Japanese, Chinese, Russian, etc. In an alternative embodiment, the administered sample is not a pool of samples.

6.12 Pharmaceutical Compositions

The invention provides methods of treatment by administration to a patient of a pharmaceutical (therapeutic) composition comprising a therapeutically effective amount of recombinant or non-recombinant Expanded HSPC produced by the methods of the present invention as described herein above.

The present invention provides pharmaceutical compositions. Such compositions comprise a therapeutically effective amount of the Expanded HSPC, and a pharmaceutically acceptable carrier or excipient. Such a carrier can be but is not limited to saline, buffered saline, dextrose, water, glycerol, ethanol, and combinations thereof. The carrier and composition preferably are sterile. Suitable pharmaceutical carriers are described in Remington: The Science and Practice of Pharmacy, 21st Edition, David B. Troy, ed., Lippicott Williams & Wilkins (2005), which is incorporated by reference herein in its entirety, and specifically for the material related to pharmaceutical carriers and compositions. The pharmaceutical compositions described herein can be formulated in any manner known in the art.

The formulations (including, e.g., carriers, excipients and medium) and modes of administration of pharmaceutical compositions described at pages 14-15 of U.S. Patent Publication No. 2010/0183564, can also be used in the methods described herein. For example, as described at page 14 of U.S. Patent Publication No. 2010/0183564, in some embodiments, the carrier or excipient is selected to minimize degradation of the active ingredient and/or to minimize adverse side effects on the cells or in the patient.

The formulation should suit the mode of administration. Expanded HSPC can be resuspended in a pharmaceutically acceptable medium suitable for administration to a mammalian host. In preferred embodiments, the pharmaceutical composition is acceptable for therapeutic use in humans. The composition, if desired, can also contain pH buffering agents.

The pharmaceutical compositions described herein can be administered via any route known to one skilled in the art to be effective. In a preferred embodiment, the composition is formulated in accordance with routine procedures as a pharmaceutical composition adapted for intravenous administration to a patient (e.g., a human). Typically, compositions for intravenous administration are solutions in sterile isotonic aqueous buffer. Where necessary, the composition may also include a solubilizing agent and a local anesthetic such as lidocaine to ease pain at the site of the injection. In one embodiment, a pharmaceutically acceptable carrier for infusion of a composition comprising the Expanded HSPC into a patient comprises buffered saline with 5% HSA or unsupplemented basal medium or any medium known in the art or described herein.

As described at page 14 of U.S. Patent Publication No. 2010/0183564, the number of the Expanded HSPC to be administered to a patient depends on such factors as sex, age, weight, the types of disease or disorder, stage of the disorder, the percentage of the desired cells in the cell population and the amount of cells needed to produce a therapeutic benefit. In one embodiment, the composition is administered by intravenous infusion and comprises at least $10^4$ cells/kg, from $10^5$ to $5 \times 10^7$ cells/kg or more cells. In one embodiment, the composition comprises $10^6$ to $10^8$ cells/ml. In a specific embodiment, all of the infused cells are derived from HSPC isolated from a single human at birth.

As described at page 15 of U.S. Patent Publication No. 2010/0183564, the compositions can be formulated for parenteral administration by injection, e.g., by bolus injection or continuous infusion. In particular embodiments, the compositions can be formulated for local administration, e.g., by injection into the bone marrow of a bone (e.g., long bone).

In specific embodiments, the compositions described herein are formulated for administration to a patient with one or more additional therapeutic active ingredients.

6.13 Therapeutic Uses of the Expanded HSPC

The Expanded HSPC of the present invention can be used to provide hematopoietic function to a patient in need thereof, preferably a human patient. In other embodiments, the patient is a cow, a pig, a horse, a dog, a cat, or any other animal, preferably a mammal.

The Expanded HSPC that are administered to a patient in need thereof can be derived from the umbilical cord blood, placental blood, peripheral blood (e.g., mobilized peripheral blood), bone marrow or other sources of HSPC. In one embodiment, the Expanded HSPC are derived from the umbilical cord blood and/or placental blood, such as the umbilical cord blood and/or placental blood of a single human at birth, or the umbilical cord blood and/or placental blood of more than 1 human at birth (pool of samples), as described above. In another embodiment, the Expanded HSPC are derived from the peripheral blood (e.g., mobilized peripheral blood).

The description of therapeutic uses of the Expanded HSPC provided herein is largely found in sec. 5.6.1 of U.S. Pat. No. 7,399,633.

In one embodiment, administration of Expanded HSPC of the invention is for the treatment of immunodeficiency. In a preferred embodiment, administration of Expanded HSPC of the invention is for the treatment of pancytopenia or for the treatment of neutropenia. The immunodeficiency in the patient, for example, pancytopenia or neutropenia, can be the result of an intensive chemotherapy regimen, myeloablative regimen for hematopoietic cell transplantation (HCT), or exposure to acute ionizing radiation. Exemplary chemotherapeutics that can cause prolonged pancytopenia or prolonged neutropenia include, but are not limited to alkylating agents such as cisplatin, carboplatin, and oxaliplatin, mechlorethamine, cyclophosphamide, chlorambucil, and ifosfamide. Other chemotherapeutic agents that can cause prolonged pancytopenia or prolonged neutropenia include azathioprine, mercaptopurine, vinca alkaloids, e.g., vincristine, vinblastine, vinorelbine, vindesine, and taxanes. In particular, a chemotherapy regimen that can cause prolonged pancytopenia or prolonged neutropenia is the administration of clofarabine and Ara-C.

In one embodiment, the patient is in an acquired or induced aplastic state.

The immunodeficiency in the patient also can be caused by exposure to acute ionizing radiation following a nuclear attack, e.g., detonation of a "dirty" bomb in a densely populated area, or by exposure to ionizing radiation due to radiation leakage at a nuclear power plant, or exposure to a source of ionizing radiation, raw uranium ore.

Transplantation of Expanded HSPC of the invention can be used in the treatment or prevention of hematopoietic disorders and diseases. In one embodiment, the Expanded HSPC are administered to a patient with a hematopoietic deficiency. In one embodiment, the Expanded HSPC are used to treat or prevent a hematopoietic disorder or disease characterized by a failure or dysfunction of normal blood cell production and cell maturation. In another embodiment, the Expanded HSPC are used to treat or prevent a hematopoietic disorder or disease resulting from a hematopoietic malignancy. In yet another embodiment, the Expanded HSPC are used to treat or prevent a hematopoietic disorder or disease resulting from immunosuppression, particularly immunosuppression in subjects with malignant, solid tumors. In yet another embodiment, the Expanded HSPC are used to treat or prevent an autoimmune disease affecting the hematopoietic system. In yet another embodiment, the Expanded HSPC are used to treat or prevent a genetic or congenital hematopoietic disorder or disease.

Examples of particular hematopoietic diseases and disorders which can be treated by the Expanded HSPC of the invention include but are not limited to those listed in Table 2, infra.

TABLE 2

DISEASES OR DISORDERS WHICH CAN BE TREATED BY ADMINISTERING EXPANDED HSPC OF THE INVENTION

I. Diseases Resulting from a Failure or Dysfunction of Normal Blood Cell Production and Maturation hyperproliferative stem cell disorders
aplastic anemia
pancytopenia
agranulocytosis
thrombocytopenia
red cell aplasia
Blackfan-Diamond syndrome due to drugs, radiation, or infection
Idiopathic
II. Hematopoietic malignancies acute lymphoblastic (lymphocytic) leukemia
chronic lymphocytic leukemia
acute myelogenous leukemia
chronic myelogenous leukemia
acute malignant myelosclerosis
multiple myeloma
polycythemia vera
agnogenic myelometaplasia
Waldenstrom's macroglobulinemia
Hodgkin's lymphoma
non-Hodgkin's lymphoma
III. Immunosuppression in patients with malignant, solid tumors malignant melanoma
carcinoma of the stomach
ovarian carcinoma
breast carcinoma
small cell lung carcinoma
retinoblastoma
testicular carcinoma TABLE 2-continued DISEASES OR DISORDERS WHICH CAN BE TREATED BY ADMINISTERING EXPANDED HSPC OF THE INVENTION glioblastoma
rhabdomyosarcoma
neuroblastoma
Ewing's sarcoma
lymphoma
IV Autoimmune diseases rheumatoid arthritis
diabetes type I
chronic hepatitis
multiple sclerosis
systemic lupus erythematosus
V. Genetic (congenital) disorders anemias
familial aplastic
Fanconi's syndrome (Fanconi anemia)
Bloom's syndrome
pure red cell aplasia (PRCA)
dyskeratosis congenital
Blackfan-Diamond syndrome
congenital dyserythropoietic syndromes I-IV
Chwachmann-Diamond syndrome
dihydrofolate reductase deficiencies
formamino transferase deficiency
Lesch-Nyhan syndrome
congenital spherocytosis
congenital elliptocytosis
congenital stomatocytosis
congenital Rh null disease
paroxysmal nocturnal hemoglobinuria
G6PD (glucose-6-phosphate dehydrogenase) variants 1, 2, 3
pyruvate kinase deficiency
congenital erythropoietin sensitivity deficiency
sickle cell disease and trait (Sickle cell anemia)
thalassemia alpha, beta, gamma
met-hemoglobinemia
congenital disorders of immunity
severe combined immunodeficiency disease (SCID)
bare lymphocyte syndrome
ionophore-responsive combined immunodeficiency
combined immunodeficiency with a capping abnormality
nucleoside phosphorylase deficiency
granulocyte actin deficiency
infantile agranulocytosis
Gaucher's disease
adenosine deaminase deficiency
Kostmann's syndrome
reticular dysgenesis
congenital leukocyte dysfunction syndromes
VI. Others osteopetrosis
myelosclerosis
acquired hemolytic anemias
acquired immunodeficiencies
infectious disorders causing primary or secondary immunodeficiencies
bacterial infections (e.g., Brucellosis, Listerosis, tuberculosis, leprosy)
parasitic infections (e.g.. malaria, Leishmaniasis)
fungal infections
disorders involving disproportions in lymphoid cell sets and impaired immune functions due to aging
phagocyte disorders
Kostmann's agranulocytosis
chronic granulomatous disease
Chediak-Higachi syndrome
neutrophil actin deficiency
neutrophil membrane GP-180 deficiency
metabolic storage diseases
mucopolysaccharidoses
mucolipidoses
miscellaneous disorders involving immune mechanisms
Wiskott-Aldrich Syndrome
α1-antitrypsin deficiency In one embodiment, the Expanded HSPC are administered to a patient with a hematopoietic deficiency. Hematopoietic deficiencies whose treatment with the Expanded HSPC of the invention is encompassed by the methods of the invention include but are not limited to decreased levels of either myeloid, erythroid, lymphoid, or megakaryocyte cells of the hematopoietic system or combinations thereof, including those listed in Table 2. In one embodiment, the Expanded HSPC are administered prenatally to a fetus diagnosed with a hematopoietic deficiency.

Among conditions susceptible to treatment with the Expanded HSPC of the present invention is leukopenia, a reduction in the number of circulating leukocytes (white cells) in the peripheral blood. Leukopenia may be induced by exposure to certain viruses or to radiation. It is often a side effect of various forms of cancer therapy, e.g., exposure to chemotherapeutic drugs, radiation and of infection or hemorrhage.

Expanded HSPC also can be used in the treatment or prevention of neutropenia and, for example, in the treatment of such conditions as aplastic anemia, cyclic neutropenia, idiopathic neutropenia, Chediak-Higashi syndrome, systemic lupus erythematosus (SLE), leukemia, myelodysplastic syndrome, myelofibrosis, thrombocytopenia. Severe thrombocytopenia may result from genetic defects such as Fanconi's Anemia, Wiscott-Aldrich, or May-Hegglin syndromes and from chemotherapy and/or radiation therapy or cancer. Acquired thrombocytopenia may result from auto- or allo-antibodies as in Immune Thrombocytopenia Purpura, Systemic Lupus Erythromatosis, hemolytic anemia, or fetal maternal incompatibility. In addition, splenomegaly, disseminated intravascular coagulation, thrombotic thrombocytopenic purpura, infection or prosthetic heart valves may result in thrombocytopenia. Thrombocytopenia may also result from marrow invasion by carcinoma, lymphoma, leukemia or fibrosis.

Many drugs may cause bone marrow suppression or hematopoietic deficiencies. Examples of such drugs are AZT, DDI, alkylating agents and anti-metabolites used in chemotherapy, antibiotics such as chloramphenicol, penicillin, gancyclovir, daunomycin and sulfa drugs, phenothiazones, tranquilizers such as meprobamate, analgesics such as aminopyrine and dipyrone, anticonvulsants such as phenyloin or carbamazepine, antithyroids such as propylthiouracil and methimazole and diuretics. Transplantation of the Expanded HSPC can be used in preventing or treating the bone marrow suppression or hematopoietic deficiencies which often occur in subjects treated with these drugs.

Hematopoietic deficiencies may also occur as a result of viral, microbial or parasitic infections and as a result of treatment for renal disease or renal failure, e.g., dialysis. Transplantation of the Expanded HSPC populations may be useful in treating such hematopoietic deficiency.

Various immunodeficiencies, e.g., in T and/or B lymphocytes, or immune disorders, e.g., rheumatoid arthritis, may also be beneficially affected by treatment with the Expanded HSPC. Immunodeficiencies may be the result of viral infections (including but not limited to HIVI, HIVII, HTLVI, HTLVII, HTLVIII), severe exposure to radiation, cancer therapy or the result of other medical treatment.

In specific embodiments, the Expanded HSPC are used for the treatment of multiple myeloma, non-Hodgkin's lymphoma, Hodgkin's disease, neuroblastoma, germ cell tumors, autoimmune disorder (e.g., Systemic lupus erythematosus (SLE) or systemic sclerosis), amyloidosis, acute myeloid leukemia, acute lymphoblastic leukemia, chronic myeloid leukemia, chronic lymphocytic leukemia, myeloproliferative disorder, myelodysplastic syndrome, aplastic anemia, pure red cell aplasia, paroxysmal nocturnal hemoglobinuria, Fanconi anemia, Thalassemia major, Sickle cell anemia, Severe combined immunodeficiency (SCID), Wiskott-Aldrich syndrome, Hemophagocytic lymphohistiocytosis (HLH), or inborn errors of metabolism (e.g., mucopolysaccharidosis, Gaucher disease, metachromatic leukodystrophies or adrenoleukodystrophies). In some embodiments, the Expanded HSPC are used for the treatment of an inherited immunodeficient disease, an autoimmune disease and/or a hematopoietic disorder.

In one embodiment, the Expanded HSPC are for replenishment of hematopoietic cells in a patient who has undergone chemotherapy or radiation treatment. In a specific embodiment, the Expanded HSPC are administered to a patient that has undergone chemotherapy or radiation treatment. In a specific embodiment, the Expanded HSPC are administered to a patient who has HIV (e.g., for replenishment of hematopoietic cells in a patient who has HIV).

In certain embodiments, the Expanded HSPC are administered into the appropriate region of a patient's body, for example, by injection into the patient's bone marrow.

In specific embodiments, a Notch agonist is inactivated or removed prior to administration of the Expanded HSPC to a patient. In other specific embodiments, an aryl hydrocarbon antagonist is inactivated or removed prior to administration of the Expanded HSPC to a patient.

In some embodiments, the patient to whom the Expanded HSPC are administered is a bone marrow donor, at risk of depleted bone marrow, or at risk for depleted or limited blood cell levels. In one embodiment, the patient to whom the Expanded HSPC is administered is a bone marrow donor prior to harvesting of the bone marrow. In one embodiment, the patient to whom the Expanded HSPC is administered is a bone marrow donor after harvesting of the bone marrow. In one embodiment, the patient to whom the Expanded HSPC is administered is a recipient of a bone marrow transplant. In one embodiment, the patient to whom the Expanded HSPC is administered is elderly, has been exposed or is to be exposed to an immune depleting or myeloablative treatment (e.g., chemotherapy, radiation), has a decreased blood cell level, or is at risk of developing a decreased blood cell level as compared to a control blood cell level. In one embodiment, the patient has anemia or is at risk for developing anemia. In one embodiment, the patient has blood loss due to, e.g., trauma, or is at risk for blood loss. The Expanded HSPC can be administered to a patient, e.g., before, at the same time, or after chemotherapy, radiation therapy or a bone marrow transplant. In specific embodiments, the patient has depleted bone marrow related to, e.g., congenital, genetic or acquired syndrome characterized by bone marrow loss or depleted bone marrow. In one embodiment, the patient is in need of hematopoiesis. In one embodiment, HSPC are isolated from peripheral blood of a patient that will undergo an immune depleting procedure (e.g., chemotherapy, radiation, or bone marrow extraction from donor), the HSPC are expanded as described herein, and after the treatment the Expanded HSPC are administered to the patient.

6.14 Kits

The invention also provides a pharmaceutical pack or kit comprising one or more containers. In a preferred embodiment, a kit of the invention comprises, in one or more containers, a Notch agonist (such as purified Notch agonist) and an aryl hydrocarbon receptor antagonist. In a specific embodiment, the Notch agonist is Delta1$^{Ext-IgG}$, and the aryl hydrocarbon receptor antagonist is SR1. In one embodiment, a Notch agonist and an aryl hydrocarbon antagonist are stored in two separate containers of the kit. In certain embodiments, each of the ingredients of the kit listed herein is provided in a separate container. In other embodiments, two or more of the ingredients of the kit listed herein are provided in a same container.

The kit may additionally comprise one or more purified growth factors, for example, one or more growth factors that promote proliferation but not differentiation of HSPC. Such one or more growth factors may be stored in a container separate from the container comprising a Notch agonist and/or in a container separate from the container comprising an aryl hydrocarbon receptor antagonist. In some embodiments, the kit may further comprise, in a separate container, one or more purified growth factors that promote the differentiation of HSPC.

In certain embodiments, cell culture medium is also provided in the kit. In other embodiments, the solid phase on which Delta1$^{Ext-IgG}$ can be coated is also provided in the kit (for example, such a kit may contain one or more tissue culture dishes coated with Delta1$^{Ext-IgG}$). In certain embodiments, the kit also comprises fibronectin (e.g., an immobilized fibronectin) or a fragment thereof (e.g., CH-296). In certain embodiments, fibronectin or a fragment thereof are provided in a separate container. In some embodiments, fibronectin or a fragment thereof is provided in the same container as a Notch agonist. In a particular embodiment, fibronectin or a fragment thereof is provided in the same container as a Notch agonist, wherein both fibronectin or a fragment thereof and the Notch agonist are coated on a solid phase.

The kit may further comprise one or more containers filled with isolated HSPC or the Enriched HSPC. The Notch agonist, the aryl hydrocarbon antagonist and the one or more growth factors provided in the described kit are together effective to expand the Enriched HSPC exposed to these ingredients of the kit in culture. In certain embodiment, a kit comprises one or more containers filled with the Enriched HSPC or with the Expanded HSPC produced by the methods of the invention and/or reagents to prepare said cells, or with reagents for the genetic manipulation of the cells.

The kit may additionally comprise a solution or a buffer (in a separate container, or in the same container as the aryl hydrocarbon receptor antagonist and/or the Notch agonist).

In some embodiments, the kit comprises a container with one or more antibodies (e.g., anti-CD34, anti-CD133, anti-CD38, anti-CD45R, anti-Thy 1 antibodies, or any other antibodies to markers/antigens described herein or known in the art).

In specific embodiments, the kit comprises a pharmaceutically acceptable carrier or a stabilizer (in a separate container, or in the same container as an aryl hydrocarbon receptor antagonist and/or a Notch agonist). Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (Uniqema, United Kingdom), polyethylene glycol (PEG), and PLURONICS™ (BASF, Germany) (U.S. Patent Publication No. 2010/0183564).

In some embodiments, an aryl hydrocarbon antagonist in the kit is formulated as a suspension, solution or emulsion in oily or aqueous vehicle that, optionally, contains a suspending, a stabilizing, a dispersing agent, and/or a preservative. The stabilizing agent can be sodium bisulfate, sodium sulfite, ascorbic acid, citric acid or its salt, and/or sodium ethylenediaminetetraacetic acid (EDTA). The preservative can be benzalkonium chloride, methyl- or propyl-paraben, or chlorobutanol. In some embodiments, an aryl hydrocarbon antagonist in the kit is formulated in a suitable carrier, e.g., in water, suitable oil, saline, aqueous dextrose (glucose), related sugar solutions or glycol (e.g., propylene glycol or polyethylene glycol). In specific embodiments, an aryl hydrocarbon antagonist in the kit is formulated in a powder form (for reconstitution with a suitable vehicle, e.g., sterile pyrogen-free water, before use).

Optionally associated with such container(s) can be a notice in the form prescribed by a governmental agency regulating the manufacture, use or sale of pharmaceuticals or biological products, which notice reflects approval by the agency of manufacture, use or sale for human administration.

7. EXAMPLES

The data presented herein show advantageous properties of a combination of an agonist of Notch function, e.g., Delta1$^{ext-IgG}$, and an aryl hydrocarbon receptor antagonist, e.g., SR1, for ex vivo expansion of HSPC. The data show that HSPC expanded using such combination of agents maintain immature progenitor cells and display superior in vivo engraftment properties relative to the engraftment properties of HSPC expanded using a Notch agonist alone or an aryl hydrocarbon receptor antagonist alone. The inventors found that expansion of HSPC using a combination of a Notch agonist alone or an aryl hydrocarbon receptor antagonist leads to superior transient myeloid and progenitor engraftment and generation of cells with multi-lineage potential capable of long-term repopulation. Data also show that HSPC that display improved engraftment properties when expanded using such combination of agents include cord blood hematopoietic stem/progenitor cells and, surprisingly, peripheral blood stem cells (in particular, mobilized peripheral blood stem cells—mPBSC). While previous attempts to expand mPBSC ex vivo generated modest expansion of progenitor cells with no difference in engraftment, the data presented herein shows that the described combination of agents leads to enhanced expansion and engraftment of mPBSC.

Materials and Methods Utilized for Examples 1-8

Cell Processing.

Human cord blood samples for research were obtained from normal deliveries under Swedish Medical Center Institutional Review Board (Seattle) approval and after consent was obtained. The units were incubated in ammonium chloride red blood cell lysis buffer (consisting of 16.6 g NH$_4$Cl, 2 g NaHCO$_3$ and 74.4 mg EDTA per 2L of water) and resuspended in PBS with 2% human AB serum. Cells were incubated with CD34 Microbeads from Miltenyi Biotec and purified with an Automacs (Miltenyi Biotec). Cells were then frozen and thawed at time of use with PBS+1% FBS. Pools of 2 or more cord blood units were used for all experiments. Peripheral blood stem cells (PBSC) were obtained from a single donor and cryopreserved after CD34$^+$ cell selection.

Cell Culture.

Cells were cultured for 16 days in non-tissue-cultured-treated tissue culture flasks (25, 75, and 175-cm$^2$). Flasks were precoated with Delta1$^{ext-IgG}$ (ligand preparation described in Delaney C. et al., 2005, Blood 106(8):2693-2699; and Varnum-Finney et al., 2000, J. Cell Science 113: 4313-4318), or human control IgG at 2.5 μg/ml and retronectin 5 μg/ml. Delta1$^{ext-IgG}$ titrations were performed with concentrations of 0.5, 1.25 (for PBSC), 2.5, or 5 μg/ml. Flasks were incubated at 4° C. overnight or 37° C. for 2 hours and then washed with PBS and blocked with PBS 2% BSA for 30 minutes at 37° C. Cells were cultured in StemSpan serum-free expansion medium in the presence of 4 growth factors (IL6 (50 ng/ml), thrombopoietin (50 ng/ml), Flt-3 ligand (50 ng/ml), stem cell factor (50 ng/ml)) or 5 growth factors (4 growth factors plus IL3 (10 ng/ml)). SR-1 was made fresh and added to cells with all feedings at a concentration of 750 nM. Cultures in 25-cm$^2$ flasks were initiated with between 7×10$^4$ and 1.3×10$^5$ CD34$^+$ cells. Cultures in 75-cm$^2$ flasks were initiated with 3×10$^5$ CD34$^+$ cells. Cells were expanded to larger flasks when they exceeded cell density >1×10$^6$ cells/ml. Expansions typically occurred on day 7 and 10 of culture. Fresh media with cytokines was added very 3-4 days including the day prior to transplantation.

Flow Cytometric Analysis.

Immunofluorescence analysis was performed as described (see Ohishi et al., 2002, J Clin Invest. 110(8): 1165-1174), with FITC-labeled antibodies against human CD3, CD14, CD15, CD33, CD34, CD90, phycoerythryin (PE)-labeled antibodies against human CD19, CD56, CD90, CD133, Glycophorin A, CXCR4, PERCP-labeled antibodies against human CD14, CD34, APC-labeled antibodies against human CD45, CD90 and PECy7 labeled antibody against mouse CD45.1.

In Vivo Repopulation Studies.

Sublethally irradiated NOD-SCID IL-2Rγ-null mice (obtained from an established breeding colony at the Fred Hutchinson Cancer Research Center and approved for use by the Fred Hutchinson Cancer Research Center Institutional Animal Care and Use Committee) were infused with the progeny 10,000 starting CD34$^+$ cells per mouse via tail vein for cord blood experiments and the progeny of 20,000 for PBSC experiments. Repopulating ability of infused cells was assessed at 2-3 weeks post-transplant by bone marrow aspiration and at 13 weeks by bone marrow harvest.

Statistical Analyses.

Data are presented graphically with means. Significance of differences between groups was determined used non-parametric two-tailed t-tests (GraphPad software).

7.1 Example 1: Delta1$^{ext-IgG}$ and SR-1 in Combination Expand CB HSPC Ex Vivo This example shows that the combination of a Notch agonist and an aryl hydrocarbon receptor antagonist, specifically the combination of Delta1$^{Ext-IgG}$ and SR1, is effective to expand CD34$^+$ CB HSPC ex vivo.

Both Delta1$^{Ext-IgG}$ and SR1 have been previously shown to generate CD34$^+$ CB HSPC ex vivo as compared to cytokine-containing control (see Boitano et al., 2010, Science 329(5997): 1345-1348; Ohishi et al., 2002, J Clin Invest. 110(8): 1165-1174; Delaney et al., 2005, Blood 106(9): 2693-2699).

To determine whether Delta1$^{Ext-IgG}$ and SR1 in combination were successfully able to expand CD34$^+$ CB HSPC ex vivo, CD34$^+$ cell generation, an HSPC enriched population routinely used in clinical application, was assessed at multiple time points in culture as compared to IgG control. CD34$^+$ CB progenitors were isolated by bead selection and Automacs and then cultured for 21 days in StemSpan serum-free expansion media supplemented with cytokines (TPO, SCF, IL-6, and Flt3-ligand at 50 ng/ml). This cytokine combination has previously been shown to optimize CD34$^+$ HSPC expansion in the presence of SR1 (see Boitano et al., 2010, Science 329(5997): 1345-1348). Cells were cultured in the presence of SR1 (750 nM) and Delta1$^{Ext-IgG}$ (0.5 or 2.5 μg/ml) or an IgG control. The engineered Notch ligand, Delta1$^{ext-IgG}$, contains the extracellular domain of Delta1 fused to the Fc portion of human IgG1 and is immobilized on the plastic surface of tissue culture flasks at varying densities. Immobilization of the Fc portion of human IgG1 served as a control construct. 7.0×10$^3$ CD34$^+$ selected cells were seeded per flask from a pool of 2 CB units. At 7, 14, 18, and 21 days in culture Delta1$^{Ext-IgG}$ and SR1 combination groups had greater CD34-fold expansion than IgG control (FIG. 1). This effect was most pronounced at later time points with 425 and 161-fold CD34 expansion in the combination groups and only 38 fold in the IgG groups. Delta1$^{Ext-IgG}$ and SR1 alone groups (data not shown) also demonstrated enhanced CD34 expansion compared to IgG control consistent with previous reports.

7.2 Example 2: Delta1$^{ext-IgG}$ and SR-1 in Combination Maintain CB HSPC with More Immature Phenotype Ex Vivo This example shows that expansion of HSPC in the presence of the combination of a Notch agonist and an aryl hydrocarbon receptor antagonist, specifically Delta1$^{Ext-IgG}$ and SR1, leads to an increase in HSPC-enriched cell population (CD34$^+$ cells), an increase in cells capable of generating long-term engraftment (CD34$^+$CD90$^+$ cells), and a decrease in differentiated myeloid cells that have lost multipotent repopulation capacity (CD34$^-$CD14$^+$ cells).

The phenotype of cells expanded ex vivo in the presence of Delta1$^{Ext-IgG}$, SR1, or the combination was evaluated to determine how the combination of these agents affected generation of CD34$^+$ and CD34$^+$CD90$^+$ CB HSPC. The CD34$^+$ cell population has previously been shown to be enriched for HSPC based on the presence of both long-term culture initiating cells (LTC-IC) and cells capable of sustained long-term in vivo repopulation (see Srour et al., 1991, Blood Cells 17(2): 287-295; Berenson et al., 1988, J Clin Invest. 81(3): 951-955). CD34$^+$CD90$^+$ cells represent a subpopulation of CD34$^+$ cells capable of generating long-term engraftment when transplanted in isolation (see Baum et al., 1992, Proc Natl Acad Sci. 89: 2804-2808; Craig et al., 1993, J Exp Med. 177: 1331-1342; Majeti et al., 2007, Cell Stem Cell 1(6): 635-645). Thus, these two phenotypes were used to determine how the culture conditions affected generation of CB HSPC.

Figures 2A, 2B, 2C:
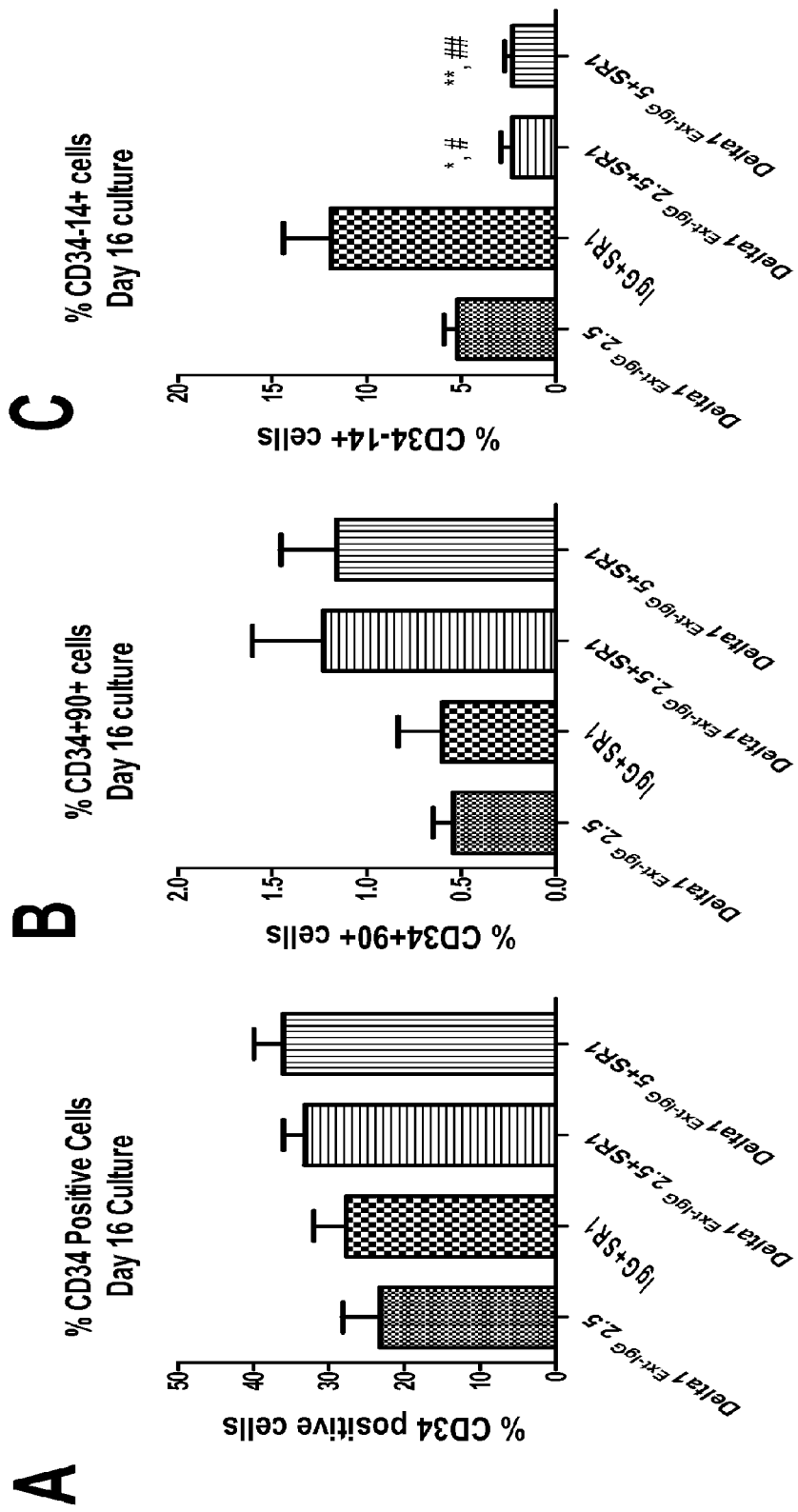

Cells were cultured in serum-free StemSpan with four cytokines (TPO, SCF, IL-6, Flt-3 ligand at 50 ng/ml) for 16 days in the presence of Delta1$^{Ext-IgG}$ 2.5 μg/ml, SR1 (with IgG), or the combination (with two Delta1$^{Ext-IgG}$ densities). Cell surface analysis by FACS of cell populations generated after 16 days in culture revealed possibly greater percentage of CD34$^+$ and CD34$^+$CD90$^+$ cells in both combination groups compared to either approach alone (FIG. 2A-B). While statistical comparisons between the combined groups and Delta1$^{Ext-IgG}$ or SR1 alone did not achieve significance, this trend was present for 6 independent experiments. Delta1$^{Ext-IgG}$ and SR1 in combination additionally result in a lower percentage of CD34$^-$CD14$^+$ cells, differentiated myeloid cells that have lost multi-potent repopulation capacity, as compared to Delta1$^{Ext-IgG}$ (not significant) or SR1 (significant) alone, suggesting maintenance of a more immature cellular phenotype (FIG. 2C).

7.3 Example 3: Maintenance of CD34$^+$CD90$^+$ Cells Ex Vivo Correlates with in Vivo Engraftment This example shows that maintenance of the CD34$^+$ CD90$^+$ cell phenotype correlates with improved in vivo repopulating ability of CB HSPC expanded in the presence of a combination of a Notch agonist and an aryl hydrocarbon receptor antagonist (Delta1$^{Ext-IgG}$ and SR1).

Figures 3A, 3B:
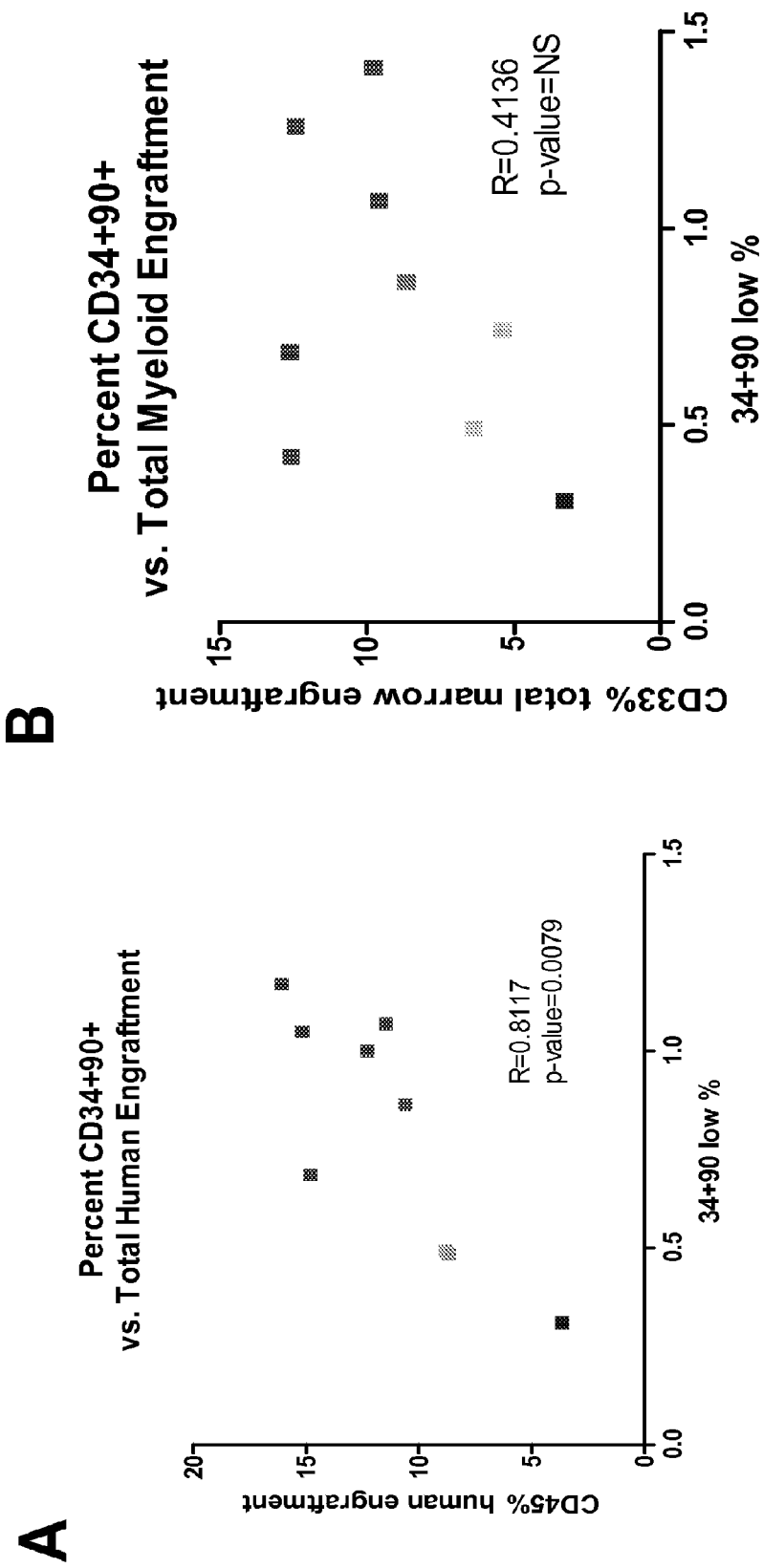

Cells were cultured as described above and transplanted into sublethally irradiated immunodeficient NSG mice. Total human engraftment was defined as percent of human CD45$^+$ murine CD45.1$^-$ cells based on bone marrow aspirate at 2 weeks post-transplant. Total myeloid engraftment was defined as percent human CD45$^+$CD33$^+$ murine CD45.1$^-$ cells on bone marrow aspirate at the same time point. Then, mean engraftment for six mice per group was compared to the percent CD34$^+$CD90$^+$ cells infused at time of transplant (FIG. 3). Total human engraftment correlated significantly with percent CD34$^+$CD90$^+$ cells infused at time of transplant (R=0.8117, p-value=0.0079, FIG. 3A). Percent CD34$^+$ CD90$^+$ cells also may predict early myeloid engraftment at this time point, although the correlation did not achieve significance (R=0.4136, p-value=0.2685, FIG. 3B). As indicated in FIG. 3, those mice receiving cells cultured in the presence of both Delta1$^{Ext-IgG}$ and SR1 maintain the highest percentage of this immature CB HSPC population and have on average higher engraftment than those cultured with either approach alone suggesting the CD34$^+$CD90$^+$ phenotype may represent or contain cells responsible for in vivo repopulation consistent with previous reports. Thus, culture with Delta1$^{Ext-IgG}$ and SR1 in combination results in generation of HSPC with a more immature cellular phenotype, and this phenotype correlates with enhanced in vivo repopulating ability.

7.4 Example 4: SR-1 Enhances Expansion of CB HSPC; Delta1$^{Ext-IgG}$ Blocks Differentiation This example shows that blockade of differentiation of progenitor cells via Notch signaling (using Notch agonist Delta1$^{Ext-IgG}$) and enhancement of cellular expansion via an AhR antagonist (SR1) may be responsible for enhanced generation of CB HSPC when Delta1$^{Ext-IgG}$ and SR1 are used in combination.

Cells were cultured as described in previous sections in the presence of SR1 (with IgG), IgG, or increasing densities of Delta1$^{Ext-IgG}$. Cells were counted at various time points in culture to determine expansion of total nucleated cells (TNC). TNC expansion was defined as cell count at given time in culture divided by starting TNC. SR1 enhanced total nucleated cell (TNC) expansion over IgG control and all Delta1$^{Ext-IgG}$ conditions (FIG. 4A). Addition of SR1 to Delta1$^{Ext-IgG}$ increased TNC generation over Delta1$^{Ext-IgG}$ alone (data not shown). While apoptosis and cell cycle studies are pending, each condition demonstrated comparable overall cell viability at each time point (data not shown) suggesting this expansion was due to enhanced cellular proliferation.

Cultured cells were analyzed after 16 days in culture for cell surface markers of immature progenitor and differentiated cell populations. Induction of Notch signaling through increasing densities of Delta1$^{Ext-IgG}$ decreased TNC generation in a stepwise manner (FIG. 4B). This was due primarily to decreased generation of mature cells of the myeloid lineage (CD34$^-$CD14$^+$) with increased induction of Notch signaling (FIG. 4C) suggesting Delta1$^{Ext-IgG}$ may be blocking or delaying differentiation of these cells in culture. The decreased number of myeloid cells generated with increasing densities of Delta1$^{Ext-IgG}$ was the result of both greater TNC generation and percentage of myeloid cells generated (FIG. 2C) suggesting a qualitative difference in cells generated in the presence of Notch signaling. This is consistent with previous data demonstrating Delta1$^{Ext-IgG}$ inhibits generation of CD14$^+$ cells by inhibiting differentiation from CD34$^+$ cells (see Delaney et al., 2005, Blood 106(9): 2693-2699).

Generation of immature progenitor and precursor cells, however, was relatively spared by increasing Delta1$^{Ext-IgG}$ signaling where total numbers of immature HSPC (CD34$^+$ CD90$^+$) and lymphoid progenitors (CD34$^+$CD7$^+$) were more equivalent between conditions despite large differences in TNC (FIG. 4D, E). In addition, greater numbers and percentages of these immature progenitor cells were generated in the presence of SR1 and Delta1$^{Ext-IgG}$ as compared to Delta1$^{Ext-IgG}$ alone (data not shown).

7.5 Example 5: Higher Densities of Delta1$^{ext-IgG}$ in Combination with SR-1 Enhance In Vivo Engraftment Despite Greater In Vitro Expansion with Lower Delta1$^{ext-IgG}$ Densities This example demonstrates optimal Delta1$^{Ext-IgG}$ densities for maximal generation of cells with in vivo repopulating ability. In particular, it shows that higher densities of Delta1$^{ext-IgG}$ in combination with SR-1 enhance in vivo engraftment despite greater in vitro expansion with lower Delta1$^{ext-IgG}$ densities.

It was noted that generation of CD34$^+$ progenitor cells was increased in the presence of SR1 and the lowest Delta1$^{Ext-IgG}$ density (0.5 µg/ml). Thus, this combination was selected for initial transplant experiments (data not shown), which showed some in vivo repopulation. Next, CB HSPC were expanded in the presence of SR1, Delta1$^{Ext-IgG}$, or the combination using varying concentrations of the immobilized Delta1$^{Ext-IgG}$. Greatest expansion of CD34$^+$ CB HSPC was noted with SR1 and the lowest Delta1$^{Ext-IgG}$ ligand density (FIG. 5A). The two groups with higher Delta1$^{Ext-IgG}$ densities (2.5 and 5 µg/ml) demonstrated inferior ex vivo CD34$^+$ cell expansion to SR1.

The progeny of 1×10$^4$ CD34$^+$ cells were then transplanted into 10 sublethally irradiated NSG mice per condition and engraftment was assessed by bone marrow aspirate at 2 weeks post-transplant. Total human engraftment was defined as percent of human CD45$^+$ murine CD45.1$^-$ cells based on bone marrow aspirate at 2 weeks post-transplant. Total myeloid engraftment was defined as percent human CD45$^+$ CD33$^+$ murine CD45.1$^-$ cells on bone marrow aspirate at the same time point. Significant enhancement of repopulating cell activity was seen for total human engraftment and total myeloid engraftment with higher densities of Delta1$^{Ext-IgG}$ as compared to the lowest density (FIG. 5B, C). Total human engraftment and total myeloid engraftment for cells cultured with Delta1$^{Ext-IgG}$ 2.5 µg/ml and SR1 were both 3.7-fold higher (p-values 0.0144, 0.0099) than the lower density combination. Total human engraftment and total myeloid engraftment for cells cultured with Delta1$^{Ext-IgG}$ 5 µg/ml and SR1 were 3 and 3.7-fold higher (p-values 0.0284, 0.0165) than the lower density combination. Furthermore, addition of SR1 to higher densities of Delta1$^{Ext-IgG}$ significantly enhanced repopulating cell activity as compared to Delta1$^{Ext-IgG}$ 2.5 µg/ml control. For example, total human engraftment was 3-fold higher for with Delta1$^{Ext-IgG}$ 2.5 µg/ml and SR1 compared to Delta1$^{Ext-IgG}$ 2.5 µg/ml alone (p-value 0.0458). Other comparisons with Delta1$^{Ext-IgG}$ 2.5 µg/ml control also reached significance. In this individual experiment, in vivo repopulating cell activity was not significantly enhanced with higher Delta1$^{Ext-IgG}$ densities and SR1 as compared to SR1 alone, although comparisons trended towards significance. For example total human engraftment with Delta1$^{Ext-IgG}$ 2.5 µg/ml and SR1 compared to SR1 alone was 2-fold higher (p-value 0.0832) and total myeloid engraftment was 2.3-fold higher (p-value 0.0732). Thus, despite increased generation of CD34$^+$ CB HSPC in vitro, the lowest dose of Delta1$^{Ext-IgG}$ ligand with SR1 resulted in inferior generation of cell with in vivo repopulating activity in comparison to the combination of SR1 and higher doses of Delta1$^{Ext-IgG}$ ligand. Thus, the combination of SR1 and higher doses of Delta1$^{Ext-IgG}$ ligand demonstrates the most robust in vivo repopulating activity.

7.6 Example 6: Delta1$^{ext-IgG}$ and SR-1 in Combination Enhance Generation of Short-Term Repopulating Cells and Maintain CB HSPC In Vivo This example demonstrates that the combination of a Notch agonist and an aryl hydrocarbon antagonist, specifically the combination of Delta1$^{ext-IgG}$ and SR1, enhances total human engraftment, enhances engraftment of myeloid cells (CD45$^+$CD33$^+$) that are capable of early short-term repopulation, and enhances engraftment of immature progenitor cells (CD45$^+$CD34$^+$).

The in vivo repopulating cell potential of cells expanded using optimized density of Delta1$^{Ext-IgG}$ and SR1 was investigated. Because delayed neutrophil recovery remains a major clinical challenge in cord blood transplantation resulting in increased morbidity and mortality from infectious complications, it was investigated whether Delta1$^{Ext-IgG}$ and SR1 in combination improved early total human (human CD45$^+$ murine CD45.1$^-$), myeloid (human CD45$^+$CD33$^+$ murine CD45.1), and progenitor cell (human CD45$^+$CD34$^+$ murine CD45.1$^-$) engraftment in immunodeficient NSG mice.

Figure 6A:
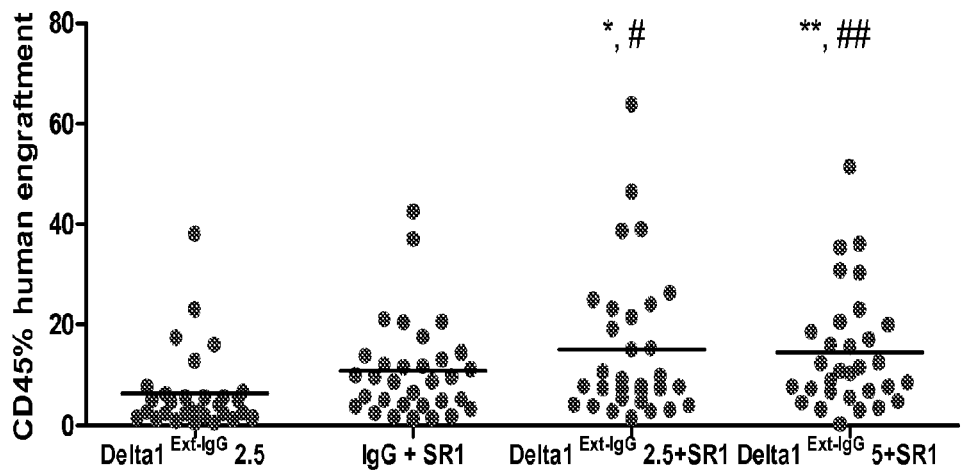

Transplants into NSG mice were performed as described above, with the cultured progeny of 1×10$^4$ CD34$^+$ cells. Cells were cultured in the presence of SR1, Delta1$^{Ext-IgG}$ 2.5 µg/ml, or SR1 and Delta1$^{Ext-IgG}$ (2.5 or 5 µg/ml) for 16 days. In four combined experiments, there was a trend towards improved total human engraftment in the combination groups compared to either control (FIG. 6A). This reached significance when compared to Delta1$^{Ext-IgG}$ 2.5 µg/ml (p-values 0.0056, 0.0026 for comparison with SR1 and Delta1$^{Ext-IgG}$ 2.5 and 5 µg/ml respectively) and approached significance compared to SR1 alone (p-values 0.1624, 0.1699 for comparison with SR1 and Delta1$^{Ext-IgG}$ 2.5 and 5 µg/ml respectively).

Figure 6B:
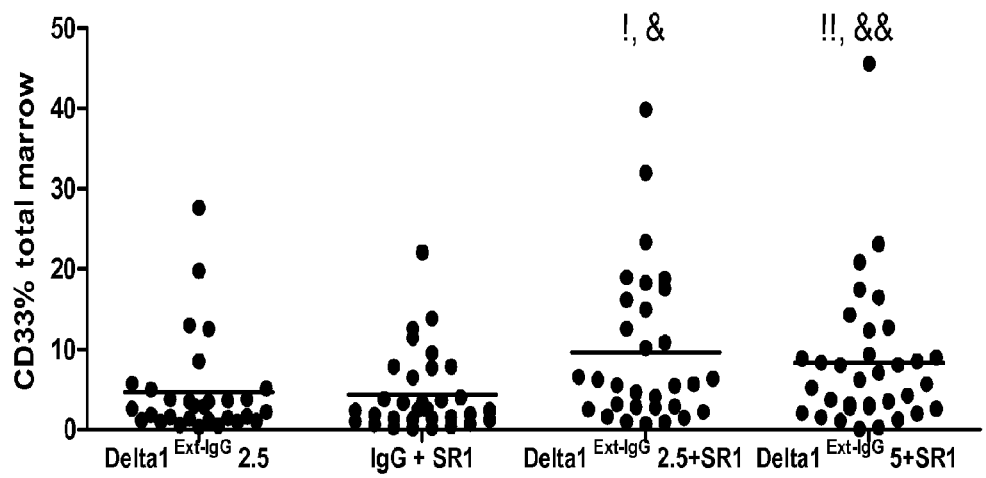
Figure 6C:
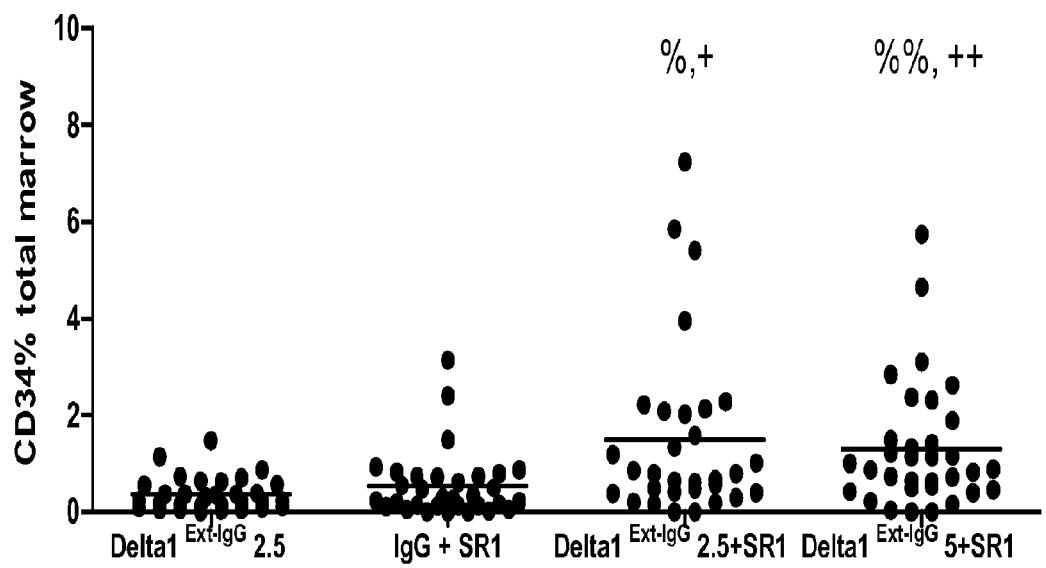
Figure 7A:
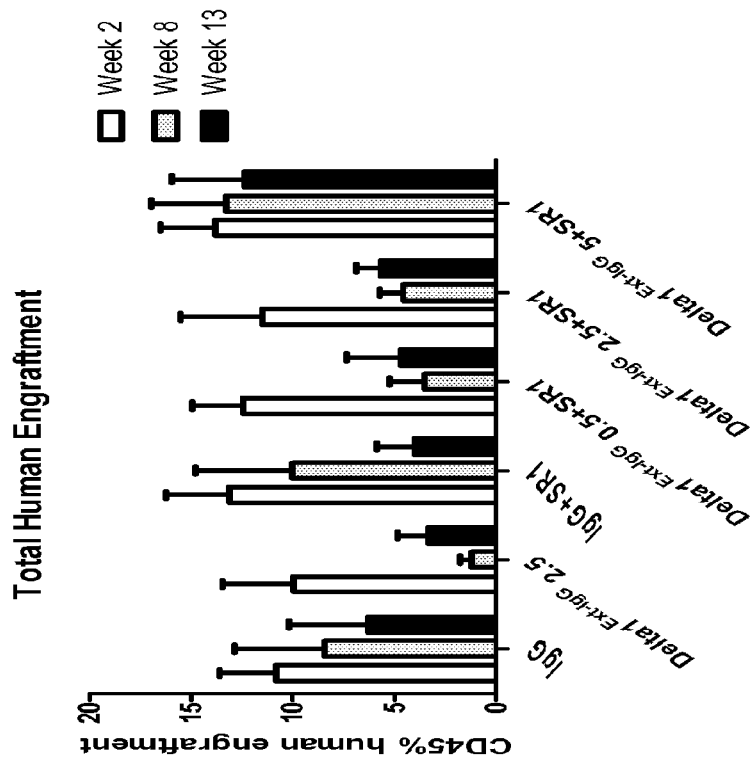
Figure 7B:
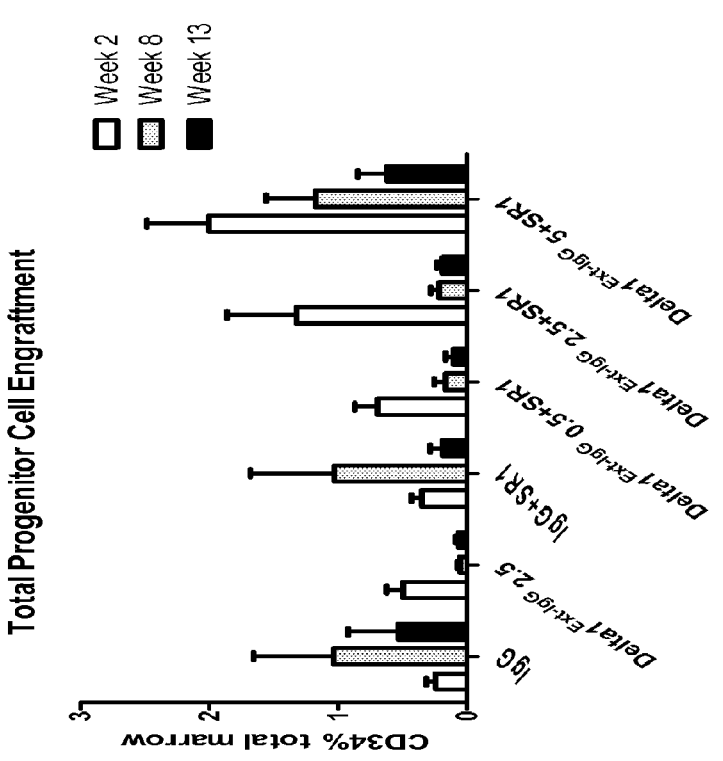
Figure 7C:
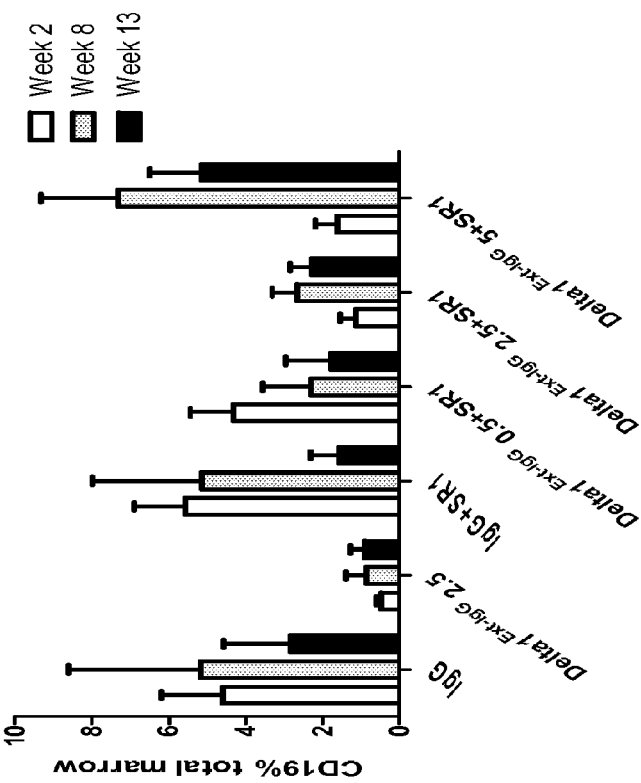
Figure 7D:
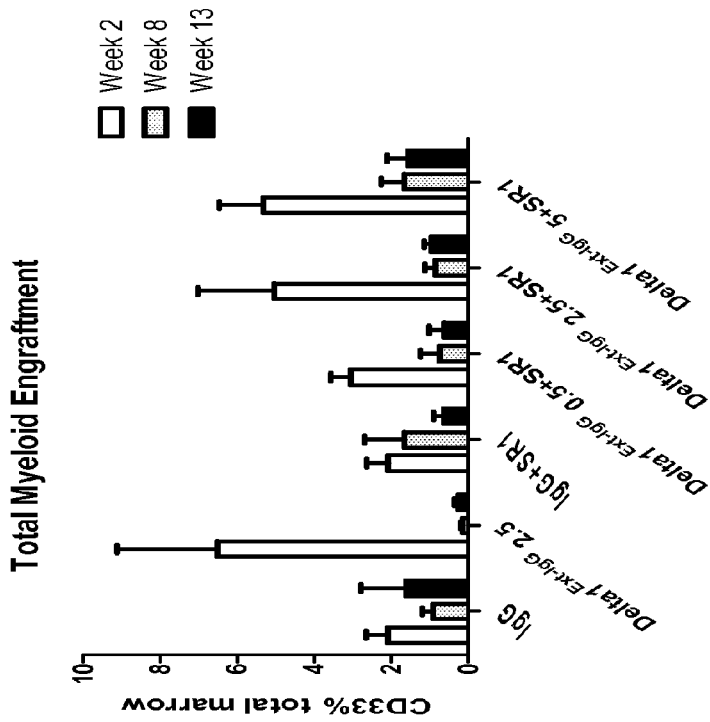

Both combination groups (SR1 and Delta1$^{Ext-IgG}$ 2.5 and 5 µg/ml) demonstrated significantly enhanced total myeloid engraftment compared to SR1 and Delta1$^{Ext-IgG}$ 2.5 µg/ml controls, an important measure of the early repopulating potential of these expanded cells (FIG. 6B). SR1 and Delta1$^{Ext-IgG}$ at 2.5 or 5 µg/ml resulted in approximately 2-fold greater generation of early myeloid repopulating cells as compared to either alone (all comparison achieve significance, p-values listed in FIG. 6B). Notably, the combination of SR1 and Delta1$^{Ext-IgG}$ also resulted in significantly enhanced engraftment of immature progenitor cells (FIG. 6C) suggesting enhanced generation of short-term repopulating cells did not result in the exhaustion of more immature HSPC. SR1 and Delta1$^{Ext-IgG}$ 2.5 and 5 µg/ml resulted in approximately 2.5-fold greater engraftment of CD34$^+$ HSPC compared to SR1 and almost 4-fold greater engraftment than Delta1$^{Ext-IgG}$ 2.5 alone (all p-values achieved significance, listed in FIG. 6C).

7.7 Example 7: Delta1$^{Ext-IgG}$ and SR1 Combination Results in Generation of Cells with Multi-Lineage Potential Capable of Long-Term Repopulation This example demonstrates that HSPC expanded in the presence of both a Notch agonist (Delta1$^{Ext-IgG}$) and an aryl hydrocarbon antagonist (SR1) are capable of long-term in vivo repopulation, long-term generation of cells of various lineage (myeloid, lymphoid, progenitor), and maintenance of long-term repopulating progenitor cells.

To determine how cells cultured in the presence of both SR1 and Delta1$^{Ext-IgG}$ contributed to engraftment over time, total human (human CD45$^+$ murine CD45.1$^-$), progenitor cell (human CD45$^+$CD34$^+$ murine CD45.1$^-$), myeloid (human CD45$^+$CD33$^+$ murine CD45.1$^-$), and lymphoid (human CD45$^+$CD19$^+$ murine CD45.1$^-$), engraftment was assessed at 2, 8, and 13 weeks post-transplant (FIG. 7). These results were compared to IgG, SR1, and Delta1$^{Ext-IgG}$ 2.5 µg/ml controls.

Cells were cultured and transplanted as described above with the progeny of 1×10$^4$ CD34$^+$ cells transplanted per mouse. Total human, progenitor cell, myeloid, and lymphoid assessments were performed on bone marrow samples. Bone marrow aspirates were performed in the mice at 2 and 8 weeks post-transplant, and mice were sacrificed for bone marrow harvest at 13 weeks. Delta1$^{Ext-IgG}$ and SR1 in combination maintained total human engraftment long-term with almost no decrease in total human engraftment in the Delta1$^{Ext-IgG}$ 5 µg/ml and SR1 13 weeks after transplant. This was in clear contrast to the control groups (IgG, SR1, and Delta1$^{Ext-IgG}$ alone) and lowest combination group where there was a clear reduction in overall long-term repopulation (as evidenced by engraftment at 8 and 13 weeks). Furthermore, engraftment was seen in the myeloid, lymphoid, and progenitor cells compartments suggesting the presence of cells with multi-lineage, long-term repopulating potential.

To determine whether generation of HSPC with long-term repopulating potential was enhanced when cultured with Delta1$^{ext-IgG}$ and SR-1 in combination, long-term engraftment at 13 weeks post-transplant was compared with either condition alone (FIG. 8). While not all comparisons were significant, there was a trend towards enhanced total human and progenitor cell engraftment in the combination groups, particularly with the highest Delta1$^{Ext-IgG}$ density (5 µg/ml) (p-values listed in FIG. 8).

7.8 Example 8: Delta1$^{ext-IgG}$ and SR1 in Combination Expand Adult HSPC Capable of Enhanced In Vivo Repopulation This example shows that, unlike Delta1$^{ext-IgG}$ alone or SR1 alone, the combination of a Notch agonist and an aryl hydrocarbon antagonist is capable of successful expansion and engraftment of adult HSPC derived from peripheral blood.

To test whether the combination of Delta1$^{ext-IgG}$ and SR1 had similar effects on adult HSPC as cord blood-derived HSPC, mobilized peripheral blood stem cells (mPBSC) were cultured in the presence of Delta1$^{ext\text{-}IgG}$, SR1 or the combination for 16 days and transplanted into immunodeficient mice. Previous attempts to expand mPBSC have met limited success including experiments using Delta alone (unpublished). In vitro, expansion with SR1 alone or lower dose Delta1$^{ext\text{-}IgG}$ (1.25 μg/ml) resulted in greatest TNC and CD34$^+$ cell expansion; however, addition of Delta1$^{ext\text{-}IgG}$ (1.25 or 5 μg/ml) resulted in greater maintenance of the immature progenitor CD34$^+$CD90$^+$ cell population (at least 2-fold higher in the presence of Delta1$^{ext\text{-}IgG}$ 5 μg/ml and SR1 as compared to SR1 alone for 4 or 5 growth factor conditions). When the progeny of 20,000 CD34$^+$ cells were transplanted into immunodeficient mice, the combination groups (cultured with 4 or 5 growth factors) had significantly greater total human and early myeloid engraftment at 3 weeks compared to SR1 alone or 20,000 non-manipulated mPBSC from the same donor (FIG. 9). Engraftment was comparable to that achieved with 250,000 starting cells.

7.9 Example 9: Enhanced Generation of Cord Blood HSPC by Expansion Using a Combination of Delta1$^{ext\text{-}IgG}$ and SR1

Delayed myeloid engraftment is a known risk factor in patients undergoing cord blood transplantation (CBT) as a consequence of inadequate cell doses provided by the stem cell graft. Furthermore, this delay in engraftment contributes to an increased risk of early transplant related mortality, primarily from infectious complications, as compared to conventional allogeneic stem cell donor transplants.

Ex vivo culture of CB HSPC in the presence of StemRegenin1 (SR1), an aryl hydrocarbon receptor antagonist, and growth factors (SCF, Flt3-ligand, IL3, and TPO) previously was shown to result in significant expansion of CD34$^+$ HSPC with enhanced in vivo repopulating capability (Boitano et al., 2010, Science 329(5997):1345-1348). Ex vivo expansion and enhanced in vivo repopulation with CD34$^+$ CB HSPC cultured in the presence of the immobilized Notch ligand Delta1$^{Ext\text{-}IgG}$ and growth factors (SCF, Flt3-ligand, IL6, IL3, TPO) has also been previously demonstrated (Delaney et al, 2010, Nat Med. 16(2):232-236; Delaney et al., 2005, Blood 106(8):2693-2699; Ohishi et al., 2002, J Clin Invest. 110(8):1165-1174). In a phase I trial, patients undergoing cord blood transplantation with cells cultured in the presence of the immobilized Notch ligand Delta1$^{Ext\text{-}IgG}$ experienced a significant reduction (50%) in time to neutrophil engraftment as compared to a concurrent cohort receiving a double cord blood transplantation of non-manipulated units (Delaney et al., 2010). However, there appears to be a dose dependent effect on reducing time to neutrophil engraftment with greater numbers of CD34+ cells infused, and thus, there is a need for methods that further enhance expansion of HSPC capable of rapid marrow repopulation until long-term engraftment occurs.

The data presented in this example demonstrate that whereas both a Notch agonist (specifically, Delta1$^{Ext\text{-}IgG}$) alone and an aryl hydrocarbon receptor antagonist (specifically, SR1) alone, enhance generation of CD34$^+$ cells, including NOD/SCID repopulating cells (SRC), the addition of a Notch agonist to an aryl hydrocarbon receptor antagonist (specifically, the addition of Delta1$^{Ext\text{-}IgG}$ to SR1) for use in expansion of cord blood HSPC further enhances the generation of rapidly repopulating myeloid cells, but not the generation of absolute numbers of CD34$^+$ cells. The analysis of developing cells within the cultures presented in this example suggests that enhanced generation of rapidly repopulating cells using the combination of a Notch agonist and an aryl hydrocarbon receptor antagonist (specifically, the combination of Delta1$^{Ext\text{-}IgG}$ and SR1) resulted from the delayed differentiation of cells due to Delta1$^{Ext\text{-}IgG}$. Further, the data presented in this example demonstrate that expanding HSPC using both a Notch agonist (specifically, Delta1$^{Ext\text{-}IgG}$) and an aryl hydrocarbon receptor antagonist (specifically, SR1) enhances generation of early myeloid and progenitor repopulating cells in vivo relative to HSPC expanded using a Notch agonist alone and/or an aryl hydrocarbon receptor antagonist alone (despite generation of fewer absolute total number of CD34$^+$ cells relative to HSPC expanded using an aryl hydrocarbon receptor antagonist alone). Furthermore, the data presented in this example demonstrate that expanding HSPC using both a Notch agonist (specifically, Delta1$^{Ext\text{-}IgG}$) and an aryl hydrocarbon receptor antagonist (specifically, SR1) enhances long-term multiple lineage engraftment and total human and B-lymphoid engraftment in vivo relative to HSPC expanded using a Notch agonist alone and/or an aryl hydrocarbon receptor antagonist alone.

Materials and Methods

Human cord blood (CB) samples for research were obtained from normal deliveries under Swedish Medical Center Institutional Review Board (Seattle) approval and after consent was obtained. CB samples were red blood cell depleted (Delaney et al., 2010, Nat Med 16(2):232-236), CD34 enriched using CD34$^+$ immunomagnetic particles (Miltenyi Biotec), purified with Automacs (Miltenyi Biotec), and cryopreserved. Cultures were performed using thawed and pooled cord blood units with Delta1$^{Ext\text{-}IgG}$ or IgG (2.5 μg/ml) (Delaney et al., 2010) in StemSpan serum-free expansion medium in the presence of four growth factors that have been previously used for SR1-induced HSPC expansion (IL6 (50 ng/ml), thrombopoietin (50 ng/ml), Flt-3 ligand (50 ng/ml), stem cell factor (50 ng/ml)) with SR-1 (750 nM) added fresh to cells with all feedings. Cultures were initiated with 7×10$^4$ to 1.3×10$^5$ CD34$^+$ cells for 25-cm$^2$ flasks and with 3×10$^5$ CD34$^+$ cells for 75-cm$^2$ flasks. Immunofluorescence analysis was performed as described (Ohishi et al., 2002, J Clin Invest. 110(8):1165-1174) with labeled antibodies: FITC (human CD14, CD33, and Lineage); PE (human CD7, CD14, CD15, CD19, CD90, and CD123); PERCP (human CD34); APC (human CD10, CD45, IL3Ra); PECy7 (mouse CD45.1, human CD34); Alexa Fluor 700 (CD38); APC-eFluor 780 (CD45RA). Transplants were performed in sublethally irradiated (275 rad) NOD-SCID IL-2Rγ-null mice (NSG). In vivo engraftment was assessed by immunofluorescence analysis of human cell subsets (human CD45$^+$ murine CD45.1). On average, the total number of cells infused was 4.25×10$^6$/mouse for Delta1$^{ext\text{-}IgG}$ alone, 1.88×10$^7$/mouse for SR1 alone, and 4.76×10$^6$/mouse for the combination. Statistical analyses were performed as indicated. For limiting dilution analysis, mice were injected with the cultured progeny of the number of CD34$^+$ cells indicated and bone marrow aspirates performed at 2 weeks. Two engraftment cut-offs were chosen based on percent engraftment observed in non-limiting transplantation studies. The frequency of SRCs was determined by the method of maximum likelihood with L-CALC software (StemCell Technologies) from the proportions of engrafted recipients (A, B).

RESULTS AND CONCLUSIONS

1. Immobilized Delta1$^{Ext-IgG}$ Delays Differentiation of CB HSPC Cultured with SR1 and Delta1$^{Ext-IgG}$ The data presented herein show that a Notch agonist (specifically, immobilized Delta1$^{Ext-IgG}$) delays differentiation of HSPC (specifically, cord blood HSPC) cultured using the combination of a Notch agonist and an aryl receptor antagonist (specifically, the combination of Delta1$^{Ext-IgG}$ and SR1).

Figure 10A:
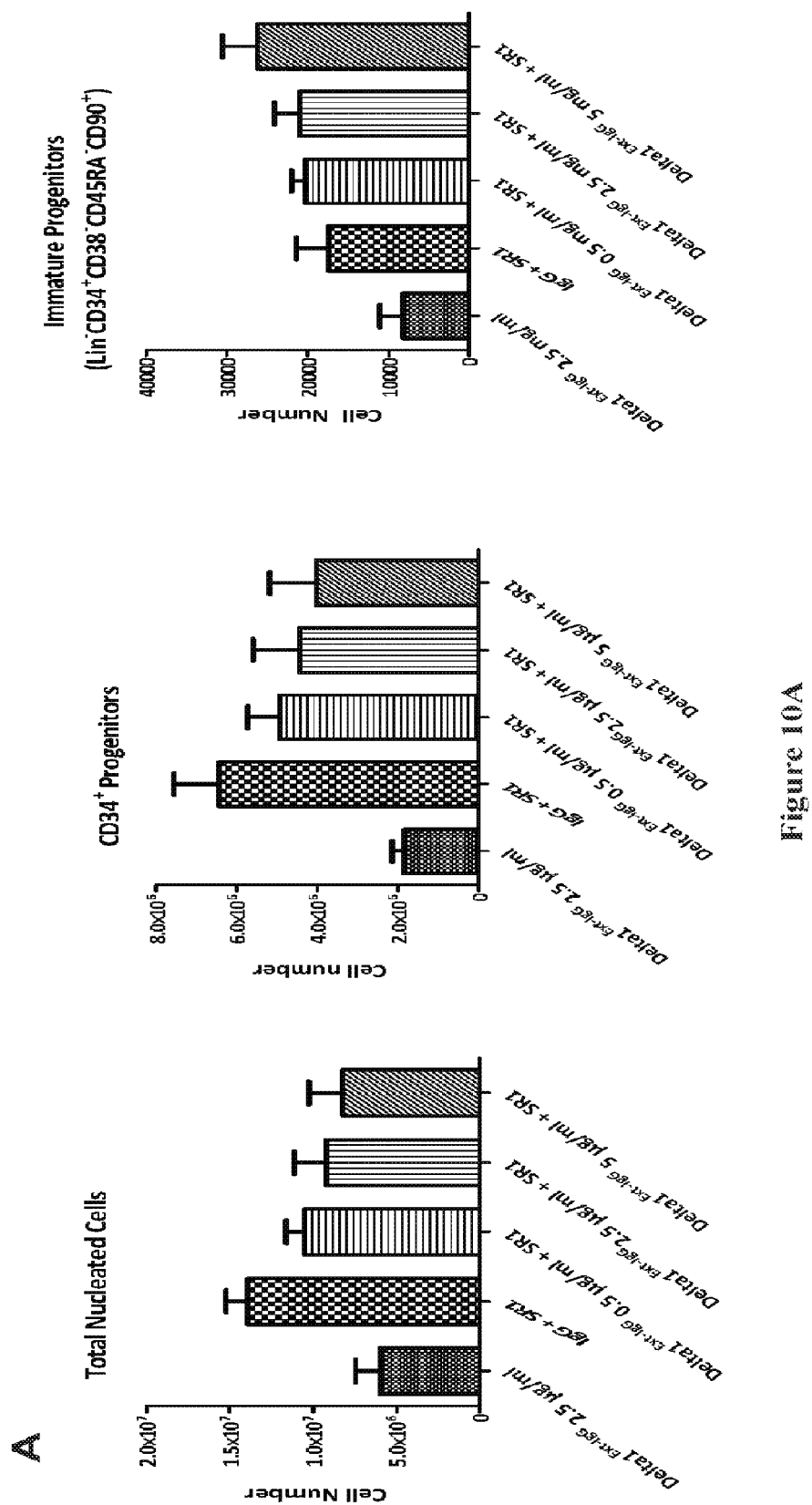
Figures 10B, 10C:
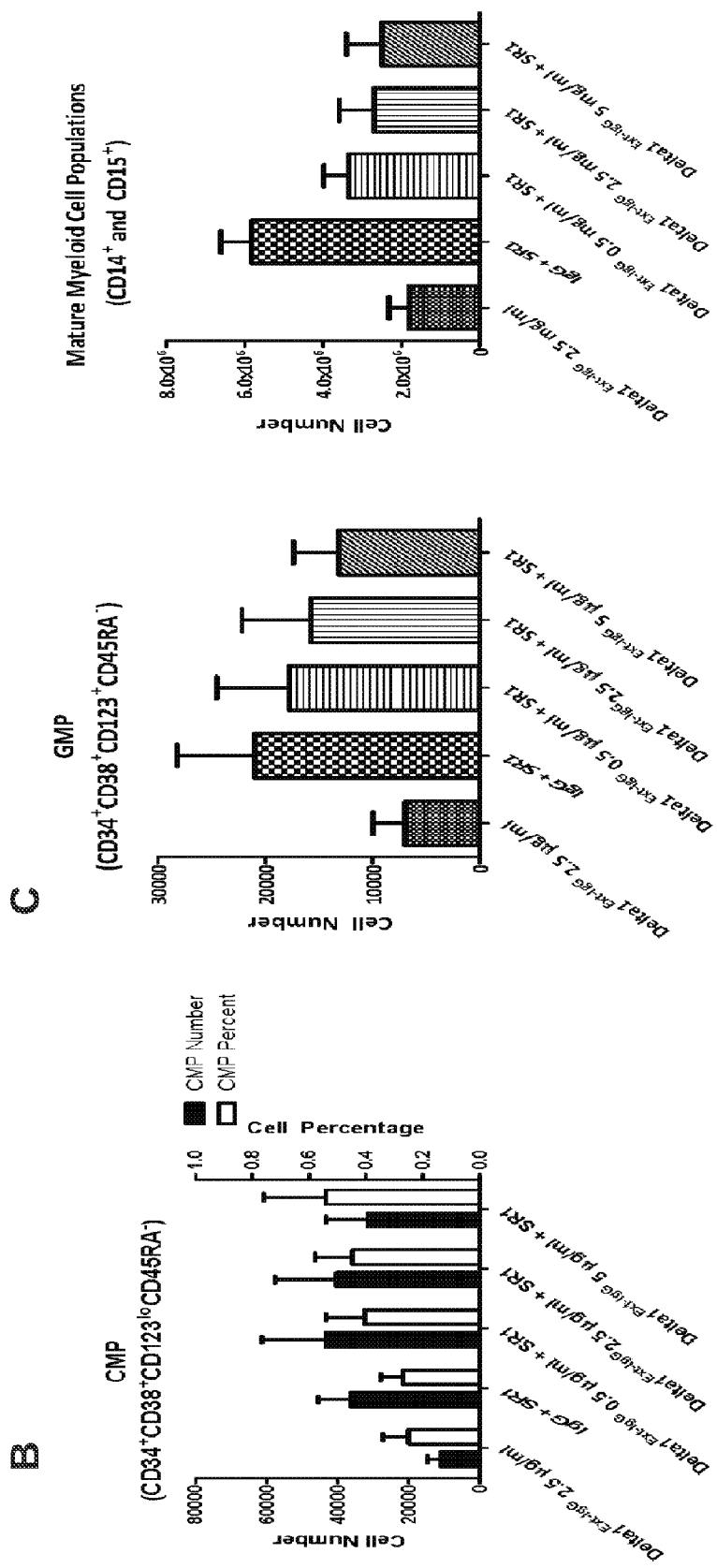
Figure 10D:
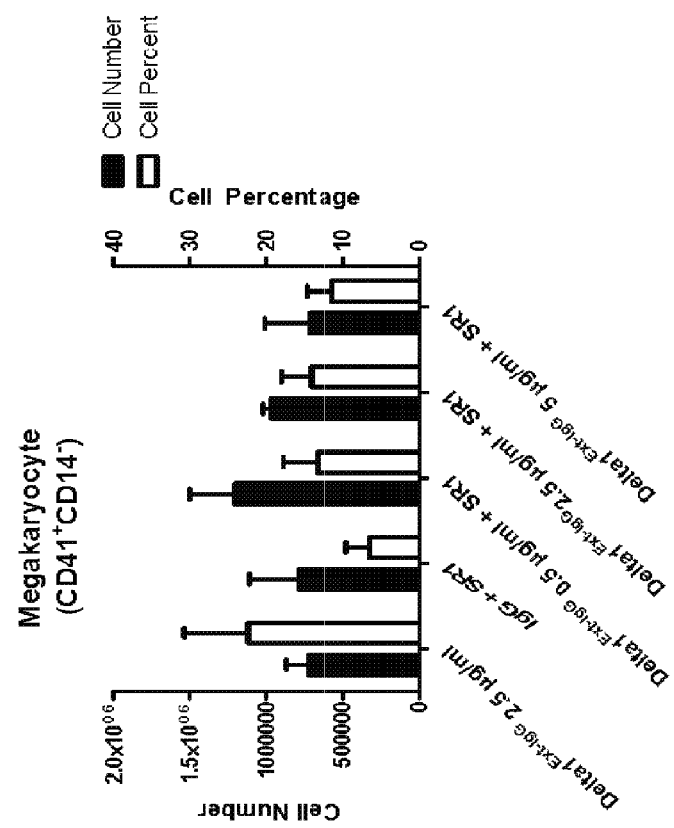
Figure 10D:
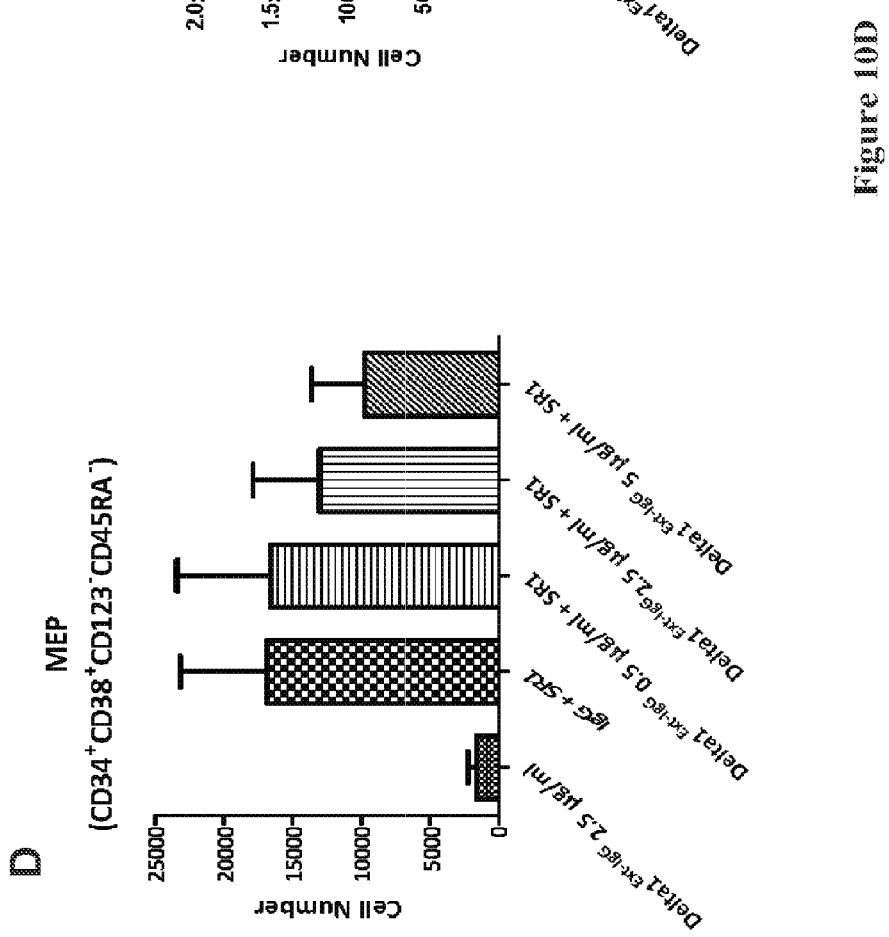

SR1 significantly enhanced the ex vivo generation of total nucleated cells (TNC) as compared to immobilized Delta1$^{Ext-IgG}$ (2.5 µg/ml) or SR1 (750 nM) and Delta1$^{Ext-IgG}$ (5 µg/ml) combined (p<0.001, p=0.04, FIG. 10A). Dose titration of Delta1$^{Ext-IgG}$ with standard dose SR1 trended towards enhanced generation of the highly immature Lin$^-$CD34$^+$CD38$^-$CD45RA$^-$CD90$^+$ subset (Majeti et al., 2007, Cell Stem Cell 1(6): 635-645) with increasing concentration of Delta1$^{ext-IgG}$ (p=0.07) while significantly decreasing TNC and total CD34$^+$ cell generation (p=0.02, p=0.04, FIG. 10A). Similar numbers of common myeloid progenitors (CMP) were generated between cultures containing SR1 or SR1 and Delta1$^{Ext-IgG}$ combined; however, there was a trend towards maintenance of greater percentages of these cells with increasing Delta1$^{Ext-IgG}$ doses (p=0.18, FIG. 10B) (Manz et al., 2002, Proc Natl Acad Sci USA. 99(18): 11872-11877). Together, these data suggest impeded differentiation of early myeloid precursors due to Delta1$^{Ext-IgG}$. Consistent with this notion were the significantly fewer CD14/15$^+$ mature myeloid cells generated with increasing Delta1$^{Ext-IgG}$ dose (p=0.005), presumably due to inhibition of precursor differentiation towards mature myeloid progeny (FIG. 10C) (Manz et al., 2002). No differences were observed for granulocyte-monocyte progenitors ("GMP," FIG. 10C) and megakaryocyte-erythrocyte progenitors ("MEP," FIG. 10D); however, there was a suggestion of decreased cell numbers generated with increased Delta1$^{Ext-IgG}$ doses in these cell populations. Megakaryocyte generation was similar across all conditions despite decreased generation of MEP with increasing doses of Delta1$^{Ext-IgG}$. Delta1$^{Ext-IgG}$ containing cultures had a greater percentage of CD41$^+$CD14$^-$ cells consistent with the role of Notch in megakaryocyte differentiation (FIG. 10D). There was no difference in generation of erythroid precursors (CD235a$^+$CD71$^+$, data not shown). Taken together, these data suggest that decreased generation of more mature myeloid cell populations together with greater maintenance of the immature Lin$^-$CD34$^+$CD38$^-$CD45RA$^-$CD90$^+$ and CMP cell populations in the presence of Delta1$^{Ext-IgG}$ results from inhibition of differentiation and potentially enhanced self-renewal of the least mature precursors.

2. Expansion of HSPC in the Presence of the Combination of Delta1$^{Ext-IgG}$ and SR1 Enhances Generation of Early Progenitor and Myeloid Repopulating Cells In Vivo The data presented herein show that expansion of HSPC (specifically, cord blood HSPC) in the presence of the combination of a Notch agonist and an aryl hydrocarbon receptor antagonist (specifically, the Delta1$^{Ext-IgG}$ and SR1) enhances generation of early progenitor and myeloid repopulating cells in vivo, and enhances long-term total and B-lymphocyte engraftment.

Figure 11A:
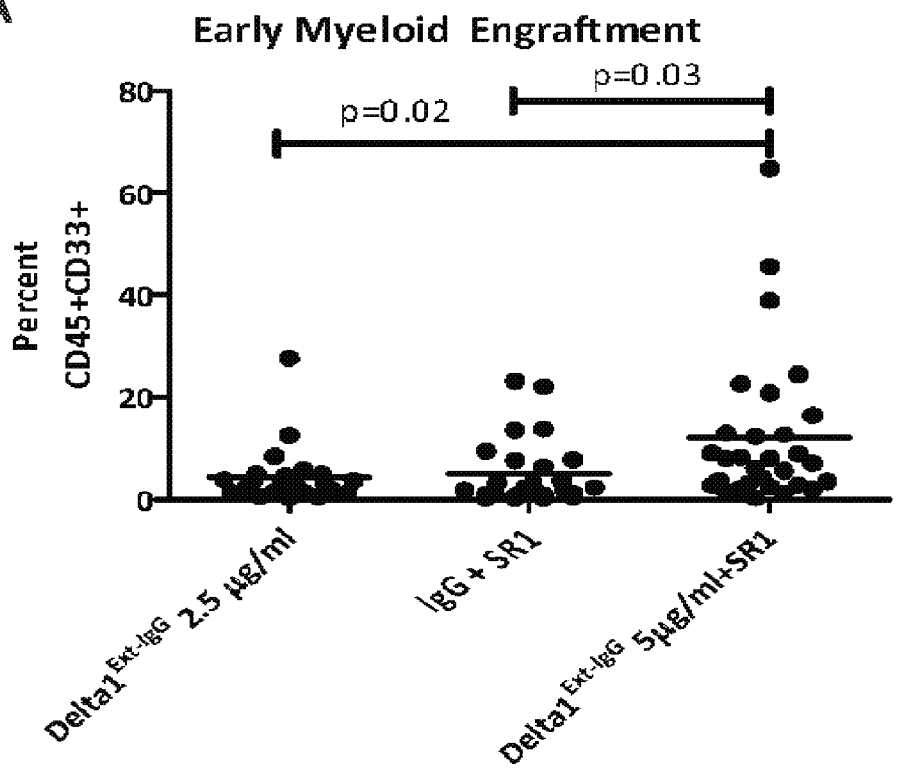

In vivo repopulating capability of HSPC generated from culture with Delta1$^{Ext-IgG}$ SR1, or the combination of Delta1$^{Ext-IgG}$ and SR1, was assessed. Using Delta1$^{Ext-IgG}$ at 5 µg/ml, concentration found to be optimal in preliminary studies (data not shown), significantly enhanced rapid myeloid reconstitution (percent CD45$^+$CD33$^+$) was observed using cells cultured in the presence of the combination of Delta1$^{Ext-IgG}$ and SR1 in comparison with cells cultured in the presence of either factor alone (FIG. 11A). Moreover, a significant, nearly 3-fold, increase in CD33$^+$ NOD/SCID repopulating cells (SRC) frequency was found in mice that received cells cultured in the presence of the combination of Delta1$^{Ext-IgG}$ and SR1 as compared to mice that received cells cultured in the presence of either factor alone, based on robust, greater than 5% marrow repopulation (FIG. 11A, and Table 3). At a more limiting level of marrow repopulation (1%), a significant 3-fold difference was also found between cells cultured in the presence of SR1 alone and the cells cultured in the presence of the combination of Delta1$^{Ext-IgG}$ and SR1. However, there was a non-significant 1½-fold difference between cells cultured in the presence of Delta1$^{Ext-IgG}$ vs. the combination of Delta1$^{Ext-IgG}$ and SR1. This suggests that the difference in SRC frequency between cells cultured in the presence of SR1 and Delta1$^{Ext-IgG}$ at a limiting level of marrow repopulation may reflect generation of cells with more robust repopulating capability when cultured in Delta1$^{Ext-IgG}$, perhaps due to retention of properties of less mature repopulating cells.

TABLE 3

| | CD33$^+$ SRC frequency determined by limiting dilution analysis | | | | | |
|---|---|---|---|---|---|---|
| | Engraftment with ≥1% CD33$^+$ cells | | | Engraftment with ≥5% CD33$^+$ cells | | |
| No. CD34$^+$ cells/mouse | Delta1$^{Ext-IgG}$ 2.5 µg/ml | IgG + SR1 | Delta1$^{Ext-IgG}$ 5 µg/ml + SR1 | Delta1$^{Ext-IgG}$ 2.5 µg/ml | IgG + SR1 | Delta1$^{Ext-IgG}$ 5 µg/ml + SR1 |
| | | No. mice engrafted | | | No. mice engrafted | |
| 1000 | 2/9 | 3/9 | 4/9 | 0/9 | 1/9 | 2/9 |
| 4000 | 9/9 | 5/9 | 9/9 | 3/9 | 1/9 | 6/9 |
| 20000 | 7/7 | 7/7 | 7/7 | 6/7 | 7/7 | 7/7 |
| SRC frequency per starting cell | 1/1719* | 1/3868** | 1/1276 | 1/11314$^\#$ | 1/10063$^{\#\#}$ | 1/3652 |

\*p = 0.47,
\*\*p = 0.02;
$^\#$p = 0.02,
$^{\#\#}$p = 0.04, reference group Delta1$^{Ext-IgG}$ 5 µg/ml + SR1

Figure 11B:
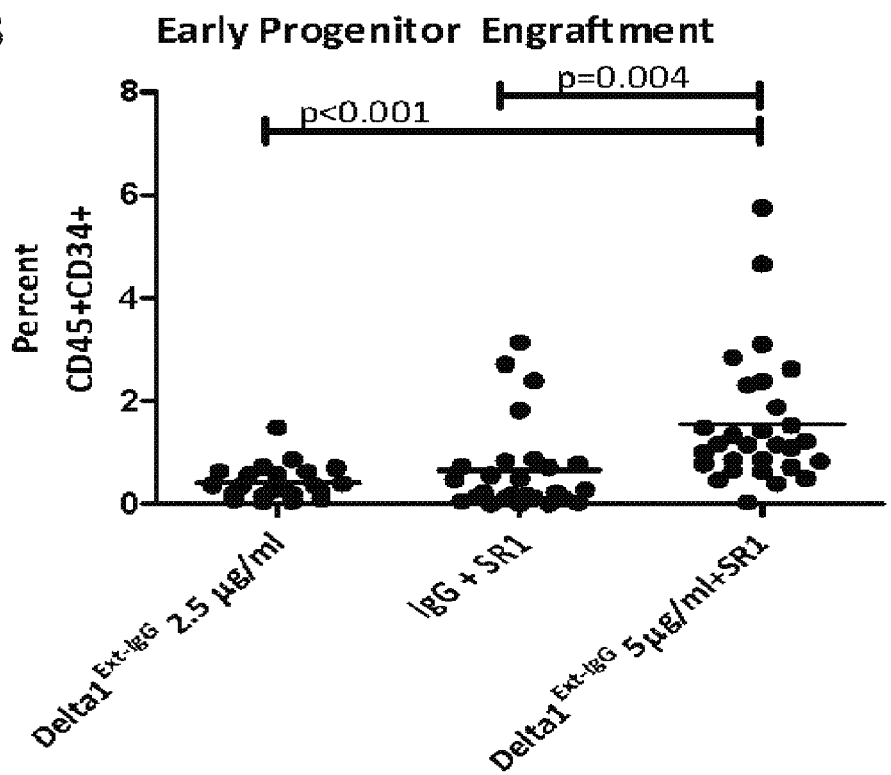

Further, progenitor cell repopulation (percent CD45$^+$ CD34$^+$) was significantly enhanced with cell cultured in the presence of the combination of Delta1$^{Ext-IgG}$ and SR1 (FIG. 11B). A 2- to 3-fold increase in CD34$^+$ SRC frequency was suggested by limiting dilution analysis at 5% marrow repopulation, with lesser differences detected at 1% repopulation (FIG. 11B, and Table 4).

TABLE 4

CD34$^+$ SRC frequency determined by limiting dilution analysis

|  | Engraftment with ≥0.5% CD34$^+$ cells | | | Engraftment with ≥1% CD34$^+$ cells | | |
|---|---|---|---|---|---|---|
| No. CD34$^+$ cells/mouse | Delta1$^{Ext-IgG}$ 2.5 μg/ml | IgG + SR1 | Delta1$^{Ext-IgG}$ 5 μg/ml + SR1 | Delta1$^{Ext-IgG}$ 2.5 μg/ml | IgG + SR1 | Delta1$^{Ext-IgG}$ 5 μg/ml + SR1 |
|  | | No. mice engrafted | | | No. mice engrafted | |
| 1000 | 0/9 | 1/9 | 1/9 | 0/9 | 1/9 | 0/9 |
| 4000 | 1/9 | 2/9 | 6/9 | 0/9 | 1/9 | 3/9 |
| 20000 | 7/7 | 7/7 | 7/7 | 6/7 | 6/7 | 7/7 |
| SRC frequency per starting cell | 1/11739* | 1/8495** | 1/4200 | 1/19121$^\#$ | 1/13514$^{\#\#}$ | 1/8273 |

*p = 0.04,
**p = 0.15;
$^\#$p = 0.11,
$^{\#\#}$p = 0.33, reference group Delta1$^{Ext-IgG}$ 5 μg/ml + SR1

Figure 11C:
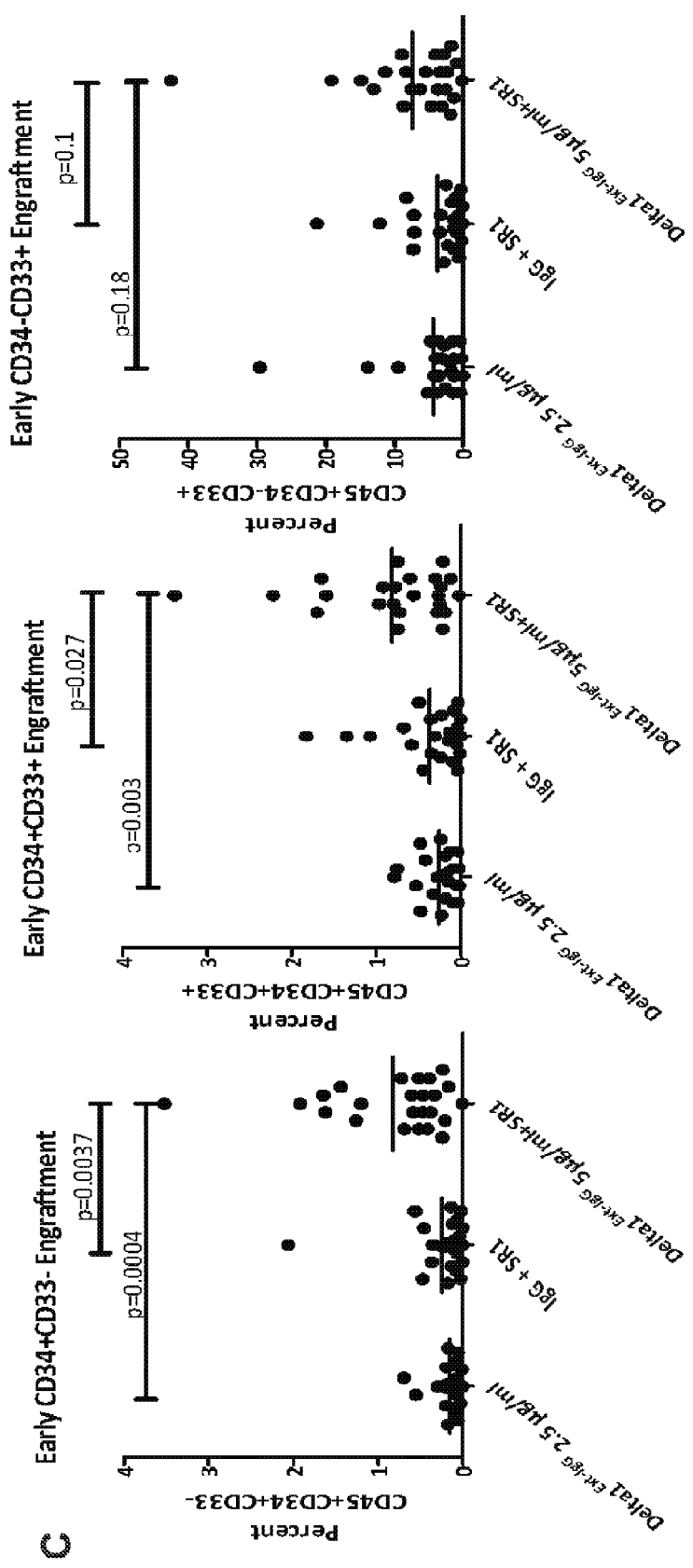
Figures 11D, 11E:
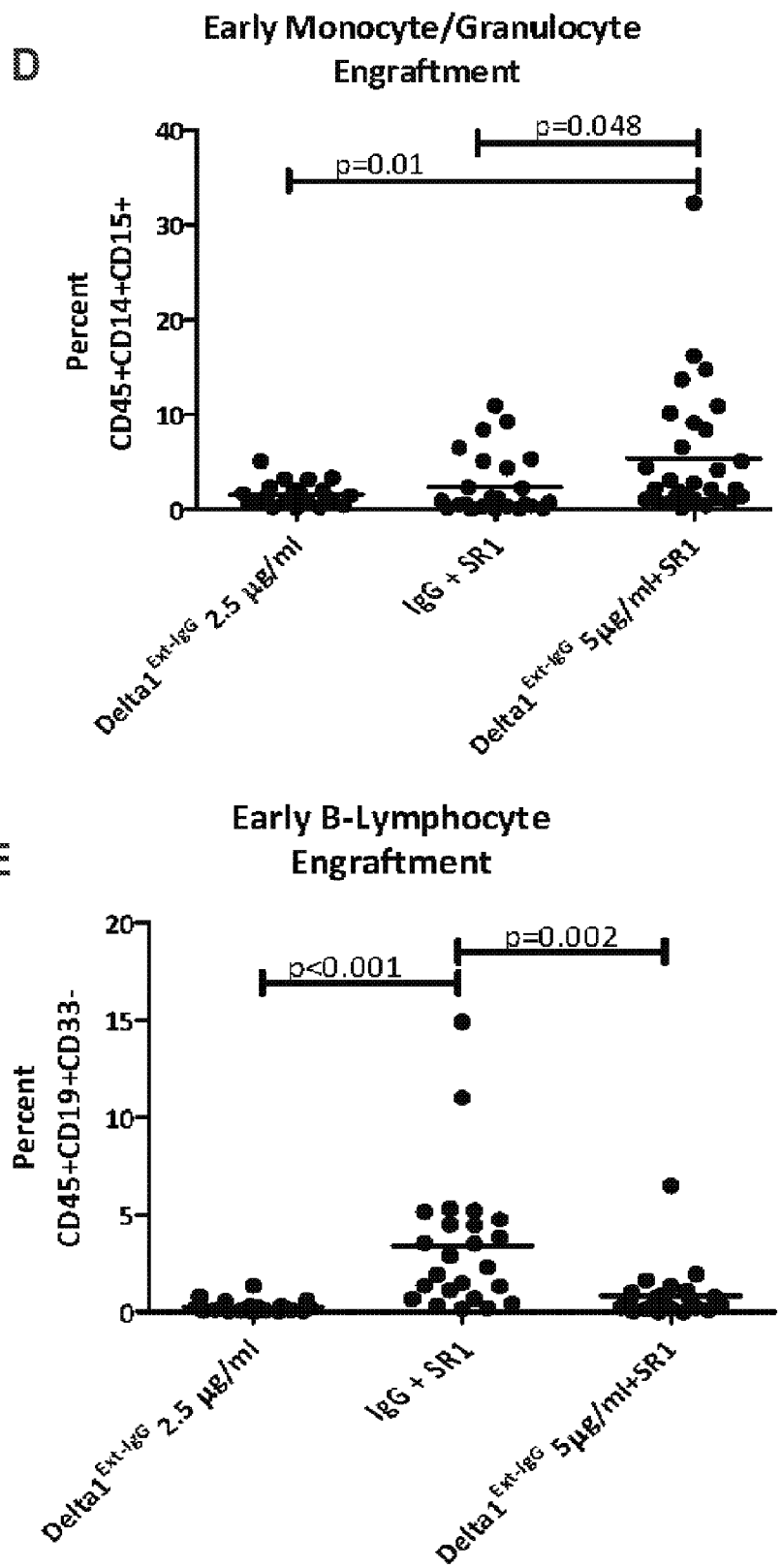

Analysis of progressively maturing precursor populations contributing to engraftment revealed that enhanced myeloid and progenitor repopulation was due to enhanced engraftment of the CD45$^+$CD34$^+$33$^-$ and CD45$^+$CD34$^+$33$^+$ cell populations but not the most mature CD45$^+$CD34$^-$CD33$^+$ cell subset, consistent with the above-presented in vitro data that addition of Delta1$^{Ext-IgG}$ to SR1 resulted in generation of more immature progenitor cells (FIG. 11C). Monocytic/granulocytic cell engraftment (percent CD45$^+$ that are CD14$^+$ and/or CD15$^+$) was also enhanced at this early time point by cells cultured in the presence of the combination of SR1 and Delta1$^{Ext-IgG}$ compared to either agent alone (FIG. 11D). In contrast, rapid repopulation by B-lymphoid cells (percent CD45$^+$CD33$^-$CD19$^+$) was significantly enhanced by cells cultured in the presence of SR1 alone in comparison with cells cultured in the presence of Delta1$^{Ext-IgG}$ alone or cultured in the presence of the combination of Delta1$^{Ext-IgG}$ and SR1 (FIG. 11E). This may be a result of Notch1-mediated inhibition of B-cell differentiation combined with greater generation of immature B-cells in the presence of aryl hydrocarbon receptor (AhR) inhibition as previously demonstrated in AhR receptor-null mice (Lehar et al., 2005, Blood 105(4): 1440-1447; Jaleco et al., 2001, J Exp Med. 194(7):991-1002; Singh et al., 2011, Stem Cells Dev. 20(5): 769-784). Minimal megakaryocyte (CD14$^-$CD41$^+$), erythroid (Glycophorin A$^+$), and T-cell (CD3$^+$) engraftment was observed at this early time point preventing in vivo comparison of these cell populations.

Figure 11F:
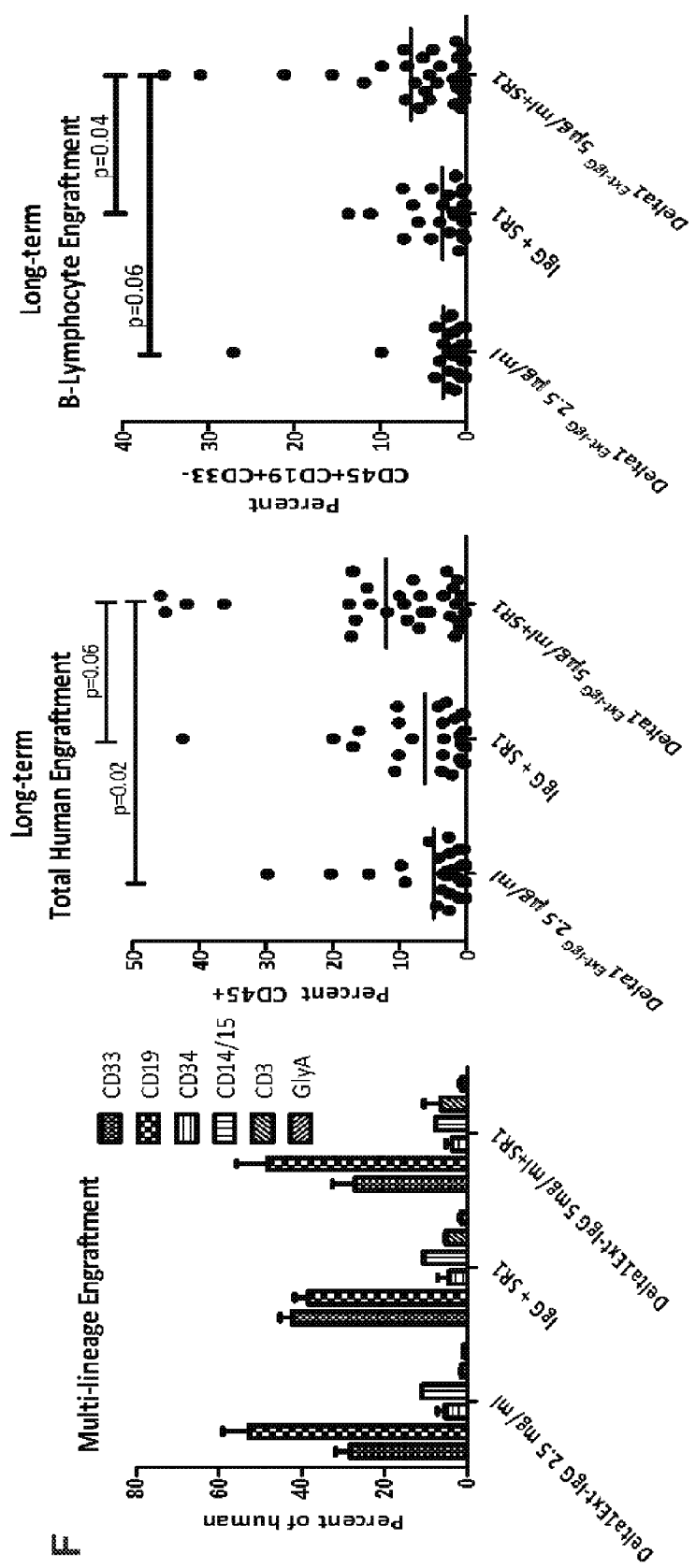

Cells cultured in the presence of the combination of SR1 and Delta1$^{Ext-IgG}$ were found to be capable of longer-term, multi-lineage engraftment (FIG. 11F). Evaluation at 12-14 weeks post-infusion revealed overall enhanced human engraftment in the combination group (FIG. 11F); however this was primarily due to enhanced B-lymphoid engraftment (FIG. 11F) as total marrow myeloid (CD33$^+$ and CD14/15$^+$), progenitor (CD34$^+$), T-lymphoid (CD3$^+$), and erythroid (Glycophorin A$^+$) cell engraftment was similar between the groups (not shown). It is not clear whether these lymphoid cells were newly derived or represented longer lived cells developed during earlier time points. Low-level human engraftment was observed in all groups upon secondary transplantation demonstrating stable, long-term engraftment of the expanded cells (average CD45$^+$ 0.22% in Delta1$^{Ext-IgG}$, 0.11% in SR1, and 0.18% in the combination); however, these differences were not statistically significant suggesting these cells have similar long-term engraftment potential.

3. Conclusions

The data presented herein show that culturing of cord blood hematopoietic stem/progenitor cells in the presence of both a Notch agonist and an aryl hydrocarbon receptor antagonist, specifically the combination of Delta1$^{ext-IgG}$ and SR1, enhances in vitro generation of a highly immature progenitor cell population (Lin$^-$CD34$^+$CD38$^-$CD45RA$^-$CD90$^+$) and decreases generation of mature myeloid populations (CD14$^+$ and CD15$^+$ cells). Importantly, greater expansion of clinically relevant, rapidly repopulating cells occurred in the presence of the combination of a Notch agonist and an aryl hydrocarbon receptor antagonist in comparison with either agent alone. In particular, the data presented herein show that combining Delta1$^{Ext-IgG}$ and SR1 achieved enhanced generation of cells capable of rapidly repopulating bone marrow with early myeloid and progenitor cells. Unexpectedly, this occurred despite decreased generation of CD34 cells in culture when Delta1$^{Ext-IgG}$ was added to SR1, indicating that generation of particular subsets of CD34$^+$ cells, rather than the absolute number of CD34$^+$ cells, may be more predictive of in vivo reconstitution. The data presented herein also suggest that a Notch agonist (specifically, Delta1$^{ext-IgG}$) enhances an aryl hydrocarbon receptor antagonist (specifically, SR1) induced generation of less mature precursors by delaying their differentiation, thereby enabling generation of greater numbers of clinically relevant repopulating cells.

The ability to significantly enhance early myeloid reconstitution has clear clinical relevance for reducing duration of neutropenia and early infectious complications in recipients of stem cell transplants or other intensive chemotherapy. Therefore, the methods presented in this example can be used for generation of increased numbers of HSPC that may be capable of achieving clinically significant reduction in time to myeloid engraftment in neutropenic patients. In particular, the inventors expect that use of the combination of a Notch agonist (e.g., Delta1$^{ext-IgG}$) and an aryl hydrocarbon receptor antagonist (e.g., SR1), such as described herein, can be used to produce an economically feasible, non-HLA matched, expanded cell product where greater numbers of repopulating cells may be required to overcome greater HLA disparity.

REFERENCES

1. Delaney C, Heimfeld S, Brashem-Stein C, Voorhies H, Manger R L, Bernstein I D. Notch-mediated expansion of human cord blood progenitor cells capable of rapid myeloid reconstitution. Nat Med. 2010; 16(2):232-236.
2. Boitano A E, Wang J, Romeo R, et al. Aryl hydrocarbon receptor antagonists promote the expansion of human hematopoietic stem cells. Science. 2010; 329(5997): 1345-1348.
3. Peled T, Mandel J, Goudsmid R N, et al. Pre-clinical development of cord blood-derived progenitor cell graft expanded ex vivo with cytokines and the polyamine copper chelator tetraethylenepentamine. Cytotherapy. 2004; 6(4):344-355.
4. de Lima M, McMannis J, Gee A, et al. Transplantation of ex vivo expanded cord blood cells using the copper chelator tetraethylenepentamine: a phase I/II clinical trial. Bone marrow transplant. 2008; 41(9):771-778.
5. Peled T, Shoham H, Aschengrau D, et al. Nicotinamide, a SIRT1 inhibitor, inhibits differentiation and facilitates expansion of hematopoietic progenitor cells with enhanced bone marrow homing and engraftment. Exp Hematol. 2012; 40(4):342-355 e341.
6. McNiece I, Harrington J, Turney J, Kellner J, Shpall E J. Ex vivo expansion of cord blood mononuclear cells on mesenchymal stem cells. Cytotherapy. 2004; 6(4):311-317.
7. De Lima M R S, McMannis J, et al. Mesenchymal stem cell based cord blood expansion leads to rapid engraftment of platelets and neutrophils [abstract]. Blood. 2010; 116:Abstract 362.
8. Dahlberg A, Delaney C, Bernstein I D. Ex vivo expansion of human hematopoietic stem and progenitor cells. Blood. 2011; 117(23):6083-6090.
9. Delaney C, Varnum-Finney B, Aoyama K, Brashem-Stein C, Bernstein I D. Dose-dependent effects of the Notch ligand Delta1 on ex vivo differentiation and in vivo marrow repopulating ability of cord blood cells. Blood. 2005; 106(8):2693-2699.
10. Ohishi K, Varnum-Finney B, Bernstein I D. Delta-1 enhances marrow and thymus repopulating ability of human CD34(+)CD38(−) cord blood cells. J Clin Invest. 2002; 110(8):1165-1174.
11. Majeti R, Park C Y, Weissman I L. Identification of a hierarchy of multipotent progenitors in human cord blood. Cell Stem Cell. 2007; 1(6): 635-645.
12. Manz M G, Miyamoto T, Akashi K, Weissman I L. Prospective isolation of human clonogenic common myeloid progenitors. Proc Natl Acad Sci USA. 2002; 99(18):11872-11877.
13. Lehar S M, Dooley J, Farr A G, Bevan M J. Notch ligands Delta 1 and Jagged1 transmit distinct signals to T-cell precursors. Blood. 2005; 105(4):1440-1447.
14. Jaleco A C, Neves H, Hooijberg E, et al. Differential effects of Notch ligands Delta-1 and Jagged-1 in human lymphoid differentiation. J Exp Med. 2001; 194(7):991-1002.
15. Singh K P, Garrett R W, Casado F L, Gasiewicz T A. Aryl hydrocarbon receptor-null allele mice have hematopoietic stem/progenitor cells with abnormal characteristics and functions. Stem Cells Dev. 2011; 20(5):769-784.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications, including patents, patent application publications, and scientific literature, are cited herein, the disclosures of which are incorporated by reference in their entireties for all purposes.

What is claimed:

1. A method of expanding hematopoietic stem/progenitor cells with improved in vivo repopulating ability, comprising culturing isolated hematopoietic stem/progenitor cells ex vivo in the presence of a composition comprising an amount of Delta$^{ext-IgG}$ and an amount of 4-(2-(2-(benzothiophen-3-yl)-9-isopropyl-9H-purin-6-ylamino)ethyl)phenol (SR1) that results in expansion of hematopoietic stem/progenitor cell sample with improved in vivo repopulating ability as compared to a hematopoietic stem/progenitor cell sample expanded in culture comprising an amount of Delta$^{ext-IgG}$ but no SR1 or an amount of SR1 but no Delta$^{ext-IgG}$, wherein the amount of SR1 is between about 200 nM and 1000 nM and wherein the amount of Delta$^{ext-IgG}$ is between about 1.25 µg/ml and 10 µg/ml, thereby expanding hematopoietic stem/progenitor cells with improved in vivo repopulating ability.

2. The method of claim 1, wherein the isolated hematopoietic stem/progenitor cells are human.

3. The method of claim 1, wherein in said culturing step, hematopoietic stem/progenitor cells are in contact with a solid phase on which the Delta$^{ext-IgG}$ is immobilized, and the SR1 is in a fluid contacting said cells.

4. The method of claim 1, wherein in said culturing step, hematopoietic stem/progenitor cells are cultured on a solid phase coated with the Delta$^{ext-IgG}$, and the SR1 is in a fluid contacting said cells.

5. The method of 1, wherein the composition or the fluid further comprises one or more growth factors.

6. The method of claim 5, wherein the one or more growth factors are selected from stem cell factor (SCF), Flt-3 ligand (Flt-3), Interleukin-6 (IL-6), Interleukin-3 (IL-3), Interleukin-11 (IL-11), thrombopoietin (TPO), Granulocyte-macrophage colony stimulating factor (GM-CSF), and granulocyte colony stimulating factor (G-CSF).

7. The method of claim 6, wherein the composition or the fluid comprises IL-6, Flt-3, SCF and TPO.

8. The method of claim 3, wherein the Delta$^{ext-IgG}$ is applied to the solid phase.

9. The method of claim 3, wherein the amount of Delta$^{ext-IgG}$ is between about 2 and 6 µg/ml applied to the solid phase.

10. The method of claim 1, wherein the composition further comprises an immobilized fibronectin or a fragment thereof.

11. The method of claim 10, wherein the fragment of fibronectin is CH-296.

12. The method of claim 1, wherein the isolated hematopoietic stem/progenitor cells are derived from umbilical cord blood and/or placental cord blood.

13. The method of claim 12, wherein the isolated hematopoietic stem/progenitor cells are derived from a pool of two or more different humans at birth.

14. The method of claim 13, wherein the isolated hematopoietic stem/progenitor cells are derived from humans of the same race.

15. The method of claim 13, wherein the isolated hematopoietic stem/progenitor cells are derived from humans of the same ethnicity.

16. The method of claim 1, wherein the percentage of CD34$^+$ cells in the expanded hematopoietic stem/progenitor cell sample is higher than the percentage of CD34$^+$ cells in the isolated hematopoietic stem/progenitor cells.

17. The method of claim 1, wherein the percentage of CD34$^+$ cells in the expanded hematopoietic stem/progenitor cell sample is higher than the percentage of CD34$^+$ cells in a sample of the hematopoietic stem/progenitor cells expanded using Delta$^{ext-IgG}$ alone and/or SR1 alone.

18. The method of claim 1, wherein the percentage of CD34$^+$CD90$^+$ cells in the expanded hematopoietic stem/progenitor cell sample is higher than the percentage of CD34$^+$CD90$^+$ cells in a sample of the hematopoietic stem/progenitor cells expanded using Delta$^{ext-IgG}$ alone and/or SR1 alone.

19. The method of claim 1, wherein the percentage of CD34$^-$CD14$^+$ cells in the expanded hematopoietic stem/progenitor cell sample is lower than the percentage of CD34$^-$CD14$^+$ cells in the isolated hematopoietic stem/progenitor cells.

20. The method of claim 1, wherein the percentage of CD34$^-$CD14$^+$ cells in the expanded hematopoietic stem/progenitor cell sample is lower than the percentage of CD34$^-$CD14$^+$ cells in a sample of the hematopoietic stem/progenitor cells expanded using Delta$^{ext-IgG}$ alone and/or SR1 alone.

21. A method of expanding human hematopoietic stem/progenitor cells with improved in vivo repopulating ability, comprising culturing isolated hematopoietic stem/progenitor cells ex vivo on a solid phase coated with (i) an amount of Delta$^{ext-IgG}$ and (ii) CH-296, and in the presence of a medium comprising (iii) an amount of an aryl hydrocarbon receptor antagonist and (iv) four or more growth factors;

wherein (i) and (iii) are provided in amounts that result in expanded human hematopoietic stem/progenitor cells with improved in vivo repopulating ability as compared to a hematopoietic stem/progenitor cell sample expanded in culture comprising an amount of Delta$^{ext-IgG}$ but no aryl hydrocarbon receptor antagonist or an amount of an aryl hydrocarbon receptor antagonist but no Delta$^{ext-IgG}$; and wherein the aryl hydrocarbon antagonist is 4-(2-(2-(benzothiophen-3-yl)-9-isopropyl-9H-purin-6-ylamino) ethyl)phenol; and wherein the four or more growth factors are selected from IL6, TPO, Flt-3 ligand, CSF and IL3;

thereby producing an expanded hematopoietic stem/progenitor cell sample with improved in vivo repopulating ability.

22. The method of claim 1, wherein the Delta$^{ext-IgG}$ is Delta$^{ext-IgG}$.

* * * * *

SEQUENCE LISTING

```
<160> NUMBER OF SEQ ID NOS: 4

<210> SEQ ID NO 1
<211> LENGTH: 61
<212> TYPE: DNA
<213> ORGANISM: Artificial Sequence
<220> FEATURE:
<223> OTHER INFORMATION: siRNA molecule capable of down-regulating the
      expression of aryl hydrocarbon receptor

<400> SEQUENCE: 1
gcggcataga gaccgactta atttcaagag aattaagtcg gtctctatgc cgcttttttg      60
g                                                                      61

<210> SEQ ID NO 2
<211> LENGTH: 65
<212> TYPE: DNA
<213> ORGANISM: Artificial Sequence
<220> FEATURE:
<223> OTHER INFORMATION: siRNA molecule capable of down-regulating the
      expression of aryl hydrocarbon receptor
```

```
<400> SEQUENCE: 2
cgcgccaaaa aagcggcata gagaccgact taattctctt gaaattaagt cggtctctat      60
gccgc                                                                  65

<210> SEQ ID NO 3
<211> LENGTH: 61
<212> TYPE: DNA
<213> ORGANISM: Artificial Sequence
<220> FEATURE:
<223> OTHER INFORMATION: siRNA molecule capable of down-regulating the
      expression of aryl hydrocarbon receptor

<400> SEQUENCE: 3
ggcttctttg atgttgcatt aattcaagag attaatgcaa catcaaagaa gccttttttg      60
g                                                                      61

<210> SEQ ID NO 4
<211> LENGTH: 65
<212> TYPE: DNA
<213> ORGANISM: Artificial Sequence
<220> FEATURE:
<223> OTHER INFORMATION: siRNA molecule capable of down-regulating the
      expression of aryl hydrocarbon receptor

<400> SEQUENCE: 4
cgcgccaaaa aaggcttctt tgatgttgca ttaatctctt gaattaatgc aacatcaaag      60
aagcc                                                                  65
```